US011753685B2

(12) United States Patent
Shultzaberger et al.

(10) Patent No.: US 11,753,685 B2
(45) Date of Patent: Sep. 12, 2023

(54) CIRCULATING RNA SIGNATURES SPECIFIC TO PREECLAMPSIA

(71) Applicant: ILLUMINA, INC., San Diego, CA (US)

(72) Inventors: Sarah E. Shultzaberger, San Diego, CA (US); Fiona Kaper, San Diego, CA (US); Sarah Kinnings, San Diego, CA (US); Suzanne Rohrback, San Diego, CA (US); Carlo Randise-Hinchliff, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/953,480

(22) Filed: Nov. 20, 2020

(65) Prior Publication Data

US 2021/0155987 A1 May 27, 2021

Related U.S. Application Data

(60) Provisional application No. 62/939,324, filed on Nov. 22, 2019.

(51) Int. Cl.
*C12Q 1/68* (2018.01)
*C12P 19/34* (2006.01)
*C12Q 1/6883* (2018.01)
*C12N 15/10* (2006.01)

(52) U.S. Cl.
CPC ....... *C12Q 1/6883* (2013.01); *C12N 15/1096* (2013.01); *C12Q 2600/118* (2013.01); *C12Q 2600/158* (2013.01)

(58) Field of Classification Search
CPC ........................ C12Q 1/6869; C12Q 2600/158
See application file for complete search history.

(56) References Cited

U.S. PATENT DOCUMENTS

| | | | |
|---|---|---|---|
| 9,657,342 | B2 | 5/2017 | Rava et al. |
| 10,240,199 | B2 | 3/2019 | Lo et al. |
| 2010/0273671 | A1 | 10/2010 | Lauwerys et al. |
| 2012/0270739 | A1 | 10/2012 | Rava et al. |
| 2014/0087967 | A1 | 3/2014 | Goren et al. |
| 2014/0243212 | A1 | 8/2014 | Lo et al. |
| 2016/0289762 | A1 | 10/2016 | Koh et al. |
| 2017/0234874 | A1 | 8/2017 | Adams et al. |

FOREIGN PATENT DOCUMENTS

| | | |
|---|---|---|
| JP | 2006/515517 | 6/2006 |
| JP | 2008/524993 | 7/2008 |
| WO | 065629 | 8/2004 |
| WO | 097051 | 9/2006 |
| WO | 132244 | 9/2014 |
| WO | 227015 | 11/2019 |

OTHER PUBLICATIONS

UBE2Q1 tissue expression data from NCBI, 2 pages printed from https://www.ncbi.nlm.nih.gov/gene/55585/?report=expression on May 24, 2022. (Year: 2022).*

Qingyan Cao et al., "Decreased levels of UBE2Q1 and CHIP in the placentas of infection related preterm birth" Clin. Exp. Obstet. Gynecol., XLV, No. 5, 2018. (Year: 2018).*

Nancy B.Y. Tsui et al., "Maternal Plasma RNA Sequencing for Genome-Wide Transcriptomic Profiling and Identification of Pregnancy-Associated Transcripts" Clinical Chemistry 60:7 954-962 (2014) (Year: 2014).*

Vivian G. Cheung, et al. "Natural variation in human gene expression assessed in lymphoblastoid cells" Nature Genetics, vol. 33, Mar. 2003. (Year: 2003).*

Yasushi Hosikawa, et al. "Hypoxia induces different genes in the lungs of rats compared with mice" Physiol Genomics 12: 209-219, 2003. (Year: 2003).*

Chen et al., "Personal Omics Profiling Reveals Dynamic Molecular and Medical Phenotypes," Cell, Mar. 16, 2012 148:1293-1307.

Chen et al., "Whole-Exome Enrichment with the Agilent SureSelect Human All Exon Platform," Cold Spring Harb Protoc, Mar. 11, 2015: 626-633.

Chen et al., "Whole-Exome Enrichment with the Roche NimbleGen SeqCap EZ Exome Library SR Platform," Cold Spring Harb Protoc, 2015(7): 11 pgs.

Chen et al., "Whole-Exome Enrichment with the Illumina TruSeq Exome Enrichment Platform," Cold Spring Harb Protoc, Mar. 11, 2015: 642-648.

Chim et al., "Detection and Characterization of Placental MicroRNAs in Maternal Plasma," Clin Chem, 2008,54(3):482-490.

Conover et al., "Pregnancy-Associated Plasma Protein-A2 (PAPP-A2): Tissue Expression and biological Consequences of Gene Knockout in Mice," Endocrinology, Jul. 2011;152(7):2837-2844.

Crosley et al., "First-Trimester Levels of Pregnancy-Associated Plasma Protein A2 (PAPP-A2) in the Maternal Circulation are Elevated in Pregnancies that Subsequently Develop Preeclampsia," Reproductive Sciences, 2014;21(6):754-760.

Diaz et al., "Performance of Streck cfDNA Blood Collection Tubes for Liquid Biopsy Testing," PLOS One, Nov. 10, 2016; 18 pgs.

Farina et al., :Quantitative distribution of a panel of circulating mRNA in preeclampsia versus controls, Prenatal Diagnosis, 2006;26:1115-1120.

Go et al., "Detection of Placental Transcription Factor mRNA in Maternal Plasma," Clinical Chemistry, 2004;50(8):1413-1414.

Huang et al., "Characterization of Human plasma-derived exosomal RNAs by deep sequencing," BMC Genomics, 2013;14:319:14 pgs.

International Search Report and Written Opinion for PCT/US2019/033964, issued by the European Patent Office dated Aug. 28, 2019; 16 pgs.

(Continued)

*Primary Examiner* — Stephen T Kapushoc
(74) *Attorney, Agent, or Firm* — Mueting Raasch Group

(57) ABSTRACT

The present invention includes methods and materials for use in the detection preeclampsia and/or determining an increased risk for preeclampsia in a pregnant female, the method including identifying in a biosample obtained from the pregnant women a plurality of circulating RNA (C-RNA) molecules.

18 Claims, 43 Drawing Sheets

(56) References Cited

OTHER PUBLICATIONS

International Search Report and Written Opinion for PCT/US2020/061466, issued by the European Patent Office dated Feb. 23, 2021; 13 pgs.
Karumanchi et al., "Preeclampsia and Pregnancy-Related Hypertensive Disorders," Hypertension, 2016;67:238-242.
Kishikawa et al., "Circulating RNAs as new biomarkers for detecting pancreatic cancer," World J Gastroenterol, Jul. 2015;28(21):8527-8540.
Koh et al., "Noninvasive in vivo monitoring of tissue-specific global gene expression in humans," PNAS, May 20, 2014;111(20):7361-7366.
Koh et al., Corrections for "Noninvasive in vivo monitoring of tissue-specific global gene expression in humans," PNAS, Jul. 29, 2014;111(30):11223.
Li et al., "Role of exosomal proteins in cancer diagnosis," Molecular Cancer, 2017;16;145: 12 pgs.
Lun et al., "Noninvasive prenatal Methylomic Analysis by Genomewide Bisulfite Sequencing of maternal Plasma DNA," ClinChem, 2013;59(11):1583-1594.
Maron et al., "Gene expression analysis in pregnant women and their infants identifies unique fetal biomarkers that circulate in maternal blood," JClinRes, Oct. 2007;117(10):3007-3019.
McCarthy and Smyth, "Testing significance relative to a fold-change threshold is a TREAT," Bioinformatics, 2009;25(6):765-771.
Muchel et al., "Circulating transcripts in maternal blood reflect a molecular signature of early-onset preeclampsia," SciTranslMed, Jul. 1, 2020;12(eaaz0131):12 pgs.
Ng et al., "The Concentration of Circulating Corticotropin-releasing Hormone mRNA in Maternal Plasma Is Increased in Preeclampsia," ClinicalChemistry, 2003;49(5):727-731.
Ng et al., mRNA of placental origin is readily detectable in maternal plasma, PNAS, Apr. 15, 2003;100(8):4748-4753.
Ngo et al., "Noninvasive blood tests for fetal development predict gestational age and preterm delivery," Science, Jun. 8, 2018; 360:1133-1136.
Poon et al., "Presence of Fetal RNA in Maternal Plasma," ClinChem, 2000;46(11):1832-1834.
"Preeclampsia-Symptoms and Causes" Mayo Clinic [On-Line], https//www.mayoclinic.org/diseases-conditions/preeclampsia/symptoms-causes/syc-20355745?p=1. 5 pgs.
Purwosunu et al., "Cell-Free mRNA Concentrations of Plasminogen Activator Inhibitor-I and tissue-Type Plasminogen Activator Are Increased in the Plasma of Pregnant Women with Preeclampsia," ClinicalChemistry, 2007;53:3:399-404.
Qin et al., "A novel blood collection device stabilizes cell-free RNA in blood during sample shipping and storage," BMC Research Notes, 2013:6;380:8 pgs.
Qin et al., "High-Throughput sequencing of human plasma RNA by using thermostable group II intron reverse transcriptases," RNA, 22:111-128.
Quinn et al., "Reprogramming of the Transcriptome in a Novel Chromosome 3 Transfer Tumor Suppressor Ovarian Cancer Cell Line Model Affected Molecular Networks That Are Characteristic of Ovarian Cancer," MolCarcinogenesis, 2009;48:648-661.
"Reviewing Maternal Deaths is First Step in Preventing Them," Mar. 6, 2018 [On Line]: https://www.preeclampsia.org/the=news/138-latest-news/677-reviewing-maternal-deaths-is-first-step-in preventing-them?tmpl=component&print=1&page=] Obtained—May 17, 2018: 1 pg.
Robinson et al., "edgeR: a Bioconductor package for differential expression analysis of digital gene expression data," Bioinformatics, 2010;26(1):139-140.
Rolnik et al., "Aspirin versus Placebo in Pregnancies at High Risk for Preterm Preeclampsia," NewEnglJMed, Aug. 17, 2017;377(7):613-622.
Sato-Kuwabara et al., "The fusion of two worlds: Non-coding RNAs and extracellular vesicles—diagnostic and therapeutic implications (Review)" Intl J of Oncology, 2015;46:17-27.
Smets et al., "Novel Biomarkers in preeclampsia," ClinicaChimicaActa, 2006;364:22-32.
Steinbrecher et al., "Pregnancy-Associated Plasma Protein-A2 and Anthropometry, Lifestyle, and Biochemical Factors in a Human Adult Population," SciRepts, 2005;7:10455.
Townsend et al., "Current best practice in the management of hypertensive disorders in pregnancy," IntBloodPressControl, 2016,9:79-94.
"TruSeq® DNA Sample Preparation Guide" Illumina Proprietary, Part # 15026486 Rev. C, Jul. 2012; 148 pgs.
"TruSeqTM Exome Enrichment Guide" Illumina Proprietary, Catalog # FC-930-1012, Part # 15013230 Rev B, Nov. 2010; 56 pgs.
"TruSeq® RNA Sample Preparation v2 Guide," Illumina Proprietary, RS-122-9001DOC, Part # 15026495 Rev. F, Mar. 2014; 132 pgs.
Tsang et al., "Integrative single-cell and cell-free plasma RNA transcriptomics elucidates placental cellular dynamics," PNAS, Aug. 22, 2017; E7786-E7795.
Tsui et al., "Systematic micro-array based identification of placental mRNA in maternal plasma: towards non-invasive prenatal gene expression profiling," J Med Genet, 2004;41:461-467.
Tsui et al., "Maternal Plasma RNA Sequencing for Genome-Wide Transcriptomic Profiling and Identification of Pregnancy-Associated Transcripts," ClinChem, 2014; 60(7):954-962.
Umu et al., "A comprehensive profile of circulating RNAs in human serum," RNABiology, 2018;15(2):242-250.
Wagner et al., "Regulation of pregnancy-associated plasma protein A2 (PAPPA2) in a human placental trophoblast cell line (BeWo)," RepBioEndo, 2011;9(4):7 pgs.
Yoffe et al., "Early Detection of Preeclampsia Using Circulating Small non-coding RNA," Scientific Reports, 2018;8:3401: 11 pgs.
U.S. Appl. No. 62/578,360, filed Oct. 27, 2017, Quake et al., "A Noninvasive Molecular Clock for Fetal Development Predicts Gestational Age and Preterm Delivery-II".
GenBank, *Homo sapiens* a disintegrin-like and metalloprotease (reprolysin type) with thrombospondin type 1 motif, 2 (ADAMTS2), mRNA, NCBI Reference Sequence: NM_014244.1, Apr. 26, 2000, 3 pages.
Textoris et al., "Evaluation of Current and New Biomarkers in Severe Preeclampsia: A Microarray Approach Reveals the VSIG4 Gene as a Potential Blood Biomarker", PLOS ONE, Dec. 2013, vol. 8, e82638.
Hansen et al., "The Genetic Components of Preeclampsia: A Whole-Exome Sequencing Study", PLoS One, 2018, 1-16.
Hansen et al., "S1 Appendix, Supplementary Methods, The Genetic Component of Preeclampsia: A Whole-Exome Sequencing Study", PLoS One, 2018, 1-36.
Lee et al., "Clinical Exome Sequencing for Genetic Identification of Rare Mendelian Disorders," 2014, *JAMA*, 312(18):1880-87.
Kaartokallio et al., "Exome Sequencing in Pooled DNA Samples to Identify Maternal Preeclampsia Risk Variants," 2016, *Scientific Reports*, vol. 6, pp. 1-9.
Kaartokallio et al., Supplemental Information, "Exome Sequencing in Pooled DNA Samples to Identify Maternal Preeclampsia Risk Variants," 2016, *Scientific Reports*, vol. 6, pp. 1-4.
UCLA Health System, UCLA Molecular Diagnostics Laboratories, Clinical Exome Sequencing, vol. 3, 2015, pp. 1-98.
UCLA, Common Tests During Pregnancy, UCLA Health, 2000-2003, pp. 1-6. Obtained online Feb. 11, 2023: https://www.uclahealth.org/departments/pathology/outreachservices/molecular-diagnostics-laboratories-pathology-outreach.
Rouillard et al., Hypertension Gene Set, 2016, *Harmonizome*. Obtained online Feb. 11, 2023: https://maayanlab.cloud/Hamonizome/gene_set/Hypertension/CTD+Gene-Disease+Associations-harmonize.
Rouillard et al., Supplemental Gene Set, Hypertension Gene Set, 2016, *Harmonizome*, Obtained online Feb. 11, 2023: https://maayanlab.cloud/Hamonizome/gene_set/Hypertension/CTD+Gene-Disease+Associations-harmonize.
Gormley et al., "Preeclampsia: novel insights from global RNA profiling of trophoblast subpopulations," Aug. 2017, Am J Obstet Gynecol, 217(2):17 pages.

(56) References Cited

OTHER PUBLICATIONS

Hui et al., "Cell-free fetal nucleic acids in amniotic fluid," Oct. 5, 2010, Human Reproduction Update, 17(3):362-71.
Paquette et al, "Comparative analysis of gene expression in maternal peripheral blood and monocytes during spontaneous preterm labor," Mar. 2018, Am J Obstet Gynecol, 218(3): page count here.

* cited by examiner

FIG. 4

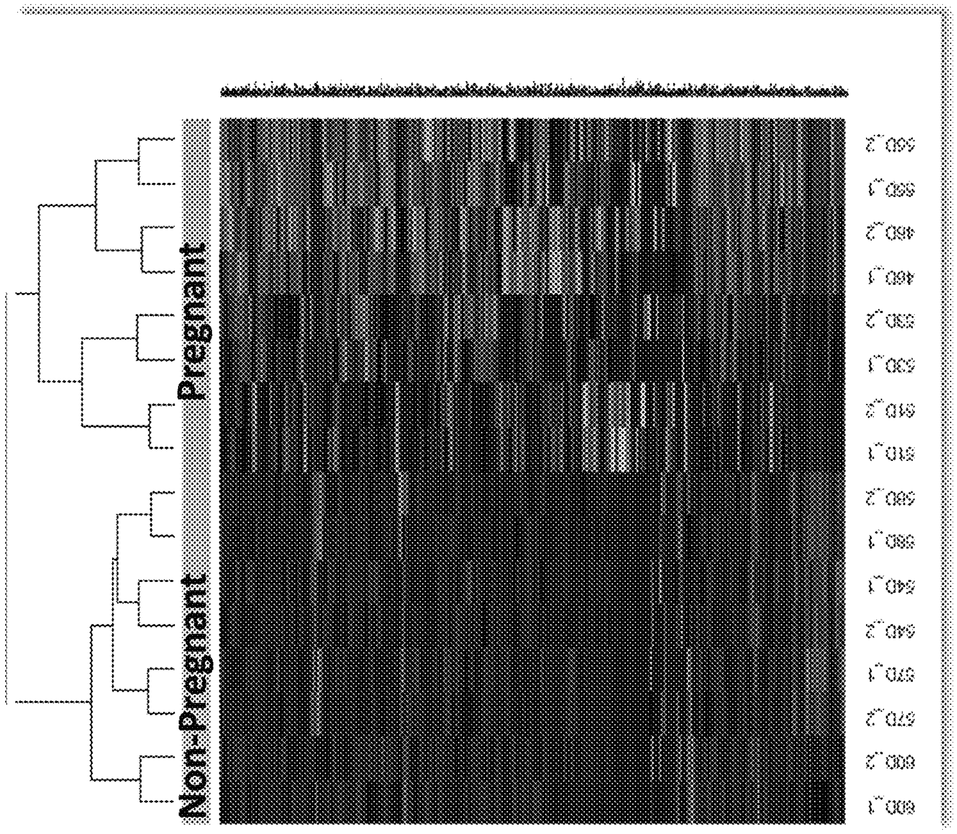

| Top 20 Differential Abundance Genes | | |
|---|---|---|
| Rank | Gene Symbol | Tissue |
| 1 | CSHL1* | Placenta |
| 2 | CSH2* | Placenta, pituitary |
| 3 | KISS1 | Placenta |
| 4 | CGA* | Pituitary, Placenta |
| 5 | PLAC4* | Placenta |
| 6 | PSG1 | Placenta |
| 7 | GH2 | Placenta |
| 8 | PSG3 | Placenta |
| 9 | PSG4* | Placenta |
| 10 | PSG7 | Placenta |
| 11 | PSG11 | Placenta |
| 12 | CSH1* | Placenta, pituitary |
| 13 | PSG2 | Placenta |
| 14 | HSD3B1* | Placenta |
| 15 | GRHL2 | Placenta, Prostate |
| 16 | LGALS14* | Placenta |
| 17 | FCGR1C | Lung |
| 18 | PSG5* | Placenta |
| 19 | LGALS1 | Placenta |
| 20 | GCM1 | Placenta |

FIG. 23A
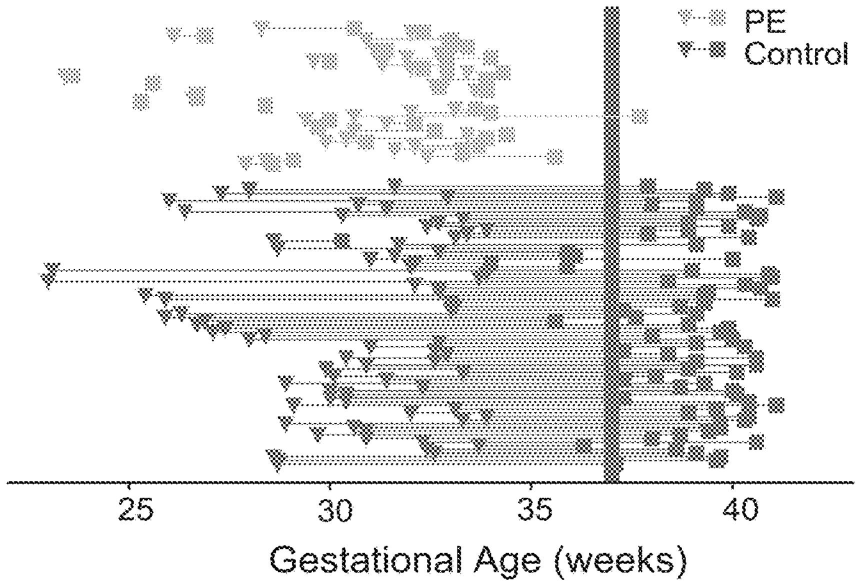
FIG. 23B
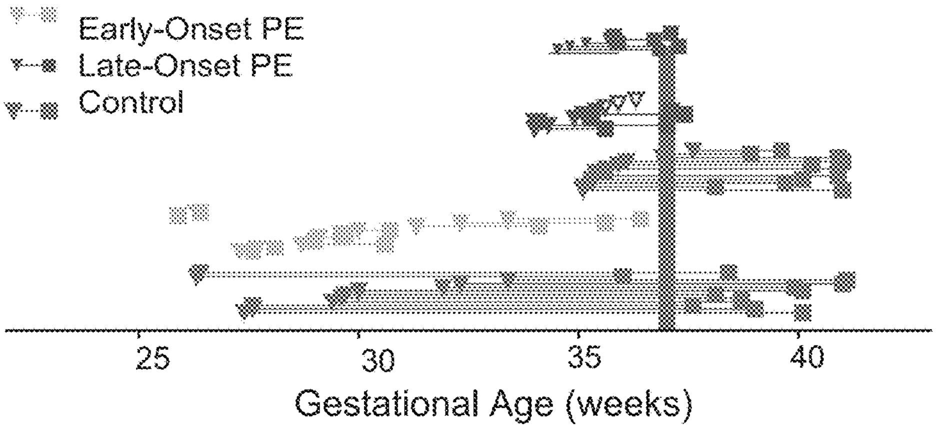
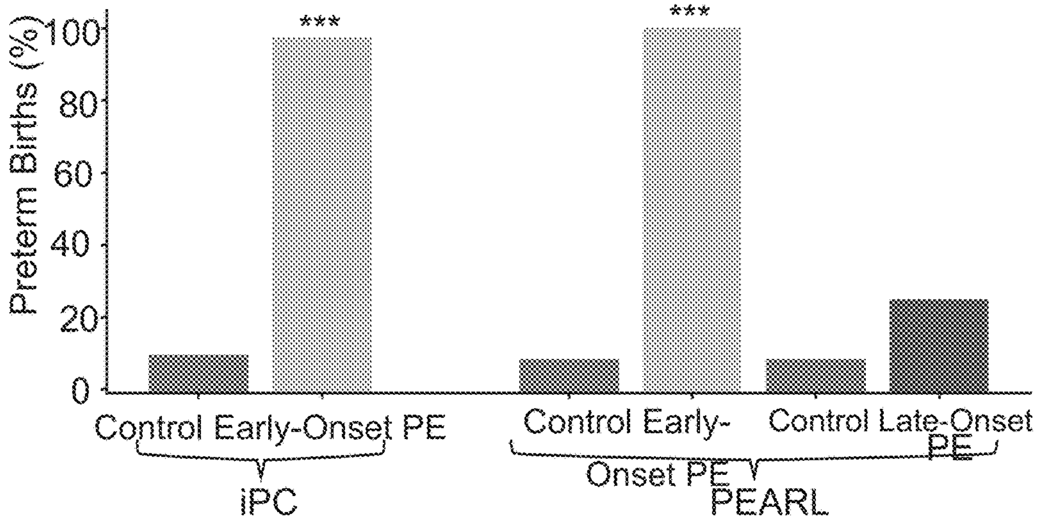
FIG. 23C low
high
EDTA Day 0
EDTA Day 1
ACD Day 1
Cell-Free RNA BCT Day 1
Cell-Free DNA BCT Day 1
Pregnant EDTA Day 1
EDTA Day 0
EDTA Day 5
cf DNA BCT Day 1
cf DNA BCT Day 0
cf DNA BCT Day 5

Pearson's R
EDTA
cf DNA BCT

Fig. 38A
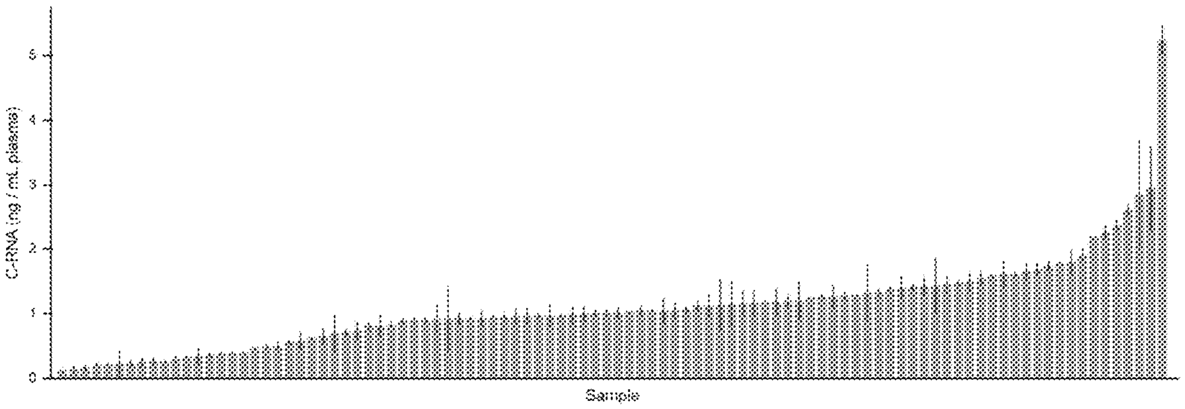
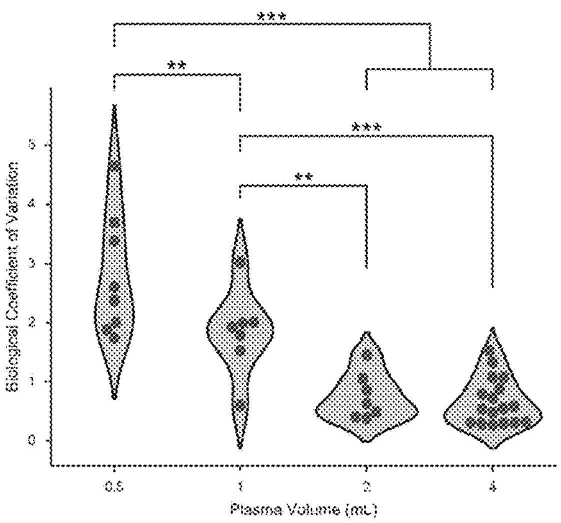
Fig. 38B
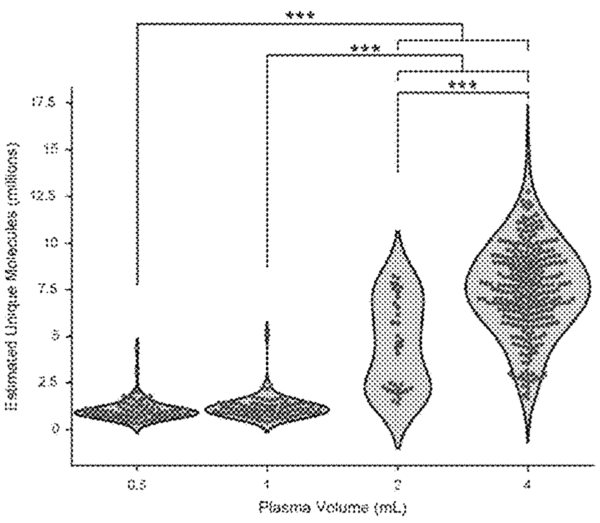
Fig. 38C

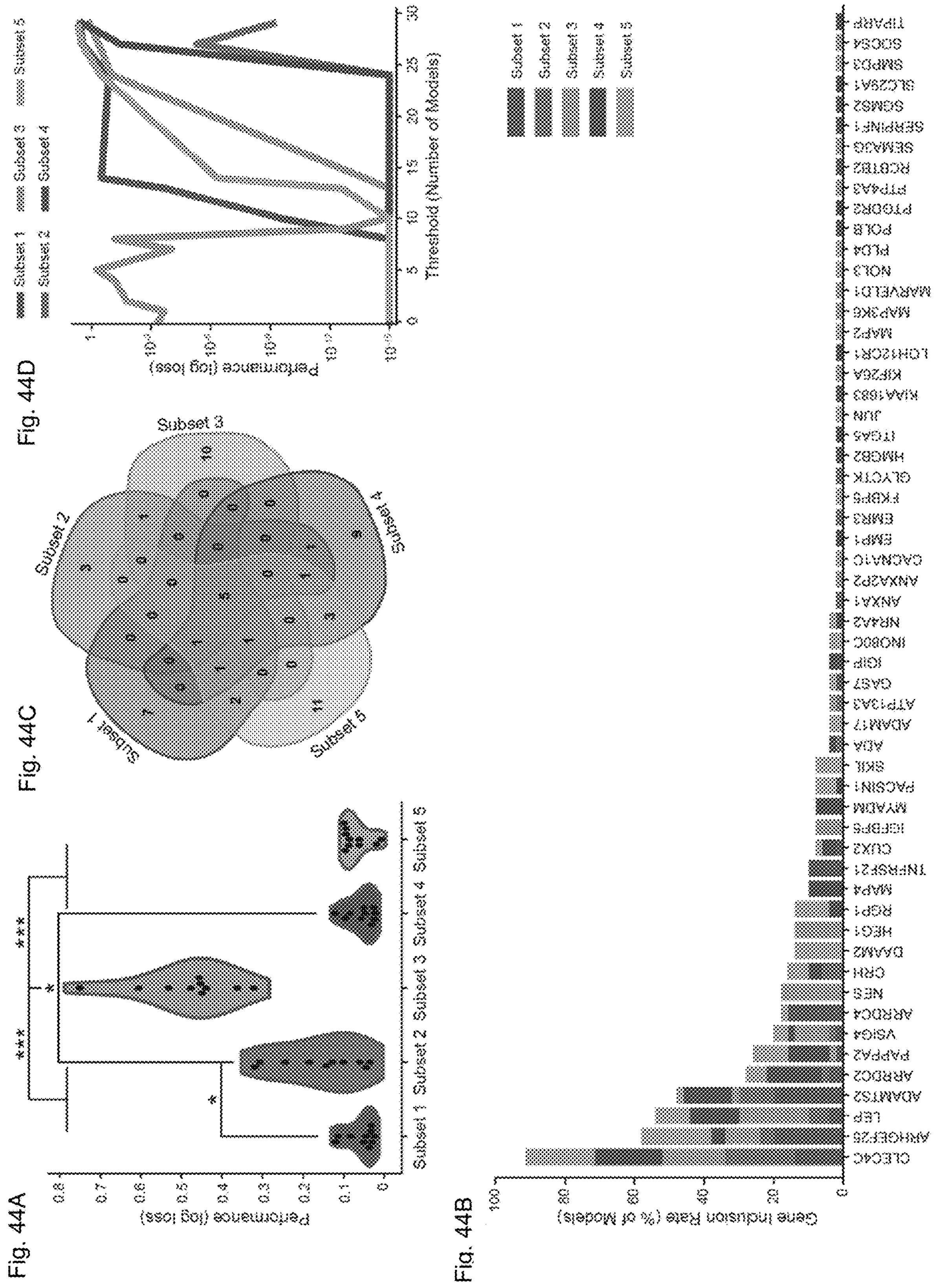
Fig. 44A
Performance (log loss)
Subset 1
Subset 2
Subset 3
Subset 4
Subset 5
Fig. 44B
Gene Inclusion Rate (% of Models)
CLEC4C
ARHGEF25
LEP
ADAMTS2
ARRDC2
PAPPA2
VSIG4
ARRDC4
NES
CRH
DAAM2
HEG1
RGP1
MAP4
TNFRSF21
CUX2
IGFBP5
MYADM
PACSIN1
SKIL
ADA
ADAM17
ATP13A3
GAS7
IQIP
INO80C
NR4A2
ANXA1
ANXA2P2
CACNA1C
EMP1
EMR3
FKBP5
GLYCTK
HMGB2
ITGA5
JUN
KIAA1683
KIF26A
LOH12CR1
MAP2
MAP3K6
MARVELD1
NOL3
PLD4
POLB
PTGDR2
PTP4A3
RCBTB2
SEMA3G
SERPINF1
SGMS2
SLC29A1
SMPD3
SOCS4
TIPARP
Fig. 44C
Fig. 44D
Performance (log loss)
Threshold (Number of Models)

CIRCULATING RNA SIGNATURES SPECIFIC TO PREECLAMPSIA

CONTINUING APPLICATION DATA

This application claims the benefit of U.S. Provisional Application Ser. No. 62/939,324, filed Nov. 22, 2019, which is incorporated by reference herein.

FIELD OF INVENTION

The present invention relates generally to methods and materials for use in the detection and early risk assessment for the pregnancy complication preeclampsia.

BACKGROUND

Preeclampsia is a condition that occurs only during pregnancy, affecting 5% to 8% of all pregnancies. It is the direct cause of 10%-15% of maternal deaths and 40% of fetal deaths. The three main symptoms of preeclampsia may include high blood pressure, swelling of hands and feet, and excess protein in the urine (proteinuria), occurring after week 20 of pregnancy. Other signs and symptoms of preeclampsia may include severe headaches, changes in vision (including temporary loss of vision, blurred vision or light sensitivity), nausea or vomiting, decreased urine output, decreased platelets levels (thrombocytopenia), impaired liver function, and shortness of breath, caused by fluid in the lung.

The more severe the preeclampsia and the earlier it occurs in pregnancy, the greater the risks for mother and baby. Preeclampsia may require induced labor and delivery or delivery by cesarean delivery. Left untreated, preeclampsia can lead to serious, even fatal, complications for both the mother and baby. Complications of preeclampsia include fetal growth restriction, low birth weight, preterm birth, placental abruption, HELLP syndrome (hemolysis, elevated liver enzymes, and low platelet count syndrome), eclampsia (a severe form of preeclampsia that leads to seizures), organ damage, including kidney, liver, lung, heart, or eye damage, stroke or other brain injury. See, for example, "Preeclampsia—Symptoms and causes—Mayo Clinic," Apr. 3, 2018, available at on the worldwide web at mayoclinic.org/diseases-conditions/preeclampsia/symptoms-causes/syc-20355745.

With early detection and treatment, most women can deliver a healthy baby if preeclampsia is detected early and treated with regular prenatal care. Although various protein biomarkers display changed levels in maternal serum at presymptomatic stages, these biomarkers lack discriminative and predictive power in individual patients (Karumanchi and Granger, 2016, *Hypertension;* 67(2): 238-242). Thus, the identification of biomarkers for the early detection of preeclampsia is critical for the early diagnosis and treatment of preeclampsia.

SUMMARY OF THE INVENTION

The present invention includes a method of detecting preeclampsia and/or determining an increased risk for preeclampsia in a pregnant female, the method including:

identifying in a biosample obtained from the pregnant women a plurality of circulating RNA (C-RNA) molecules;

wherein a plurality of C-RNA molecules is selected from:

(a) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5; or (d) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) a plurality of C-RNA molecules encoding at least a portion of a protein selected from any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1; or (i) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or (j) a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

The present invention includes a method of detecting preeclampsia and/or determining an increased risk for preeclampsia in a pregnant female, the method including:

obtaining a biosample from the pregnant female;

purifying a population of circulating RNA (C-RNA) molecules from the biosample;

identifying protein coding sequences encoded by the C-RNA molecules within the purified population of C-RNA molecules;

wherein protein coding sequences encoded by the C-RNA molecules encoding at least a portion of a protein is selected from:

(a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy or more, or all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy-five or more, any one hundred or more, or all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5; or (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1; or (i) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or (j) any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

In some aspects, identifying protein coding sequences encoded by C-RNA molecules within the biosample includes hybridization, reverse transcriptase PCR, microarray chip analysis, or sequencing.

In some aspects, identifying protein coding sequences encoded by the C-RNA molecules within the biosample includes sequencing, including, for example, massively parallel sequencing of clonally amplified molecules and/or RNA sequencing.

In some aspects, the method further includes removing intact cells from the biosample; treating the biosample with a deoxynuclease (DNase) to remove cell free DNA (cfDNA); synthesizing complementary DNA (cDNA) from C-RNA molecules in the biosample; and/or enriching the cDNA sequences for DNA sequences that encode proteins by exome enrichment prior to identifying protein coding sequence encoded by the circulating RNA (C-RNA) molecules.

The present invention includes a method of detecting preeclampsia and/or determining an increased risk for preeclampsia in a pregnant female, the method including:

obtaining a biological sample from the pregnant female;

removing intact cells from the biosample;

treating the biosample with a deoxynuclease (DNase) to remove cell free DNA (cfDNA);

synthesizing complementary DNA (cDNA) from RNA molecules in the biosample;

enriching the cDNA sequences for DNA sequences that encode proteins (exome enrichment);

sequencing the resulting enriched cDNA sequences; and identifying protein coding sequences encoded by enriched C-RNA molecules;

wherein protein coding sequences encoded by the C-RNA molecules encoding at least a portion of a protein selected from:

(a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all seventy-five of ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5; or (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1; or (i) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or (j) any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

The present invention includes a method of identifying a circulating RNA signature associated with an increased risk of preeclampsia, the method including obtaining a biological sample from the pregnant female; removing intact cells from the biosample; treating the biosample with a deoxynuclease (DNase) to remove cell free DNA (cfDNA); synthesizing complementary DNA (cDNA) from RNA molecules in the biosample; enriching the cDNA sequences for DNA sequences that encode proteins (exome enrichment); sequencing the resulting enriched cDNA sequences; and identifying protein coding sequences encoded by enriched C-RNA molecules.

The present invention includes a method including:

obtaining a biological sample from the pregnant female;

removing intact cells from the biosample;

treating the biosample with a deoxynuclease (DNase) to remove cell free DNA (cfDNA);

synthesizing complementary DNA (cDNA) from RNA molecules in the biosample;

enriching the cDNA sequences for DNA sequences that encode proteins (exome enrichment);

sequencing the resulting enriched cDNA sequences; and identifying protein coding sequences encoded by the enriched C-RNA molecules;

wherein the protein coding sequences include at least a portion of a protein selected from:

(a) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five up to all seventy-five ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3; or (b) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4; or (c) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, up to all one hundred twenty-two of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5; or (d) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4; or (e) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4; or (f) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4; or (g) any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES (including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL); or (h) any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1; or (i) any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or (j) any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768.

In some aspects, the biosample includes plasma.

In some aspects, the biosample is obtained from a pregnant female at less than 16 weeks gestation or at less than 20 weeks gestation.

In some aspects, the biosample is obtained from a pregnant female at greater than 20 weeks gestation.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any fifty or more, any seventy or more, up to all seventy-five ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty six of more, or all twenty-seven of TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4.

The present invention includes a circulating RNA (C-RNA) signature for an elevated risk of preeclampsia, the C-RNA signature encoding a least a portion of a plurality of CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRF1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, any twenty-six or more, any twenty-seven or more, any twenty-eight or more, any twenty-nine or more, or all thirty of VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, any twenty-four or more, any twenty-five or more, or all twenty-six of ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, or all twenty-two of ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, or all eleven of CLEC4C, ARHGEF25, ADAMTS2, LEP, ARRDC2, SKIL, PAPPA2, VSIG4, ARRDC4, CRH, and NES, including in some embodiments, the seven of ADAMTS2, ARHGEF25, ARRDC2, CLEC4C, LEP, PAPPA2, and VSIG4; the eight of ADAMTS2, ARHGEF25, ARRDC2, CLEC4C, LEP, PAPPA2, SKIL, and VSIG4; the eight of ADAMTS2, ARHGEF25, ARRDC4, CLEC4C, LEP, NES, SKIL, and VSIG4; the ten of ADAMTS2, ARHGEF25, ARRDC2, ARRDC4, CLEC4C, CRH, LEP, PAPPA2, SKIL, and VSIG4; the of six of ADAMTS2, ARHGEF25, ARRDC2, CLEC4C, LEP, and SKIL; or the eight of ADAMTS2, ARHGEF25, ARRDC2, ARRDC4, CLEC4C, LEP, PAPPA2, and SKIL.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, any thirteen or more, any fourteen or more, any fifteen or more, any sixteen or more, any seventeen or more, any eighteen or more, any nineteen or more, any twenty or more, any twenty-one or more, any twenty-two or more, any twenty-three or more, or all twenty-four of LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7.

The present invention includes a circulating RNA (C-RNA) signature for an elevated risk of preeclampsia, the C-RNA signature encoding at least a portion of any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768.

The present invention includes a solid support array comprising a plurality of agents capable of binding and/or identifying a C-RNA signature as described herein.

The present invention includes a kit comprising a plurality of probes capable of binding and/or identifying a C-RNA signature as described herein.

The present invention includes a kit comprising a plurality of primers for selectively amplifying a C-RNA signature as described herein.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "template" and "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, "amplify," "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the target nucleic acid molecule. The target nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as Mg' or Mn' and can also include various modifiers of ionic strength.

As used herein, the term "polymerase chain reaction" (PCR) refers to the method of K. B. Mullis U.S. Pat. Nos. 4,683,195 and 4,683,202, which describes a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double-stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified." In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. The terms should be understood to include, as equivalents, analogs of either DNA or RNA made from nucleotide analogs and to be applicable to single stranded (such as sense or antisense) and double-stranded polynucleotides. The term as used herein also encompasses cDNA, that is complementary or copy DNA produced from an RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, the terms "library" and "sequencing library" refer to a collection or plurality of template molecules which share common sequences at their 5' ends and common sequences at their 3' ends. The collection of template molecules containing known common sequences at their 3' and 5' ends may also be referred to as a 3' and 5' modified library.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, PCR, rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complimentary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "sensitivity" as used herein is equal to the number of true positives divided by the sum of true positives and false negatives.

The term "specificity" as used herein is equal to the number of true negatives divided by the sum of true negatives and false positives.

The term "enrich" herein refers to the process of amplifying nucleic acids contained in a portion of a sample. Enrichment includes specific enrichment that targets specific sequences, e.g., polymorphic sequences, and non-specific enrichment that amplifies the whole genome of the DNA fragments of the sample.

As used herein, the term "each," when used in reference to a collection of items, is intended to identify an individual item in the collection but does not necessarily refer to every item in the collection unless the context clearly dictates otherwise.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4. Validation of C-RNA approach comparing 3rd trimester pregnant and non-pregnant samples.

FIG. 22A is a schematic of the sequencing library preparation method; all steps after blood collection can be performed in a centralized processing lab. Temporal changes of transcripts altered throughout the course of pregnancy (FIG. 22B). Overlap of genes identified in C-RNA pregnancy progression studies (FIG. 22C). Tissues expressing the 91 genes unique to the pregnancy time course study (FIG. 22D).

FIGS. 23A-23C. Sample collection for PE clinical studies. Panels illustrate the time of blood collection (triangles) and gestational age at birth (squares) for each individual in the iPC study (FIG. 23A) and the PEARL study (FIG. 23B). The red line indicates the threshold for term birth. Preterm birth rates are significantly elevated in early-onset PE cohorts (FIG. 23C). *** $p<0.001$ by Fisher's exact test.

FIG. 31C shows the impact of pruning individual AdaBoost models on performance (as in FIG. 30B). Solid lines are the average for all 10 models, and the shaded region shows the standard deviation. The number of AdaBoost models using each gene observed in the pre-pruned ensemble (FIG. 31D). Model performance when pruning the combined AdaBoost ensemble (FIG. 31E). The orange lines in FIG. 31D and FIG. 31E show the threshold applied to generate the final AdaBoost model.

FIG. 32A shows temporal changes in transcripts significantly altered throughout the course of pregnancy. Each row corresponds to a transcript, the abundance of which was normalized across all samples (N=152) prior to clustering. Orange signifies elevated abundance; purple indicates decreased abundance. FIG. 32B shows the overlap of transcripts identified in three independent C-RNA pregnancy progression analyses. N=number of plasma samples collected from a pregnant woman in cohort. FIG. 32C shows tissues expressing the 91 genes that were only detected with the PEARL HCC cohort.

As shown in FIG. 33C, preterm birth rates are significantly elevated in early-onset PE cohorts. *** $p<0.001$ by Fisher's exact test. iPEC, Control N=73, PE N=40; PEARL PEC, N=12 for each group.

FIG. 34A shows fold change and abundance of transcripts altered in PE. FIG. 34B shows one-sided, normal-based 95% confidence intervals of the p-value for each transcript that was detected as altered by standard analyses. FIG. 34C is a schematic of the jackknifing approach, wherein 90% of samples were randomly selected for analysis over many iterations to quantify p-value stability. FIG. 34D shows average abundance and noise for each differentially abundant gene ($p>0.05$ for both variables by Mann-Whitney U; N=30,12). FIG. 34E shows ROC area under the curve values for each affected transcript reflect how separated C-RNA transcript abundance distributions are for control versus PE samples (* $p<0.05$ by Mann-Whitney U; Included, N=30; Excluded, N=12). FIG. 34F shows hierarchical clustering of iPEC samples using the genes excluded after jackknifing (sensitivity=73%; specificity=99%; N=113). For FIGS. 34A, 34B, 34D, and 34E orange and blue datapoints reflect transcripts considered statistically altered in PE by standard differential expression analysis, but only orange datapoint were identified by the jackknifing approach. Sample status is shown by the blue (PE) and gray (control) rectangles along the right side of the heatmap.

FIG. 35A shows the fold-change between PE and control pregnancies was assessed both by sequencing (orange) and by qPCR (purple) for 20 transcripts (* $p<0.05$ by Student's T-test; N=19 for control and for PE). FIG. 35B shows tissue expression of affected genes. FIG. 35C shows hierarchical clustering of the iPEC samples (average linkage, squared Euclidean distance; PE, N=40; control, N=73). Clustering of early-onset (FIG. 35D) and late-onset (FIG. 35E) PE and control pregnancy samples from the PEARL PEC (N=12 for each group).

FIG. 36A shows average ROC curve for iPEC validation samples (dashed line=SD; N=10). FIG. 36B shows accuracy, sensitivity and specificity measurements if iPEC hold out samples and independent PEARL PEC samples (N=10). FIG. 36C is a heatmap of the relative transcript abundance in the iPEC cohort for the genes used by AdaBoost model. The graph on the right indicates how many cross-validation models a given transcript appeared in. FIG. 36D shows concordance of transcripts identified by differential analysis and AdaBoost. FIG. 36E shows tissue expressing elevated levels of transcripts selected by AdaBoost models.

FIG. 37A shows the approach used for sequencing library preparation. Blood is shipped overnight prior to plasma processing and nucleic acid extraction. cfDNA is digested with Dnase, then cDNA is synthesized from all RNA. Whole transcriptome enrichment is performed prior to sequencing. In FIG. 37B, three methods were assessed for C-RNA transcriptome analyses. rRNA depletion did not consistently enrich the exonic C-RNA fraction; many libraries contain numerous unaligned reads. Likewise, rRNA overwhelmed sequencing datasets when not removed. Enrichment generated libraries with the highest proportion of reads from exonic C-RNA. For all bar graphs, orange shows reads aligned to the human genome, gray shows reads aligned to an rRNA sequence, and pink shows reads that do not align to the human genome (including both non-human RNA and low quality sequences).

FIGS. 38A-38C. The effect of plasma volume on C-RNA data quality. FIG. 38A shows the C-RNA yield in plasma from 122 samples was quantified with the Quant-iT RiboGreen assay (Thermo Fisher). Measurements from 23 samples were below the detection threshold and are excluded from the graph. Bars show mean±SD from 2 technical replicates. Data from 9 independent experiments was used for a meta-analysis evaluating the effect of plasma input on data quality. FIG. 38B shows noise (biological coefficient of variation, edgeR) calculated from biological replicates within each study. FIG. 38C shows library complexity (bound population, preseq) of each sample.  $p<0.01$, * $p<0.001$ by ANOVA with Tukey's HSD correction, using the study as a blocking variable. 0.5 mL, N=8, 95; 1 mL, N=7, 83; 2 mL, N=7, 33; 4 mL, N=17, 267 for FIGS. 38B and 38C, respectively.

FIG. 39A is a heatmap of the abundance of known C-RNA pregnancy markers after overnight storage in 4 BCTs compared to immediate processing from EDTA BCTs. FIG. 39B shows an integrated measure of pregnancy signal obtained by summing transcript abundance in FIG. 39A discriminates between pregnant and non-pregnant samples.  $p<0.01$, * $p<0.001$ by ANOVA with Tukey's HSD correction. EDTA immediate, N=4, 8; EDTA overnight, N=7, 7; ACD overnight, N=16, 16; Cell-Free RNA overnight, N=10, 9; Cell-Free DNA overnight, N=8, 8; for non-pregnant and pregnant groups, respectively. FIG. 39C shows correlation of transcriptomic profiles from blood samples collected from the same individual and stored for 0, 1 or 5 days in Cell-free DNA BCTs (Streck, Inc) prior to processing. Bars show mean±range; N=2. The AdaBoost scores assigned to control samples (FIG. 39D) or to PE samples (FIG. 39E) from the iPEC cohort versus the number of days blood was stored at room temperature prior to plasma processing. AdaBoost scores are normalized to range from −1 to +1, with control samples expected to have a score <0, and PE samples to have a score >0. No significant differences in AdaBoost score were observed (ANOVA for controls; T-Test for PE). Control 1 day, N=60; 2 days, N=4; 3 days, N=1, 5 days, N=2. PE 1 day, N=37; 2 days, N=3.

FIG. 40D is an ontology and pathway enrichment analysis for transcripts which change during healthy pregnancy. Each filled in box signifies significant enrichment of the corresponding term or pathway. "All Genes" shows analysis of all 156 differentially abundant transcripts. Too few genes were altered late in pregnancy to perform ontological analysis.

FIG. 41A shows tissue specificity for the full set of genes detected in each study. FIG. 41B shows the transcripts unique to each study. FIG. 41C shows intersecting gene sets.

In FIG. 43A, the training samples are divided into 5 evenly sized subsets, corresponding to five iterations of model construction. For the first iteration, the samples in subset 1 are used for pruning while the samples in subsets 2, 3, 4, and 5 are combined for AdaBoost fitting; for the second iteration the samples in subset 2 are used for pruning while those in subsets 1, 3, 4, and 5 are used for AdaBoost fitting; and so on for the remaining 3 iterations. As shown in FIG. 43B, for each iteration, an AdaBoost model is fit to the "Fitting Samples." Then the impact of removing genes below an incrementally increasing importance threshold on classification performance is assessed with the "Pruning Samples." The model with the best performance and fewest genes is retained. In FIG. 43C, the process in FIG. 43B is repeated 10 times for each set of fitting and pruning samples, generating a total of 50 models. In FIG. 43D, estimators from all models are then aggregated into a single AdaBoost ensemble. Feature pruning of the aggregate model is performed to identify the minimal gene set required for optimal classification.

FIGS. 44A-44D. AdaBoost output is significantly impacted by sample selection. FIG. 44A shows classification performance (log-loss) of the individual models generated from each AdaBoost subset (* $p<0.05$, * $p<0.001$ by ANOVA with Tukey's HSD correction; N=10 each). In FIG. 44B, the frequency each transcript was included in one of the 50 separate AdaBoost models. FIG. 44C is a Venn diagram of the transcripts incorporated in each training subset's models. While 5 transcripts are utilized in models from all subsets, 40 are unique to a single subset. FIG. 44D shows the effect of pruning estimators on classification performance (log-loss) for the final, fully aggregated AdaBoost model also shows distinct behavior for each set of samples. These trends are particularly striking when considering that 75% of the data used for fitting AdaBoost models were shared by any two sets of samples used for fitting AdaBoost. Note these data were generated separately from the final machine learning analysis presented in FIG. 41**.

Figure 1:
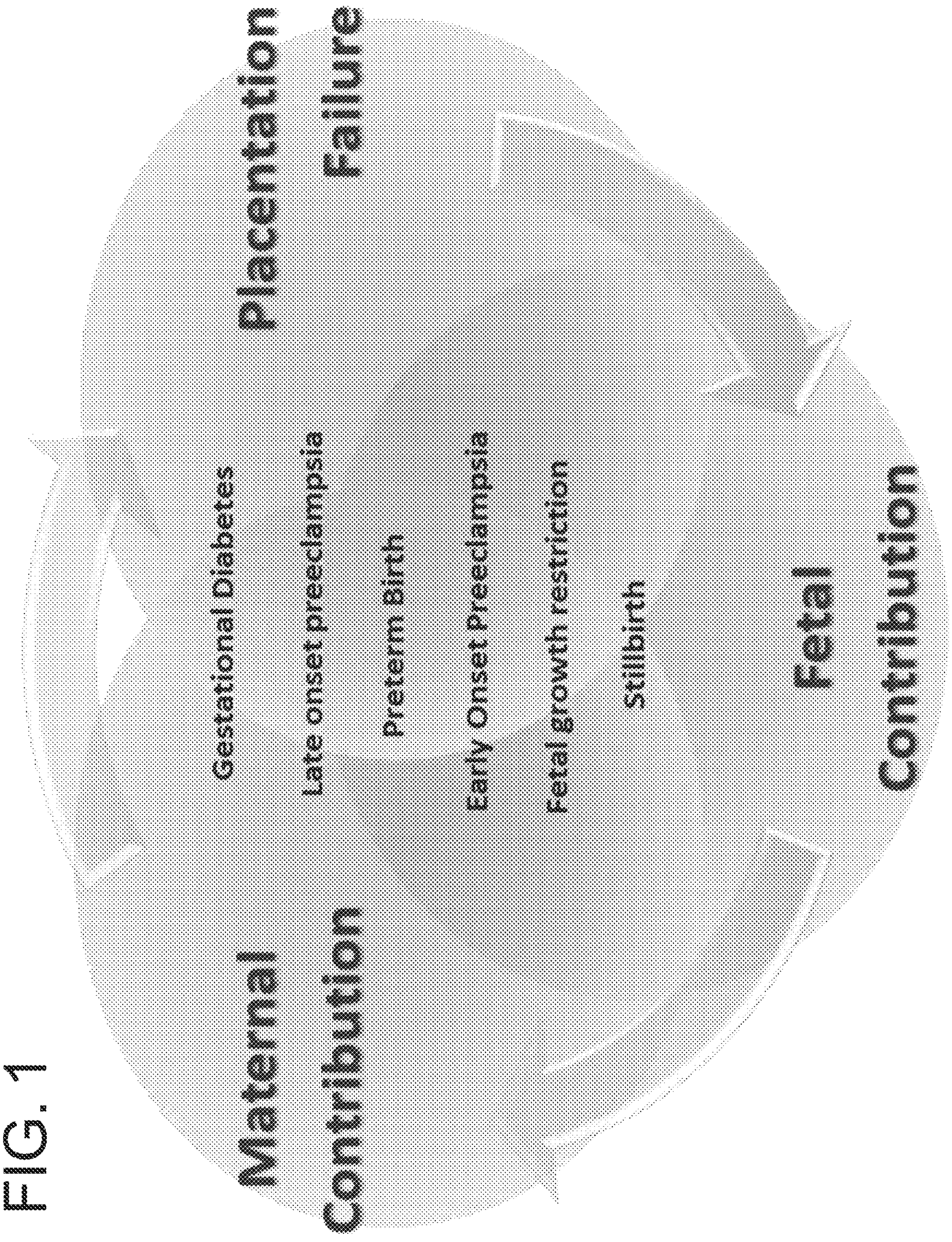
FIG. 1. A schematic of the relationships between placental health, maternal response, and fetal response.

The schematic drawings are not necessarily to scale. Like numbers used in the figures may refer to like components. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Provided herein are signatures of circulating RNA found in the maternal circulation that are specific to preeclampsia and the use of such signatures in noninvasive methods for the diagnosis of preeclampsia and the identification of pregnant women at risk for developing preeclampsia.

While most of the DNA and RNA in the body is located within cells, extracellular nucleic acids can also be found circulating freely in the blood. Circulating RNA, also referred to herein as "C-RNA," refers to extracellular segments of RNA found in the bloodstream. C-RNA molecules originate predominately from two sources: one, released into the circulation from dying cells undergoing apoptosis, and two, contained within exosomes shed by living cells into the circulation. Exosomes are small membranous vesicles about 30-150 nm of diameter released from many cell types into the extracellular space and are found in a wide variety of body fluids, including serum, urine, and breast milk and carrying protein, mRNA, and microRNA. The lipid bilayer structure of exosomes protects the RNAs contained within from degradation by RNases, providing for stability in blood. See, for example, Huang et al., 2013, *BMC Genomics;* 14:319; And Li et al., 2017, *Mol Cancer;* 16:145). Evidence is accumulating that exosomes have specialized functions and play a role in such processes as coagulation, intercellular signaling, and waste management (van der Pol et al., 2012, *Pharmacol Rev;* 64(3):676-705). See, also, Samos et al., 2006, *Ann N Y Acad Sci;* 1075:165-173; Zernecke et al., 2009, *Sci Signal;* 2:ra81; Ma et al., 2012, *J Exp Clin Cancer Res;* 31:38; and Sato-Kuwabara et al., 2015, *Int J Oncol;* 46:17-27.

With the methods described herein, the C-RNA molecules found in maternal circulation function as biomarkers of fetal, placental, and maternal health and provide a window into the progression of pregnancy. Described herein are C-RNA signatures within the maternal circulation that are indicative of pregnancy, C-RNA signatures within the maternal circulation that are temporally associated with the gestational stage of pregnancy, and C-RNA signatures within the maternal circulation that are indicative of the pregnancy complication preeclampsia.

A C-RNA signature within the maternal circulation indicative of preeclampsia includes a plurality of C-RNA molecules encoding at least a portion of a plurality of proteins selected from ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3. This C-RNA signature is the Adaboost General signature obtained with the TruSeq library prep method shown in Table 1 below, also referred to herein as "list (a)" or "(a)."

A C-RNA signature within the maternal circulation indicative of preeclampsia includes a plurality of C-RNA molecules encoding at least a portion of a plurality of proteins selected from TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4. This C-RNA signature is the Bootstrapping signature obtained with the TruSeq library prep method shown in Table 1 below, also referred to herein as "list (b)" or "(b)."

A C-RNA signature within the maternal circulation indicative of preeclampsia includes a plurality of C-RNA molecules encoding at least a portion of a protein selected from CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5. This C-RNA signature is the Standard DEX Treat signature obtained with the TruSeq library prep method shown in Table 1 below, also referred to herein as "list (c)" or "(c)."

A C-RNA signature within the maternal circulation indicative of preeclampsia includes a plurality of C-RNA molecules encoding at least a portion of a protein selected from VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, and HTRA4. This C-RNA signature is the Jacknifing signature obtained with the TruSeq library prep method shown in Table 1 below, also referred to herein as "list (d)" or "(d)."

A C-RNA signature within the maternal circulation indicative of preeclampsia includes a plurality of C-RNA molecules encoding at least a portion of a protein selected from ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, and VSIG4. This C-RNA signature is the Standard DEX Treat signature obtained with the Nextera Flex for Enrichment library prep method shown in Table 1 below, also referred to herein as "list (e)" or "(e)."

A C-RNA signature within the maternal circulation indicative of preeclampsia includes a plurality of C-RNA molecules encoding at least a portion of a protein selected from ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, and VSIG4. This C-RNA signature is the Jacknifing signature obtained with the Nextera Flex for Enrichment library prep method shown in Table 1 below, also referred to herein as "list (f)" or "(f)."

A C-RNA signature within the maternal circulation indicative of preeclampsia includes a plurality of C-RNA molecules encoding at least a portion of a protein selected from CLEC4C, ARHGEF25, ADAMTS2, LEP, ARRDC2, SKIL, PAPPA2, VSIG4, ARRDC4, CRH, and NES.

This C-RNA signature is the Adaboost Refined TruSeq signature obtained with the TruSeq library prep method shown in Table 1 below, also referred to herein as "AdaBoost Refined 1," "list (g)," or "(g)."

In some embodiments, a C-RNA signature within the maternal circulation indicative of preeclampsia includes C-RNA molecules encoding at least a portion of a protein selected from ADAMTS2, ARHGEF25, ARRDC2, CLEC4C, LEP, PAPPA2, and VSIG4 (also referred to herein as "AdaBoost Refined 2"), ADAMTS2, ARHGEF25, ARRDC2, CLEC4C, LEP, PAPPA2, SKIL, and VSIG4 (also referred to herein as "AdaBoost Refined 3"), ADAMTS2, ARHGEF25, ARRDC4, CLEC4C, LEP, NES, SKIL, and VSIG4 (also referred to herein as "AdaBoost Refined 4"), ADAMTS2, ARHGEF25, ARRDC2, ARRDC4, CLEC4C, CRH, LEP, PAPPA2, SKIL, and VSIG4 (also referred to herein as "AdaBoost Refined 5"), ADAMTS2, ARHGEF25, ARRDC2, CLEC4C, LEP, and SKIL (also referred to herein as "AdaBoost Refined 6"), or ADAMTS2, ARHGEF25, ARRDC2, ARRDC4, CLEC4C, LEP, PAPPA2, and SKIL (also referred to herein as "AdaBoost Refined 7").

A C-RNA signature within the maternal circulation indicative of preeclampsia includes a plurality of C-RNA molecules encoding at least a portion of a protein selected from LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMA3G, TIPARP, LRRC26, PHEX, LILRA4, and PER1. This C-RNA signature is the Adaboost Refined Nextera Flex signature obtained with the Nextera Flex for Enrichment library prep method shown in Table 1 below, also referred to herein as "list (h)" or "(h)."

A C-RNA signature within the maternal circulation indicative of preeclampsia includes a plurality of C-RNA molecules encoding at least a portion of a protein selected from any of those shown Table S9 of Example 7, also referred to herein as "list (i)" or "(i)."

A C-RNA signature within the maternal circulation indicative of preeclampsia includes a plurality of C-RNA molecules encoding at least a portion of a protein selected from AKAP2, ARRB1, CPSF7, INO80C, JAG1, MSMP, NR4A2, PLEK, RAP1GAP2, SPEG, TRPS1, UBE2Q1, and ZNF768, also referred to herein as "list (j)" or "(j)."

In some embodiments, a C-RNA signature within the maternal circulation indicative of preeclampsia includes a plurality of C-RNA molecules encoding at least a portion of a protein selected from of any one or more of any of (a), (b), (c), (d), (e), (f), (g), (h), (i), and/or (j) in combination with any one or more of any of (a), (b), (c), (d), (e), (f), (g), (h), (i), and/or (j).

The Examples provided herewith describe the eight gene lists summarized above that distinguish preeclampsia and control pregnancies. Each was identified by using different analysis methods and/or distinct datasets. However, there is a high degree of concordance between many of these gene sets. Identifying a transcript as altered in preeclampsia C-RNA with multiple approaches indicates that said transcript has higher predictive value for classification of this disease. Thus, the importance of the transcripts identified by all differential expression analyses and by all AdaBoost models was combined and ranked. Genes assigned lower ranks are not unimportant or uninformative, but they may be less robust for classification of preeclampsia across cohorts and sample preparations.

First, the transcripts identified when using all differential expression analyses (Standard DEX Treat, bootstrapping and the jackknifing) for both library preparation methods (TruSeq and Nextera Flex for Enrichment) were combined. Table 2 below shows the relative importance for all of the 125 transcripts identified by the different analysis methods. Transcripts identified across every analysis method and both library preparations are the strongest classifiers and assigned an importance ranking of 1. Transcripts that were identified by three or more analysis methods and were detected with both library preparations were given an importance ranking of 2. Transcripts identified by the most stringent analysis method, jackknifing but only one of the library preparations were assigned an importance ranking of 3. Transcripts identified in two of the five analysis methods were given an importance ranking of 4. Transcripts that were only identified in the Standard DEX Treat method, the most broad and inclusive analysis, were given the lowest importance ranking of 5.

Then, the 91 transcripts identified across all AdaBoost models (AdaBoost General and AdaBoost Refined) and both library preparations (Table 3 below) were combined. When generating the refined AdaBoost models for each library preparation, observed slight variations had been observed in the gene set obtained each time a model was built from the same data. This is a natural result of randomness used by AdaBoost to search through the large whole-exome C-RNA data. To obtain a representative list of genes, model building for refined AdaBoost was run a minimum of nine separate times and all genes used by one or more models reported. The percent of models that included each transcript are reported in Table 3 (Frequency Used By AdaBoost). AdaBoost assigns its own "importance" value to each transcript, which reflects how much the abundance of that transcript influences determining whether a sample is from a preeclampsia patient. These AdaBoost importance values were averaged across each refined AdaBoost model a given transcript was used by (Table 3, Average AdaBoost Model Importance).

Transcripts identified across all AdaBoost analyses and library preparations were assigned the highest importance ranking of 1. Transcripts identified in the refined AdaBoost model for a single library preparation method with over 90% frequency used by AdaBoost were assigned an importance ranking of 2. Generally, these transcripts also have higher AdaBoost model importance, consistent with increased predictive capabilities. Transcripts identified in the refined AdaBoost model for a single library preparation method but used by less than 90% of AdaBoost models were assigned an importance ranking of 3. Transcripts identified only in the general AdaBoost model for a single library preparation were given the lowest importance ranking of 4.

Table 2 lists every gene identified by DEX analysis across all analysis approaches and library preps. Rank 1=Transcript identified across every analysis method and library prep method. Rank 2=Transcript identified both library preps, and 3/5 analysis methods. Rank 3=Identified in one library prep method, in jacknifing, are most stringent analysis. Rank 4=identified in 2/5 analyses. And Rank 5=Only identified in Standard DEX Treat method, our most relaxed analysis method.

Table 3 lists every gene identified by Adaboost analysis across both library preps. Rank 1=identified in both library prep methods and the refined adaboost models. Rank 2=Identified in one library prep method, present in refined adaboost model with high model importance and frequency. Rank 3=identified in one library prep method, present in refined adaboost model with medium model importance and frequency. And Rank 4=Identified in one library prep, not present in the refined adaboost model.

Table 4 below is a glossary of all of the various genes recited herein. The information was obtained from the HUGO Gene Nomenclature Committee at the European Bioinformatics Institute.

TABLE 1

| Composite Gene Listing | | | | | | | |
|---|---|---|---|---|---|---|---|
| DIFFERENTIAL EXPRESSION APPROACHES | | | | | Machine Learning Approaches | | |
| | | | | | | Adaboost Refined | Adaboost Refined Nextera Flex |
| Standard DEX TREAT Library Prep: TruSeq Broadest DEX list for TST170 122 genes | Bootstrapping Library Prep: TruSeq Refined subset of Standard DEX TREAT 27 genes | Jackknifing Library Prep: TruSeq Refined subset of Standard DEX TREAT 30 genes | Standard DEX TREAT Library Prep: Nextera Flex for Enrichment Broadest DEX list for Nextera 26 genes | Jackknifing Library Prep: Nextera Flex for Enrichment Refined subset of Standard DEX TREAT for Nextera 22 genes | Adaboost General Library Prep: TruSeq Broadest adaboost 75 genes | TruSeq Library Prep: TruSeq Imrpoved model building for Adaboost, to improve unverisal signal 11 genes | Library Prep: Nextera Flex for Enrichment Imrpoved model building for Adaboost, to improve unverisal signal 24 genes |
| FLG | FLG | VSIG4 | ADAMTS1 | ADAMTS1 | ARHGEF25 | CLEC4C | LEP |
| KRT5 | KRT5 | ADAMTS2 | ADAMTS2 | ADAMTS2 | CLEC4C | ARHGEF25 | PAPPA2 |
| HBG2 | CLEC4C | NES | ALOX15B | ALOX15B | CRH | ADAMTS2 | KCNA5 |
| NXF3 | TEAD4 | FAM107A | AMPH | ARHGEF25 | CUX2 | LEP | ADAMTS2 |
| CLEC4C | SEMA3G | LEP | ARHGEF25 | CELF4 | LEP | ARRDC2 | MYOM3 |
| BPIFB3 | ADAMTS1 | DAAM2 | CELF4 | DAAM2 | NES | SKIL | ATP13A3 |
| LAMP5 | IGFBP5 | ARHGEF25 | DAAM2 | FAM107A | PAPPA2 | PAPPA2 | ARHGEF25 |
| CADM2 | HSPA12B | TIMP3 | FAM107A | HTRA4 | PRG2 | VSIG4 | ADA |
| CUX2 | SLC9A3R2 | PRX | HSPA12B | IGFBP5 | ACY3 | ARRDC4 | HTRA4 |
| PACSIN1 | PRX | ALOX15B | HTRA4 | KCNA5 | ADA | CRH | NES |
| PTGDR2 | TIMP3 | HSPA12B | IGFBP5 | KRT5 | ADAM17 | NES | CRH |
| PLD4 | ARHGEF25 | IGFBP5 | KCNA5 | LCN6 | ARFGAP3 | | ACY3 |
| NOMO1 | HTRA4 | CLEC4C | KRT5 | LEP | ARRDC2 | | PLD4 |
| SH3RF2 | NES | SLC9A3R2 | LCN6 | LRRC26 | ARRDC3 | | SCT |
| ZNF366 | TIMP4 | ADAMTS1 | LEP | NES | ASTE1 | | NOX4 |
| SH3PXD2A | PAPPA2 | SEMA3G | LRRC26 | OLAH | ATOH8 | | PACSIN1 |
| SULT2A1 | FAM107A | KRT5 | NES | PRX | ATP13A3 | | SERPINF1 |
| FAM219A | PRG2 | AMPH | OLAH | PTGDR2 | C10orf2 | | SKIL |
| PPP1R3C | AMPH | PRG2 | PACSIN1 | SEMA3G | C22orf39 | | SEMA3G |
| NFE2L1 | DAAM2 | PAPPA2 | PAPPA2 | SLC9A3R2 | CCDC151 | | TIPARP |
| PODXL | LCN6 | TEAD4 | PRX | TIMP3 | CD63 | | LRRC26 |
| HTRA1 | ALOX15B | CRH | PTGDR2 | VSIG4 | CKAP4 | | PHEX |
| EMP1 | CRH | PITPNM3 | SEMA3G | | CLCN1 | | LILRA4 |
| H19 | VSIG4 | TIMP4 | SLC9A3R2 | | CLEC4M | | PER1 |
| IGIP | LEP | PNMT | TIMP3 | | CLIC5 | | |
| SSUH2 | ADAMTS2 | ZEB1 | VSIG4 | | CNFN | | |
| C6 | ARMS2 | APOLD1 | | | CPAMD8 | | |
| ARHGEF15 | | PLD4 | | | DDI2 | | |
| IRF6 | | CUX2 | | | EBI3 | | |
| NPR1 | | HTRA4 | | | ELMO3 | | |
| ALPK3 | | | | | ENC1 | | |
| ZCCHC24 | | | | | ETV3 | | |
| SAMD4A | | | | | FAR2 | | |
| STAG3 | | | | | FOS | | |
| RP1L1 | | | | | FSTL3 | | |
| A1CF | | | | | GATSL2 | | |
| MN1 | | | | | GBP2 | | |
| CD34 | | | | | GINS4 | | |
| MYH14 | | | | | GSTA3 | | |
| TENC1 | | | | | HEATR9 | | |
| FSTL3 | | | | | HEG1 | | |
| PRDM16 | | | | | HIPK2 | | |
| FMO3 | | | | | JUN | | |
| UACA | | | | | LILRA4 | | |
| TEK | | | | | MRPS35 | | |
| SOX17 | | | | | MTRNR2L6 | | |
| FLNC | | | | | ORAI3 | | |
| TMC7 | | | | | PARN | | |
| KIF1C | | | | | PDE8B | | |
| CLIC5 | | | | | PI4KAP1 | | |
| SYNPO | | | | | PPP1R17 | | |
| CACNA1C | | | | | PSMD11 | | |
| ERG | | | | | RGP1 | | |
| PTPN21 | | | | | RNF6 | | |
| NTRK2 | | | | | SCAMP1 | | |
| WWTR1 | | | | | SERPINF1 | | |
| CYP26B1 | | | | | SKIL | | |
| ZEB1 | | | | | SLC26A2 | | |
| AIF1L | | | | | SLC4A3 | | |
| C8B | | | | | SLIT3 | | |
| KIF26A | | | | | SMPD3 | | |
| ZBTB16 | | | | | SPDYE5 | | |

TABLE 1-continued

| Composite Gene Listing | | | | | | | |
|---|---|---|---|---|---|---|---|
| DIFFERENTIAL EXPRESSION APPROACHES | | | | | Machine Learning Approaches | | |
| | | | | | | Adaboost Refined | Adaboost Refined Nextera Flex |
| Standard DEX TREAT Library Prep: TruSeq Broadest DEX list for TST170 122 genes | Bootstrapping Library Prep: TruSeq Refined subset of Standard DEX TREAT 27 genes | Jackknifing Library Prep: TruSeq Refined subset of Standard DEX TREAT 30 genes | Standard DEX TREAT Library Prep: Nextera Flex for Enrichment Broadest DEX list for Nextera 26 genes | Jackknifing Library Prep: Nextera Flex for Enrichment Refined subset of Standard DEX TREAT for Nextera 22 genes | Adaboost General Library Prep: TruSeq Broadest adaboost 75 genes | TruSeq Library Prep: TruSeq Imrpoved model building for Adaboost, to improve unverisal signal 11 genes | Library Prep: Nextera Flex for Enrichment Imrpoved model building for Adaboost, to improve unverisal signal 24 genes |
| BCL6B | | | | | ST6GALNAC3 | | |
| FKBP5 | | | | | THTPA | | |
| FN1 | | | | | TIPARP | | |
| AQP7 | | | | | TMEM108 | | |
| IL1R2 | | | | | TMEM11 | | |
| ERRFI1 | | | | | TNFRSF21 | | |
| SRPX | | | | | TPCN1 | | |
| GJA5 | | | | | TPST1 | | |
| GPR116 | | | | | TRAF3IP1 | | |
| JAG2 | | | | | TRUB1 | | |
| MYL2 | | | | | TTC21A | | |
| ADCY1 | | | | | USP54 | | |
| NRG3 | | | | | ZMYM6 | | |
| GPR4 | | | | | | | |
| PITPNM3 | | | | | | | |
| SERPINA3 | | | | | | | |
| CPB2 | | | | | | | |
| ADRA2C | | | | | | | |
| ANO1 | | | | | | | |
| CA3 | | | | | | | |
| C14orf37 | | | | | | | |
| TEAD4 | | | | | | | |
| TAT | | | | | | | |
| LEAP2 | | | | | | | |
| HAO2 | | | | | | | |
| SEMA3G | | | | | | | |
| ADAMTS1 | | | | | | | |
| APOLD1 | | | | | | | |
| IGFBP5 | | | | | | | |
| HSPA12B | | | | | | | |
| GATA5 | | | | | | | |
| SLC9A3R2 | | | | | | | |
| RSPO3 | | | | | | | |
| AQP7P1 | | | | | | | |
| PRX | | | | | | | |
| PNMT | | | | | | | |
| MYOM3 | | | | | | | |
| HRG | | | | | | | |
| TIMP3 | | | | | | | |
| ARHGEF25 | | | | | | | |
| HTRA4 | | | | | | | |
| SCN5A | | | | | | | |
| OLAH | | | | | | | |
| NES | | | | | | | |
| TIMP4 | | | | | | | |
| PAPPA2 | | | | | | | |
| AZGP1 | | | | | | | |
| FAM107A | | | | | | | |
| PRG2 | | | | | | | |
| AMPH | | | | | | | |
| AP3B2 | | | | | | | |
| KRT17 | | | | | | | |
| DAAM2 | | | | | | | |
| LCN6 | | | | | | | |
| ALOX15B | | | | | | | |
| CRH | | | | | | | |
| VSIG4 | | | | | | | |
| LEP | | | | | | | |
| ADAMTS2 | | | | | | | |
| ARMS2 | | | | | | | |

TABLE 2

| | | | | | | | | |
|---|---|---|---|---|---|---|---|---|
| DEX Analysis | | | | | | | | |
| | | TruSeq | | | | | | |
| | | Standard | | | | Nextera Flex for enrichment | | |
| Gene | Importance Ranking | DEX TREAT | Fold Change | Bootstrapping | Jackknifing | Standard DEX | Fold Change | Jackknifing |
| ADAMTS1 | 1 | Y | 1.79 | Y | Y | Y | +3.2 | Y |
| ADAMTS2 | 1 | Y | 3.61 | Y | Y | Y | +12.2 | Y |
| ALOX15B | 1 | Y | 2.51 | Y | Y | Y | +5.3 | Y |
| ARHGEF25 | 1 | Y | 2.02 | Y | Y | Y | +3.8 | Y |
| DAAM2 | 1 | Y | 2.48 | Y | Y | Y | +5.4 | Y |
| FAM107A | 1 | Y | 2.31 | Y | Y | Y | +4.3 | Y |
| HTRA4 | 1 | Y | 2.03 | Y | Y | Y | +4.0 | Y |
| IGFBP5 | 1 | Y | 1.81 | Y | Y | Y | +3.4 | Y |
| KRT5 | 1 | Y | −2.52 | Y | Y | Y | −4.8 | Y |
| LEP | 1 | Y | 3.48 | Y | Y | Y | +8.1 | Y |
| NES | 1 | Y | 2.15 | Y | Y | Y | +4.2 | Y |
| PRX | 1 | Y | 1.93 | Y | Y | Y | +3.3 | Y |
| SEMA3G | 1 | Y | 1.78 | Y | Y | Y | +3.5 | Y |
| SLC9A3R2 | 1 | Y | 1.85 | Y | Y | Y | +3.4 | Y |
| TIMP3 | 1 | Y | 2.01 | Y | Y | Y | +3.7 | Y |
| VSIG4 | 1 | Y | 3.03 | Y | Y | Y | +8.2 | Y |
| PAPPA2 | 2 | Y | 2.20 | Y | Y | Y | +4.2 | N |
| AMPH | 2 | Y | 2.37 | Y | Y | Y | +4.1 | N |
| HSPA12B | 2 | Y | 1.82 | Y | Y | Y | +3.2 | N |
| PTGDR2 | 2 | Y | −1.67 | N | N | Y | −3.5 | Y |
| LCN6 | 2 | Y | 2.49 | Y | N | Y | +4.4 | Y |
| OLAH | 2 | Y | 2.07 | N | N | Y | +5.2 | Y |
| APOLD1 | 3 | Y | 1.80 | N | Y | N | NA | N |
| CUX2 | 3 | Y | −1.73 | N | Y | N | NA | N |
| PITPNM3 | 3 | Y | 1.66 | N | Y | N | NA | N |
| PLD4 | 3 | Y | −1.59 | N | Y | N | NA | N |
| PNMT | 3 | Y | 1.98 | N | Y | N | NA | N |
| CLEC4C | 3 | Y | −1.86 | Y | Y | N | NA | N |
| CRH | 3 | Y | 2.54 | Y | Y | N | NA | N |
| PRG2 | 3 | Y | 2.36 | Y | Y | N | NA | N |
| TEAD4 | 3 | Y | 1.74 | Y | Y | N | NA | N |
| TIMP4 | 3 | Y | 2.17 | Y | Y | N | NA | N |
| CELF4 | 3 | N | NA | N | N | Y | +5.3 | Y |
| KCNA5 | 3 | N | NA | N | N | Y | −4.0 | Y |
| LRRC26 | 3 | N | NA | N | N | Y | −4.4 | Y |
| ARMS2 | 4 | Y | 4.43 | Y | N | N | NA | N |
| FLG | 4 | Y | −3.05 | Y | N | N | NA | N |
| PACSIN1 | 4 | Y | −1.70 | N | N | Y | −3.4 | N |
| A1CF | 5 | Y | 1.37 | N | N | N | NA | N |
| ADCY1 | 5 | Y | 1.62 | N | N | N | NA | N |
| ADRA2C | 5 | Y | 1.69 | N | N | N | NA | N |
| AIF1L | 5 | Y | 1.48 | N | N | N | NA | N |
| ALPK3 | 5 | Y | 1.35 | N | N | N | NA | N |
| ANO1 | 5 | Y | 1.69 | N | N | N | NA | N |
| AP3B2 | 5 | Y | 2.40 | N | N | N | NA | N |
| AQP7 | 5 | Y | 1.51 | N | N | N | NA | N |
| AQP7P1 | 5 | Y | 1.88 | N | N | N | NA | N |
| ARHGEF15 | 5 | Y | 1.33 | N | N | N | NA | N |
| AZGP1 | 5 | Y | 2.27 | N | N | N | NA | N |
| BCL6B | 5 | Y | 1.50 | N | N | N | NA | N |
| BPIFB3 | 5 | Y | −1.80 | N | N | N | NA | N |
| C14orf37 | 5 | Y | 1.73 | N | N | N | NA | N |
| C6 | 5 | Y | 1.33 | N | N | N | NA | N |
| C8B | 5 | Y | 1.49 | N | N | N | NA | N |
| CA3 | 5 | Y | 1.72 | N | N | N | NA | N |
| CACNA1C | 5 | Y | 1.42 | N | N | N | NA | N |
| CADM2 | 5 | Y | −1.76 | N | N | N | NA | N |
| CD34 | 5 | Y | 1.37 | N | N | N | NA | N |
| CLIC5 | 5 | Y | 1.41 | N | N | N | NA | N |
| CPB2 | 5 | Y | 1.69 | N | N | N | NA | N |
| CYP26B1 | 5 | Y | 1.48 | N | N | N | NA | N |
| EMP1 | 5 | Y | 1.30 | N | N | N | NA | N |
| ERG | 5 | Y | 1.43 | N | N | N | NA | N |
| ERRFI1 | 5 | Y | 1.54 | N | N | N | NA | N |
| FAM219A | 5 | Y | 1.24 | N | N | N | NA | N |
| FKBP5 | 5 | Y | 1.50 | N | N | N | NA | N |
| FLNC | 5 | Y | 1.40 | N | N | N | NA | N |
| FMO3 | 5 | Y | 1.39 | N | N | N | NA | N |
| FN1 | 5 | Y | 1.51 | N | N | N | NA | N |
| FSTL3 | 5 | Y | 1.38 | N | N | N | NA | N |
| GATA5 | 5 | Y | 1.82 | N | N | N | NA | N |

TABLE 2-continued

| DEX Analysis | | | | | | | | |
|---|---|---|---|---|---|---|---|---|
| | | TruSeq | | | | | | |
| | | Standard | | | | Nextera Flex for enrichment | | |
| Gene | Importance Ranking | DEX TREAT | Fold Change | Bootstrapping | Jackknifing | Standard DEX | Fold Change | Jackknifing |
| GJA5 | 5 | Y | 1.55 | N | N | N | NA | N |
| GPR116 | 5 | Y | 1.56 | N | N | N | NA | N |
| GPR4 | 5 | Y | 1.65 | N | N | N | NA | N |
| H19 | 5 | Y | 1.32 | N | N | N | NA | N |
| HAO2 | 5 | Y | 1.75 | N | N | N | NA | N |
| HBG2 | 5 | Y | −2.15 | N | N | N | NA | N |
| HRG | 5 | Y | 1.99 | N | N | N | NA | N |
| HTRA1 | 5 | Y | 1.29 | N | N | N | NA | N |
| IGIP | 5 | Y | 1.32 | N | N | N | NA | N |
| IL1R2 | 5 | Y | 1.53 | N | N | N | NA | N |
| IRF6 | 5 | Y | 1.34 | N | N | N | NA | N |
| JAG2 | 5 | Y | 1.57 | N | N | N | NA | N |
| KIF1C | 5 | Y | 1.41 | N | N | N | NA | N |
| KIF26A | 5 | Y | 1.49 | N | N | N | NA | N |
| KRT17 | 5 | Y | 2.47 | N | N | N | NA | N |
| LAMP5 | 5 | Y | −1.77 | N | N | N | NA | N |
| LEAP2 | 5 | Y | 1.74 | N | N | N | NA | N |
| MN1 | 5 | Y | 1.37 | N | N | N | NA | N |
| MYH14 | 5 | Y | 1.38 | N | N | N | NA | N |
| MYL2 | 5 | Y | 1.60 | N | N | N | NA | N |
| MYOM3 | 5 | Y | 1.99 | N | N | N | NA | N |
| NFE2L1 | 5 | Y | 1.26 | N | N | N | NA | N |
| NOMO1 | 5 | Y | −1.49 | N | N | N | NA | N |
| NPR1 | 5 | Y | 1.34 | N | N | N | NA | N |
| NRG3 | 5 | Y | 1.62 | N | N | N | NA | N |
| NTRK2 | 5 | Y | 1.45 | N | N | N | NA | N |
| NXF3 | 5 | Y | −1.96 | N | N | N | NA | N |
| PODXL | 5 | Y | 1.27 | N | N | N | NA | N |
| PPP1R3C | 5 | Y | 1.25 | N | N | N | NA | N |
| PRDM16 | 5 | Y | 1.38 | N | N | N | NA | N |
| PTPN21 | 5 | Y | 1.44 | N | N | N | NA | N |
| RP1L1 | 5 | Y | 1.36 | N | N | N | NA | N |
| RSPO3 | 5 | Y | 1.87 | N | N | N | NA | N |
| SAMD4A | 5 | Y | 1.35 | N | N | N | NA | N |
| SCN5A | 5 | Y | 2.03 | N | N | N | NA | N |
| SERPINA3 | 5 | Y | 1.67 | N | N | N | NA | N |
| SH3PXD2A | 5 | Y | 1.23 | N | N | N | NA | N |
| SH3RF2 | 5 | Y | 1.18 | N | N | N | NA | N |
| SOX17 | 5 | Y | 1.40 | N | N | N | NA | N |
| SRPX | 5 | Y | 1.55 | N | N | N | NA | N |
| SSUH2 | 5 | Y | 1.33 | N | N | N | NA | N |
| STAG3 | 5 | Y | 1.36 | N | N | N | NA | N |
| SULT2A1 | 5 | Y | 1.23 | N | N | N | NA | N |
| SYNPO | 5 | Y | 1.42 | N | N | N | NA | N |
| TAT | 5 | Y | 1.74 | N | N | N | NA | N |
| TEK | 5 | Y | 1.39 | N | N | N | NA | N |
| TENC1 | 5 | Y | 1.38 | N | N | N | NA | N |
| TMC7 | 5 | Y | 1.40 | N | N | N | NA | N |
| UACA | 5 | Y | 1.39 | N | N | N | NA | N |
| WWTR1 | 5 | Y | 1.47 | N | N | N | NA | N |
| ZBTB16 | 5 | Y | 1.50 | N | N | N | NA | N |
| ZCCHC24 | 5 | Y | 1.35 | N | N | N | NA | N |
| ZEB1 | 5 | Y | 1.48 | N | Y | N | NA | N |
| ZNF366 | 5 | Y | 1.23 | N | N | N | NA | N |

TABLE 3

| Adaboost Analysis | | | | | | | |
|---|---|---|---|---|---|---|---|
| | Importance | Fold Change in Preeclampsia | | Frequency Used By Adaboost | | Average AdaBoost Model Importance | |
| | Ranking | TruSeq | Nextera Flex | TruSeq | Nextera Flex | TruSeq | Nextera Flex |
| ADAMTS2 | 1 | +11.6 | +12.2 | 100% | 100% | 9% | 8% |
| ARHGEF25 | 1 | +4.1 | +3.8 | 100% | 100% | 11% | 5% |
| CRH | 1 | +5.7 | +3.9 | 14% | 100% | 2% | 4% |
| LEP | 1 | +10.7 | +8.1 | 100% | 100% | 8% | 17% |

TABLE 3-continued

| Adaboost Analysis | | | | | | | |
|---|---|---|---|---|---|---|---|
| | Importance | Fold Change in Preeclampsia | | Frequency Used By Adaboost | | Average AdaBoost Model Importance | |
| | Ranking | TruSeq | Nextera Flex | TruSeq | Nextera Flex | TruSeq | Nextera Flex |
| NES | 1 | +4.5 | +4.2 | 7% | 100% | 4% | 4% |
| PAPPA2 | 1 | +4.9 | +4.2 | 64% | 100% | 3% | 8% |
| SKIL | 1 | +1.5 | +1.4 | 86% | 78% | 3% | 3% |
| ACY3 | 2 | ND | −2.3 | ND | 100% | ND | 3% |
| ADA | 2 | ND | −1.6 | ND | 100% | ND | 5% |
| ARRDC2 | 2 | +1.8 | ND | 93% | ND | 3% | ND |
| ATP13A3 | 2 | ND | +1.5 | ND | 100% | ND | 5% |
| CLEC4C | 2 | −3.6 | ND | 100% | ND | 18% | ND |
| HTRA4 | 2 | ND | +4.0 | ND | 100% | ND | 5% |
| KCNA5 | 2 | ND | −4.0 | ND | 100% | ND | 8% |
| MYOM3 | 2 | ND | +4.2 | ND | 100% | ND | 7% |
| NOX4 | 2 | ND | −1.8 | ND | 100% | ND | 2% |
| PACSIN1 | 2 | ND | −3.4 | ND | 100% | ND | 2% |
| PLD4 | 2 | ND | −2.7 | ND | 100% | ND | 3% |
| SCT | 2 | ND | −3.3 | ND | 100% | ND | 3% |
| SERPINF1 | 2 | ND | −1.6 | ND | 100% | ND | 2% |
| VSIG4 | 3 | +8.1 | ND | 43% | ND | 3% | ND |
| ARRDC4 | 3 | +2.0 | ND | 36% | ND | 4% | ND |
| LILRA4 | 3 | ND | −2.7 | ND | 33% | ND | 1% |
| LRRC26 | 3 | ND | −4.4 | ND | 56% | ND | 2% |
| PER1 | 3 | ND | +2.2 | ND | 33% | ND | 1% |
| PHEX | 3 | ND | −2.2 | ND | 56% | ND | 2% |
| SEMA3G | 3 | ND | +3.5 | ND | 67% | ND | 5% |
| TIPARP | 3 | ND | +1.2 | ND | 67% | ND | 2% |
| ADAM17 | 4 | ND | ND | ND | ND | ND | ND |
| ARFGAP3 | 4 | ND | ND | ND | ND | ND | ND |
| ARRDC3 | 4 | ND | ND | ND | ND | ND | ND |
| ASTE1 | 4 | ND | ND | ND | ND | ND | ND |
| ATOH8 | 4 | ND | ND | ND | ND | ND | ND |
| C10orf2 | 4 | ND | ND | ND | ND | ND | ND |
| C22orf39 | 4 | ND | ND | ND | ND | ND | ND |
| CCDC151 | 4 | ND | ND | ND | ND | ND | ND |
| CD63 | 4 | ND | ND | ND | ND | ND | ND |
| CKAP4 | 4 | ND | ND | ND | ND | ND | ND |
| CLCN1 | 4 | ND | ND | ND | ND | ND | ND |
| CLEC4M | 4 | ND | ND | ND | ND | ND | ND |
| CLIC5 | 4 | ND | ND | ND | ND | ND | ND |
| CNFN | 4 | ND | ND | ND | ND | ND | ND |
| CPAMD8 | 4 | ND | ND | ND | ND | ND | ND |
| CUX2 | 4 | ND | ND | ND | ND | ND | ND |
| DDI2 | 4 | ND | ND | ND | ND | ND | ND |
| EBI3 | 4 | ND | ND | ND | ND | ND | ND |
| ELMO3 | 4 | ND | ND | ND | ND | ND | ND |
| ENC1 | 4 | ND | ND | ND | ND | ND | ND |
| ETV3 | 4 | ND | ND | ND | ND | ND | ND |
| FAR2 | 4 | ND | ND | ND | ND | ND | ND |
| FOS | 4 | ND | ND | ND | ND | ND | ND |
| FSTL3 | 4 | ND | ND | ND | ND | ND | ND |
| GATSL2 | 4 | ND | ND | ND | ND | ND | ND |
| GBP2 | 4 | ND | ND | ND | ND | ND | ND |
| GINS4 | 4 | ND | ND | ND | ND | ND | ND |
| GSTA3 | 4 | ND | ND | ND | ND | ND | ND |
| HEATR9 | 4 | ND | ND | ND | ND | ND | ND |
| HEG1 | 4 | ND | ND | ND | ND | ND | ND |
| HIPK2 | 4 | ND | ND | ND | ND | ND | ND |
| JUN | 4 | ND | ND | ND | ND | ND | ND |
| MRPS35 | 4 | ND | ND | ND | ND | ND | ND |
| MTRNR2L6 | 4 | ND | ND | ND | ND | ND | ND |
| ORAI3 | 4 | ND | ND | ND | ND | ND | ND |
| PARN | 4 | ND | ND | ND | ND | ND | ND |
| PDE8B | 4 | ND | ND | ND | ND | ND | ND |
| PI4KAP1 | 4 | ND | ND | ND | ND | ND | ND |
| PPP1R17 | 4 | ND | ND | ND | ND | ND | ND |
| PRG2 | 4 | ND | ND | ND | ND | ND | ND |
| PSMD11 | 4 | ND | ND | ND | ND | ND | ND |
| RGP1 | 4 | ND | ND | ND | ND | ND | ND |
| RNF6 | 4 | ND | ND | ND | ND | ND | ND |
| SCAMP1 | 4 | ND | ND | ND | ND | ND | ND |
| SLC26A2 | 4 | ND | ND | ND | ND | ND | ND |
| SLC4A3 | 4 | ND | ND | ND | ND | ND | ND |
| SLIT3 | 4 | ND | ND | ND | ND | ND | ND |
| SMPD3 | 4 | ND | ND | ND | ND | ND | ND |
| SPDYE5 | 4 | ND | ND | ND | ND | ND | ND |

TABLE 3-continued

| Adaboost Analysis | | | | | | | |
|---|---|---|---|---|---|---|---|
| | Importance | Fold Change in Preeclampsia | | Frequency Used By Adaboost | | Average AdaBoost Model Importance | |
| | Ranking | TruSeq | Nextera Flex | TruSeq | Nextera Flex | TruSeq | Nextera Flex |
| ST6GALNAC3 | 4 | ND | ND | ND | ND | ND | ND |
| THTPA | 4 | ND | ND | ND | ND | ND | ND |
| TMEM108 | 4 | ND | ND | ND | ND | ND | ND |
| TMEM11 | 4 | ND | ND | ND | ND | ND | ND |
| TNFRSF21 | 4 | ND | ND | ND | ND | ND | ND |
| TPCN1 | 4 | ND | ND | ND | ND | ND | ND |
| TPST1 | 4 | ND | ND | ND | ND | ND | ND |
| TRAF3IP1 | 4 | ND | ND | ND | ND | ND | ND |
| TRUB1 | 4 | ND | ND | ND | ND | ND | ND |
| TTC21A | 4 | ND | ND | ND | ND | ND | ND |
| USP54 | 4 | ND | ND | ND | ND | ND | ND |
| ZMYM6 | 4 | ND | ND | ND | ND | ND | ND |

TABLE 4

| Gene Glossary | | | | |
|---|---|---|---|---|
| Gene Symbol Used in Patent | Official Gene Symbol | Approved Name | HGNC ID | Location |
| KRT5 | KRT5 | keratin 5 | HGNC:6442 | 12q13.13 |
| CUX2 | CUX2 | cut like homeobox 2 | HGNC:19347 | 12q24.11-q24.12 |
| CLEC4C | CLEC4C | C-type lectin domain family 4 member C | HGNC:13258 | 12p13.31 |
| PLD4 | PLD4 | phospholipase D family member 4 | HGNC:23792 | 14q32.33 |
| ALOX15B | ALOX15B | arachidonate 15-lipoxygenase type B | HGNC:434 | 17p13.1 |
| PRG2 | PRG2 | proteoglycan 2, pro eosinophil major basic protein | HGNC:9362 | 11q12.1 |
| HTRA4 | HTRA4 | HtrA serine peptidase 4 | HGNC:26909 | 8p11.22 |
| AMPH | AMPH | amphiphysin | HGNC:471 | 7p14.1 |
| PNMT | PNMT | phenylethanolamine N-methyltransferase | HGNC:9160 | 17q12 |
| LEP | LEP | leptin | HGNC:6553 | 7q32.1 |
| PAPPA2 | PAPPA2 | pappalysin 2 | HGNC:14615 | 1q25.2 |
| CRH | CRH | corticotropin releasing hormone | HGNC:2355 | 8q13.1 |
| TIMP4 | TIMP4 | TIMP metallopeptidase inhibitor 4 | HGNC:11823 | 3p25.2 |
| APOLD1 | APOLD1 | apolipoprotein L domain containing 1 | HGNC:25268 | 12p13.1 |
| ARHGEF25 | ARHGEF25 | Rho guanine nucleotide exchange factor 25 | HGNC:30275 | 12q13.3 |
| TIMP3 | TIMP3 | TIMP metallopeptidase inhibitor 3 | HGNC:11822 | 22q12.3 |
| SEMA3G | SEMA3G | semaphorin 3G | HGNC:30400 | 3p21.1 |
| IGFBP5 | IGFBP5 | insulin like growth factor binding protein 5 | HGNC:5474 | 2q35 |
| PRX | PRX | periaxin | HGNC:13797 | 19q13.2 |
| PITPNM3 | PITPNM3 | PITPNM family member 3 | HGNC:21043 | 17p13.2-p13.1 |
| FAM107A | FAM107A | family with sequence similarity 107 member A | HGNC:30827 | 3p14.3-p14.2 |
| TEAD4 | TEAD4 | TEA domain transcription factor 4 | HGNC:11717 | 12p13.33 |
| HSPA12B | HSPA12B | heat shock protein family A (Hsp70) member 12B | HGNC:16193 | 20p13 |
| NES | NES | nestin | HGNC:7756 | 1q23.1 |
| SLC9A3R2 | SLC9A3R2 | SLC9A3 regulator 2 | HGNC:11076 | 16p13.3 |
| ZEB1 | ZEB1 | zinc finger E-box binding homeobox 1 | HGNC:11642 | 10p11.22 |
| ADAMTS1 | ADAMTS1 | ADAM metallopeptidase with thrombospondin type 1 motif 1 | HGNC:217 | 21q21.3 |
| DAAM2 | DAAM2 | dishevelled associated activator of morphogenesis 2 | HGNC:18143 | 6p21.2 |
| ADAMTS2 | ADAMTS2 | ADAM metallopeptidase with thrombospondin type 1 motif 2 | HGNC:218 | 5q35.3 |
| VSIG4 | VSIG4 | V-set and immunoglobulin domain containing 4 | HGNC:17032 | Xq12 |
| ARRDC2 | ARRDC2 | arrestin domain containing 2 | HGNC:25225 | 19p13.11 |
| SKIL | SKIL | SKI like proto-oncogene | HGNC:10897 | 3q26.2 |
| ARRDC4 | ARRDC4 | arrestin domain containing 4 | HGNC:28087 | 15q26.2 |
| KCNA5 | KCNA5 | potassium voltage-gated channel subfamily A member 5 | HGNC:6224 | 12p13.32 |
| MYOM3 | MYOM3 | myomesin 3 | HGNC:26679 | 1p36.11 |
| ATP13A3 | ATP13A3 | ATPase 13A3 | HGNC:24113 | 3q29 |
| ADA | ADA | adenosine deaminase | HGNC:186 | 20q13.12 |
| ACY3 | ACY3 | aminoacylase 3 | HGNC:24104 | 11q13.2 |
| SCT | SCT | secretin | HGNC:10607 | 11p15.5 |
| NOX4 | NOX4 | NADPH oxidase 4 | HGNC:7891 | 11q14.3 |
| PACSIN1 | PACSIN1 | protein kinase C and casein kinase substrate in neurons 1 | HGNC:8570 | 6p21.3 |
| SERPINF1 | SERPINF1 | serpin family F member 1 | HGNC:8824 | 17p13.3 |
| TIPARP | TIPARP | TCDD inducible poly(ADP-ribose) polymerase | HGNC:23696 | 3q25.31 |
| LRRC26 | LRRC26 | leucine rich repeat containing 26 | HGNC:31409 | 9q34.3 |
| PHEX | PHEX | phosphate regulating endopeptidase homolog X-linked | HGNC:8918 | Xp22.11 |
| LILRA4 | LILRA4 | leukocyte immunoglobulin like receptor A4 | HGNC:15503 | 19q13.42 |
| PER1 | PER1 | period circadian regulator 1 | HGNC:8845 | 17p13.1 |
| CELF4 | CELF4 | CUGBP Elav-like family member 4 | HGNC:14015 | 18q12.2 |
| LCN6 | LCN6 | lipocalin 6 | HGNC:17337 | 9q34.3 |
| OLAH | OLAH | oleoyl-ACP hydrolase | HGNC:25625 | 10p13 |

TABLE 4-continued

Gene Glossary

| Gene Symbol Used in Patent | Official Gene Symbol | Approved Name | HGNC ID | Location |
|---|---|---|---|---|
| PTGDR2 | PTGDR2 | prostaglandin D2 receptor 2 | HGNC:4502 | 11q12.2 |
| JUN | JUN | Jun proto-oncogene, AP-1 transcription factor subunit | HGNC:6204 | 1p32.1 |
| PDE8B | PDE8B | phosphodiesterase 8B | HGNC:8794 | 5q13.3 |
| GSTA3 | GSTA3 | glutathione S-transferase alpha 3 | HGNC:4628 | 6p12.2 |
| RGP1 | RGP1 | RGP1 homolog, RAB6A GEF complex partner 1 | HGNC:21965 | 9p13.3 |
| USP54 | USP54 | ubiquitin specific peptidase 54 | HGNC:23513 | 10q22.2 |
| MRPS35 | MRPS35 | mitochondrial ribosomal protein S35 | HGNC:16635 | 12p11.22 |
| HEATR9 | HEATR9 | HEAT repeat containing 9 | HGNC:26548 | 17q12 |
| FSTL3 | FSTL3 | follistatin like 3 | HGNC:3973 | 19p13.3 |
| DDI2 | DDI2 | DNA damage inducible 1 homolog 2 | HGNC:24578 | 1p36.21 |
| ZMYM6 | ZMYM6 | zinc finger MYM-type containing 6 | HGNC:13050 | 1p34.3 |
| ST6GALNAC3 | ST6GALNAC3 | ST6 N-acetylgalactosaminide alpha-2,6-sialyltransferase 3 | HGNC:19343 | 1p31.1 |
| GBP2 | GBP2 | guanylate binding protein 2 | HGNC:4183 | 1p22.2 |
| ETV3 | ETV3 | ETS variant 3 | HGNC:3492 | 1q23.1 |
| ADAM17 | ADAM17 | ADAM metallopeptidase domain 17 | HGNC:195 | 2p25.1 |
| ATOH8 | ATOH8 | atonal bHLH transcription factor 8 | HGNC:24126 | 2p11.2 |
| SLC4A3 | SLC4A3 | solute carrier family 4 member 3 | HGNC:11029 | 2q35 |
| TRAF3IP1 | TRAF3IP1 | TRAF3 interacting protein 1 | HGNC:17861 | 2q37.3 |
| TTC21A | TTC21A | tetratricopeptide repeat domain 21A | HGNC:30761 | 3p22.2 |
| HEG1 | HEG1 | heart development protein with EGF like domains 1 | HGNC:29227 | 3q21.2 |
| ASTE1 | ASTE1 | asteroid homolog 1 | HGNC:25021 | 3q22.1 |
| TMEM108 | TMEM108 | transmembrane protein 108 | HGNC:28451 | 3q22.1 |
| ENC1 | ENC1 | ectodermal-neural cortex 1 | HGNC:3345 | 5q13.3 |
| SCAMP1 | SCAMP1 | secretory carrier membrane protein 1 | HGNC:10563 | 5q14.1 |
| ARRDC3 | ARRDC3 | arrestin domain containing 3 | HGNC:29263 | 5q14.3 |
| SLC26A2 | SLC26A2 | solute carrier family 26 member 2 | HGNC:10994 | 5q32 |
| SLIT3 | SLIT3 | slit guidance ligand 3 | HGNC:11087 | 5q34-q35.1 |
| CLIC5 | CLIC5 | chloride intracellular channel 5 | HGNC:13517 | 6p21.1 |
| TNFRSF21 | TNFRSF21 | TNF receptor superfamily member 21 | HGNC:13469 | 6p12.3 |
| PPP1R17 | PPP1R17 | protein phosphatase 1 regulatory subunit 17 | HGNC:16973 | 7p14.3 |
| TPST1 | TPST1 | tyrosylprotein sulfotransferase 1 | HGNC:12020 | 7q11.21 |
| GATSL2 | CASTOR2 | cytosolic arginine sensor for mTORC1 subunit 2 | HGNC:37073 | 7q11.23 |
| SPDYE5 | SPDYE5 | speedy/RINGO cell cycle regulator family member E5 | HGNC:35464 | 7q11.23 |
| HIPK2 | HIPK2 | homeodomain interacting protein kinase 2 | HGNC:14402 | 7q34 |
| MTRNR2L6 | MTRNR2L6 | MT-RNR2 like 6 | HGNC:37163 | 7q34 |
| CLCN1 | CLCN1 | chloride voltage-gated channel 1 | HGNC:2019 | 7q34 |
| GINS4 | GINS4 | GINS complex subunit 4 | HGNC:28226 | 8p11.21 |
| C10orf2 | TWNK | twinkle mtDNA helicase | HGNC:1160 | 10q24.31 |
| TRUB1 | TRUB1 | TruB pseudouridine synthase family member 1 | HGNC:16060 | 10q25.3 |
| FAR2 | FAR2 | fatty acyl-CoA reductase 2 | HGNC:25531 | 12p11.22 |
| CD63 | CD63 | CD63 molecule | HGNC:1692 | 12q13.2 |
| CKAP4 | CKAP4 | cytoskeleton associated protein 4 | HGNC:16991 | 12q23.3 |
| TPCN1 | TPCN1 | two pore segment channel 1 | HGNC:18182 | 12q24.13 |
| RNF6 | RNF6 | ring finger protein 6 | HGNC:10069 | 13q12.13 |
| THTPA | THTPA | thiamine triphosphatase | HGNC:18987 | 14q11.2 |
| FOS | FOS | Fos proto-oncogene, AP-1 transcription factor subunit | HGNC:3796 | 14q24.3 |
| PARN | PARN | poly(A)-specific ribonuclease | HGNC:8609 | 16p13.12 |
| ORAI3 | ORAI3 | ORAI calcium release-activated calcium modulator 3 | HGNC:28185 | 16p11.2 |
| ELMO3 | ELMO3 | engulfment and cell motility 3 | HGNC:17289 | 16q22.1 |
| SMPD3 | SMPD3 | sphingomyelin phosphodiesterase 3 | HGNC:14240 | 16q22.1 |
| TMEM11 | TMEM11 | transmembrane protein 11 | HGNC:16823 | 17p11.1 |
| PSMD11 | PSMD11 | proteasome 26S subunit, non-ATPase 11 | HGNC:9556 | 17q11.2 |
| EBI3 | EBI3 | Epstein-Barr virus induced 3 | HGNC:3129 | 19p13.3 |
| CLEC4M | CLEC4M | C-type lectin domain family 4 member M | HGNC:13523 | 19p13.2 |
| CCDC151 | CCDC151 | coiled-coil domain containing 151 | HGNC:28303 | 19p13.2 |
| CPAMD8 | CPAMD8 | C3 and PZP like alpha-2-macroglobulin domain containing 8 | HGNC:23228 | 19p13.11 |
| CNFN | CNFN | cornifelin | HGNC:30183 | 19q13.2 |
| C22orf39 | C22orf39 | chromosome 22 open reading frame 39 | HGNC:27012 | 22q11.21 |
| PI4KAP1 | PI4KAP1 | phosphatidylinositol 4-kinase alpha pseudogene 1 | HGNC:33576 | 22q11.21 |
| ARFGAP3 | ARFGAP3 | ADP ribosylation factor GTPase activating protein 3 | HGNC:661 | 22q13.2 |
| FLG | FLG | filaggrin | HGNC:3748 | 1q21.3 |
| ARMS2 | ARMS2 | age-related maculopathy susceptibility 2 | HGNC:32685 | 10q26.13 |
| CYP26B1 | CYP26B1 | cytochrome P450 family 26 subfamily B member 1 | HGNC:20581 | 2p13.2 |
| IRF6 | IRF6 | interferon regulatory factor 6 | HGNC:6121 | 1q32.2 |
| MYH14 | MYH14 | myosin heavy chain 14 | HGNC:23212 | 19q13.33 |
| PODXL | PODXL | podocalyxin like | HGNC:9171 | 7q32.3 |
| PPP1R3C | PPP1R3C | protein phosphatase 1 regulatory subunit 3C | HGNC:9293 | 10q23.32 |
| SH3RF2 | SH3RF2 | SH3 domain containing ring finger 2 | HGNC:26299 | 5q32 |
| TMC7 | TMC7 | transmembrane channel like 7 | HGNC:23000 | 16p12.3 |
| ZNF366 | ZNF366 | zinc finger protein 366 | HGNC:18316 | 5q13.1 |
| ADCY1 | ADCY1 | adenylate cyclase 1 | HGNC:232 | 7p12.3 |
| C6 | C6 | complement C6 | HGNC:1339 | 5p13.1 |
| FAM219A | FAM219A | family with sequence similarity 219 member A | HGNC:19920 | 9p13.3 |
| HAO2 | HAO2 | hydroxyacid oxidase 2 | HGNC:4810 | 1p12 |
| IGIP | IGIP | IgA inducing protein | HGNC:33847 | 5q31.3 |

TABLE 4-continued

Gene Glossary

| Gene Symbol Used in Patent | Official Gene Symbol | Approved Name | HGNC ID | Location |
|---|---|---|---|---|
| IL1R2 | IL1R2 | interleukin 1 receptor type 2 | HGNC:5994 | 2q11.2 |
| NTRK2 | NTRK2 | neurotrophic receptor tyrosine kinase 2 | HGNC:8032 | 9q21.33 |
| SH3PXD2A | SH3PXD2A | SH3 and PX domains 2A | HGNC:23664 | 10q24.33 |
| SSUH2 | SSUH2 | ssu-2 homolog | HGNC:24809 | 3p25.3 |
| SULT2A1 | SULT2A1 | sulfotransferase family 2A member 1 | HGNC:11458 | 19q13.33 |
| FMO3 | FMO3 | flavin containing dimethylaniline monoxygenase 3 | HGNC:3771 | 1q24.3 |
| GATA5 | GATA5 | GATA binding protein 5 | HGNC:15802 | 20q13.33 |
| HTRA1 | HTRA1 | HtrA serine peptidase 1 | HGNC:9476 | 10q26.13 |
| C8B | C8B | complement C8 beta chain | HGNC:1353 | 1p32.2 |
| H19 | H19 | H19 imprinted maternally expressed transcript | HGNC:4713 | 11p15.5 |
| MN1 | MN1 | MN1 proto-oncogene, transcriptional regulator | HGNC:7180 | 22q12.1 |
| NFE2L1 | NFE2L1 | nuclear factor, erythroid 2 like 1 | HGNC:7781 | 17q21.3 |
| PRDM16 | PRDM16 | PR/SET domain 16 | HGNC:14000 | 1p36.32 |
| AP3B2 | AP3B2 | adaptor related protein complex 3 subunit beta 2 | HGNC:567 | 15q25.2 |
| EMP1 | EMP1 | epithelial membrane protein 1 | HGNC:3333 | 12p13.1 |
| FLNC | FLNC | filamin C | HGNC:3756 | 7q32.1 |
| STAG3 | STAG3 | stromal antigen 3 | HGNC:11356 | 7q22.1 |
| CPB2 | CPB2 | carboxypeptidase B2 | HGNC:2300 | 13q14.13 |
| TENC1 | TNS2 | tensin 2 | HGNC:19737 | 12q13.13 |
| RP1L1 | RP1L1 | RP1 like 1 | HGNC:15946 | 8p23.1 |
| A1CF | A1CF | APOBEC1 complementation factor | HGNC:24086 | 10q11.23 |
| NPR1 | NPR1 | natriuretic peptide receptor 1 | HGNC:7943 | 1q21.3 |
| TEK | TEK | TEK receptor tyrosine kinase | HGNC:11724 | 9p21.2 |
| ERRFI1 | ERRFI1 | ERBB receptor feedback inhibitor 1 | HGNC:18185 | 1p36.23 |
| ARHGEF15 | ARHGEF15 | Rho guanine nucleotide exchange factor 15 | HGNC:15590 | 17p13.1 |
| CD34 | CD34 | CD34 molecule | HGNC:1662 | 1q32.2 |
| RSPO3 | RSPO3 | R-spondin 3 | HGNC:20866 | 6q22.33 |
| ALPK3 | ALPK3 | alpha kinase 3 | HGNC:17574 | 15q25.3 |
| SAMD4A | SAMD4A | sterile alpha motif domain containing 4A | HGNC:23023 | 14q22.2 |
| ZCCHC24 | ZCCHC24 | zinc finger CCHC-type containing 24 | HGNC:26911 | 10q22.3 |
| LEAP2 | LEAP2 | liver enriched antimicrobial peptide 2 | HGNC:29571 | 5q31.1 |
| MYL2 | MYL2 | myosin light chain 2 | HGNC:7583 | 12q24.11 |
| NRG3 | NRG3 | neuregulin 3 | HGNC:7999 | 10q23.1 |
| ZBTB16 | ZBTB16 | zinc finger and BTB domain containing 16 | HGNC:12930 | 11q23.2 |
| SERPINA3 | SERPINA3 | serpin family A member 3 | HGNC:16 | 14q32.13 |
| AQP7 | AQP7 | aquaporin 7 | HGNC:640 | 9p13.3 |
| SRPX | SRPX | sushi repeat containing protein X-linked | HGNC:11309 | Xp11.4 |
| UACA | UACA | uveal autoantigen with coiled-coil domains and ankyrin repeats | HGNC:15947 | 15q23 |
| ANO1 | ANO1 | anoctamin 1 | HGNC:21625 | 11q13.3 |
| FKBP5 | FKBP5 | FKBP prolyl isomerase 5 | HGNC:3721 | 6p21.31 |
| SCN5A | SCN5A | sodium voltage-gated channel alpha subunit 5 | HGNC:10593 | 3p22.2 |
| PTPN21 | PTPN21 | protein tyrosine phosphatase non-receptor type 21 | HGNC:9651 | 14q31.3 |
| CACNA1C | CACNA1C | calcium voltage-gated channel subunit alpha1 C | HGNC:1390 | 12p13.33 |
| ERG | ERG | ETS transcription factor ERG | HGNC:3446 | 21q22.2 |
| SOX17 | SOX17 | SRY-box 17 | HGNC:18122 | 8q11.23 |
| WWTR1 | WWTR1 | WW domain containing transcription regulator 1 | HGNC:24042 | 3q25.1 |
| AIF1L | AIF1L | allograft inflammatory factor 1 like | HGNC:28904 | 9q34.12-q34.13 |
| CA3 | CA3 | carbonic anhydrase 3 | HGNC:1374 | 8q21.2 |
| HRG | HRG | histidine rich glycoprotein | HGNC:5181 | 3q27.3 |
| TAT | TAT | tyrosine aminotransferase | HGNC:11573 | 16q22.2 |
| AQP7P1 | AQP7P1 | aquaporin 7 pseudogene 1 | HGNC:32048 | 9q13 |
| ADRA2C | ADRA2C | adrenoceptor alpha 2C | HGNC:283 | 4p16.3 |
| SYNPO | SYNPO | synaptopodin | HGNC:30672 | 5q33.1 |
| FN1 | FN1 | fibronectin 1 | HGNC:3778 | 2q35 |
| GPR116 | ADGRF5 | adhesion G protein-coupled receptor F5 | HGNC:19030 | 6p12.3 |
| KRT17 | KRT17 | keratin 17 | HGNC:6427 | 17q21.2 |
| AZGP1 | AZGP1 | alpha-2-glycoprotein 1, zinc-binding | HGNC:910 | 7q22.1 |
| BCL6B | BCL6B | BCL6B transcription repressor | HGNC:1002 | 17p13.1 |
| KIF1C | KIF1C | kinesin family member 1C | HGNC:6317 | 17p13.2 |
| GPR4 | GPR4 | G protein-coupled receptor 4 | HGNC:4497 | 19q13.32 |
| GJA5 | GJA5 | gap junction protein alpha 5 | HGNC:4279 | 1q21.2 |
| C14orf37 | ARMH4 | armadillo like helical domain containing 4 | HGNC:19846 | 14q23.1 |
| JAG2 | JAG2 | jagged canonical Notch ligand 2 | HGNC:6189 | 14q32.33 |
| KIF26A | KIF26A | kinesin family member 26A | HGNC:20226 | 14q32.33 |
| HBG2 | HBG2 | hemoglobin subunit gamma 2 | HGNC:4832 | 11p15.4 |
| CADM2 | CADM2 | cell adhesion molecule 2 | HGNC:29849 | 3p12.1 |
| LAMP5 | LAMP5 | lysosomal associated membrane protein family member 5 | HGNC:16097 | 20p12.2 |
| NOMO1 | NOMO1 | NODAL modulator 1 | HGNC:30060 | 16p13.11 |
| NXF3 | NXF3 | nuclear RNA export factor 3 | HGNC:8073 | Xq22.1 |
| BPIFB3 | BPIFB3 | BPI fold containing family B member 3 | HGNC:16178 | 20q11.21 |
| CGB8 | CGB8 | chorionic gonadotropin subunit beta 8 | HGNC:16453 | 19q13.33 |
| CGB5 | CGB5 | chorionic gonadotropin subunit beta 5 | HGNC:16452 | 19q13.33 |
| ZSCAN23 | ZSCAN23 | zinc finger and SCAN domain containing 23 | HGNC:21193 | 6p22.1 |
| HSPA1A | HSPA1A | heat shock protein family A (Hsp70) member 1A | HGNC:5232 | 6p21.33 |
| PMAIP1 | PMAIP1 | phorbol-12-myristate-13-acetate-induced protein 1 | HGNC:9108 | 18q21.32 |

TABLE 4-continued

Gene Glossary

| Gene Symbol Used in Patent | Official Gene Symbol | Approved Name | HGNC ID | Location |
|---|---|---|---|---|
| C8orf4 | TCIM | transcriptional and immune response regulator | HGNC:1357 | 8p11.21 |
| ITM2B | ITM2B | integral membrane protein 2B | HGNC:6174 | 13q14.2 |
| IFIT2 | IFIT2 | interferon induced protein with tetratricopeptide repeats 2 | HGNC:5409 | 10q23.31 |
| CD74 | CD74 | CD74 molecule | HGNC:1697 | 5q33.1 |
| HSPA6 | HSPA6 | heat shock protein family A (Hsp70) member 6 | HGNC:5239 | 1q23.3 |
| TFAP2A | TFAP2A | transcription factor AP-2 alpha | HGNC:11742 | 6p24.3 |
| TRPV6 | TRPV6 | transient receptor potential cation channel subfamily V member 6 | HGNC:14006 | 7q34 |
| EXPH5 | EXPH5 | exophilin 5 | HGNC:30578 | 11q22.3 |
| CAPN6 | CAPN6 | calpain 6 | HGNC:1483 | Xq23 |
| ALDH3B2 | ALDH3B2 | aldehyde dehydrogenase 3 family member B2 | HGNC:411 | 11q13.2 |
| RAB3B | RAB3B | RAB3B, member RAS oncogene family | HGNC:9778 | 1p32.3 |
| MUC15 | MUC15 | mucin 15, cell surface associated | HGNC:14956 | 11p14.3 |
| GRHL2 | GRHL2 | grainyhead like transcription factor 2 | HGNC:2799 | 8q22.3 |
| CSHL1 | CSHL1 | chorionic somatomammotropin hormone like 1 | HGNC:2442 | 17q23.3 |
| CSH2 | CSH2 | chorionic somatomammotropin hormone 2 | HGNC:2441 | 17q23.3 |
| KISS1 | KISS1 | KiSS-1 metastasis suppressor | HGNC:6341 | 1q32.1 |
| CGA | CGA | glycoprotein hormones, alpha polypeptide | HGNC:1885 | 6q14.3 |
| PLAC4 | PLAC4 | p1acenta enriched 4 | HGNC:14616 | 21q22.2 |
| PSG1 | PSG1 | pregnancy specific beta-1-glycoprotein 1 | HGNC:9514 | 19q13.2 |
| GH2 | GH2 | growth hormone 2 | HGNC:4262 | 17q23.3 |
| PSG3 | PSG3 | pregnancy specific beta-1-glycoprotein 3 | HGNC:9520 | 19q13.2 |
| PSG4 | PSG4 | pregnancy specific beta-1-glycoprotein 4 | HGNC:9521 | 19q13.31 |
| PSG7 | PSG7 | pregnancy specific beta-1-glycoprotein 7 (gene/pseudogene) | HGNC:9524 | 19q13.31 |
| PSG11 | PSG11 | pregnancy specific beta-1-glycoprotein 11 | HGNC:9516 | 19q13.31 |
| CSH1 | CSH1 | chorionic somatomammotropin hormone 1 | HGNC:2440 | 17q23.3 |
| PSG2 | PSG2 | pregnancy specific beta-1-glycoprotein 2 | HGNC:9519 | 19q13.31 |
| HSD3B1 | HSD3B1 | hydroxy-delta-5-steroid dehydrogenase, 3 beta- and steroid delta-isomerase 1 | HGNC:5217 | 1p12 |
| LGALS14 | LGALS14 | galectin 14 | HGNC:30054 | 19q13.2 |
| FCGR1C | FCGR1CP | Fc fragment of IgG receptor Ic, pseudogene | HGNC:3615 | 1q21.1 |
| PSG5 | PSG5 | pregnancy specific beta-l-glycoprotein 5 | HGNC:9522 | 19q13.31 |
| LAGALS13 | LGALS13 | galectin 13 | HGNC:15449 | 19q13.2 |
| GCM1 | GCM1 | glial cells missing transcription factor 1 | HGNC:4197 | 6p12.1 |

The term “plurality” refers to more than one element. For example, the term is used herein in reference to a number of C-RNA molecules that serve as a signature indicative of preeclampsia.

A plurality may include any two, any three, any four, any five, any six, any seven, any eight, any nine, any ten, any eleven, any twelve, any thirteen, any fourteen, any fifteen, any sixteen, any seventeen, any eighteen, any nineteen, any twenty, any twenty-one, any twenty-two, any twenty-three, any twenty-four, any twenty-five, any twenty-six, any twenty-seven, any twenty-eight, any twenty-nine, any thirty, any thirty-one, any thirty-two, any thirty-three, any thirty-four, any thirty-five, any thirty-six, any thirty-seven, any thirty-eight, any thirty-nine, any forty, any forty-one, any forty-two, any forty-three, any forty-four, any forty-five, any forty-six, any forty-seven, any forty-eight, any forty-nine, any fifty, any fifty-one, any fifty-two, any fifty-three, any fifty-four, any fifty-five, any fifty-six, any fifty-seven, any fifty-eight, any fifty-nine, any sixty, any sixty-one, any sixty-two, any sixty-three, any sixty-four, any sixty-five, any sixty-six, any sixty-seven, any sixty-eight, any sixty-nine, any seventy, any seventy-one, any seventy-two, any seventy-three, any seventy-four, any seventy-five, any seventy-six, any seventy-seven, any seventy-eight, any seventy-nine, any eighty, any eighty-one, any eighty-two, any eighty-three, any eighty-four, any eighty-five, any eighty-six, any eighty-seven, any eighty-eight, any eighty-nine, any ninety, any ninety-one, any ninety-two, any ninety-three, any ninety-four, any ninety-five, any ninety-six, any ninety-seven, any ninety-eight, any ninety-nine, any one hundred, any one hundred and one, any one hundred and two, any one hundred and three, any one hundred and four, any one hundred and five, any one hundred and six, any one hundred and seven, any one hundred and eight, any one hundred and nine, any one hundred ten, any one hundred eleven, any one hundred twelve, any one hundred thirteen, any one hundred fourteen, any one hundred fifteen, any one hundred sixteen, any one hundred seventeen, any one hundred eighteen, any one hundred nineteen, any one hundred twenty, any one hundred twenty-one, or any one hundred twenty-two of the molecules recited in a list described herein. A plurality may include a least any of the numbers recited above. A plurality may include more than any of the numbers recited above. A plurality may include a range of any of those recited above. In some embodiments, a C-RNA signature indicative of preeclampsia includes just one of the biomarkers recited above.

The identification and/or quantification of one of these C-RNA signatures within a sample obtained from a subject can be used to determine that the subject suffers from preeclampsia or is at a risk of developing preeclampsia.

A sample may be a biological sample or biosample, including but not limited to blood, serum, plasma, sweat, tears, urine, sputum, lymph, saliva, amniotic fluid, a tissue biopsy, swab, or smear, including for example, but not limited to, a placental tissue sample. In some preferred embodiments, a biological sample is a cell free plasma sample. A biological sample may be a maternal sample obtained from a pregnant female subject.

As used herein, the term “subject” refers to a human subject as well as a non-human mammalian subject. Although the examples herein concern humans and the language is primarily directed to human concerns, the concept of this disclosure is applicable to any mammal, and is useful in the fields of veterinary medicine, animal sciences, research laboratories and such.

A subject may be a pregnant female, including a pregnant female in any gestational stages of pregnancy. The gestational stage of pregnancy may be, for example, the first trimester, the second trimester, including late second trimester, or the third trimester, including early third trimester. The gestational stage of pregnancy may be, for example, before 16 weeks of pregnancy, before 20 weeks of pregnancy, or after 20 weeks of pregnancy. The gestational stage of pregnancy may be, for example, 8-18 weeks of pregnancy, 10-14 weeks of pregnancy, 11-14 weeks of pregnancy, 11-13 weeks, or 12-13 weeks of pregnancy.

The discovery of cell-free fetal nucleic acids in maternal plasma has opened up new possibilities for noninvasive prenatal diagnosis. Over the last few years, a number of approaches have been demonstrated to allow such circulating fetal nucleic acids to be used for the prenatal detection of chromosomal aneuploidies. Any of the methods described for example in Poon et al., 2000, *Clin Chem;* 1832-4; Poon et al., 2001, *Ann N Y Acad Sci;* 945:207-10; Ng et al., 2003, *Clin Chem;* 49(5):727-31; Ng et al., 2003, *Proc Natl Acad Sci USA;*100(8):4748-53; Tsui et al., 2004, *J Med Genet;* 41(6):461-7; Go et al., 2004, *Clin Chem;* 50(8):1413-4; Smets et al., 2006, *Clin Chim Acta;* 364(1-2):22-32; Tsui et al., 2006, *Methods Mol Biol;* 336:123-34; Purwosunu et al., 2007, *Clin Chem;* 53(3):399-404; *Chim* et al., 2008, *Clin Chem;* 54(3):482-90; Tsui and Lo, 2008, *Methods Mol Biol;* 444:275-89; Lo, 2008, *Ann N Y Acad Sci;* 1137:140-143; Miura et al., 2010, *Prenat Diagn;* 30(9):849-61; Li et al., 2012, *Clin Chim Acta;* 413(5-6):568-76; Williams et al., 2013, *Proc Natl Acad Sci USA;* 110(11):4255-60; Tsui et al., 2014, *Clin Chem;* 60(7):954-62; Tsang et al., 2017, *Proc Natl Acad Sci USA;* 114(37):E7786-E7795, and US Patent Publication US 2014/0243212 may be used in the methods described herein.

The detection and identification of biomarkers of a C-RNA signature within the maternal circulation indicative of preeclampsia or a risk for developing preeclampsia may involve any of a variety of technologies. For example, biomarkers may be detected in serum by radioimmunoassay or the polymerase chain reaction (PCR) technique may be used.

In various embodiments, the identification of the biomarkers of a C-RNA signature within the maternal circulation indicative of preeclampsia or a risk for developing preeclampsia may involve sequencing the C-RNA molecules. Any of a number of sequencing technologies can be utilized, including, but not limited to, any of a variety of high-throughput sequencing techniques.

In some embodiments, the C-RNA population within a maternal biosample may be subject to enrichment of RNA sequences the include protein-coding sequences prior to sequencing. Any of a variety of platforms available for whole-exome enrichment and sequencing may be used, including but not limited to the Agilent SureSelect Human All Exon platform (Chen et al., 2015a, *Cold Spring Harb Protoc;* 2015(7):626-33. doi: 10.1101/pdb.prot083659); the Roche NimbleGen SeqCap EZ Exome Library SR platform (Chen et al., 2015b, *Cold Spring Harb Protoc;* 2015(7):634-41. doi: 10.1101/pdb.prot084855); or the Illumina TruSeq Exome Enrichment platform (Chen et al., 2015c, *Cold Spring Harb Protoc;* 2015(7):642-8. doi:10.1101/pdb-.prot084863). See also "TruSeq™ Exome Enrichment Guide," Catalog # FC-930-1012 Part #15013230 Rev. B November 2010 and Illumina's "TruSeq™ RNA Sample Preparation Guide," Catalog #RS-122-9001DOC Part #15026495 Rev. F March 2014.

In particular embodiments, biomarkers of a C-RNA signature within the maternal circulation indicative of preeclampsia or a risk for developing preeclampsia may be detected and identified using microarray techniques. In this method, polynucleotide sequences of interest are plated, or arrayed, on a microchip substrate. The arrayed sequences are then hybridized with a maternal biosample, or a purified and/or enriched portion thereof. Microarrays may include a variety of solid supports including, but not limited to, beads, glass microscope slides, glass wafers, gold, silicon, microchips, and other plastic, metal, ceramic, or biological surfaces. Microarray analysis can be performed by commercially available equipment, following manufacturer's protocols, such as by using Illumina's technology.

With obtaining, shipping, storing, and/or processing blood samples for the preparation of circulating RNA, steps may be taken to stabilize the sample and/or prevent the disruption of cell membranes resulting in the release of cellular RNAs into the sample. For example, in some embodiments, blood samples may be collected, shipped, and/or stored in tubes that have cell- and DNA-stabilizing properties, such as Streck Cell-Free DNA BCT® blood collection tubes, prior to processing into plasma. In some embodiments, blood samples are not exposed to EDTA. See, for example, Qin et al., 2013, *BMC Research Notes;* 6:380 and Medina Diaz et al., 2016, *PLoS ONE;* 11(11):e0166354.

In some embodiments, blood samples are processed into plasma within about 24 to about 72 hours of the blood draw, and in some embodiments, within about 24 hours of the blood draw. In some embodiments, blood samples are maintained, stored, and/or shipped at room temperature prior to processing into plasma.

In some embodiments, blood samples are maintained, stored, and/or shipped without exposure to chilling (for example, on ice) or freezing prior to processing into plasma.

The disclosure includes kits for use in the diagnosis of preeclampsia and the identification of pregnant women at risk for developing preeclampsia. A kit is any manufacture (e.g. a package or container) including at least one reagent, e.g. a probe, for specifically detecting a C-RNA signature within the maternal circulation as described herein that is indicative of preeclampsia or a risk for developing preeclampsia. The kit may be promoted, distributed, or sold as a unit for performing the methods of the present disclosure.

The use of signatures of circulating RNA found in the maternal circulation specific to preeclampsia in noninvasive methods for the diagnosis of preeclampsia and the identification of pregnant women at risk for developing preeclampsia may be combined with appropriate monitoring and medical management. For example, further tests may be ordered. Such test may include, for example, blood tests to measure liver function, kidney function, and/or platelet and various clotting proteins, urine analysis to measure protein or creatinine levels, fetal ultrasound to measure monitor fetal growth, weight, and amniotic fluid, a nonstress test to measure how fetal heart rate with fetal movement, and/or a biophysical profile using ultrasound to measure your fetal breathing, muscle tone, and movement and the volume of amniotic fluid may be ordered. Therapeutic interventions may include, for example, increasing the frequency of prenatal visits, antihypertensive medications to lower blood pressure, corticosteroid medications, anticonvulsant medications, bed rest, hospitalization, and/or early delivery. See, for example, Townsend et al., 2016 "Current best practice in the management of hypertensive disorders in pregnancy," *Integr Blood Press Control;* 9: 79-94.

Therapeutic interventions may include the administration of low dose aspirin to pregnant women identified at risk of for developing preeclampsia. A recent multicenter, double-blind, placebo-controlled trial demonstrated that treatment of women at high risk for preterm preeclampsia with low-dose aspirin resulted in a lower incidence of this diagnosis compared to placebo (Rolnik et al., 2017, "Aspirin versus Placebo in Pregnancies at High Risk for Preterm Preeclampsia," *N Engl J Med;* 377(7):613-622). Dosages of low dose aspirin include, but are not limited to, about 50 to about 150 mg per day, about 60 to about 80 mg per day, about 100 or more mg per day, or about 150 mg per day. Administration may begin, for example, at or before 16 weeks of gestation or from 11 to 14 weeks of gestation. Administration may continue thru 36 weeks of gestation.

The invention is defined in the claims. However, below is provided a non-exhaustive list of non-limiting embodiments. Any one or more of the features of these embodiments may be combined with any one or more features of another example, embodiment, or aspect described herein.

Embodiment 1 includes a method of detecting preeclampsia and/or determining an increased risk for preeclampsia in a pregnant female, the method comprising:

identifying in a biosample obtained from the pregnant women a plurality of circulating RNA (C-RNA) molecules;

wherein a plurality of C-RNA molecules selected from:

a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or a plurality of C-RNA molecules encoding at least a portion of a protein selected from any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

Embodiment 2 includes a method of detecting preeclampsia and/or determining an increased risk for preeclampsia in a pregnant female, the method comprising:

obtaining a biosample from the pregnant female;

purifying a population of circulating RNA (C-RNA) molecules from the biosample;

identifying protein coding sequences encoded by the C-RNA molecules within the purified population of C-RNA molecules;

wherein the protein coding sequences encoded by the C-RNA molecules encoding at least a portion of a protein are selected from:

any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

Embodiment 3 includes a method of Embodiment 1 or 2, wherein identifying protein coding sequences encoded by C-RNA molecules within the biosample comprises hybridization, reverse transcriptase PCR, microarray chip analysis, or sequencing.

Embodiment 4 includes the method of Embodiment 1 or 2, wherein identifying protein coding sequences encoded by the C-RNA molecules within the biosample comprises sequencing.

Embodiment 4 includes the method of Embodiment 4, wherein sequencing comprises massively parallel sequencing of clonally amplified molecules.

Embodiment 6 includes the method of Embodiment 4 or 5, wherein sequencing comprises RNA sequencing.

Embodiment 7 includes the method of any one of Embodiments 1 to 6, further comprising:

removing intact cells from the biosample;

treating the biosample with a deoxynuclease (DNase) to remove cell free DNA (cfDNA);

synthesizing complementary DNA (cDNA) from C-RNA molecules in the biosample; and/or enriching the cDNA sequences for DNA sequences that encode proteins by exome enrichment;

prior to identifying protein coding sequence encoded by the circulating RNA (C-RNA) molecules.

Embodiment 8 includes a method of detecting preeclampsia and/or determining an increased risk for preeclampsia in a pregnant female, the method comprising:

obtaining a biological sample from the pregnant female;

removing intact cells from the biosample;

treating the biosample with a deoxynuclease (DNase) to remove cell free DNA (cfDNA);

synthesizing complementary DNA (cDNA) from RNA molecules in the biosample;

enriching the cDNA sequences for DNA sequences that encode proteins (exome enrichment);

sequencing the resulting enriched cDNA sequences; and identifying protein coding sequences encoded by enriched C-RNA molecules;

wherein protein coding sequences encoded by the C-RNA molecules encoding at least a portion of a protein selected from:

any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768 is indicative of preeclampsia and/or an increased risk for preeclampsia in the pregnant women.

Embodiment 9 includes a method comprising:

obtaining a biological sample from the pregnant female;

removing intact cells from the biosample;

treating the biosample with a deoxynuclease (DNase) to remove cell free DNA (cfDNA);

synthesizing complementary DNA (cDNA) from RNA molecules in the biosample;

enriching the cDNA sequences for DNA sequences that encode proteins (exome enrichment);

sequencing the resulting enriched cDNA sequences; and identifying protein coding sequences encoded by the enriched C-RNA molecules;

wherein the protein coding sequences encoded by the C-RNA molecules includes at least a portion of a protein are selected from:

any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7; or any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768.

Embodiment 10 includes the method of any one of Embodiments 1 to 9, wherein the biosample comprises plasma.

Embodiments 11 includes the method of any one of Embodiments 1 to 10, wherein the biosample is obtained from a pregnant female at less than 16 weeks gestation or at less than 20 weeks gestation.

Embodiment 12 includes the method of any one of Embodiments 1 to 10, wherein the biosample is obtained from a pregnant female at greater than 20 weeks gestation.

Embodiment 13 includes a circulating RNA (C-RNA) signature for an elevated risk of preeclampsia, the C-RNA signature comprising any one or more, any two or more, any three or more, any four or more, any five or more, any six or more, any seven or more, any eight or more, any nine or more, any ten or more, any eleven or more, any twelve, any thirteen or more, any fourteen or more, any fifteen or more, any sixteen or more, any seventeen or more, any eighteen or more, any nineteen or more, any twenty or more, any twenty one or more, any twenty two or more, any twenty three or more, any twenty four or more, any twenty five or more, any twenty-six or more, any twenty-seven or more, any twenty-eight or more, any twenty-nine or more, any thirty or more, any thirty-one or more, any thirty-two or more, any thirty-three or more, any thirty-four or more, any thirty-five or more, any thirty-six or more, any thirty-seven or more, any thirty-eight or more, any thirty-nine or more, any forty or more, any forty-one or more, any forty-two or more, any forty-three or more, any forty-four or more, any forty-five or more, any forty-six or more, any forty-seven or more, any forty-eight or more, or all forth-nine of those listed in Table S9 of Example 7.

Embodiment 14 includes a circulating RNA (C-RNA) signature for an elevated risk of preeclampsia, the C-RNA signature comprising any one or more, any two or more, any three or more, any four or more, any five or more, any six or more, any seven or more, any eight or more, any nine or more, any ten or more, any eleven or more, any twelve or more, or all thirteen of AKAP2, ARRB1, CPSF7, INO80C, JAG1, MSMP, NR4A2, PLEK, RAP1GAP2, SPEG, TRPS1, UBE2Q1, and ZNF768.

Embodiment 15 includes a solid support array comprising a plurality of agents capable of binding and/or identifying a C-RNA signature of Embodiment 13 or 14.

Embodiment 16 includes a kit comprising a plurality of probes capable of binding and/or identifying a C-RNA signature of Embodiment 13 or 14.

Embodiment 17 includes a kit comprising a plurality of primers for selectively amplifying a C-RNA signature of Embodiment 13 or 14.

Embodiment 18 includes the method of any one of Embodiments 1 to 12, wherein sample is a blood sample and the blood samples is collected, shipped, and/or stored in a tube that has cell- and DNA-stabilizing properties prior to processing the blood sample into plasma.

Embodiment 19 includes the method of Embodiment 18, wherein the tube comprises a Streck Cell-Free DNA BCT® blood collection tube.

The present invention is illustrated by the following examples. It is to be understood that the particular examples, materials, amounts, and procedures are to be interpreted broadly in accordance with the scope and spirit of the invention as set forth herein.

EXAMPLES

Example 1

C-RNA Signatures Unique to Pregnancy

Figure 2:
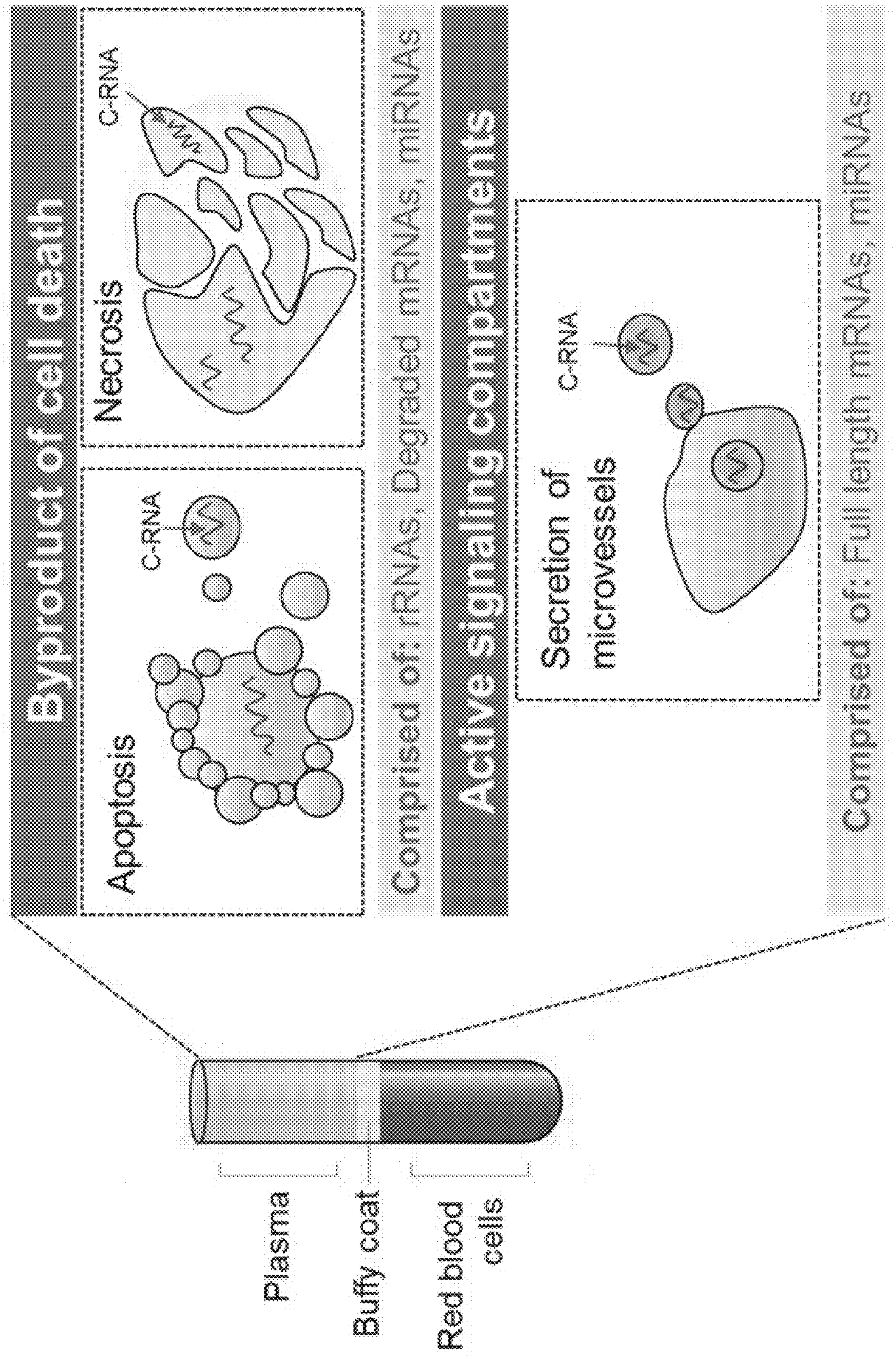
FIG. 2. Origins of circulating RNA (C-RNA).

The presence of circulating nucleic acid in maternal plasma provides a window into the progression and health of the fetus and the placenta (FIG. 1). Circulating RNA (C-RNA) is detected in maternal circulation and originates from two predominant sources. A significant fraction of C-RNA originates from apoptotic cells, which release vesicles containing C-RNA into the blood stream. C-RNA also enters maternal circulation through the shedding of active signaling vesicles such as exosomes and microvesicles from a variety of cell types. As shown in FIG. 2, C-RNA is therefore comprised of the byproducts of cell death as well as active signaling products. Characteristics of C-RNA include generation through common processes, release from cells throughout the body, and stable and contained in vesicles. It represents a circulating transcriptome that reflects tissue-specific changes in gene expression, signaling, and cell death.

C-RNA has the potential to be an excellent biomarker for at least the following reasons:

1) All C-RNA is contained within membrane bound vesicles, which protects the C-RNA from degradation, making it quite stable in the blood.

2) C-RNA originates from all cell types. For example, C-RNA has been shown to contain transcripts from both the placenta and the developing fetus. The diverse origins of C-RNA give it the potential to be a rich repository for accessing information on both fetal and overall maternal health.

Figure 3:
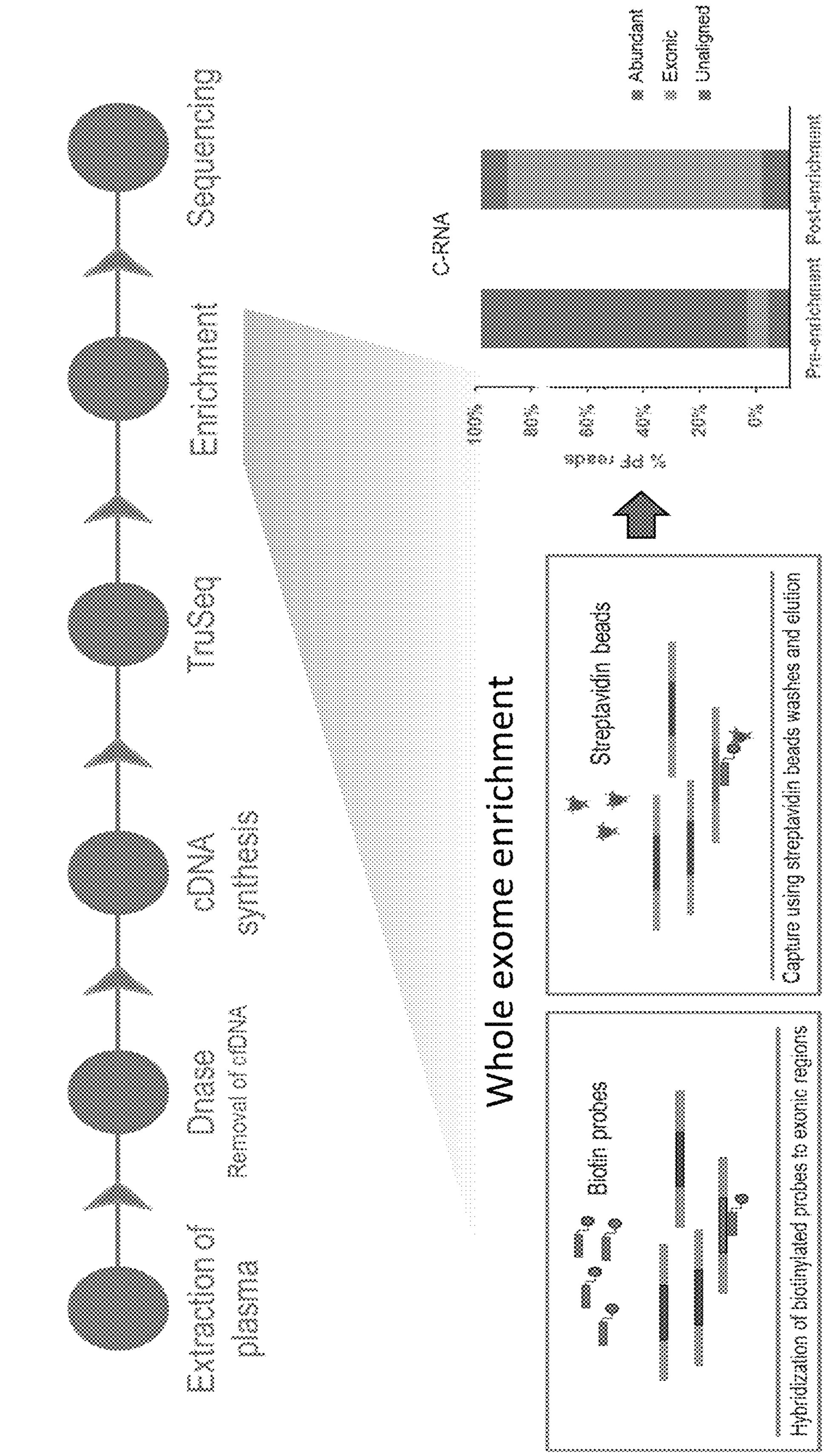
FIG. 3. Library prep workflow for C-RNA.
Figure 7:
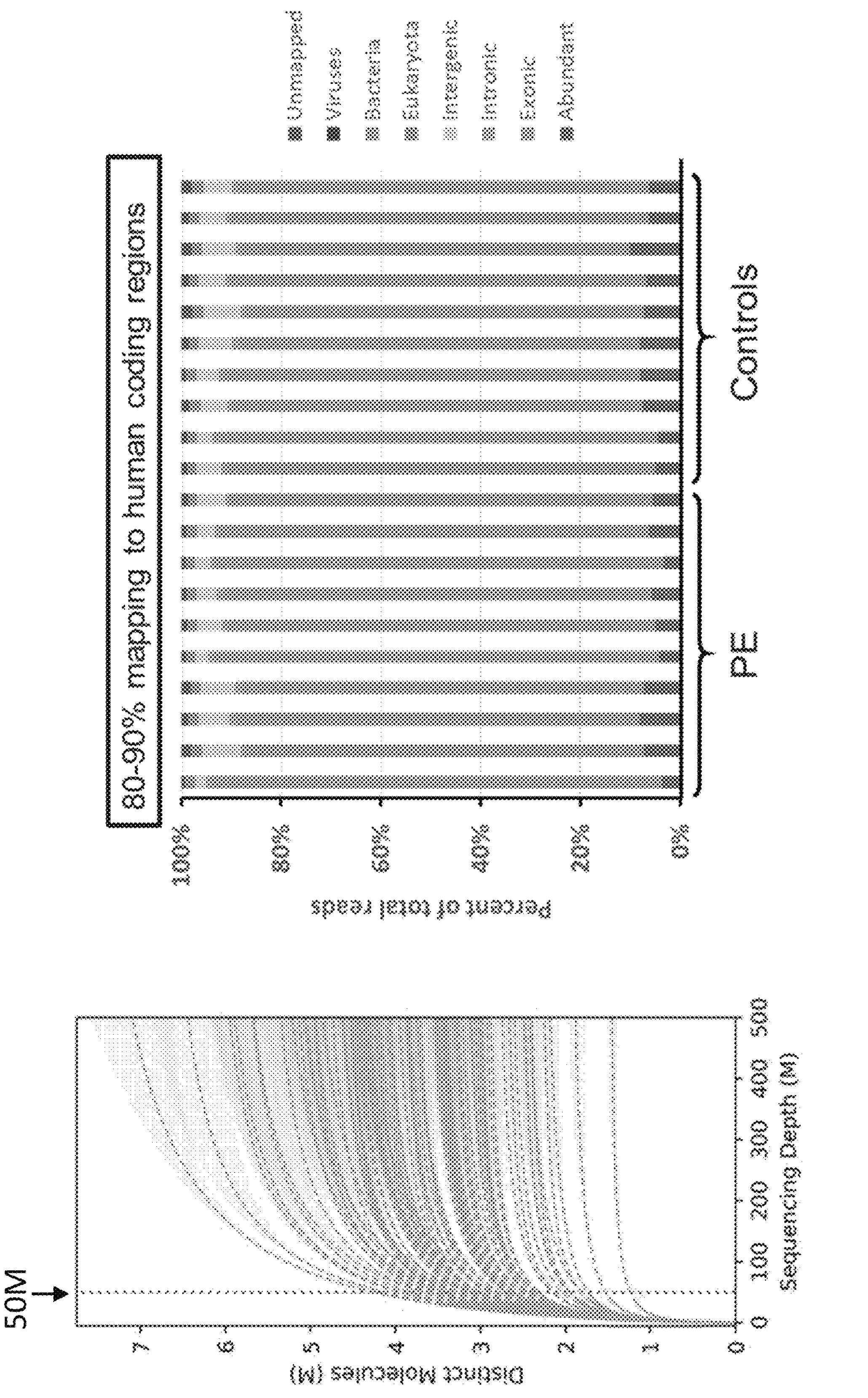
FIG. 7. Sequencing data characteristics.

C-RNA libraries were prepared from plasma samples using standard Illumina library prep and whole exome enrichment technology. This is shown in FIG. 3. Specifically, Illumina TruSeq™ library prep and RNA Access Enrichment were used. Using this approach, libraries were generated that have 90% of the reads aligning to the human coding region (FIG. 3 and FIG. 7). Samples were down-sampled to 50 M reads and ≥40 M mapped reads were used for downstream analysis. Samples were processed using the C-RNA workflow shown in FIG. 3. Dual Indexed libraries. Sequenced 50X50 on Hiseq2000

As shown in FIG. 4, comparing results from plasma samples from third trimester pregnant women to plasma samples from non-pregnant women provides a clear signature unique to pregnancy. The top twenty differential abundance genes of this signature are CSHL1, CSH2, KISS1, CGA, PLAC4, PSG1, GH2, PSG3, PSG4, PSG7, PSG11, CSH1, PSG2, HSD3B1, GRHL2, LGALS14, FCGR1C, PSG5, LGALS13, and GCM1. The majority of the genes identified in the pregnancy signature are placentally expressed and also correlate with published data. These results also confirm that placental RNA can be accessed in in the maternal circulation.

Example 2

C-RNA Signatures Across Gestational Age

Figure 5:
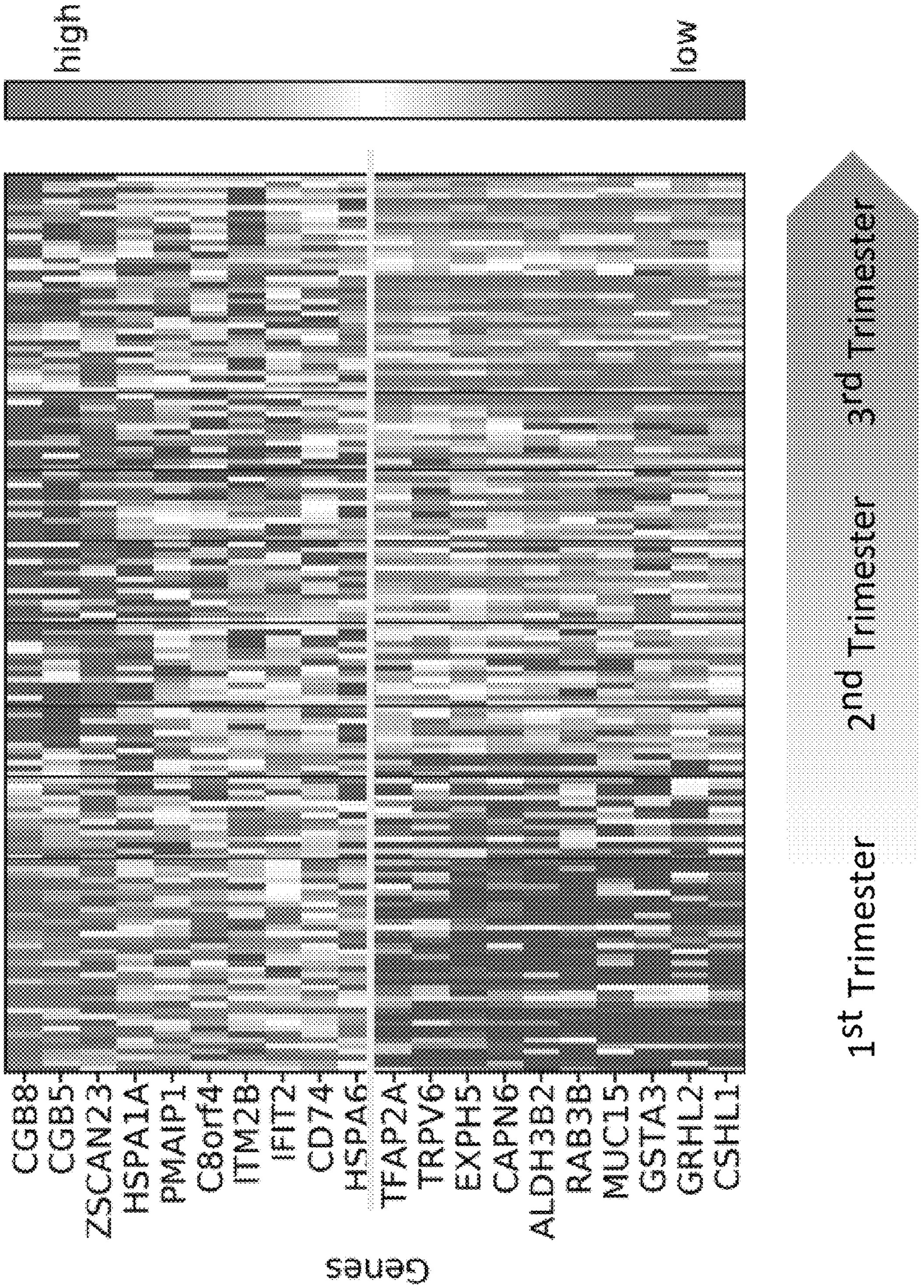
FIG. 5. Validation of C-RNA approach using longitudinal pregnancy samples.

This example characterized C-RNA signatures across different gestational ages throughout pregnancy. It is expected that the changes in C-RNA signatures at different time points longitudinally across pregnancy will be more subtle than the differences between C-RNA signatures of pregnant and non-pregnant samples noted in Example 1. As shown in FIG. 5, clear temporal changes in C-RNA profiles of the signature genes were observed as pregnancy progressed, with a clear group of genes upregulated in the first trimester and clear group of genes that increase in the third trimester.

These genes included CGB8, CGB5, ZSCAN23, HSPA1A, PMAIP1, C8orf4, ITM2B, IFIT2, CD74, HSPA6, TFAP2A, TRPV6, EXPH5, CAPN6, ALDH3B2, RAB3B, MUC15, GSTA3, GRHL2, and CSHL1, as listed in FIG. 5.

These genes may also include CSHL1, CSH2, KISS1, CGA, PLAC4, PSG1, GH2, PSG3, PSG4, PSG7, PSG11, CSH1, PSG2, HSD3B1, GRHL2, LGALS14, FCGR1C, PSG5, LGALS13, and GCM1.

These changes throughout the course of pregnancy correlate with published data from both Steve Quake and Dennis Lo. See, for example, Maron et al., 2007, "Gene expression analysis in pregnant women and their infants identifies unique fetal biomarkers that circulate in maternal blood," *J Clin Invest;* 117(10):3007-3019; Koh et al., 2014, "Noninvasive in vivo monitoring of tissue-specific global gene expression in humans," *Proc Natl Acad Sci USA;* 111(20):7361-6; and Ngo et al., 2018, "Noninvasive blood tests for fetal development predict gestational age and preterm delivery," *Science;* 360(6393):1133-1136. C-RNA signatures correlating with patterns of gene expression of the placenta were found. Thus, this approach is able to detect subtle changes within pregnancy and provides non-invasive means to monitor placental health.

Example 3

C-RNA Signatures of Preeclampsia

Figure 6:
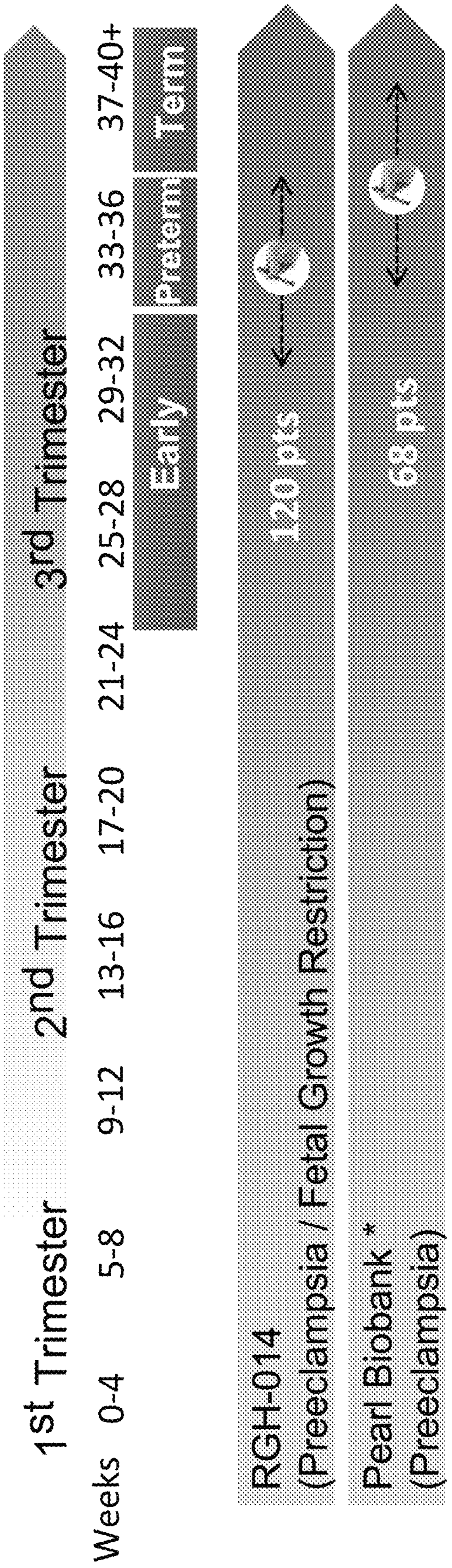
FIG. 6. Description of clinical studies.

With this example, C-RNA signatures unique to preeclampsia were identified. C-RNA signatures were determined in samples collected from pregnant women diagnosed with preeclampsia from two studies, the RGH14 Study (registered with clinical trials.gov as NCT0208494) and the Pearl Study (also referred to herein as the Pearl Biobank; registered with clinical trials.gov as NCT02379832)), were assayed (FIG. 6). Two tubes of blood were collected at the time of diagnosis for preeclampsia. Eighty controls samples matched for gestational age were collected to minimize transcriptional variability not related to the preeclampsia disease state and to control for gestational age differences in C-RNA signatures. Samples from the RGH14 study were used to identify a set of biologically relevant genes, and the predictive value of these biomarkers was validated in an independent cohort of samples from the Pearl Biobank.

In the analysis of the RGH14 data, C-RNA signatures unique to preeclampsia (PE) were identified using four different methods, the TREAT method, a Bootstrap method, a jackknifing method, and the Adaboost method. Example 3 focuses on the first 3 analysis methods and Example four focuses on the Adaboost method.

The t-test relative to threshold (TREAT) statistical method utilizing the EDGR program allows researchers to formally test (with associated p-values) whether the differential expression in a microarray experiment is greater than a given (biologically meaningful) threshold. See McCarthy and Smyth, 2009 "Testing significance relative to a fold-change threshold is a TREAT," *Bioinformatics;* 25(6):765-71 for a more detailed description of the TREAT statistical method and Robinson et al., 2010, "edgeR: a Bioconductor package for differential expression analysis of digital gene expression data," *Bioinformatics;* 26:139-140 for a more detailed description of the EDGR program. See Freund and Schapire, 1997, "A Decision-Theoretic Generalization of On-Line Learning and an Application to Boosting," *Journal of Computer and Systems Sciences;* 55(1):119-139 and Pedregosa et al., 2011, "Scikit-learn: Machine Learning in Python," *JMLR;* 12:2825-2830 for a more detailed description of the Adaboost method. The Adaboost method will be discussed in Example 4.

Figure 8:
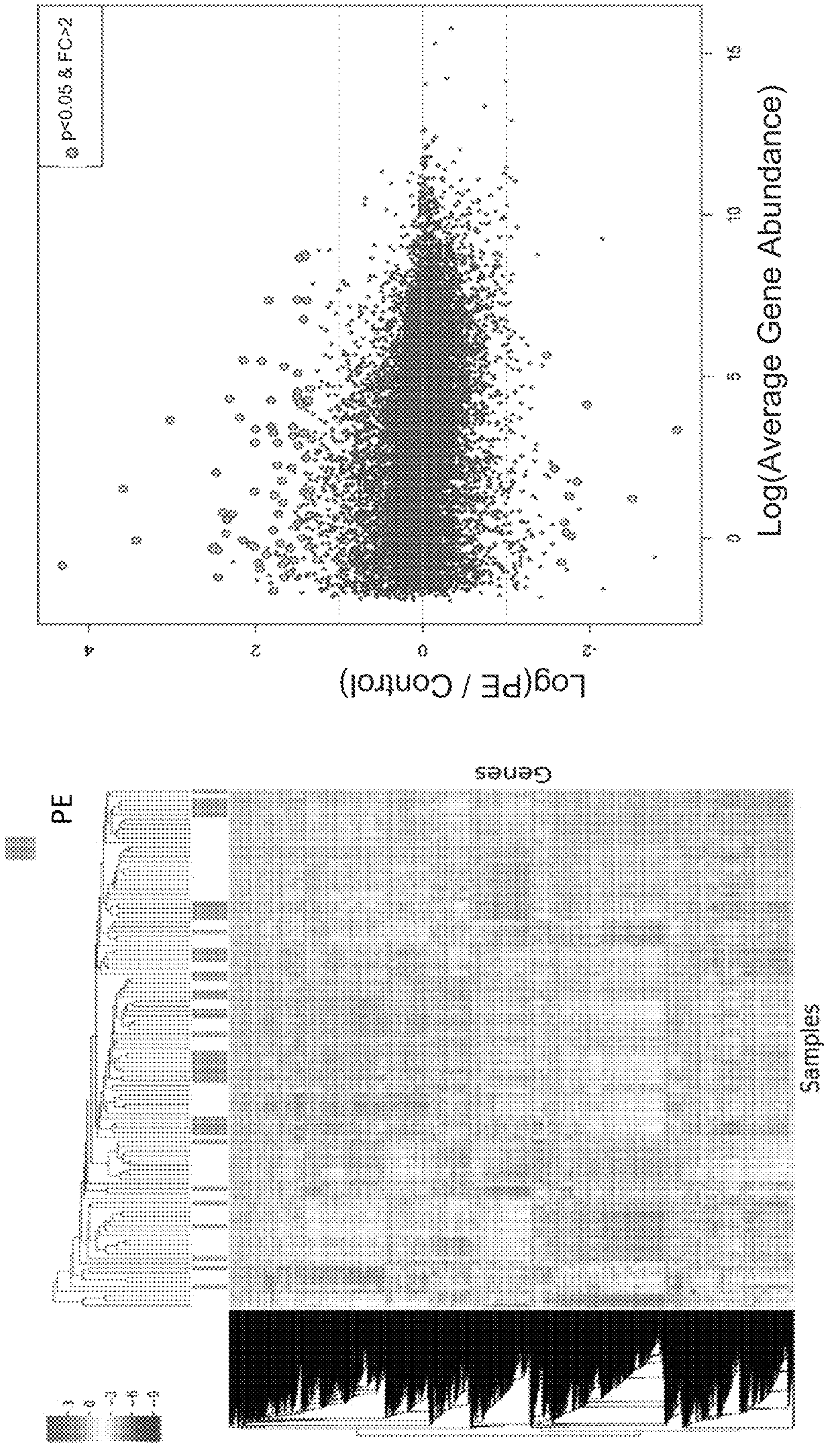
FIG. 8. Classification of PE without any selection of genes, relying of entire data set.

In the first method, standard statistical testing (TREAT method) was used to identify genes that are statistically different in the RGH14 preeclampsia cohort of 40 patients as compared to a subset of matched controls (40 patients). 122 genes were identified as statistically different in the preeclampsia cohort (40 patients) as compared to a subset of matched controls (40 patients) (FIG. 8, right panel). These genes include CYP26B1, IRF6, MYH14, PODXL, PPP1R3C, SH3RF2, TMC7, ZNF366, ADCY1, C6, FAM219A, HAO2, IGIP, IL1R2, NTRK2, SH3PXD2A, SSUH2, SULT2A1, FMO3, FSTL3, GATA5, HTRA1, C8B, H19, MN1, NFE2L1, PRDM16, AP3B2, EMP1, FLNC, STAG3, CPB2, TENC1, RP1L1, A1CF, NPR1, TEK, ERRFI1, ARHGEF15, CD34, RSPO3, ALPK3, SAMD4A, ZCCHC24, LEAP2, MYL2, NRG3, ZBTB16, SERPINA3, AQP7, SRPX, UACA, ANO1, FKBP5, SCN5A, PTPN21, CACNA1C, ERG, SOX17, WWTR1, AIF1L, CA3, HRG, TAT, AQP7P1, ADRA2C, SYNPO, FN1, GPR116, KRT17, AZGP1, BCL6B, KIF1C, CLIC5, GPR4, GJA5, OLAH, C14orf37, ZEB1, JAG2, KIF26A, APOLD1, PNMT, MYOM3, PITPNM3, TIMP4, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, PRG2, PRX, ARHGEF25, ADAMTS2, DAAM2, FAM107A, LEP, NES, VSIG4, HBG2, CADM2, LAMPS, PTGDR2, NOMO1, NXF3, PLD4, BPIFB3, PACSIN1, CUX2, FLG, CLEC4C, and KRT5.

Figure 15:
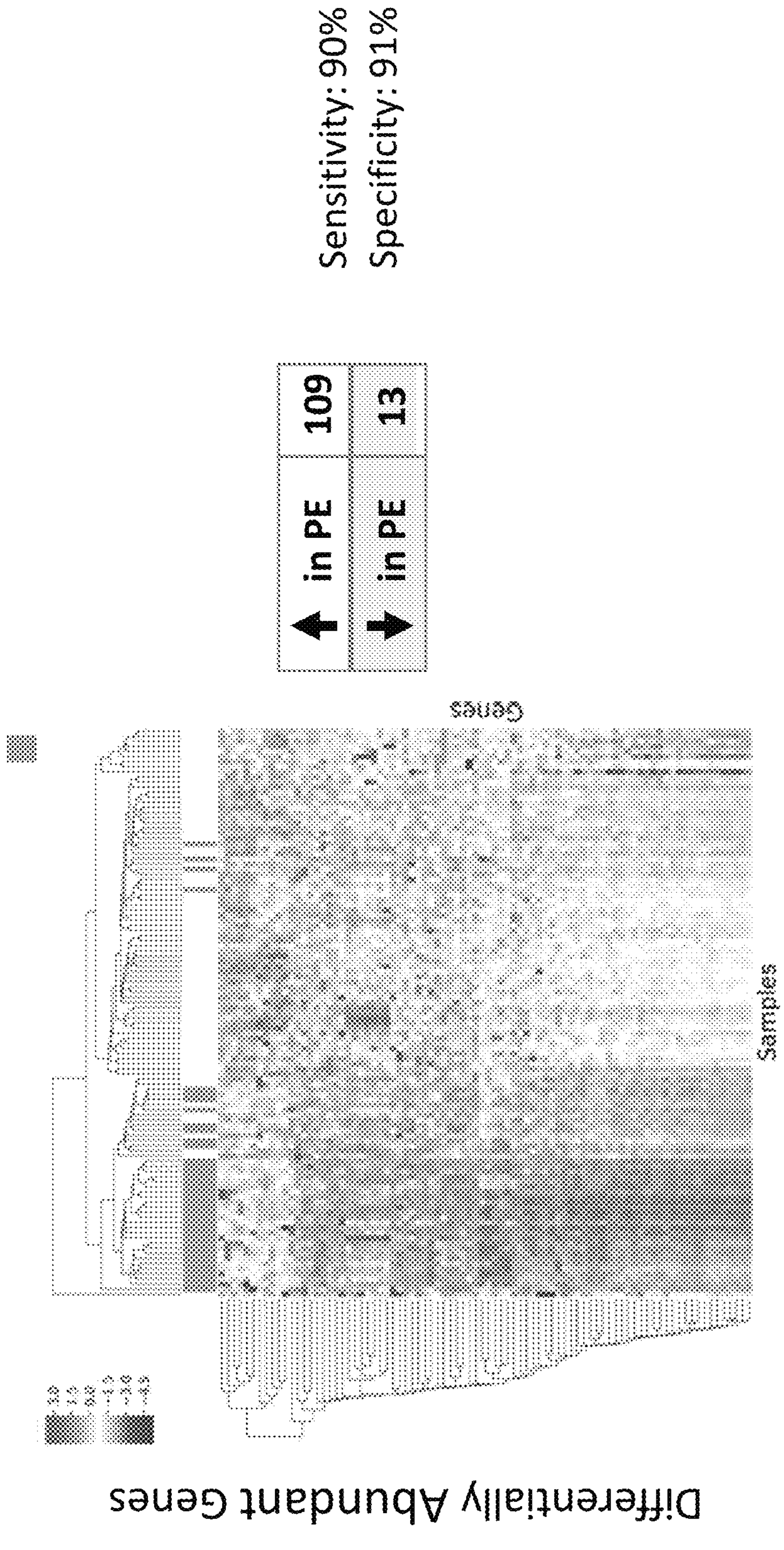
FIG. 15. Classification of preeclampsia with standard DEX TREAT analysis.

The TREAT method did not identify a set of genes that 100% accurately classifies the preeclampsia patients into a separate group (FIG. 15). However, focusing in on these identified genes did improve classification compared to using the entire data set of all measured genes (FIG. 8, left panel). This highlights the value of focusing in on a subset of genes for prediction. However, with the TREAT method, a significant amount of variability was observed in the genes identified depending on which controls were selected. To deal with this biological variability and further improve the predictive value of our gene list, a second bootstrapping approach was developed.

Figure 9:
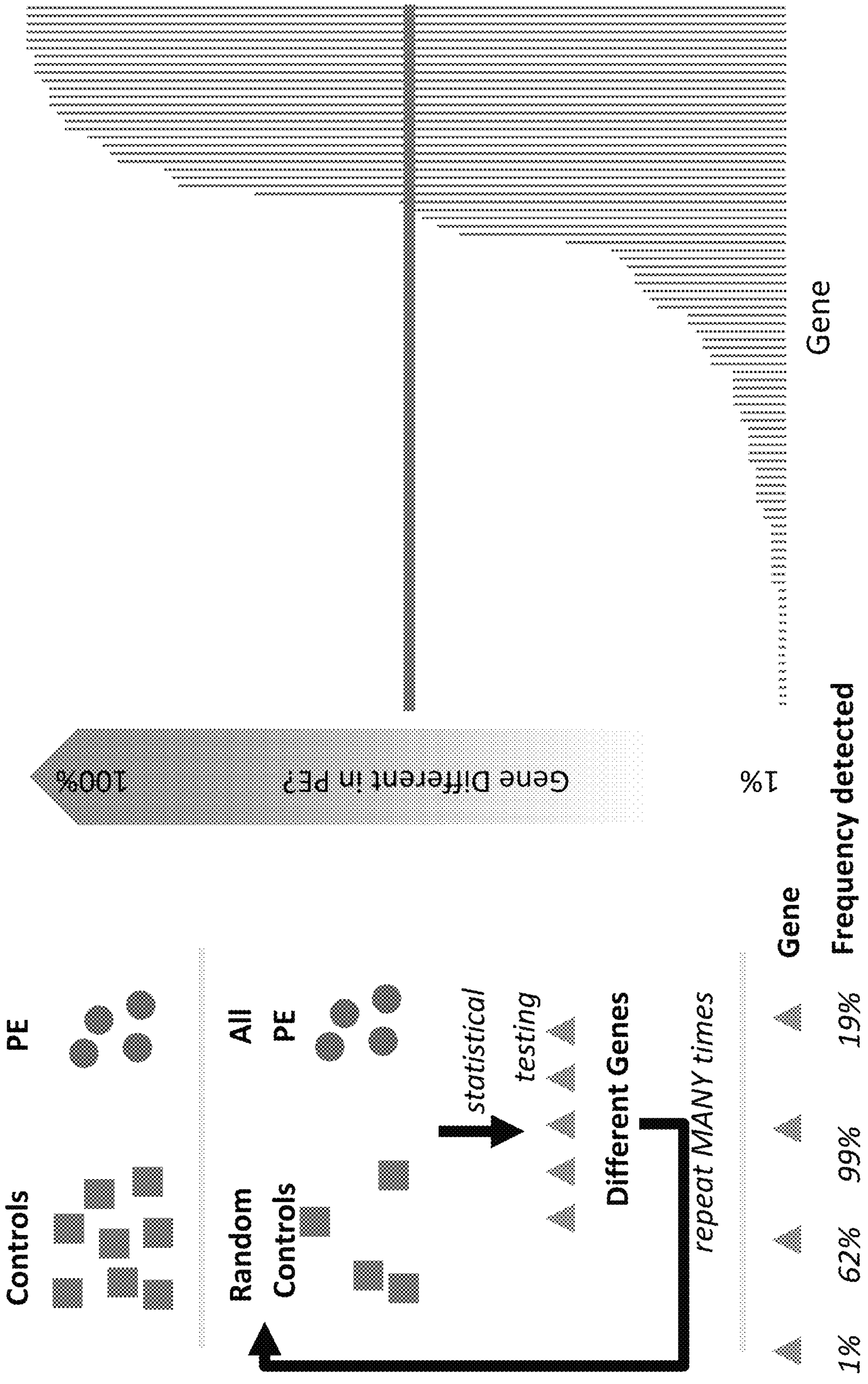
FIG. 9. Description of bootstrapping method.
Figure 10:
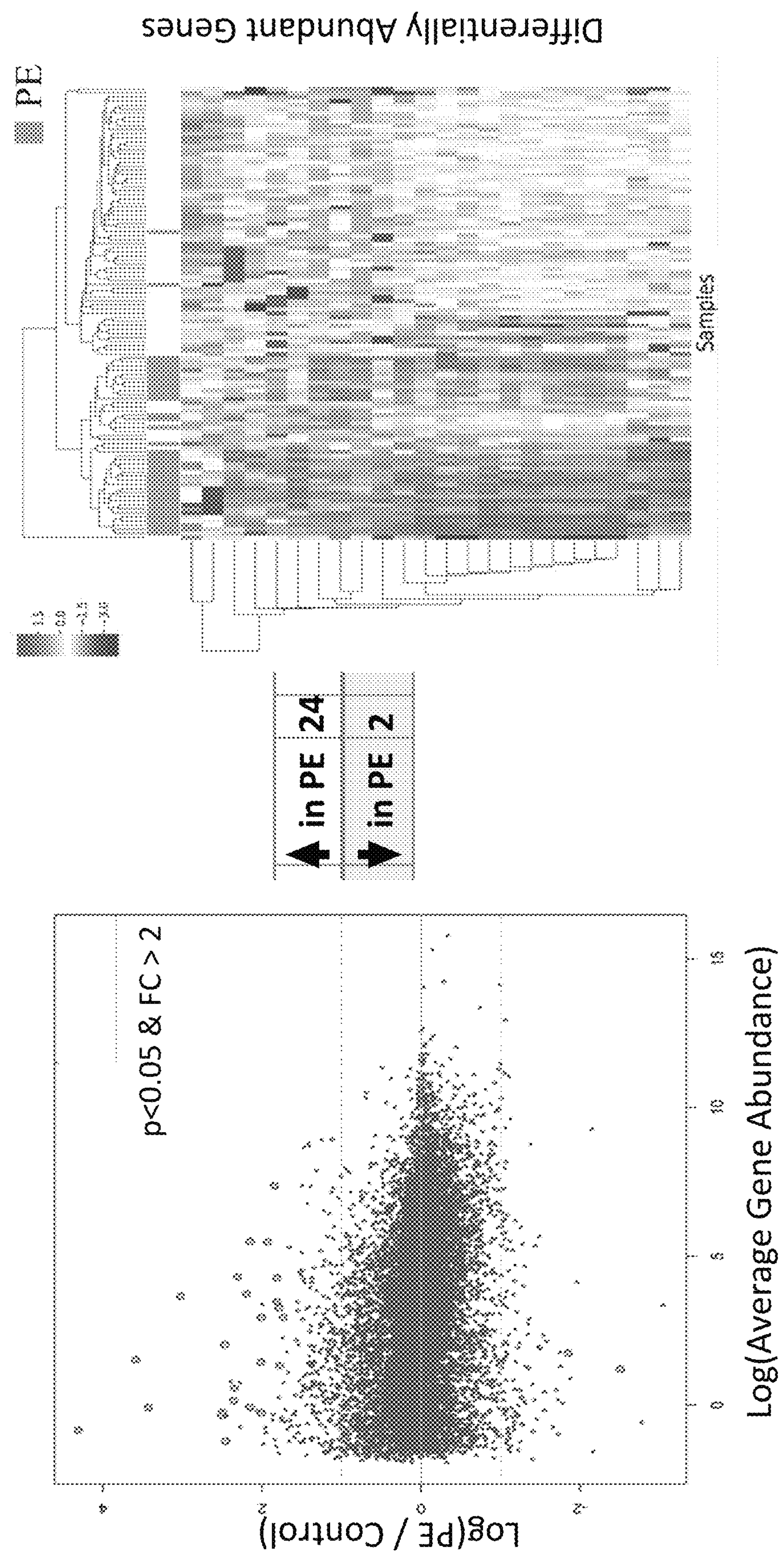
FIG. 10. Classification of preeclampsia samples with bootstrapping approach.

In the RGH14 study more control samples (80) are available than preeclampsia patient samples (40). Thus, the RGH14 cohort of 40 preeclampsia patient samples was compared to a random selection of 40 controls samples (still matched for gestational age) and a gene list that is statistically different in the preeclampsia cohort was identified. As shown in FIG. 9, this was then repeated 1,000 times, to identify how often a set of genes was identified. A significant subset of genes only show up less than 10 times out of the 1,000 iterations (less than 1% of the 1,000 iterations). These low frequency genes most likely are due to biological noise and may not reflect a gene that is universally specific to preeclampsia. So, the gene list was further downselected by requiring a gene to be considered as statistically different in the preeclampsia cohort only if identified in 50% of the 1,000 iterations performed (FIG. 9, right panel). As shown in FIG. 10, differential transcript abundance with the additional bootstrapping selection distinguishes preeclampsia samples from healthy controls. Using this additional requirement helped address biological variability and further improved the ability to classify preeclampsia samples correctly.

Figure 11:
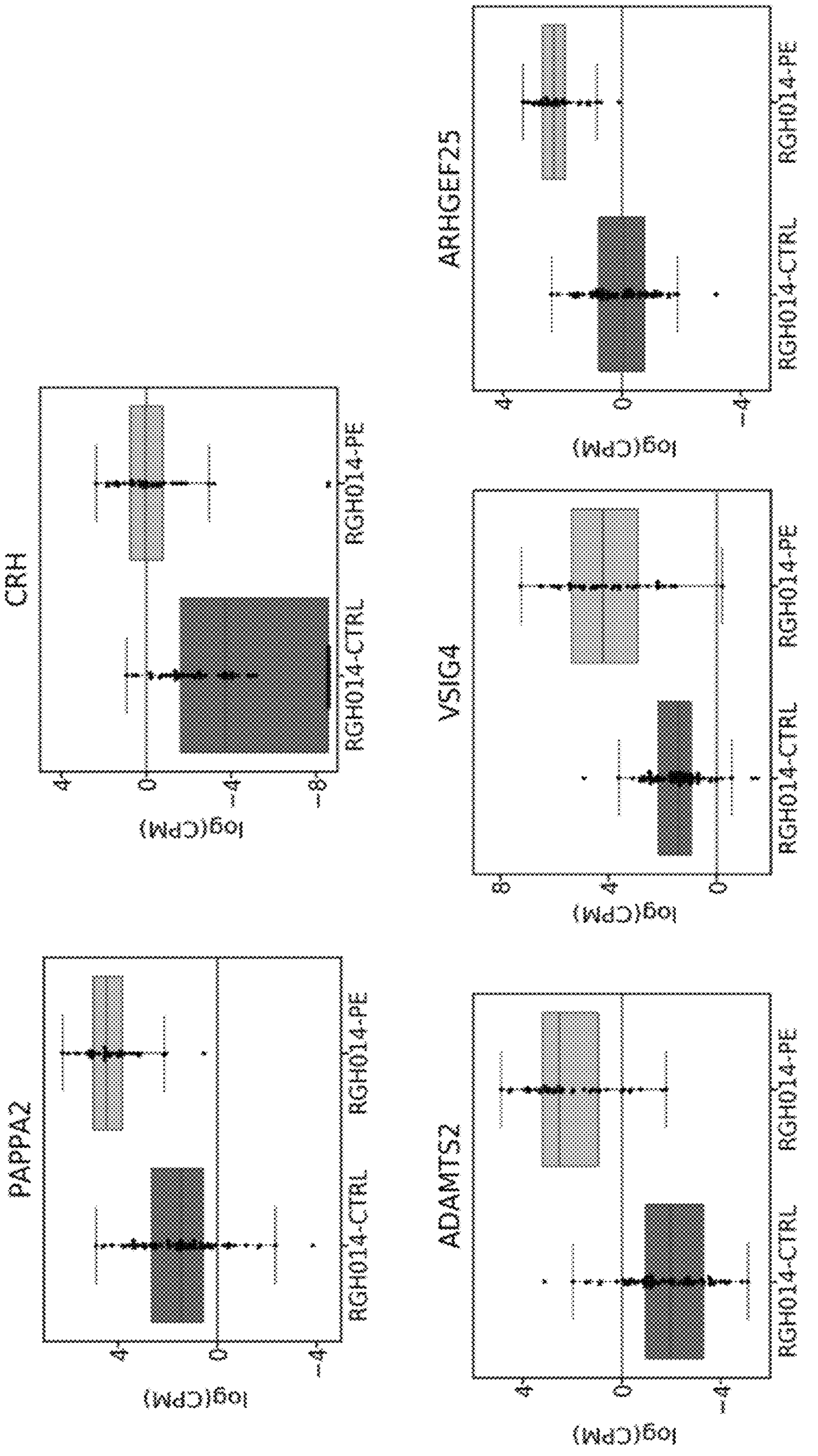
FIG. 11. Examination of over-abundant preeclampsia genes.

Using this Bootstrap method, 27 genes were identified as statistically associated with preeclampsia. These genes include TIMP4, FLG, HTRA4, AMPH, LCN6, CRH, TEAD4, ARMS2, PAPPA2, SEMA3G, ADAMTS1, ALOX15B, SLC9A3R2, TIMP3, IGFBP5, HSPA12B, CLEC4C, KRT5, PRG2, PRX, ARHGEF25, ADAMTS2, DAAM2, FAM107A, LEP, NES, and VSIG4. The genes identified with this bootstrapping method had excellent concordance with published data. Approximately 75% of these genes are expressed by the placenta. As shown in FIG. 11, there is overlap with known markers of preeclampsia, including PAPPA and CRH. And, a significant number of these genes are involved in embryo development, extracellular matrix remodeling, immune regulation, and cardiovascular function, all pathways known to be dysregulated in preeclampsia.

A third jackknifing approach was also developed to capture the subset of genes with the highest predictive value. This approach is similar to the bootstrapping method. Patients from both preeclampsia and control groups were randomly subsampled and differentially abundant genes identified 1,000 times. Instead of using the frequency with which a gene is identified as statistically different, the jackknifing approach calculated confidence intervals (95%, one-sided) for the p-value of each transcript. Genes where this confidence interval exceeded 0.05 were excluded. (FIG. 16, left panel).

Using the jackknifing approach, 30 genes were identified as predictive of preeclampsia: VSIG4, ADAMTS2, NES, FAM107A, LEP, DAAM2, ARHGEF25, TIMP3, PRX, ALOX15B, HSPA12B, IGFBP5, CLEC4C, SLC9A3R2, ADAMTS1, SEMA3G, KRT5, AMPH, PRG2, PAPPA2, TEAD4, CRH, PITPNM3, TIMP4, PNMT, ZEB1, APOLD1, PLD4, CUX2, HTRA4.

Figure 16:
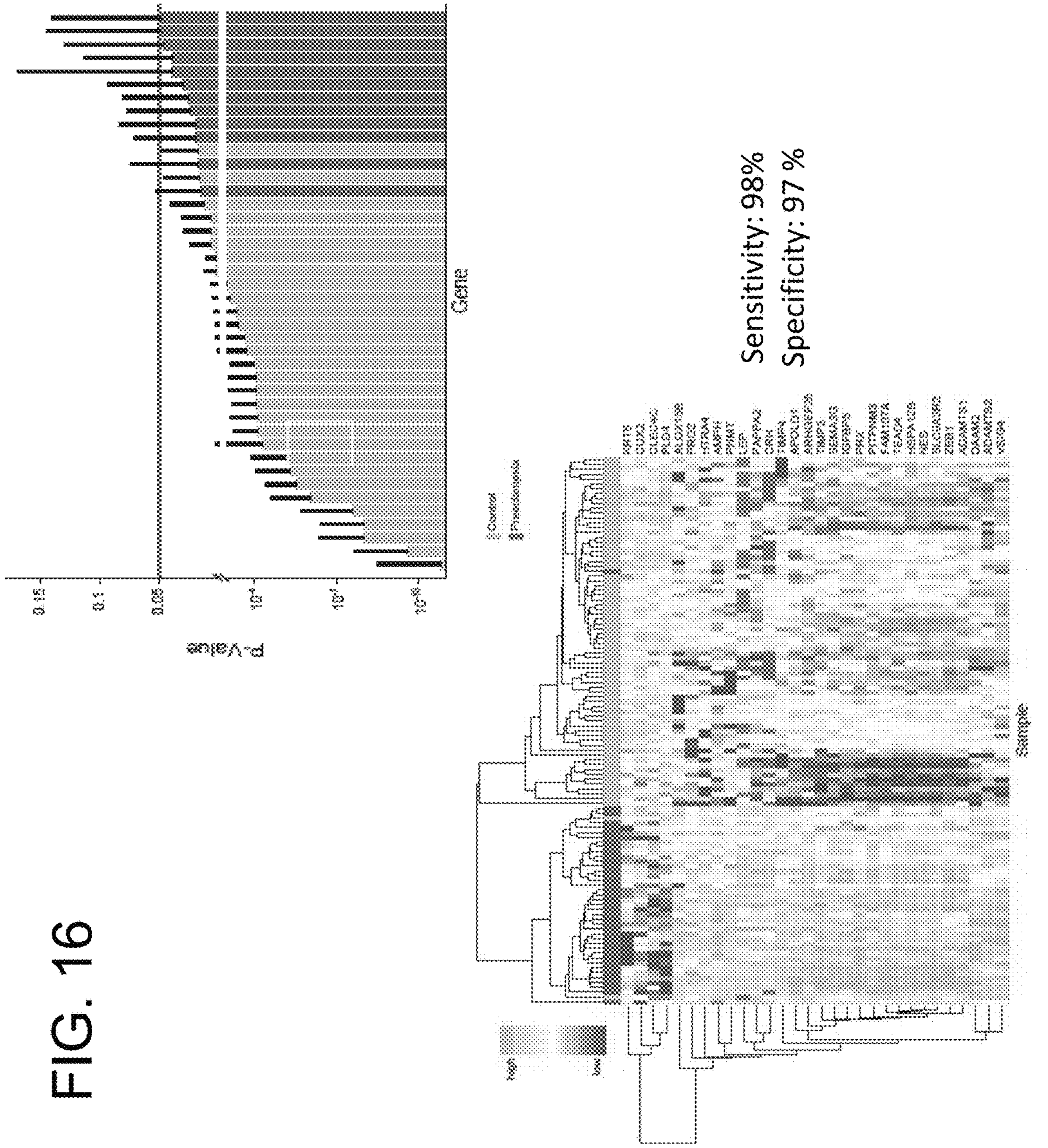
FIG. 16. Selection of genes and classification of preeclampsia with jackknifing approach.
Figure 17:
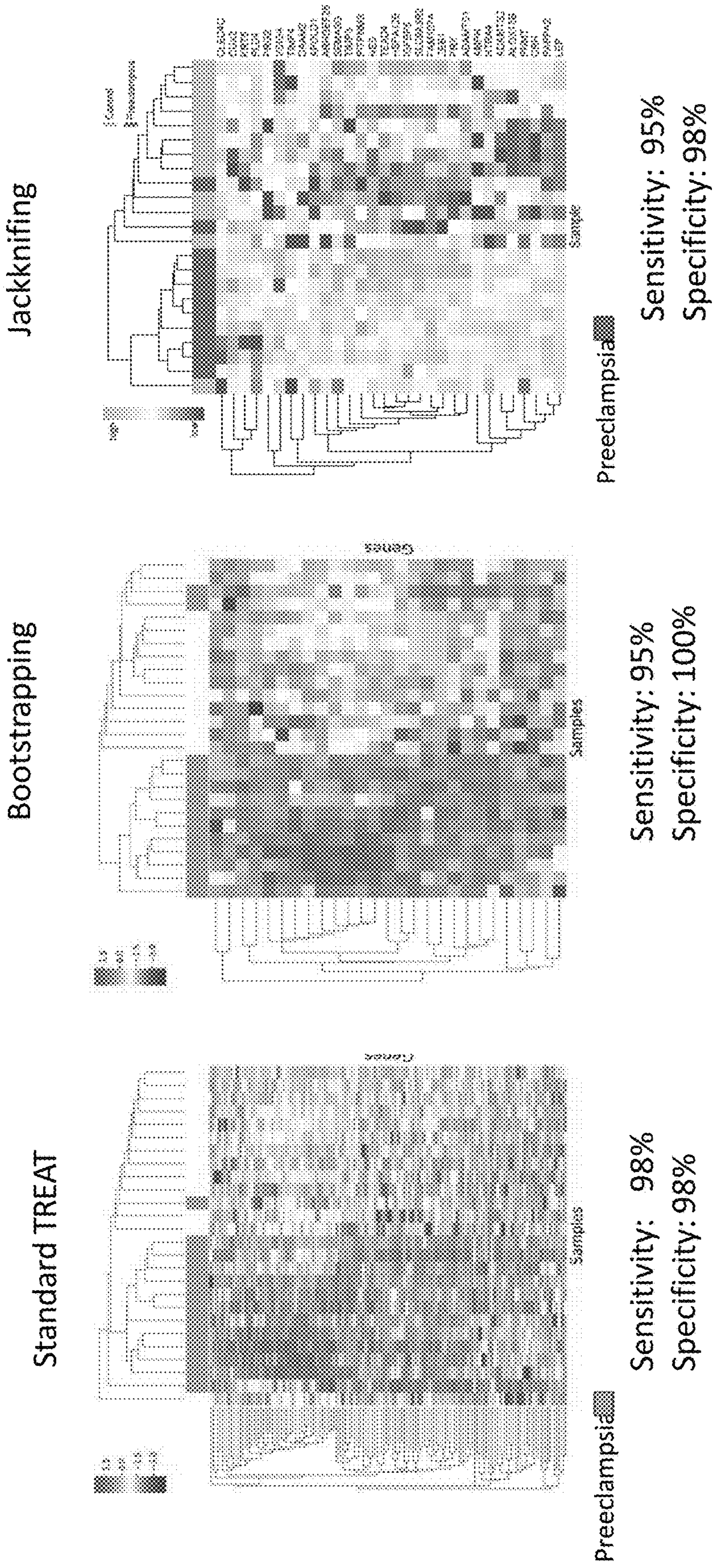
FIG. 17. Validation of TREAT, Bootstrapping, and Jackknifing approaches in independent PEARL biobank cohort.

As shown in FIG. 16 right panel, this approach gave good classification of preeclampsia patients in the RGH14 data set (compare FIG. 15 (TREAT), FIG. 10 (bootstrapping) and FIG. 16 (jackknifing)). Each identified gene list was also used to classify preeclampsia samples in the independent Pearl Biobank dataset. As shown in FIG. 17, each gene list was able to classify preeclampsia samples.

All genes identified by the bootstrapping and jackknifing methods are represented in the 122 TREAT method genes (Table 2, DEX analysis, TruSeq library prep method). The bootstrapping and jackknifing approach gene lists are highly concordant, with over 70% of genes in common. Nearly 90% of transcripts identified by any approach exhibit increased transcript abundance in preeclampsia patients, consistent with elevated signaling and/or cell death in this disease.

Example 4

Identification of C-RNA Signatures with Adaboost

Figure 12:
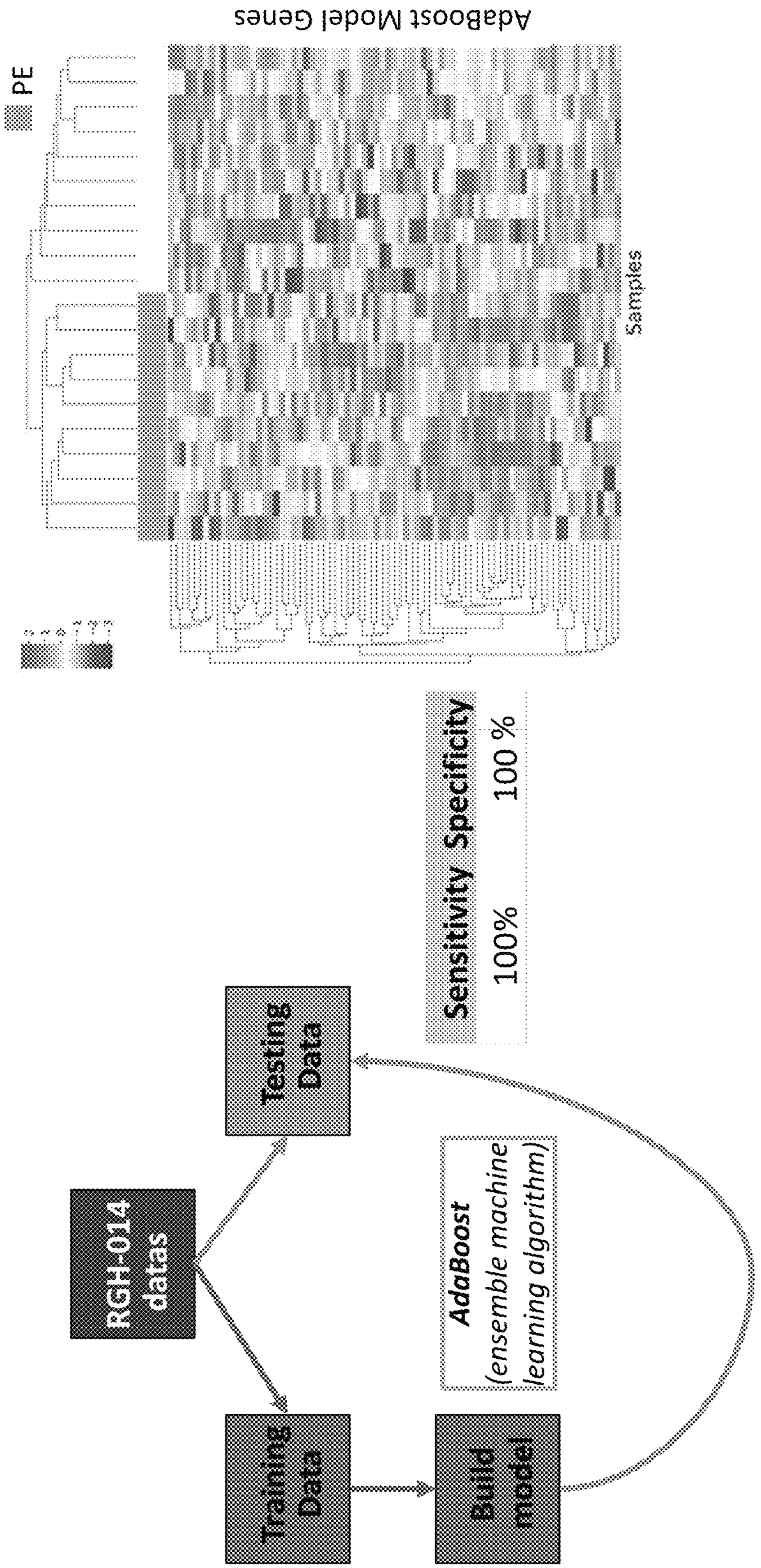
FIG. 12. Standard Adaboost Model.
Figure 13:
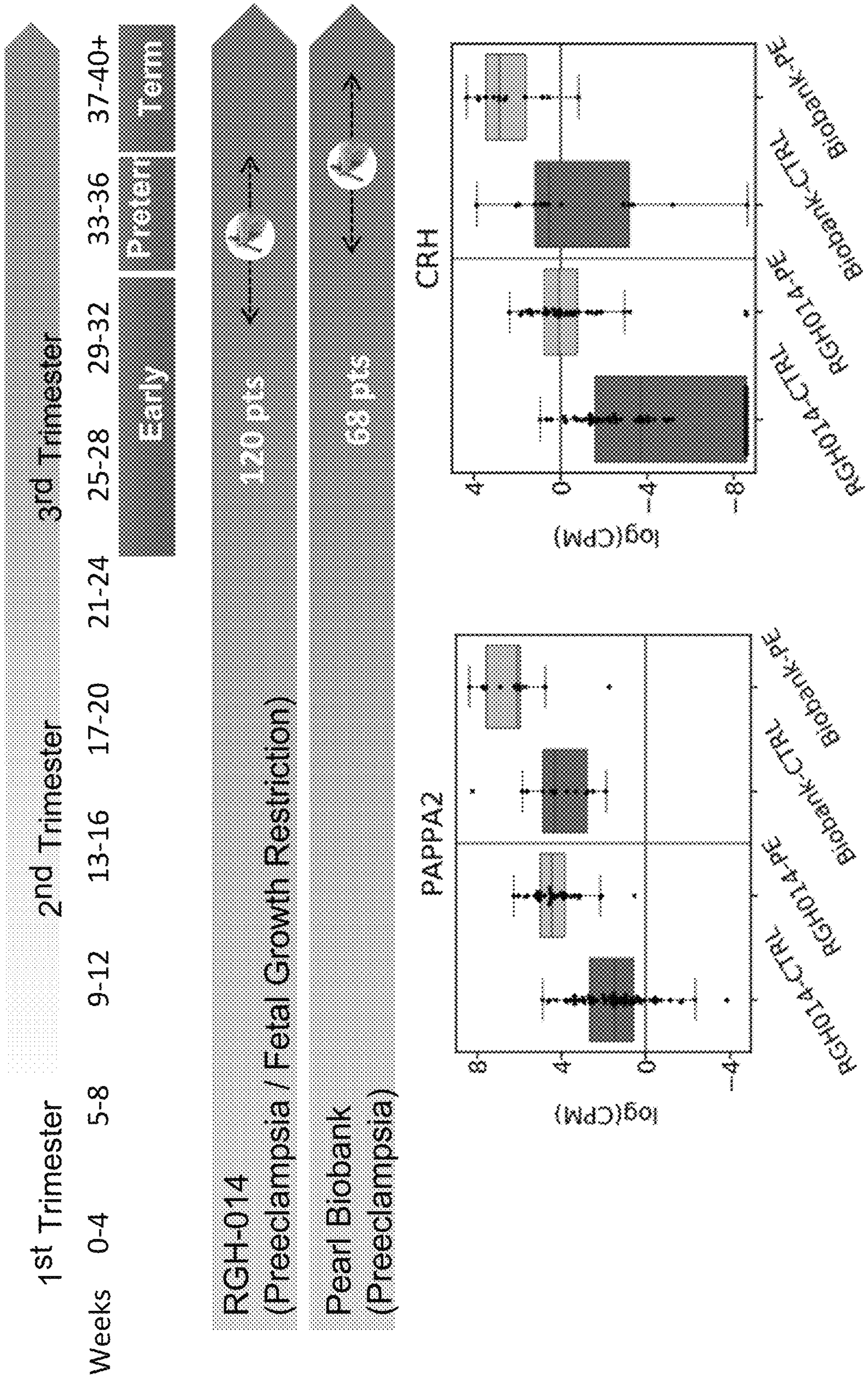
FIG. 13. Independent cohort allows further validation of preeclampsia signature.
Figure 14:
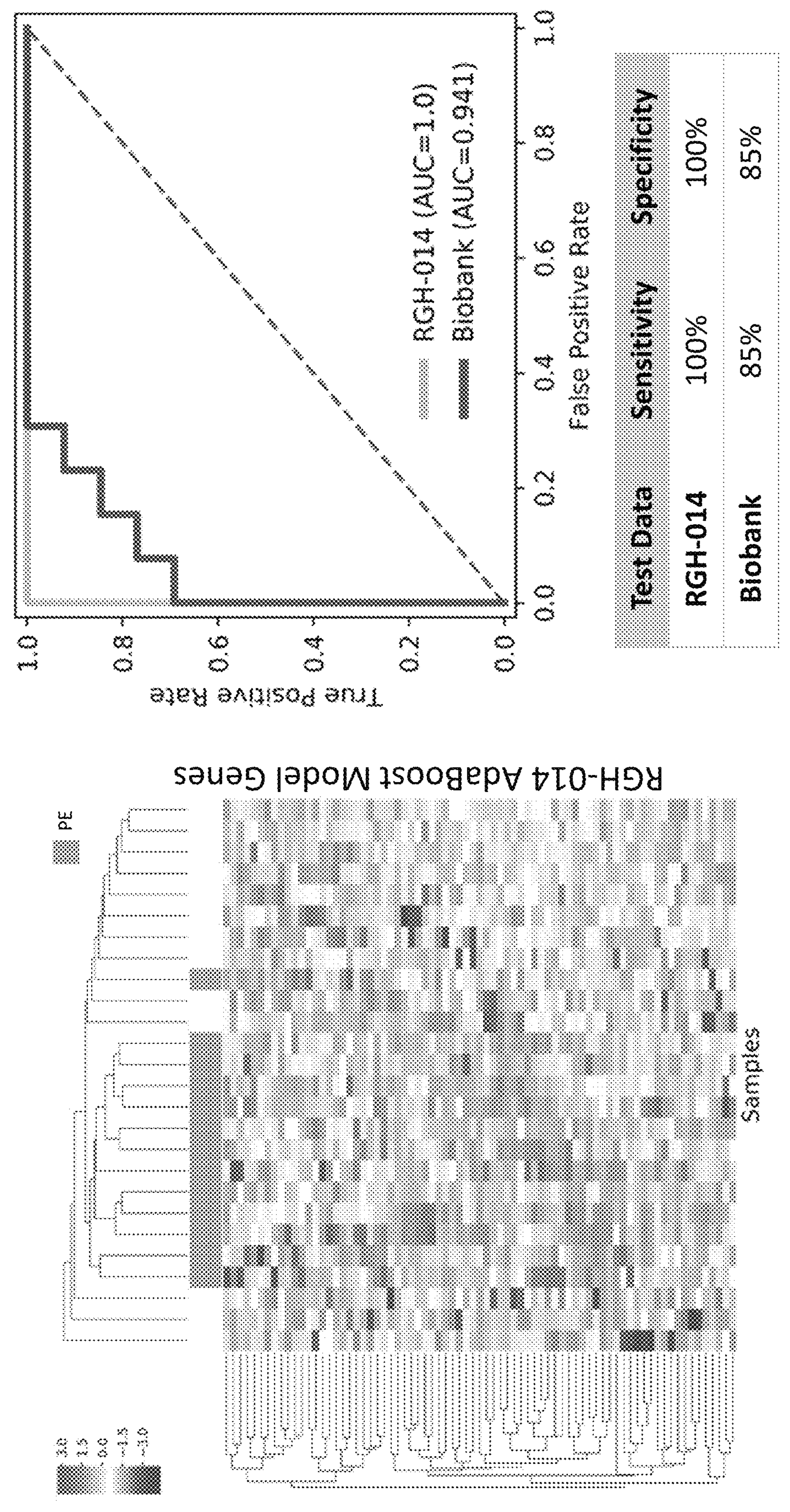
FIG. 14. Performance of standard adaboost model in classification of preeclampsia.

With this example an alternative approach, a publicly available machine learning algorithm called adaboost, was used to identify a specific C-RNA signature associated with preeclampsia. As shown in FIG. 12, this approach identifies a set of genes that has the most predictive power to classify a sample as preeclampsia (PE) or normal. Using this gene list, the clearest separation of a preeclampsia cohort from healthy controls was observed. However, this approach can also be very susceptible to overtraining to the samples used to build the model. Thus, the predictive model was validated using a completely independent data set from the PEARL study (FIG. 13). Using this Adaboost gene list, 85% of the preeclampsia samples were accurately classify with 85% specificity (FIG. 14). Overall, the Adaboost machine learning approach built the most accurate predictive model for preeclampsia.

Using the Adaboost method, 75 genes were identified as statistically associated with preeclampsia (Table 3, AdaBoost Analysis, TruSeq library prep method). These genes include ARRDC2, JUN, SKIL, ATP13A3, PDE8B, GSTA3, PAPPA2, TIPARP, LEP, RGP1, USP54, CLEC4C, MRPS35, ARHGEF25, CUX2, HEATR9, FSTL3, DDI2, ZMYM6, ST6GALNAC3, GBP2, NES, ETV3, ADAM17, ATOH8, SLC4A3, TRAF3IP1, TTC21A, HEG1, ASTE1, TMEM108, ENC1, SCAMP1, ARRDC3, SLC26A2, SLIT3, CLIC5, TNFRSF21, PPP1R17, TPST1, GATSL2, SPDYE5, HIPK2, MTRNR2L6, CLCN1, GINS4, CRH, C10orf2, TRUB1, PRG2, ACY3, FAR2, CD63, CKAP4, TPCN1, RNF6, THTPA, FOS, PARN, ORAI3, ELMO3, SMPD3, SERPINF1, TMEM11, PSMD11, EBI3, CLEC4M, CCDC151, CPAMD8, CNFN, LILRA4, ADA, C22orf39, PI4KAP1, and ARFGAP3.

Figure 18:
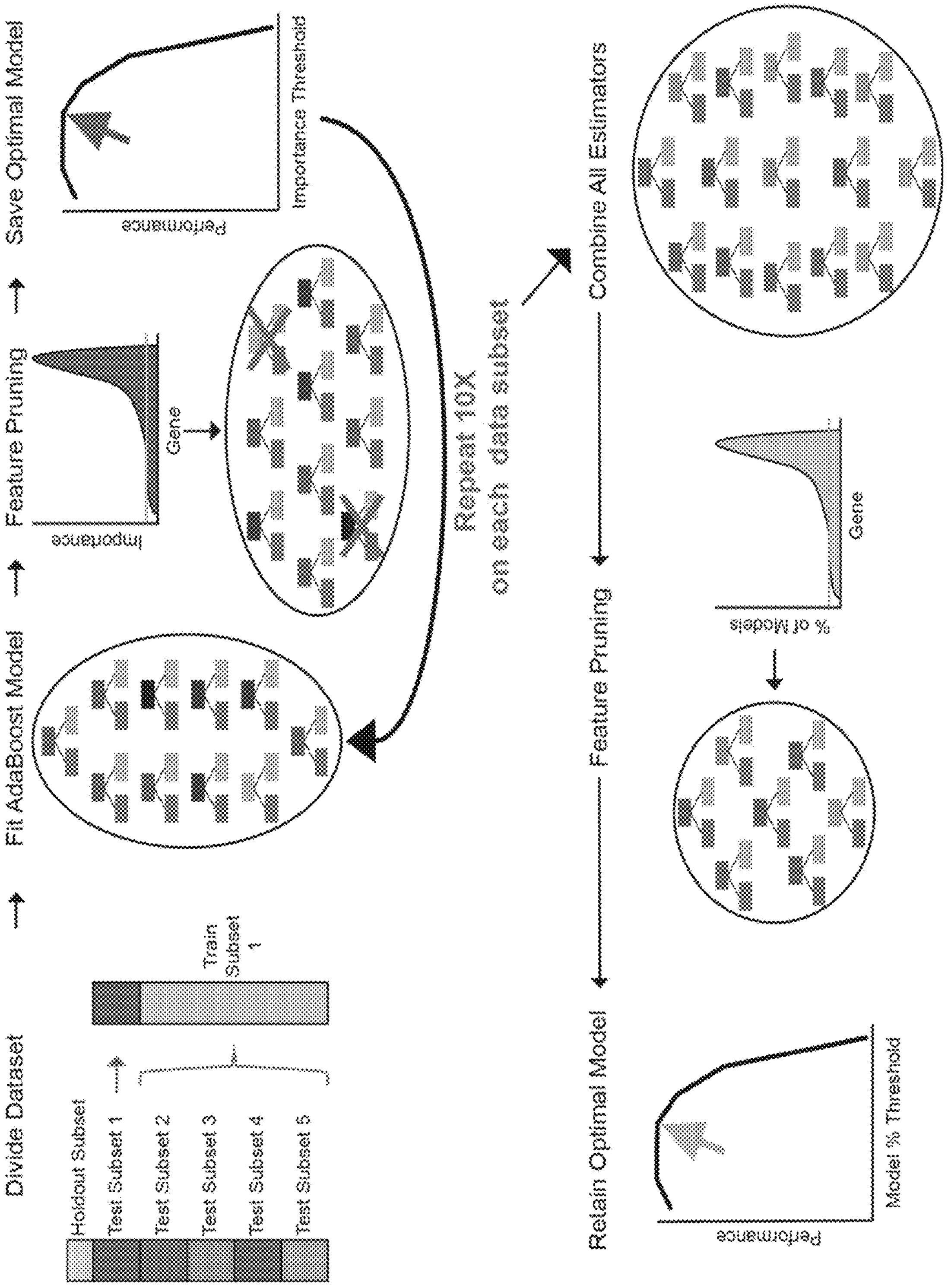
FIG. 18. A diagram of the bioinformatic approach to build AdaBoost Refined models.

A refined AdaBoost model was also developed for robust classification of PE samples. In order to create a generalized machine learning model that could accurately predict new samples, we used a rigorous approach that avoided overfitting to a single dataset and validated the final classifier with samples not used for model building. As illustrated in FIG. 18, the RGH14 dataset was divided into 6 pieces by random selection: a holdout subset with 12% of samples which was excluded from model building, and 5 evenly sized test subsets. For each iteration subsets were designated as training data or test samples. This process, starting at building the AdaBoost model was repeated for a minimum of 10 times on this data subset. After 50 high performing models were built for the 5 test-train subsets, the estimators from all models were merged into a single AdaBoost model.

Figure 19:
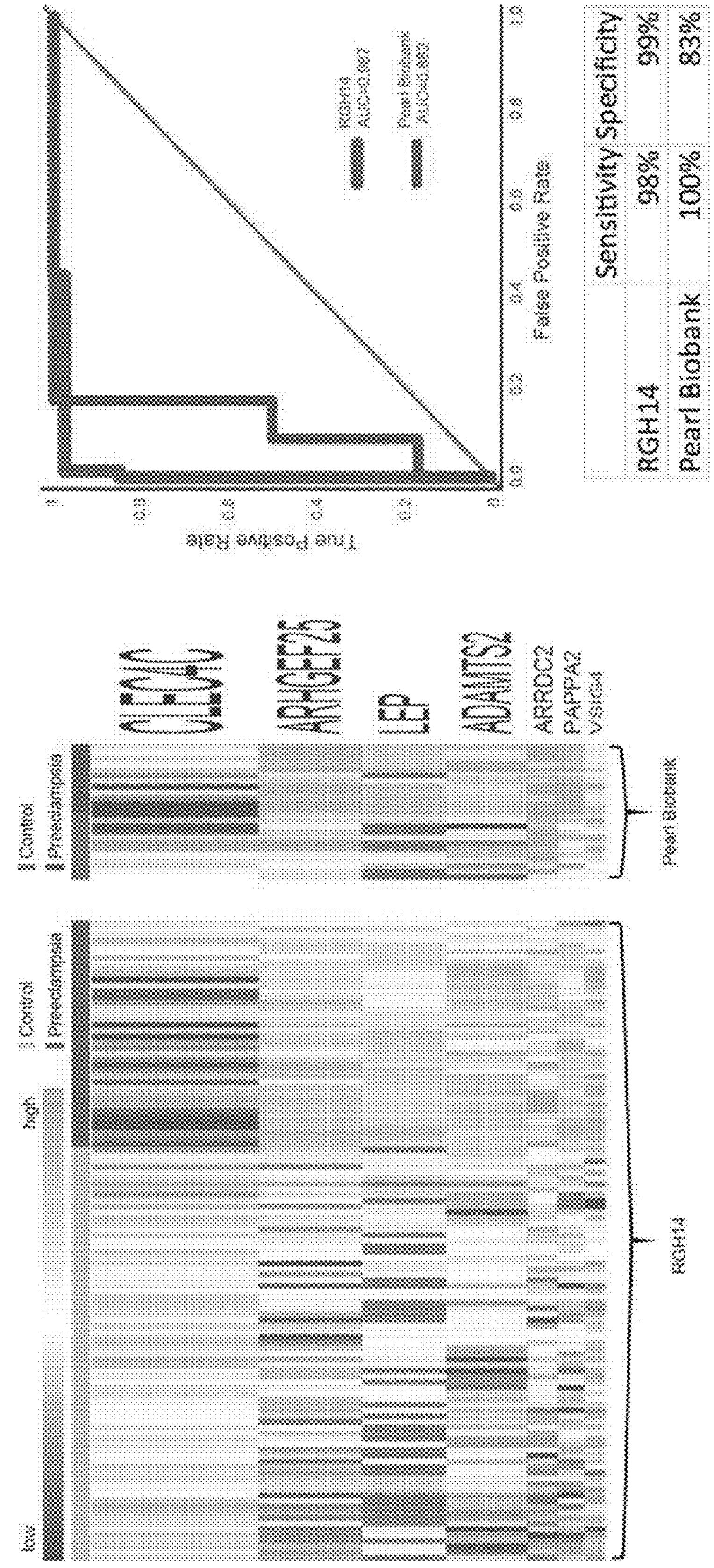
FIG. 19. Relative abundance of genes utilized by AdaBoost Refined model and their predictive capability on independent datasets.

Using the refined AdaBoost model, 11 genes were identified as statically associated with preeclampsia. These genes include CLEC4C, ARHGEF25, ADAMTS2, LEP, ARRDC2, SKIL, PAPPA2, VSIG4, ARRDC4, CRH and NES. The performance of this predictive model was validated using the hold out data set from RGH14 as well as in the completely independent Pearl Biobank cohort (FIG. 19).

AdaBoost Model Creation Description. The AdaBoost classification approach was refined in order to obtain more specific gene sets (AdaBoost Refined 1-7) by the following approach, also illustrated in FIG. 18. The RGH14 dataset was divided into 6 pieces by random selection: a holdout subset with 12% of samples which was excluded from model building, and 5 evenly sized test subsets.

For each of the test subsets, training data was assigned as all samples in neither the holdout or test samples. Gene counts for the test and training samples were TMM-normalized in edgeR, then standardized such that the training data has mean of 0 and standard deviation of 1 for each gene. An AdaBoost model with 90 estimators and 1.6 learning rate was then fit to the training data. Feature pruning was then performed by determining the feature importance of each gene in the model and testing the impact of eliminating estimators using genes with importance below a threshold value. The threshold resulting in the best performance (as measured by Matthew's correlation coefficient on test data classification) with the fewest genes was selected, and that model retained. This process, starting at building the AdaBoost model was repeated for a minimum of 10 times on this data subset.

After all 50 plus models were built for the 5 test-train subsets, the estimators from all models were merged into a single AdaBoost model. Feature pruning was performed again, this time using the percent of models incorporating a gene to for threshold values and assessing performance with the average negative log loss value for the classification of each test subset. The model which obtained the maximal negative log loss value with the fewest genes was selected as the final AdaBoost model.

AdaBoost Gene Lists. Upon repetition of this process, slight variations were observed in the genes selected for the final model, due to innate randomization in the AdaBoost algorithm implementation, however performance remained high for predicting the test data, holdout data, and independent (Pearl) datasets.

Eleven total genes were observed in at least one of 14 AdaBoost Refined models generated: ADAMTS2, ARHGEF25, ARRDC2, ARRDC4, CLEC4C, CRH, LEP, NES, PAPPA2, SKIL, VSIG4 (AdaBoost Refined 1), although no models were generated that included all simultaneously.

Two observed gene sets offered the highest performance on classification of independent data. These are AdaBoost Refined 2: ADAMTS2, ARHGEF25, ARRDC2, CLEC4C, LEP, PAPPA2, VSIG4 and AdaBoost Refined 3: ADAMTS2, ARHGEF25, ARRDC2, CLEC4C, LEP, PAPPA2, SKIL, VSIG4.

Four additional gene sets performed almost as highly as AdaBoost Refined 2-3. These are AdaBoost Refined 4: ADAMTS2, ARHGEF25, ARRDC4, CLEC4C, LEP, NES, SKIL, VSIG4; AdaBoost Refined 5: ADAMTS2, ARHGEF25, ARRDC2, ARRDC4, CLEC4C, CRH, LEP, PAPPA2, SKIL, VSIG4; AdaBoost Refined 6: ADAMTS2, ARHGEF25, ARRDC2, CLEC4C, LEP, SKIL; and AdaBoost Refined 7: ADAMTS2, ARHGEF25, ARRDC2, ARRDC4, CLEC4C, LEP, PAPPA2, SKIL.

Example 5

Identification of C-RNA Signature with Transposome Based Library Prep

The RGH14 samples were also processed through the Illumina Nextera Flex for Enrichment protocol, enriched for whole exome and sequenced to >40 million reads. This approach is more sensitive and robust for low inputs, thus likely to identify additional genes predictive of preeclampsia. This dataset was run through three analysis methods, standard differential expression analysis (TREAT), jackknifing, and the refined Adaboost model. See Example 3 and Example 4 for detailed description of these analysis methods.

Figure 20:
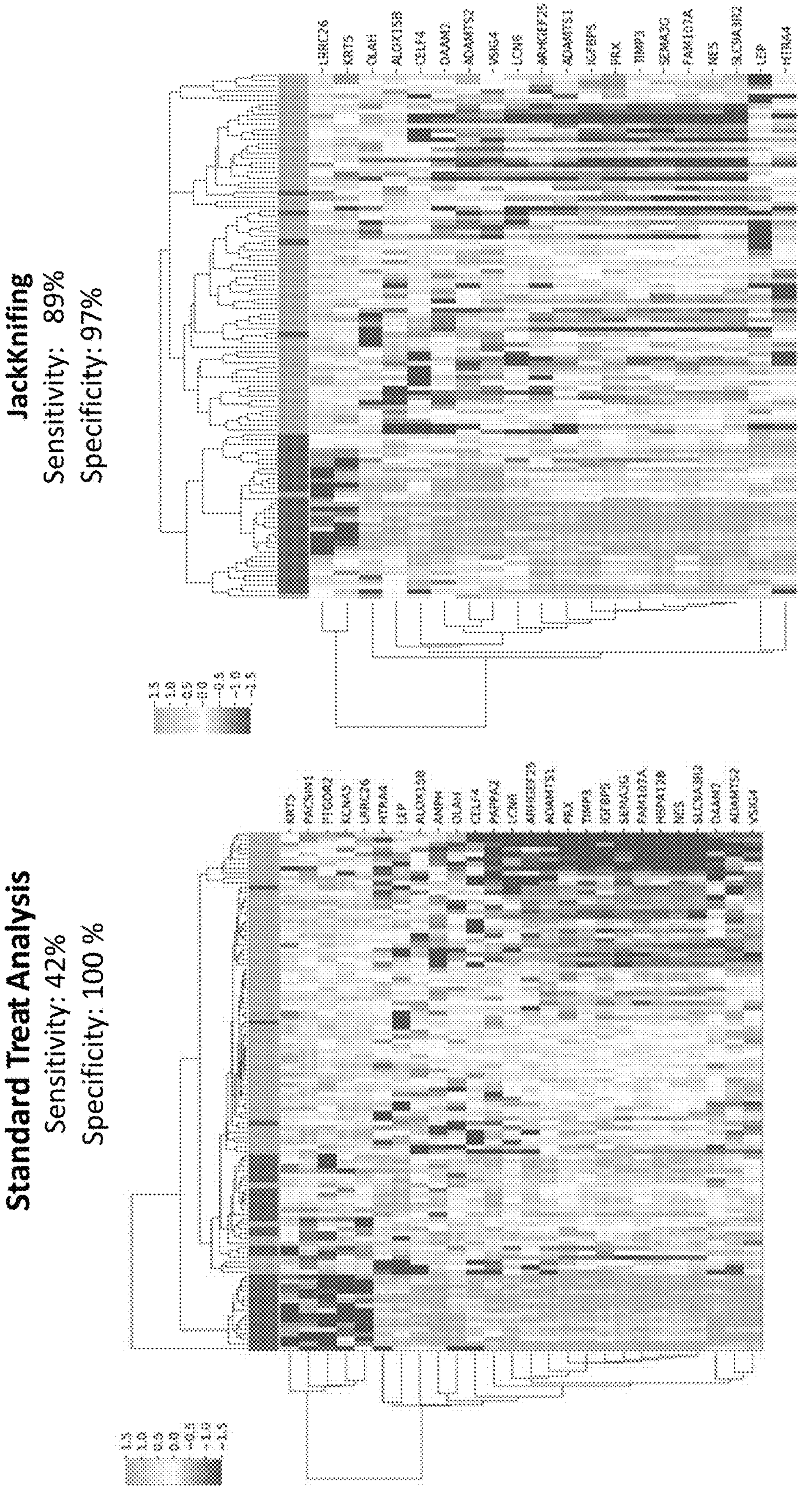
FIG. 20. Identifying C-RNA signatures specific to preeclampsia in Nextera Flex generated libraries using standard TREAT analysis and jackknifing approach.

Changing the method for generating libraries altered the genes detected in all three analysis methods. For the TREAT method, 26 genes were identified as differentially abundant in preeclampsia, with the majority again showing elevated abundance in preeclampsia (See Table 2, DEX Analysis, Nextera Flex for Enrichment library prep method). These genes include ADAMTS1, ADAMTS2, ALOX15B, AMPH, ARHGEF25, CELF4, DAAM2, FAM107A, HSPA12B, HTRA4, IGFBP5, KCNA5, KRT5, LCN6, LEP, LRRC26, NES, OLAH, PACSIN1, PAPPA2, PRX, PTGDR2, SEMA3G, SLC9A3R2, TIMP3, VSIG4. FIG. 20 shows classification of the RGH14 samples with this gene list.

Applying the jackknifing analysis method downselected the TREAT list to 22 genes identified as differentially abundant in preeclampsia. These genes included ADAMTS1, ADAMTS2, ALOX15B, ARHGEF25, CELF4, DAAM2, FAM107A, HTRA4, IGFBP5, KCNA5, KRT5, LCN6, LEP, LRRC26, NES, OLAH, PRX, PTGDR2, SEMA3G, SLC9A3R2, TIMP3, VSIG4. The improved performance of this list is shown in FIG. 20.

Figure 21:
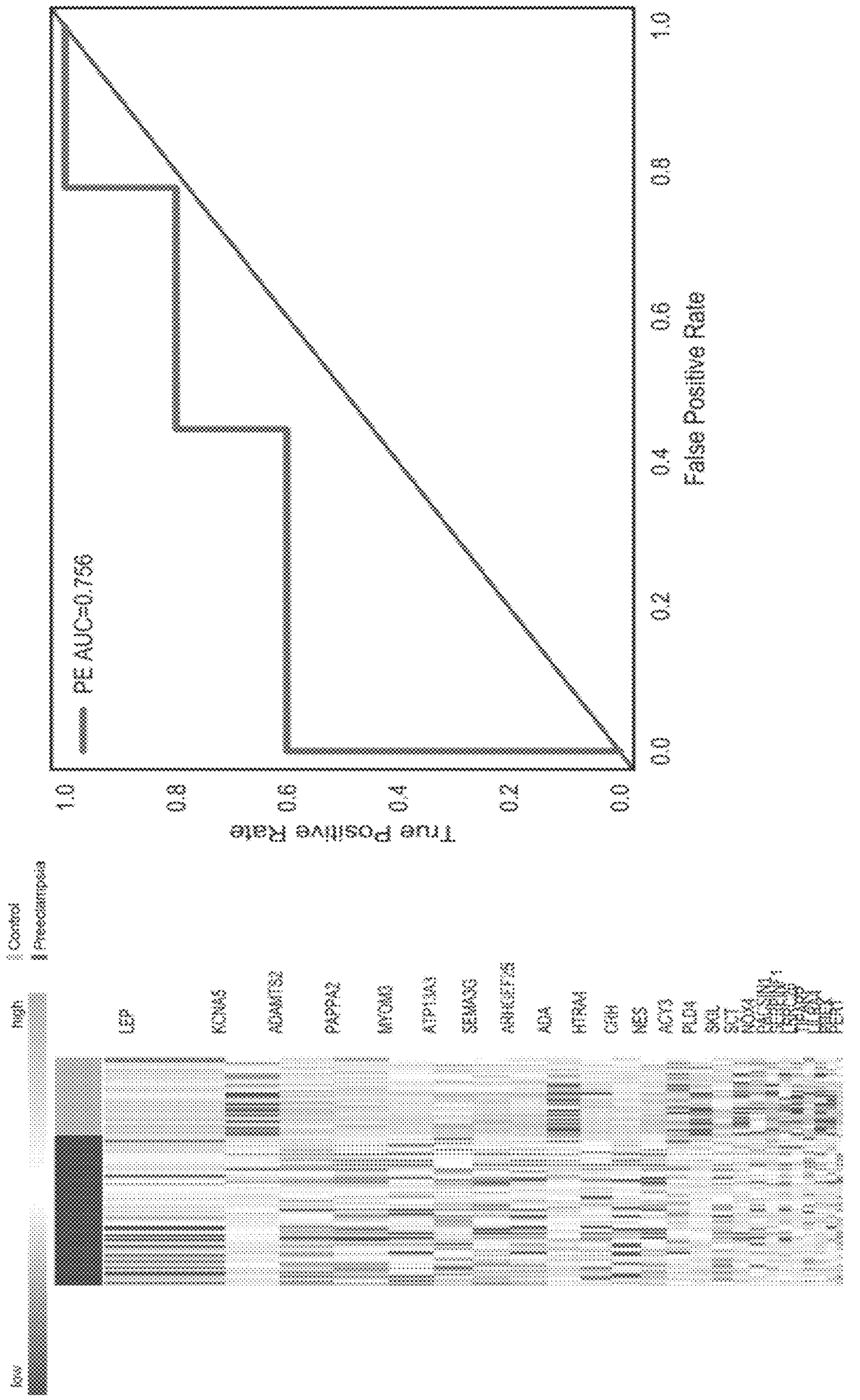
FIG. 21. Relative abundance of genes utilized by AdaBoost Refined model on Nextera Flex generated libraries and their predictive power in RGH14 dataset.

The refined AdaBoost model approach was applied to this data, as described in Example 4. Using this method, 24 genes are identified as statically associated with preeclampsia (Table 3, AdaBoost Analysis, Nextera Flex for Enrichment library prep method). These genes include LEP, PAPPA2, KCNA5, ADAMTS2, MYOM3, ATP13A3, ARHGEF25, ADA, HTRA4, NES, CRH, ACY3, PLD4, SCT, NOX4, PACSIN1, SERPINF1, SKIL, SEMAG3, TIPARP, LRRC26, PHEX, LILRA4, and PER1. The performance of this predictive model is indicated in FIG. 21.

Example 6

Circulating Transcriptome Measurements from Maternal Blood Detects Early-Onset Preeclampsia Signature Molecular tools to non-invasively monitor pregnancy health from conception to birth would enable accurate detection of pregnancies at risk for adverse outcomes. Circulating RNA (C-RNA) is released by all tissues into the bloodstream, offering an accessible, comprehensive measurement of placental, fetal and maternal health (Koh et al., 2014, *Proceedings of the National Academy of Sciences;* 111:7361-7366; and Tsui et al., 2014, *Clinical Chemistry;* 60:954-962). Preeclampsia (PE), a prevalent and potentially fatal pregnancy complication, is placental in origin but gains a substantial maternal component as the disease progresses (Staff et al., 2013, *Hypertension;* 61:932-942; and Chaiworapongsa et al., 2014, *Nature Reviews Nephrology;* 10, 466-480). Yet purported biomarkers have shown limited clinical utility (Poon and Nicolaides, 2014, *Obstetrics and Gynecology International;* 2014:1-11; Zeisler et al., 2016, *N Engl J Med;* 374:13-22; and Duhig et al., 2018, F1000Research; 7:242). Hypothesizing that characterization of the circulating transcriptome may identify better biomarkers, C-RNA was analyzed from 113 pregnancies, 40 at the time of early-onset PE diagnosis. Using a novel workflow, differences were identified in the abundance of 30 transcripts which are consistent with the biology of PE and represent placental, fetal, and maternal contributions. Further, a machine learning model was developed, demonstrating that only seven C-RNA transcripts are required to classify PE in two independents cohorts (92-98% accuracy). The global measurements of C-RNA disclosed in this example highlight the utility in monitoring both maternal and fetal health and hold great promise for the diagnosis and prediction of at-risk pregnancies.

Figures 22A, 22B, 22C, 22D:
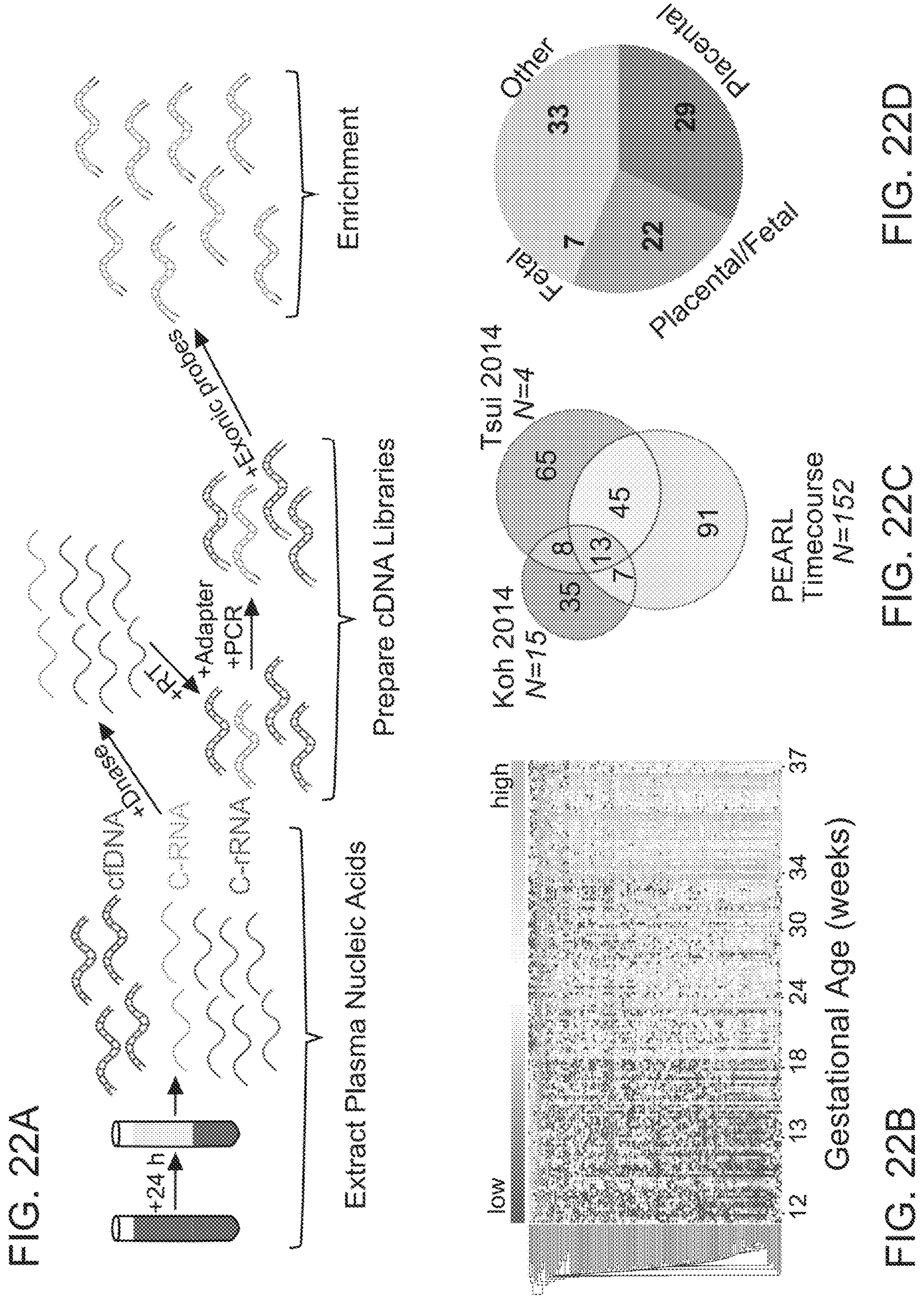
FIGS. 22A-22D. Validation of a clinic-friendly, whole-exome C-RNA analysis method.

Several studies have begun to investigate and identify potential biomarkers in C-RNA for a range of pregnancy complications (Pan et al., 2017, *Clinical Chemistry;* 63:1695-1704; Whitehead et al., 2016, *Prenatal Diagnosis;* 36:997-1008; Tsang et al., 2017, *Proc Natl Acad Sci USA;* 114: E7786-E7795; and Ngo et al., 2018, *Science;* 360:1133-1136). However, these studies have involved few patients and have been limited to monitoring small numbers of genes—almost exclusively placental and fetal derived transcripts. Measurements of the entire circulating transcriptome are difficult to perform because they require specific upfront sample collection and processing to minimize variability and contamination from cell lysis (Chiu et al., 2001, *Clinical Chemistry;* 47:1607-1613; and Page et al., 2013, *PLoS ONE;* 8: e77963). This complex workflow makes large clinical sample collections difficult to achieve because the labor required for immediate processing of blood samples is infeasible for many clinics (Marton and Weiner, 2013, *BioMed Research International;* 2013:891391). Therefore, with this example, a method was established that allows overnight shipment of blood to a processing lab where every step of sample preparation is performed in a controlled environment, providing a scalable platform for clinical trial level assessments (FIG. 22A).

Figures 26A, 26B, 26C:
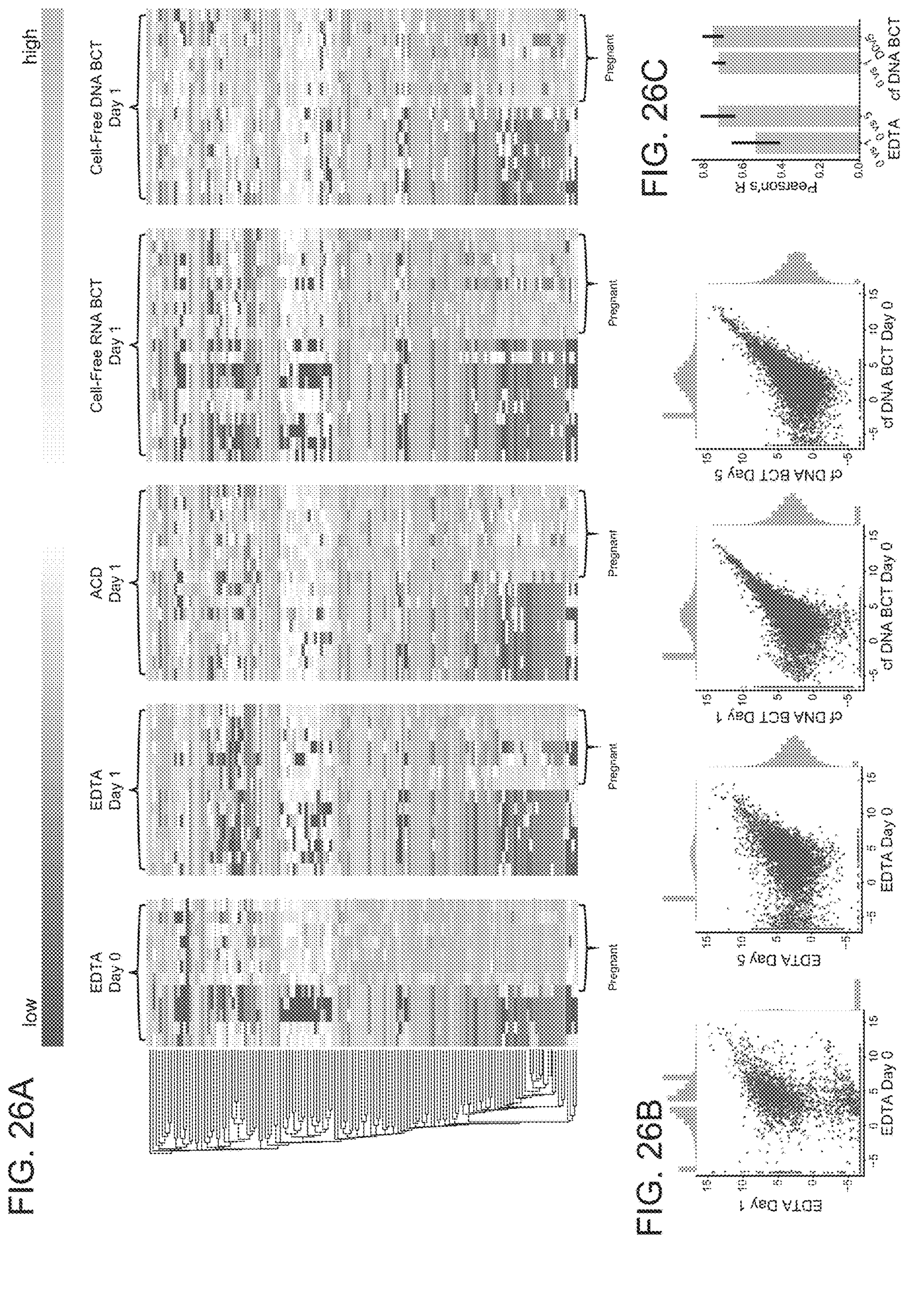
FIGS. 26A-26C. C-RNA data integrity when blood is stored in different collection tubes. Comparing the abundance of previously detected C-RNA pregnancy markers from blood stored overnight in different tube types to immediate processing after collection in EDTA tubes (FIG. 26A). Scatterplots comparing transcript FPKM values for C-RNA prepared from the same individual after different blood storage durations (FIG. 26B). Pearson's correlation coefficient, R, is more variable when using EDTA tubes (cf, Cell-Free) (FIG. 26C).

The lynchpin of this method is the ability to ship blood overnight to a processing lab. The C-RNA pregnancy signal was assessed after overnight, room-temperature shipping in several tube types (FIGS. 26A-26C). Blood stored in EDTA tubes, the gold standard used by prior C-RNA studies, exhibited a reduction in the abundance of pregnancy-associated transcripts and overall instability of the transcriptomic profile (Qin et al., 2013, *BMC Research Notes;* 6:380). In contrast, the predominant tube type used for Non-Invasive Prenatal Testing (NIPT), Cell-Free DNA BCT (Streck), retained the signal from placental transcripts and had improved technical reproducibility (FIG. 26B) (Medina Diaz et al., 2016, *PLoS ONE;* 11:e0166354).

Figure 27B:
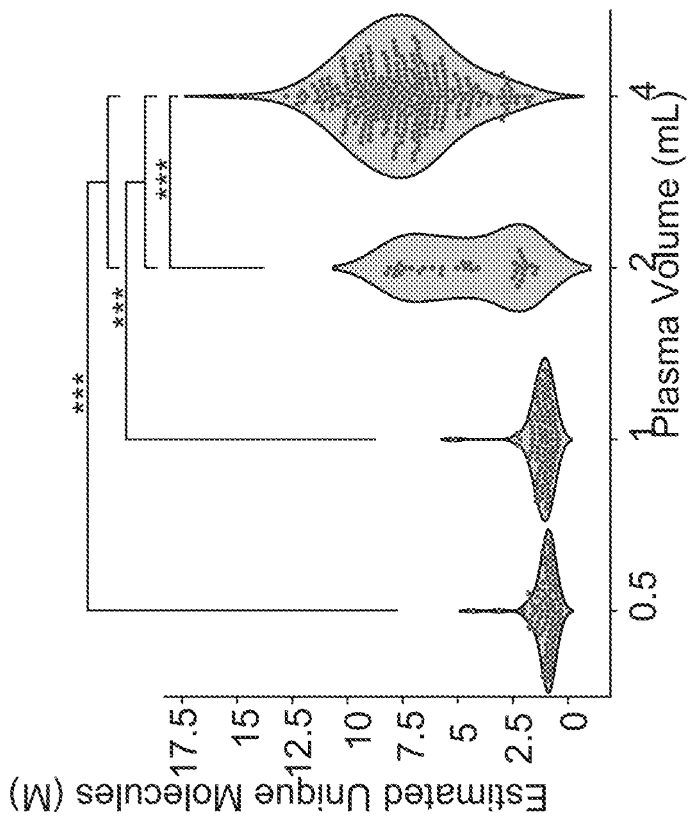
FIGS. 27A and 27B. The effect of plasma volume on C-RNA data quality. A meta-analysis was performed with data from nine independent studies to determine the appropriate plasma input for the protocol. Noise (biological coefficient of variation, EdgeR) was calculated from biological replicates within each study (FIG. 27A). Library complexity (bound population, Preseq) was calculated for each sample (FIG. 27B).  $p<0.01$, * $p<0.001$ by ANOVA with Tukey's HSD correction, with study as a blocking variable.
Figure 27A:
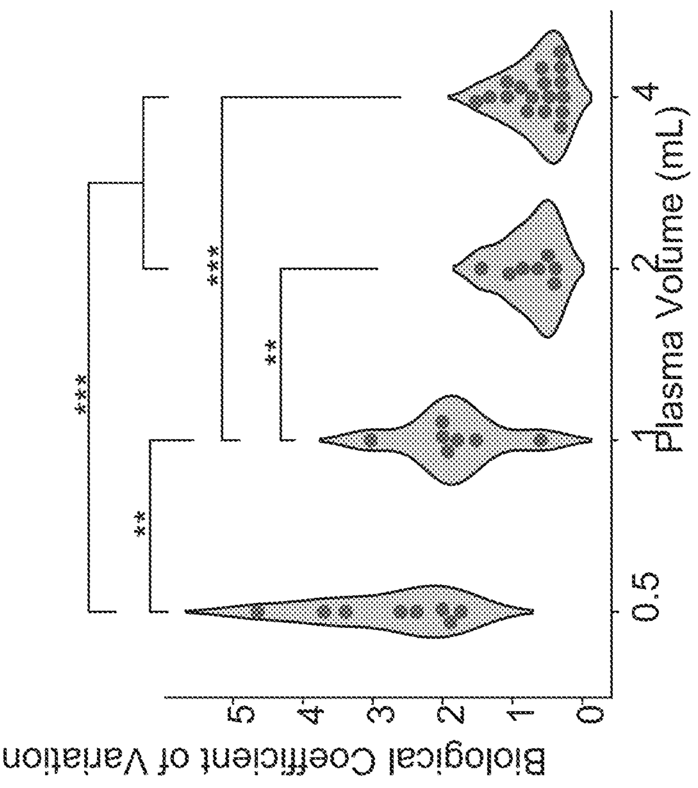
Figure 28A:
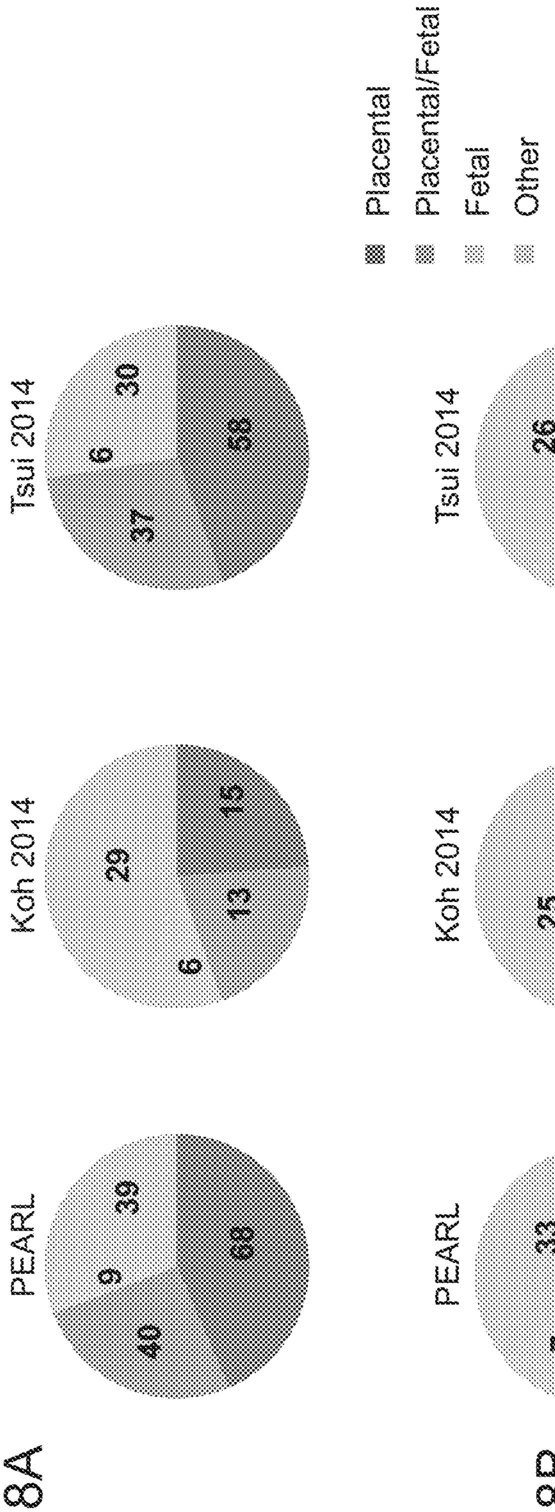
FIGS. 28A-28C. Pregnancy marker tissue specificity. Pie charts showing tissue specificity of the genes detected in pregnancy by three independent studies, using either the full set of altered genes (FIG. 28A), the transcripts unique to each study (FIG. 28B), or intersecting gene sets (FIG. 28C).
Figure 28B:
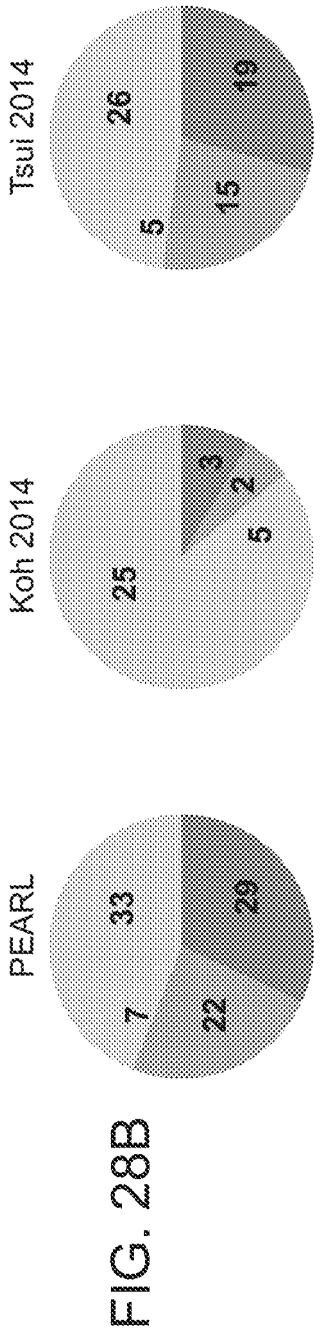
Figure 28C:
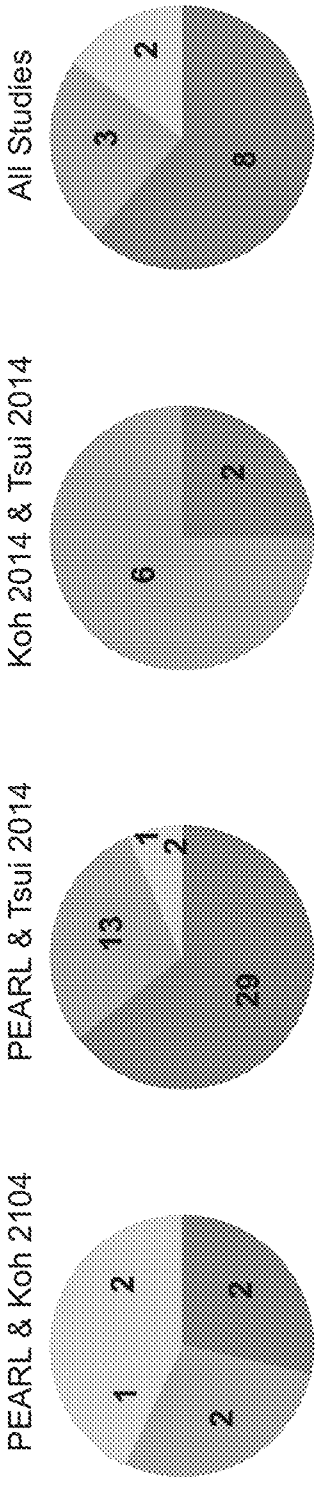

Shipment of blood allowed us to easily obtain an average of 5 mL plasma per patient from a single tube of blood. The difference in C-RNA data quality was assessed when using varying plasma volumes and determined that using <2 mL plasma significantly increased noise and decreased library complexity (FIGS. 27A and 27B). Thus 4 mL of plasma was used for the studies of this example to maximize confidence in data quality.

This novel workflow was validated by recapitulating previous work monitoring C-RNA dynamics of >10,000 transcripts per healthy pregnancy from first to third trimester. Using 152 samples collected serially from 45 healthy pregnancies (Pre-Eclampsia and Growth Restriction Longitudinal Study Control Cohort—PEARL; NCT02379832; Table 5), 156 significantly altered transcripts were identified, with the majority increasing in abundance as pregnancy progresses (FIG. 22B). 42% of the altered genes were identified in prior C-RNA studies (FIG. 22C) (Koh et al., 2014, *Proceedings of the National Academy of Sciences;* 111:7361-7366; and Tsui et al., 2014, *Clinical Chemistry;* 60:954-962). Of the 91 transcripts identified only in this study, 64% are expressed by placental and/or fetal tissues (FIGS. 22D and 28A-28C). Presumably, the remaining genes reflect the maternal response to pregnancy.

Study Design

For the next phase of investigation, the workflow was applied on clinical samples to measure C-RNA changes in PE (iPC, Illumina Preeclampsia Cohort). PE is a heterogeneous disorder and associated with different severity and patient outcomes based on whether it manifests before (early-onset) or after (late-onset) 34 gestational weeks (Staff et al., 2013, *Hypertension;* 61:932-942; Chaiworapongsa et al., 2014, *Nature Reviews Nephrology;* 10, 466-4803; and Dadelszen et al., 2003, *Hypertension in Pregnancy;* 22:143-148). This study to focused on the more severe early-onset form of PE and defined strict diagnostic criteria with clear inclusion and exclusion requirements—most critically excluding any individuals with a history of chronic hypertension—in order to obtain a clean cohort (Table 6) (Nakanishi et al., 2017, *Pregnancy Hypertension;* 7:39-43; and Hiltunen et al., 2017, *PLoS ONE;* 12:e0187729). Maternal characteristics, pregnancy outcomes, and medications in use were recorded throughout the study (Table 7). 113 samples were collected across 8 sites (Table 8), 40 at the time of PE diagnosis, and 73 controls gestationally-age matched within 1 week (FIG. 23A). All but one woman with PE gave birth prematurely, in contrast to 9.5% of controls, confirming these diagnostic criteria as identifying individuals severely impacted by this disease (FIG. 23C).

Figures 24A, 24B, 24C, 24D, 24E, 24F, 24G:
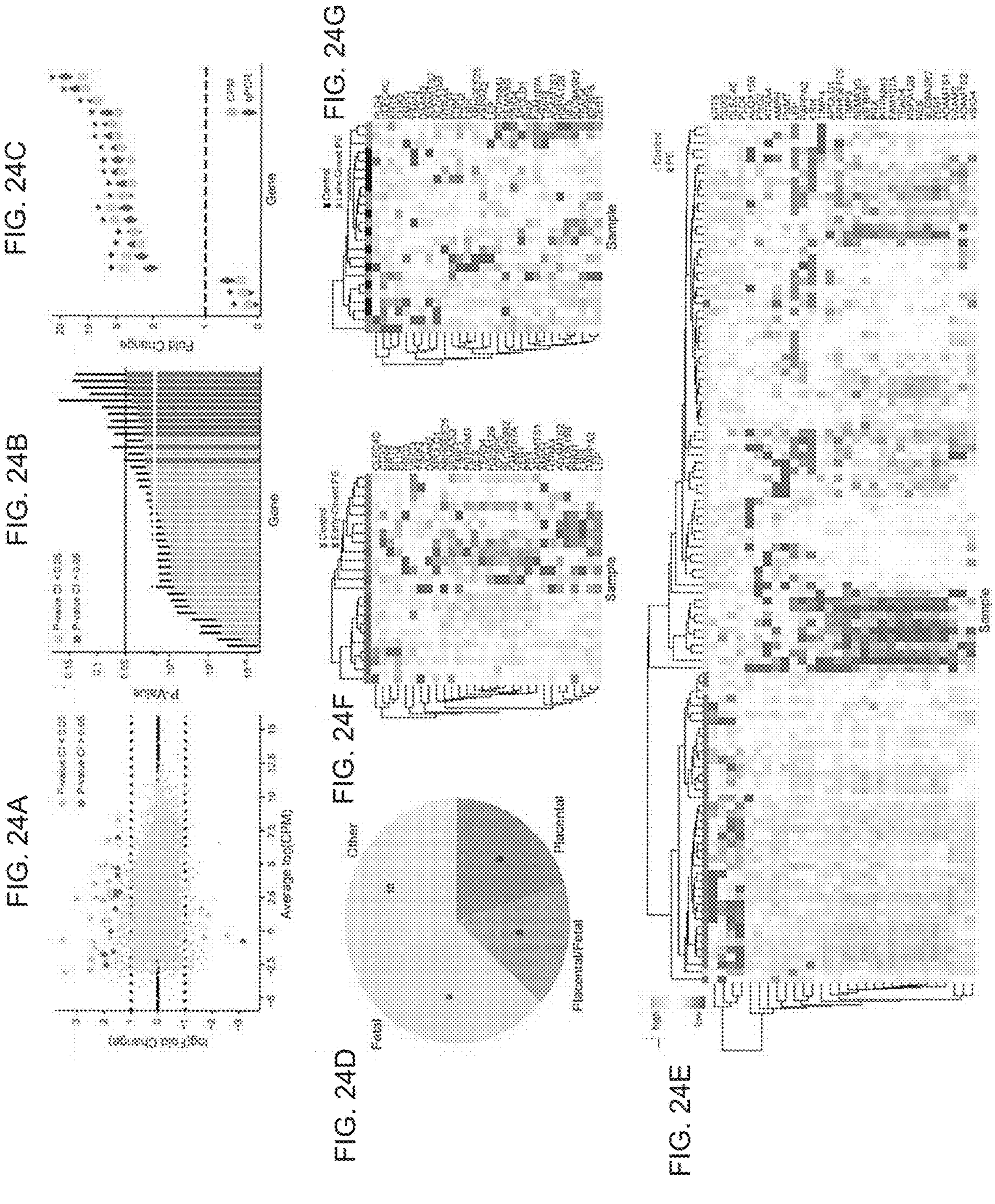
FIGS. 24A-24G. Differential analysis of C-RNA identifies preeclampsia biomarkers. Fold change and abundance of transcripts altered in PE (FIG. 24A). One-sided confidence p-value intervals were calculated after jackknifing for each gene detected by standard analysis methods (FIG. 24B). Transcript abundance fold-change determined by whole exome sequencing and by qPCR for (21) genes (FIG. 24C). * $p<0.05$ by Student's T-test. Tissue distribution of affected genes (FIG. 24D). Hierarchical clustering of iPC samples (average linkage, squared Euclidean distance) (FIG. 24E). Clustering of early-onset PE (FIG. 24F) and late-onset PE (FIG. 24G) samples from the PEARL study.

All samples were randomly distributed across multiple processing batches, then sequenced to ≥40 M reads. Standard differential expression analysis using the full cohort identified 42 altered transcripts, with 37 increased in PE (FIG. 24A, blue and orange). However, of concern was the high variability observed in the genes detected as altered when different subsets of controls were selected for analysis.

Figure 29A:
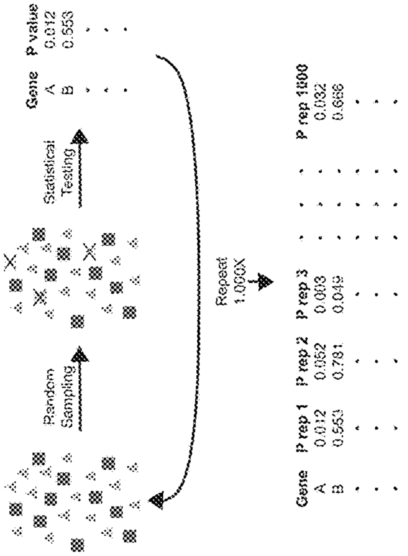
FIGS. 29A-29E. Jackknifing excludes genes that are not universally altered in preeclampsia. Schematic of the jackknifing approach used to determine how consistently transcripts were altered across PE samples (FIG. 29A). Average abundance and noise for each differentially abundant gene (FIG. 29B). ROC area under the curve values for each affected transcript provide a measure of how separated C-RNA transcript abundance distributions are for control and PE samples (FIG. 29C). * $p<0.05$ by Mann-Whitney U test. Hierarchical clustering of iPC samples using the genes excluded after jackknifing (FIG. 29D). Tissue distribution of excluded transcripts (FIG. 29E). The decreased contribution of the fetus and placenta may suggest the maternal component of PE is most variable between individuals.
Figure 29B:
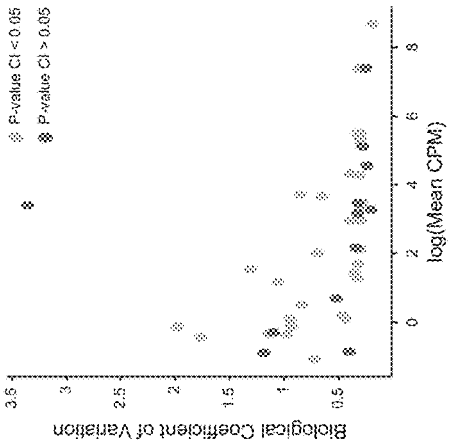
Figure 29C:
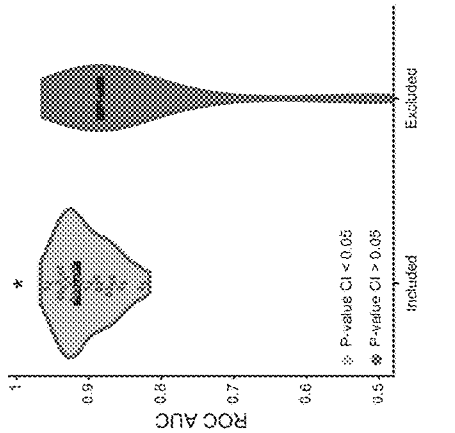
Figure 29D:
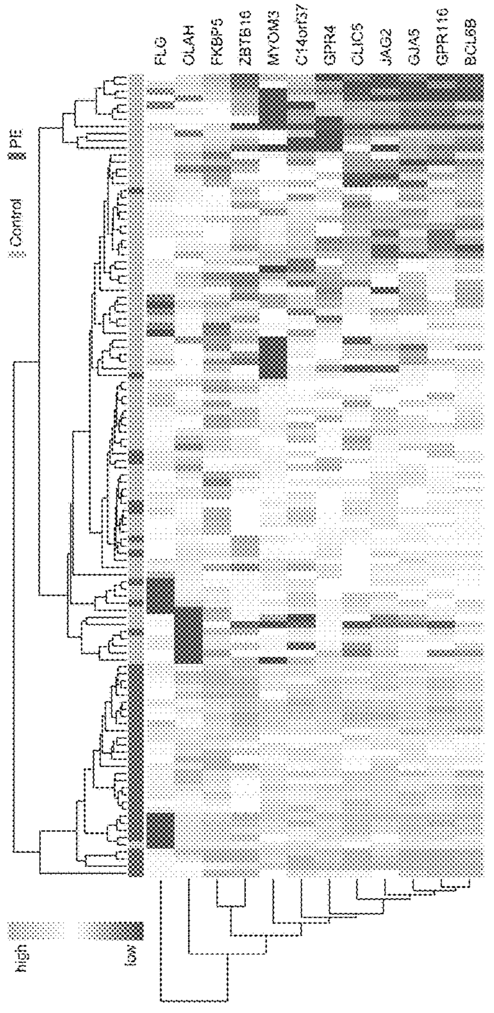
Figure 29E:
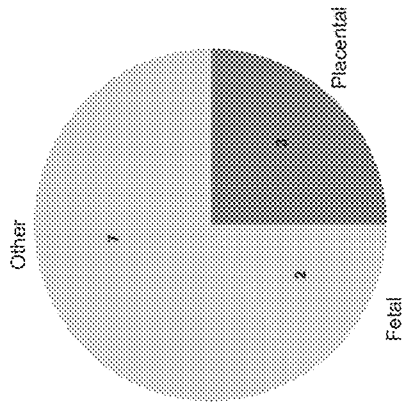
Figures 30A, 30B, 30C, 30D:
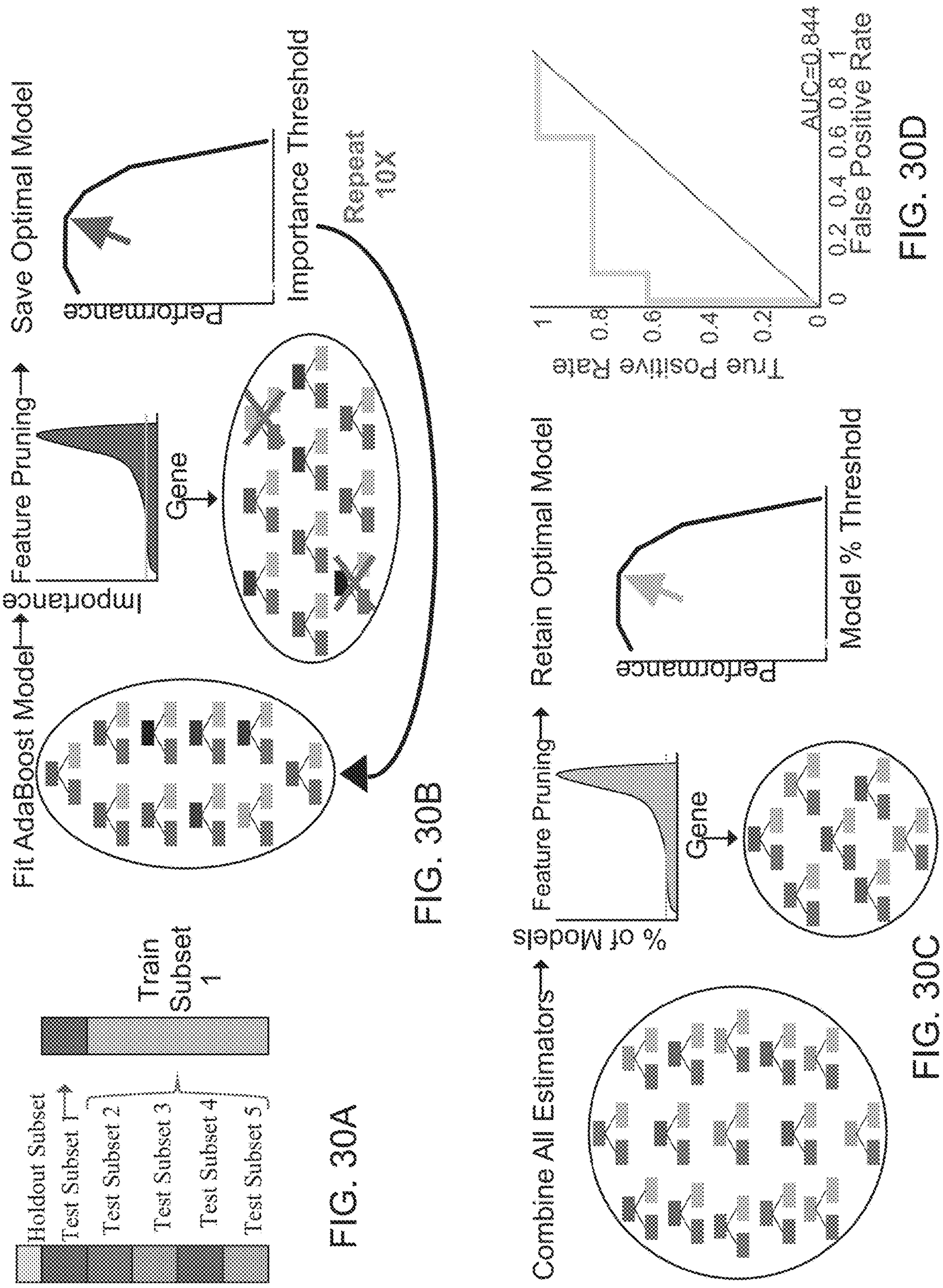
FIGS. 30A-30D. AdaBoost model development strategy. The RGH014 dataset was divided into 6 pieces (FIG. 30A). The "Holdout Subset" contained 10% of the samples (randomly selected) as well as the 3 samples which were incorrectly clustered when using differentially abundant genes (as with FIG. 24C) and was fully excluded from model building. The remaining samples were divided at random into 5 evenly sized "Test Subsets." For each test subset, training data was composed of all non-holdout and non-testing samples. Gene counts for training and testing data were TMM-normalized in edgeR, and then standardized to mean 0 and standard deviation 1 for each gene. For each train/test sample set, AdaBoost models (90 estimators, 1.6 learning rate) were built 10 times from the training data (FIG. 30B). Feature pruning was performed, removing genes below an incrementally increasing importance threshold and assessing performance by Matthew's correlation coefficient when predicting testing data. The model with the best performance—and fewest genes, in the case of a tie—was retained. Estimators from all 50 independent models were combined into a single AdaBoost model (FIG. 30C). Feature pruning was performed on the resulting ensemble, this time using the percent of models which used a gene to set threshold values and performance measured by average log loss value across test subsets. ROC curve after applying the final AdaBoost model to the holdout data (FIG. 30D). All samples segregated correctly, except for two of the three samples which also misclustered by HCA.
Figure 31A:
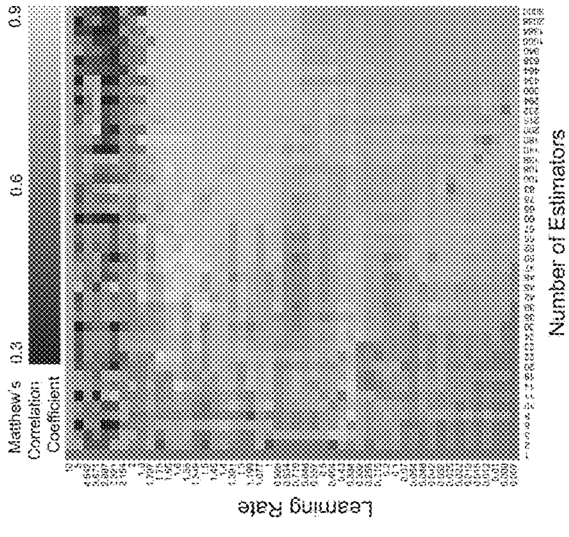
FIGS. 31A-31E. The effect of hyperparameter selection and feature pruning on machine learning performance. Heatmap of a grid search to identify the optimal hyperparameters for AdaBoost (FIG. 31A). Matthew's correlation coefficient was used as a measure of performance. Flattened views of performance for each hyperparameter (FIG. 31B). Arrows indicate the values selected for model construction.
Figure 31B:
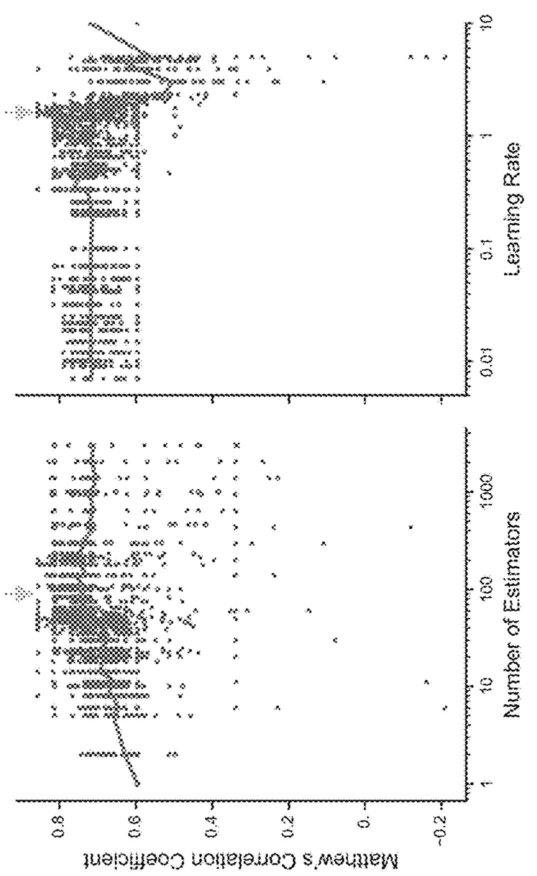
Figure 31C:
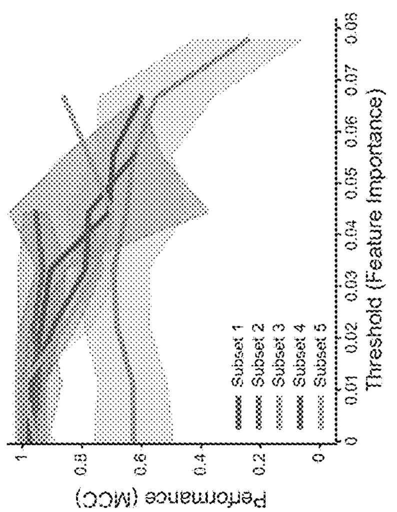
Figure 31D:
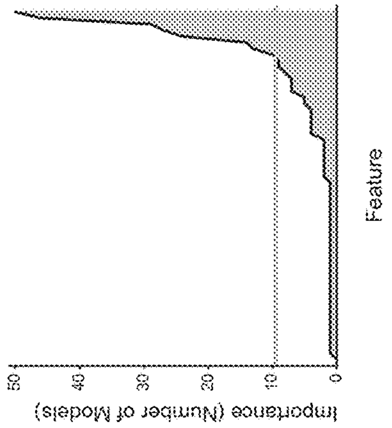
Figure 31E:
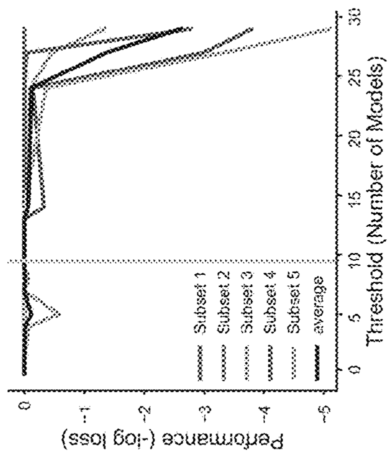

To address this discrepancy, a jackknifing approach was incorporated which allowed the identification of the genes that are most consistently altered (FIGS. 24A and 24B, orange). 1,000 iterations of differential analysis with randomly selected sample subsets were performed, which allowed the construction of confidence intervals for the p-values associated with each putatively altered transcript (FIG. 29A). 12 genes whose confidence interval exceeded 0.05 were excluded (FIG. 24B). These genes would not have been excluded by simply setting a threshold for baseline abundance or biological variance (FIG. 29B), however it was observed that these transcripts have lower predictive value (FIG. 29C). Hierarchical clustering indicates these genes are not altered universally in the PE cohort, and thus lack sensitivity (73%) for accurate classification of this condition (FIG. 29D).

The analysis then focused on the refined 30 gene set, 60% of which have previously been associated with PE (Namli et al., 2018, *Hypertension in Pregnancy;* 37: 9-17; Than et al., 2018, *Frontiers in Immunology;* 9:1661; Kramer et al., 2016, *Placenta;* 37:19-25; Winn et al., 2008, *Endocrinology;* 150:452-462; and Liu et al., 2018, *Molecular Medicine Reports;* 18:2937-2944). qPCR analysis confirmed 19 of 20 genes as significantly altered in PE (FIG. 24C, Table 9). Strikingly, 40% of these genes encode for extracellular or secreted protein products. Additionally, nearly all genes are involved in PE relevant processes, including extracellular matrix (ECM) remodeling, pregnancy duration, placental/fetal development, angiogenesis, and hypoxia response (Table 10). 67% of these transcripts were expressed by the placenta and/or fetus (FIG. 24D). In the remaining maternally expressed transcripts, cardiovascular and immune functions were well represented (Table 10). Hierarchical clustering of these genes effectively segregated PE and control samples with 98% sensitivity and 97% specificity (FIG. 24E). Intriguingly, clinical data for the two misidentified controls indicated potentially confounding health problems, as suggested by their use of hypertensive medication (Table 7).

Using the genes identified in iPC, the ability to cluster a cohort of samples obtained from an independent biobank was assessed—the Pre-Eclampsia and Growth Restriction Longitudinal Study (PEARL; NCT02379832; FIGS. 23B and 23C, Table 11). This cohort consisted of both early-(diagnosed at <34 weeks); and late-onset PE with gestationally age-matched controls. Early-onset PE samples clustered separately from matched controls with 83% sensitivity and 92% specificity, further validating the relevance of these transcripts (FIG. 24F). In contrast, no clustering was observed for the late-onset PE and matched control samples (FIG. 24G).

Figures 25A, 25B, 25C, 25D, 25E:
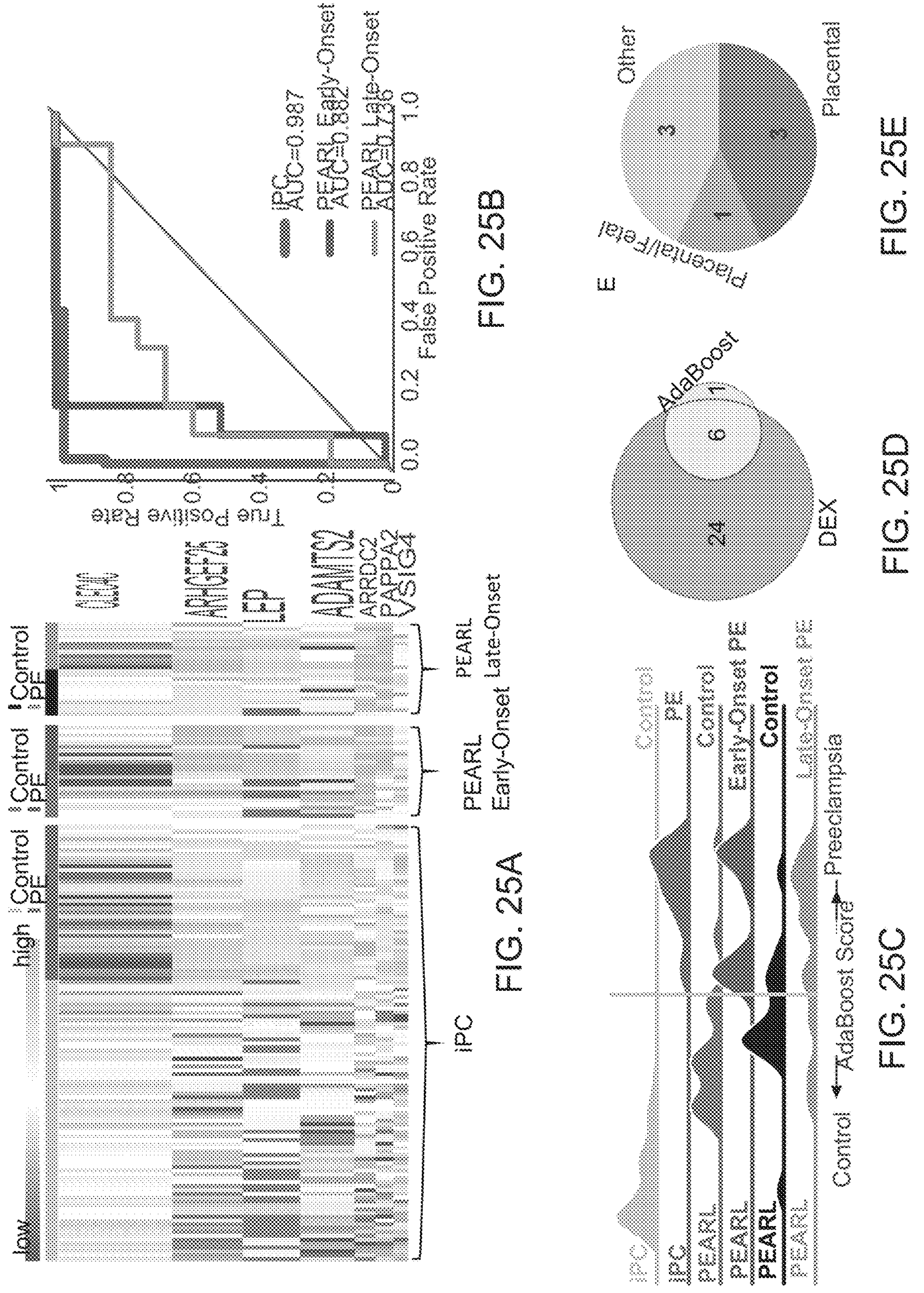
FIGS. 25A-25E. AdaBoost classifies preeclampsia samples across cohorts. Heatmap illustrating the relative abundance of the transcripts used by machine learning in each cohort (FIG. 25A). The height of each block reflects each gene's importance. ROC curves for each dataset (FIG. 25B). Distributions (KDE) of AdaBoost Scores. The orange line indicates the optimal boundary to discriminate PE and control samples (FIG. 25C). Concordance of genes identified by differential analysis and those used in AdaBoost (FIG. 25D). Tissue distribution of AdaBoost genes (FIG. 25E).

The iPC data was then used to build an AdaBoost model for robust classification of PE samples. In order to create a generalized machine learning model that could accurately predict new samples, a rigorous approach was used that avoided overfitting to a single dataset and validated the final classifier with samples not used for model building (FIGS. 30A-30D and FIGS. 31A-31E). Surprisingly, the final model only utilized 7 genes, 3 of which have not been previously reported (FIG. 25A). For the entire iPC cohort, this model classified samples with extremely high accuracy (AUC=0.99, sensitivity=98%, specificity=99%; FIGS. 25B and 25C, blue). Early-onset PE PEARL samples were also accurately classified (AUC=0.88, sensitivity=100%, specificity=83%; FIGS. 25B and 25C, pink). Unexpectedly, late-onset PE PEARL samples were also classified with reasonable accuracy (AUC=0.74, sensitivity=75%, specificity=67%; FIGS. 25B and 25C, green).

This gene set was highly concordant with transcripts identified by differential abundance analysis (FIG. 25D; Table 10). The classifier relied on both placentally and maternally expressed transcripts (FIG. 25E). All genes used by the model form protein products that are either extracellular or membrane bound. Despite the small number of genes selected by AdaBoost, a diversity of PE-relevant functions was observed, specifically cardiovascular function and angiogenesis, immune regulation, fetal development, and ECM remodeling.

Methods

Prospective Clinical Sample Collection. Pregnant patients were recruited in an Illumina sponsored clinical study protocol in compliance with the International Conference on Harmonization for Good Clinical Practice. Following informed consent, 20 mL whole blood samples were collected from 40 pregnant women with a diagnosis of preeclampsia before 34 weeks gestation with severe features defined per ACOG guidelines (Table 6). Samples from 76 healthy pregnancies were also collected and were matched for gestational age to the preeclampsia group. Three control samples developed term preeclampsia after blood collection and were excluded from data analysis. For detailed inclusion and exclusion criteria, see Table 6. Patient clinical history, treatment and birth outcome information were also recorded (Table 7).

Patients were recruited across 8 different clinical sites, including University of Texas Medical Branch (Galveston, Tex.), Tufts Medical Center (Boston, Mass.), Columbia University Irving Medical Center (New York, N.Y.), Winthrop University Hospital (Mineola, N.Y.), St. Peter's University Hospital (New Brunswick, N.J.), Christiana Care (Newark, Del.), Rutgers University Robert Wood Johnson Medical School (New Brunswick, N.J.) and New York Presbyterian/Queens (New York, N.Y.). The clinical protocol and informed consent were approved by each clinical site's Institutional Review Board. See Table 8 for patient distribution across clinical sites.

PEARL Validation Cohort Study Design. Illumina obtained plasma samples from the Preeclampsia and Growth Restriction Longitudinal study (PEARL; NCT02379832) to be used as an independent validation cohort. Plasma samples were obtained after the study had reached completion. PEARL samples were collected at the Centre hospitalier universitaire de Québec (CHU de Québec) with principal investigator Emmanual Buj old, MD, MSc. A group of 45 control pregnancies and 45 case pregnancies were recruited in this study and written informed consent was obtained for all patients. Only participants above 18 years of age were eligible, and all pregnancies were singleton.

Preeclampsia Group. The criteria for preeclampsia was defined based on the Society of Obstetricians and Gynecologists of Canada (SOGC) June 2014 criteria for preeclampsia, with a gestational age requirement between 20 and 41 weeks. A blood sample was taken once at the time of diagnosis.

Control Group. 45 pregnant women who were expected to have a normal pregnancy were recruited between 11 and 13 weeks gestational age. Each enrolled patient was followed longitudinally with blood drawn at 4 timepoints throughout pregnancy until birth. The control women were divided into three subgroups and subsequent follow up blood draws were staggered to cover the entire range of gestational ages throughout pregnancy (Table 5).

The PEARL control samples were used for two purposes. 153 longitudinal samples from 45 individual women were used to monitor placental dynamics throughout pregnancy. Additionally, control samples were selected for comparison to the preeclampsia cohort, which were matched for gestational age and used to validate the model.

Study Sample Processing. All samples from the Illumina prospective collection and the PEARL samples were processed identically by investigators blinded to disease status. Two tubes of blood were collected per patient in Cell-Free DNA BCT tubes (Streck) following the manufacturer instructions. Blood samples were stored and shipped at room temperature overnight and processed within 72 hours. Blood was centrifuged at 1,600×g for 20 minutes at room temperature, plasma transferred to a new tube and centrifuged additional 10 minutes at 16,000×g to remove residual cells. Plasma was stored at −80° C. until use. Circulating RNA was extracted from 4.5 mL of plasma using the Circulating Nucleic Acid Kit (Qiagen) followed by DNAse I digestion (Thermofisher) according to manufacturer's instructions.

cDNA Synthesis and Library Prep. Circulating RNA was fragmented at 94° C. for 8 minutes followed by random hexamer primed cDNA synthesis using the Illumina TruSight Tumor 170 Library Prep kit (Illumina). Illumina sequencing library prep was carried out according to TST170 Tumor Library Prep Kit for RNA, with the following modifications to accommodate low RNA inputs. All reactions were reduced to 25% of original volume and the ligation adaptor was used at 1 in 10 dilution. Library quality was assessed using High Sensitivity DNA Analysis kits on the Agilent Bioanalzyer 2100 (Agilent).

Whole Exome Enrichment. Sequencing libraries were quantified using Quant-iT PicoGreen dsDNA Kit (ThermoFisher Scientific), normalized to 200 ng input and pooled to 4 samples per enrichment reaction. Whole exome enrichment was carried out according to the TruSeq RNA Access Library Prep guide (Illumina). Additional blocking oligos lacking the 5' biotin designed against hemoglobin genes HBA1, HBA2, and HBB were included in the enrichment reaction to reduce enrichment of these genes in the sequencing libraries. Final enrichment libraries were quantified using Quant-IT Picogreen dsDNA Kit (ThermoFisher Scientific), normalized and pooled for paired end 50 by 50 sequencing on Illumina HiSeq 2000 platforms to a minimum depth of 40 million reads per sample.

Data Analysis. Unless otherwise noted, all statistical testing was two-sided. Non-parametric testing was used when data were not normally distributed. Sequencing reads were mapped to human reference genome (hg19) with tophat (v2.0.13), and transcript abundance quantified with featureCounts (subread-1.4.6) against RefGene coordinates (obtained Oct. 27, 2014). Tissue expression data were obtained from Body Atlas (CorrelationEngine, BaseSpace, Illumina, Inc) (Kupershmidt, et al., 2010, PLoS ONE 5; 10.1371/journal.pone.0013066). vGenes with expression ≥2-fold higher than the median expression across all tissues in the placenta or any of the fetal tissues (brain, liver, lung, and thyroid) were assigned to that group. Subcellular localization was obtained from UniProt.

Differential expression analysis was performed in R (v3.4.2) with edgeR (v3.20.9), after exclusion of genes with a CPM ≤0.5 in <25% of samples. The dataset was normalized by the TMM method, and differentially abundant genes identified by the glmTreat test for a log fold change ≥1 followed by Bonferroni-Holm p-value correction. The same process was used for each jackknifing iteration, using 90% of samples in each group selected by random sampling without replacement. After 1,000 jackknifing iterations, the one-sided 95% confidence interval for gene-wise p-values was calculated with statsmodels (v0.8.0). Hierarchical clustering analysis was performed with squared Euclidean distance and average linkage.

AdaBoost was performed in python with scikit-learn (v0.19.1, sklearn.ensemble. AdaBoostClassifier). Optimal hyperparameter values (90 estimators, 1.6 learning rate) were determined by grid search, using Matthew's correlation coefficient to quantify performance. The overall AdaBoost model development strategy is illustrated in FIGS. 31A-31E. Datasets (TMM-normalized log CPM values of genes with a CPM ≤0.5 in <25% of samples) were standardized (sklearn.preprocessing. StandardScaler) prior to fitting classifiers. The same scaler fit on training data was applied to the corresponding testing dataset; all 5 scalers for the 5 training datasets were averaged for use with the final model. The decision function score was used to construct ROC curves and determine sample classification.

RT-qPCR validation assay and analysis. C-RNA was isolated and converted to cDNA from 2mls of plasma from 19 Preeclampsia (PE) and 19 matched control samples, which were selected randomly. The cDNA was pre-amplified using the TaqMan Preamp master Mix (cat: 4488593) for 16 cycles and diluted 10-fold to a final volume of 500 μL. For qPCR, the reaction mixture contained 54, of diluted pre-amplified cDNA, 104, of TaqMan gene expression master mix (cat: 4369542), 1 μL of TaqMan Probe, and 44, of water using the manufacturer's instructions. For each TaqMan probe (Table 9), three qPCR reactions were carried out per diluted cDNA sample and the Cq values were determined using Bio-Rad CFX manager software. To determine gene abundance for each target gene, the $\Delta\Delta Cq = 2^{\wedge}-(\text{target } Cq - \text{ref } Cq_{avg})$ was calculated using the mean Cq values between five reference gene probes (ref $Cq_{avg}$). To determine the fold change (PE/CTRL) for each probe, the ΔΔCq values for each sample was divided by the average ΔΔCq value for the matched control group.

Tube type study. To assess the effects of tube type and overnight shipping on circulating RNA quality, blood was drawn from pregnant and non-pregnant females in the following tube types: K2 EDTA (Beckton Dickinson), ACD (Beckton Dickinson), Cell Free RNA BCT tube (Streck), and 1 Cell Free DNA BCT tube (Streck). 8 mL of blood was drawn into each tube and shipped overnight either on ice packs (EDTA and ACD) or shipped at room temperature (Cell Free RNA and DNA BCT tubes). All shipped blood tubes were processed into plasma within 24 hours of the blood draw. As a reference, 8 mL of blood was also drawn into K2 EDTA tubes and processed within 4 hours into plasma on site and shipped as plasma on dry ice. All plasma processing and circulating RNA extraction was carried out as described in the methods section. 3 mL of plasma was used per condition to generate sequencing libraries for enrichment using Illumina protocols as described.

Reproducibility Study. Plasma was obtained from 10 individuals and split into 4 mL, 1 mL, and 0.5 mL volumes, with 3 replicates for each volume. Circulating RNA extraction (Qiagen Circulating Nucleic Acid Kit) and random primed cDNA synthesis were carried out on all samples as previously described. For libraries using 4.5 mL plasma inputs, sequencing libraries were generated using the TST170 Tumor Library Prep Kit as described above. For 1 mL and 0.5 mL inputs, the Accel-NGS 1S Plus DNA Library Kit (Swift Biosciences) was used to generate libraries. Whole exome enrichment and sequencing was carried out on all samples using as described above.

Discussion

This study focused on identifying differences that are universal to early-onset PE, supporting the ultimate goal of clinically actionable biomarker discovery. This required tailoring the analysis methods to account for the variability observed in the data. This variance stems from both the substantial biological noise in C-RNA measurements as well as the phenotypic diversity of PE. C-RNA is inherently more variable than single tissue transcriptomics because it represents a combination of cell death, signaling, and gene expression across all organs. Furthermore, PE exhibits a wide range of maternal and fetal outcomes which may be associated with different underlying molecular causes. While the genes that were eliminated may be biologically relevant in PE, they were not universal in the cohort. Interestingly, the excluded transcripts were elevated in specific women, who may represent a molecular subset of PE.

Larger cohorts will help elucidate if C-RNA can delineate PE subtypes, which is crucial to understanding the diverse pathophysiology of this condition.

The most universal set of transcripts was identified by AdaBoost. The success of this method was underscored by highly accurate classification of an independent early-onset PE cohort (PEARL). These samples were collected from a different population with significantly relaxed inclusion and exclusion criteria, for instance including women in the control group who had chronic hypertension, gestational diabetes, or Alport syndrome—none of which were misidentified as having PE. In contrast to hierarchical clustering, 17 of 24 individuals from the late-onset PE cohort were correctly classified by machine learning model of this example, surprising given the suggestion that early- and late-onset PE are distinct conditions. The findings of this example suggest there may be some pathways universally altered in all PE.

In every assessment, C-RNA revealed changes in placental, fetal, and maternally expressed transcripts. One of the most striking trends observed in PE samples was the increased abundance of myriad ECM remodeling and cell migration/invasion proteins (FAM107A, SLC9A3R2, TIMP4, ADAMTS1, PRG2, TIMP3, LEP, ADAMTS2, ZEB1, HSPA12B), tracking with dysfunctional extravillous trophoblast invasion and remodeling of maternal vessels characteristic in this disease. The maternal side of early-onset PE manifests as cardiovascular dysfunction, inflammation, and preterm birth (PNMT, ZEB1, CRH), all of which show molecular signs of aberrant behavior in the data of this example.

TABLE 5

PEARL Control Cohort Gestational Age Distribution for 45 healthy pregnancies

| Control Groups | Recruitment | Follow up visit #1 | Follow up visit #2 | Follow up visit #3 |
|---|---|---|---|---|
| Group 1 (n = 15) | $11^{0/7}$-$13^{6/7}$ weeks | $14^{0/7}$-$17^{6/7}$ weeks | $26^{0/7}$-$28^{6/7}$ weeks | $35^{0/7}$-$37^{6/7}$ weeks |
| Group 2 (n = 15) | $11^{0/7}$-$13^{6/7}$ weeks | $18^{0/7}$-$21^{6/7}$ weeks | $29^{0/7}$-$31^{6/7}$ weeks | $35^{0/7}$-$37^{6/7}$ weeks |
| Group 3 (n = 15) | $11^{0/7}$-$13^{6/7}$ weeks | $22^{0/7}$-$25^{6/7}$ weeks | $32^{0/7}$-$34^{6/7}$ weeks | $35^{0/7}$-$37^{6/7}$ weeks |

TABLE 6

Diagnostic Criteria for Preeclampsia with Severe Features and Inclusion/Exclusion Criteria

| | |
|---|---|
| Blood Pressure | 1) Systolic BP ≥160 mmHG or diastolic BP ≥110 mmHg measured on at least 2 occasions 4 hours apart while on bedrest but before the onset of labor or measured on 1 occasion only, if antihypertensive therapy is initiated due to severe hypertension |
| | Measured by one of the following: |
| Proteinuria | 1) Excretion of ≥300 mg of protein in a 24 hr period |
| | 2) Protein/creatinine value of at least 0.3 |
| | 3) qualitative determination with urine dipstick of ≥1+ |
| | OR |
| Blood Pressure | 1) Systolic BP ≥140 mmHg or diastolic ≥90 mmHG |
| With one of the following features | 1) Thombocytopenia (<100,000 platelets/mL) |
| | 2) Impaired liver function |
| | 3) Newly developed renal insufficiency |

TABLE 6-continued

| Diagnostic Criteria for Preeclampsia with Severe Features and Inclusion/Exclusion Criteria |
|---|
| 4) Pulmonary edema<br>5) New onset cerebral disturbances or scotomata |

| Preeclampsia Cohort | |
|---|---|
| Inclusion Criteria | Exclusion Criteria |
| 1. Women 18 years of age or older<br>2. Pregnant women with a viable singleton gestation<br>3. Gestational age between 20 0/7 and 33 6/7 weeks determined by ultrasound and/or LMP per ACOG guidelines.<br>4. Preeclampsia diagnosed with severe features per ACOG guidelines | 1. Known Malignancy<br>2. History of maternal organ or bone marrow transp1ant<br>3. Maternal blood transfusion in the last 8 weeks<br>4. Chronic Hypertension diagnosed prior to current pregnancy<br>5. Type I, II or gestational diabetes<br>6. Fetal anomaly or known chromosome abnonnality<br>7. Active Labor |

| Control Cohort | |
|---|---|
| Inclusion Criteria | Exclusion Criteria |
| 1. Women 18 years of age or older<br>2. Pregnant women with a viable singleton gestation<br>3. Gestational age between 20 0/7 and 33 6/7 weeks determined by ultrasound and/or LMP per ACOG guidelines. | 1. Known Malignancy<br>2. History of maternal organ or bone marrow transp1ant<br>3. Maternal blood transfusion in the last 8 weeks<br>4. Chronic Hypertension diagnosed prior to current pregnancy<br>5. Type I, II or gestational diabetes<br>6. Fetal anomaly or known chromosome abnormality<br>7. Active Labor<br>8. Thrombocytopenia (<100,000 plts/mL)<br>9. Impaired liver function<br>10. Newly developed renal insufficiency (serum creatine >1.1 mg/dL)<br>11. Pulmonary edema<br>12. New Onset cerebral disturbances or scotomata<br>13. Preeclampsia in prior or current pregnancy<br>14. Fetal growth restriction |

TABLE 7

| Study characteristics for Illumina Preeclampsia Cohort | | | |
|---|---|---|---|
| | | Early Onset PE Cohort | Control Cohort |
| Sample Size | | n = 40 | n = 73 |
| Gestational Age at Sample Collection (weeks · days) | | 30.5 (+/−2.6) | 30.5 (+/−2.6) |
| Maternal Characteristics | | | |
| Ethnicity | (% Hispanic) | 35% (n = 14) | 41.1% (n = 30) |
| Race | % Caucasian | 35% (n = 14) | 46.6% (n = 34) |
| | % African American | 27.5% (n = 11) | 17.8% (n = 13) |
| | % Asian | 7.5% (n = 3) | 13.7% (n = 10) |
| | % Unknown | 30% (n = 12) | 20.5% (n = 15) |
| | % Other | 0.0% | 1.4% (n = 1) |
| Maternal Age (years, mean +/− SD) | | 30.4 (+/−5.7) | 29.7 (+/−5.3) |
| Maternal BMI (kg/m2, mean +/− SD) | | 34.2 (+/−5.8) | 30.1 (+/−5.6) |
| Gravida (% Nulliparous) | | 32.5% (n = 13) | 38.4% (n = 28) |
| Chronic Hypertension | | 0% (n = 0) | 0% (n = 0) |
| Type I, II Diabetes | | 0% (n = 0) | 0% (n = 0) |
| Gestational Diabetes | | 0% (n = 0) | 0% (n = 0) |
| Birth Outcomes | | | |
| Gestational Age at Birth (weeks · days) | | 31.5 (+/−3.1) | 38.9 (+/−1.8) |
| Full Term | | 2.5% (n = 1) | 90.4% (n = 66) |

TABLE 7-continued

| Study characteristics for Illumina Preeclampsia Cohort | | | |
|---|---|---|---|
| | | Early Onset PE Cohort | Control Cohort |
| Preterm (<37 weeks) | | 97.5% (n = 39) | 9.6% (n = 7) |
| Sex (% male) | | 37.5% (n = 15) | 42.5% (n = 31) |
| Birth Weight (kg) | | 1.4 (+/−0.52) | 3.2 (+/−0.55) |
| Small for Gestational Age* | | 45% (n = 18) | 9.6% (n = 7) |
| Stillbirth | | 2.5% (n = 1) | 0% (n = 0) |
| Medications for treatment of: | | | |
| PE/Hypertension | MgSO4 | 82.5% (n = 33) | 4.1% (n = 3) |
| | Antenatal Steroids | 95.0% (n = 38) | 6.8% (n = 5) |
| | Anti-Hypertensive | 75.0% (n = 30) | 5.3% (n = 4) |
| | Aspirin | 20.0% (n = 8) | 0% (n = 0) |
| Other Conditions | Analgesics | 60.0% (n = 24) | 11.8% (n = 9) |
| | Antimicrobials | 12.5% (n = 5) | 5.5% (n = 4) |
| | Antihistamines | 32.5% (n = 13) | 13.7% (n = 10) |
| | Asthma | 10.0% (n = 4) | 2.7% (n = 2) |
| | Psychoactive | 15.0% (n = 6) | 5.5% (n = 4) |
| | Hypothyroidism | 7.5% (n = 3) | 2.7% (n = 2) |
| | Antiemetics | 25.0% (n = 10) | 5.5% (n = 4) |
| Pregnancy | Antacids | 27.5% (n = 11) | 8.2% (n = 6) |
| Symptoms | Anti-constipation | 15.0% (n = 6) | 11.8% (n = 9) |
| | Prenatal Vitamins | 17.5% (n = 7) | 31.5% (n = 23) |
| | Iron Supplement | 10% (n = 4) | 12.3% (n = 9) |

*Defined as birthweight <10% of population for male or female fetus

TABLE 8

| Medical Center Collection Site Patient Distribution | | | |
|---|---|---|---|
| Clinical Site | Location | Number PE patients | Number of controls |
| University of Texas Medical Branch | Galveston, Texas | 4 | 11 |
| Tufts Medical Center | Boston, MA | 10 | 17 |
| Columbia University Irving Medical Center | New York, NY | 4 | 9 |
| Winthrop University Hospital | Mineola, NY | 5 | 9 |
| St. Peter's University Hospital | New Brunswick, NJ | 3 | 6 |
| Christiana Care | Newark, DE | 7 | 13 |
| Rutgers University Robert Wood Johnson Medical School | New Brunswick, NJ | 5 | 8 |
| New York Presbyterian/Queens | New York, NY | 2 | 3 |
| | Total Samples collected | 40 | 76 |

TABLE 9

| Genes validated by TaqMan qPCR | | | |
|---|---|---|---|
| Gene Name | Assay ID | Type | RefSeq |
| ABHD12 | Hs01018050_m1 | Reference | NM_001042472.2 |
| ABHD12 | Hs01018050_m1 | Target | NM_001042472.2 |
| ADAMTS2 | Hs01029111_m1 | Target | NM_014244.4 |
| ALOX15B | Hs00153988_m1 | Target | NM_001039130.1 |
| ARHGEF25 | Hs00384780_g1 | Target | NM_001111270.2 |
| ARRDC2 | Hs01006434_g1 | Target | NM_001286826.1 |
| CLEC4C | Hs01092460_m1 | Target | NM_130441.2 |
| DAAM2 | Hs00322497_m1 | Target | NM_001201427.1 |
| FAM107A | Hs00200376_m1 | Target | NM_001076778.2 |
| HSPA12B | Hs00369554_m1 | Target | NM_001197327.1 |
| HTRA4 | Hs00538137_m1 | Target | NM_153692.3 |
| IGFBP5 | Hs00181213_m1 | Target | NM_000599.3 |
| KRBOX4 | Hs01063506_gH | Reference | NM_001129898.1 |
| KRT5 | Hs00361185_m1 | Target | NM_000424.3 |
| LEP | Hs00174877_m1 | Target | NM_000230.2 |
| NES | Hs00707120_s1 | Target | NM_006617.1 |

TABLE 9-continued

| Genes validated by TaqMan qPCR | | | |
|---|---|---|---|
| Gene Name | Assay ID | Type | RefSeq |
| NME3 | Hs01573872_g1 | Reference | NM_002513.2 |
| PAPPA2 | Hs01060983_m1 | Target | NM_020318.2 |
| PITPNM3 | Hs01107787_m1 | Target | NM_001165966.1 |
| PLD4 | Hs00975488_m1 | Target | NM_001308174.1 |
| PRG2 | Hs00794928_m1 | Target | NM_001243245.2 |
| TIMP3 | Hs00165949_m1 | Target | NM_000362.4 |
| TIMP4 | Hs00162784_m1 | Target | NM_003256.3 |
| VSIG4 | Hs00907325_m1 | Target | NM_001184830.1 |
| WNT7A | Hs00171699_m1 | Reference | NM_004625.3 |
| ZEB1 | Hs01566408_m1 | Target | NM_001128128.2 |
| ZNF138 | Hs00864088_gH | Reference | NM_001271638.1 |

TABLE 10

| Gene Symbol | Analysis | Previous Literature Reports | Change in PE | Tissue Expression Category | Sub-Cellular Location | Function(s) |
|---|---|---|---|---|---|---|
| ARRDC2 | AdaBoost | No | Increase* | Other (Skeletal Muscle; Globus Pallidus; Lung) | Membrane | Protein Trafficking |
| ALOX15B | DEX | Yes | Increase | Fetal | Nucleus; Cytoskeleton; Cytosol; Membrane | Cell Cycle; Immune Function; Cardiovascular Function |
| AMPH | DEX | No | Increase | Fetal | Cytoskeleton; Membrane | Synaptic Vesicle Endocytosis |
| CUX2 | DEX | No | Decrease | Fetal | Nucleus | Cell Cycle; Fetal Development; DNA Damage Response |
| FAM107A | DEX | No | Increase | Fetal | Cytoskeleton; Membrane; Nucleus | Cell Migration/Invasion; Cell Cycle; ECM Regulation |
| IGFBP5 | DEX | Yes | Increase | Fetal | Extracellular or Secreted | Fetal Development; IGF Signaling |
| NES | DEX | Yes | Increase | Fetal | Cytoskeleton | Fetal Development; Cell Cycle |
| PITPNM3 | DEX | No | Increase | Fetal | Membrane | Phosphatidylinositol Regulation |
| PRX | DEX | Yes | Increase | Fetal | Membrane | Cell Structure/Composition |
| TEAD4 | DEX | Yes | Increase | Fetal | Nucleus | Placental Development |
| PNMT | DEX | Yes | Increase | Other (Adrenal Gland Cortex; Adrenal Gland; Skeletal Muscle Psoas) | Cytosol | Epinephrine Synthesis; Cardiovascular Function; Pregnancy Duration |
| DAAM2 | DEX | Yes | Increase | Other (Corpus Callosum; Globus Pallidum External; Nodose Nucleus) | Extracellular or Secreted | Fetal Development |
| SLC9A3R2 | DEX | No | Increase | Other (Heart Ventricle; Liver; Parotid Gland) | Membrane; Nucleus | ECM Regulation; Cell Structure/Composition |
| HSPA12B | DEX | No | Increase | Other (Heart Ventricle; Lung; Spleen) | unknown | Angiogenesis; Cardiovascular Function; Cell Migration/Invasion; Hypoxia Response |
| PLD4 | DEX | No | Decrease | Other (Nodose Nucleus; Subthalamic Nucleus; Corpus Callosum) | Membrane | Phosphatidylinositol Regulation; Immune Function |
| TIMP4 | DEX | No | Increase | Other (Omental Adipose Tissue; Subcutaneous Adipose Tissue; Joint Synovium) | Extracellular or Secreted | ECM Regulation; Immune Function |
| KRT5 | DEX | Yes | Decrease | Other (Oral Mucosa; Pharyngeal Mucosa; Esophagus) | Cytoskeleton | Cell Structure/Composition |
| ZEB1 | DEX | No | Increase | Other (Synovial Membrane; Aorta; Myometrium) | Nucleus | Immune Function; Cell Migration/Invasion; Fetal Development; Pregnancy Duration |
| APOLD1 | DEX | Yes | Increase | Placental | Plasma Membrane | Angiogenesis; Cardiovascular Function; Hypoxia Response; Fetal Development |
| HTRA4 | DEX | Yes | Increase | Placental | Extracellular or Secreted | IGF Signaling; Placental Development |
| SEMA3G | DEX | No | Increase | Placental | Extracellular or Secreted | Cell Migration/Invasion |
| ADAMTS1 | DEX | Yes | Increase | Placental/Fetal | Extracellular or Secreted | ECM Regulation; Fetal Development; Angiogenesis |
| CRH | DEX | Yes | Increase | Placental/Fetal | Extracellular or Secreted | Pregnancy Duration; Fetal Development; Cardiovascular Function |
| PRG2 | DEX | Yes | Increase | Placental/Fetal | Extracellular or Secreted | Immune Function; ECM Regulation; IGF Signaling |
| TIMP3 | DEX | Yes | Increase | Placental/Fetal | Extracellular or Secreted | ECM Regulation; Immune Function; Angiogenesis |
| ARHGEF25 | DEX & AdaBoost | No | Increase | Other (Hippocampus; Myometrium; Cerebellum) | Membrane; Sarcomere | |
| CLEC4C | DEX & AdaBoost | Yes | Decrease | Other (Rectum Colon; Ascending Colon; Substantia Nigra Reticulata) | Membrane | Immune Function |
| LEP | DEX & AdaBoost | Yes | Increase | Placental | Extracellular or Secreted | Energy Homeostasis; Immune Function; Angiogenesis; Fetal Development; ECM Regulation |
| PAPPA2 | DEX & AdaBoost | Yes | Increase | Placental | Extracellular or Secreted | Fetal Development; IGF Signaling |
| VSIG4 | DEX & AdaBoost | Yes | Increase | Placental | Membrane | Immune Function |

TABLE 10-continued

| Gene Symbol | Analysis | Previous Literature Reports | Change in PE | Tissue Expression Category | Sub-Cellular Location | Function(s) |
|---|---|---|---|---|---|---|
| ADAMTS2 | DEX & AdaBoost | No | Increase | Placental/Fetal | Extracellular or Secreted | ECM Regulation; Angiogenesis; Fetal Development |

Key
Increase* indicates the change was not statistically different
CorrelationEngine Body Atlas was used to find the 3 top tissues expressing genes in the "Other" category
UniProt was used to determine sub-cellular localization . . . as a note; I merged all "membrane" classifications to one category (so Plasma Membrane; ER Membrane; etc are not distinct)

TABLE 11

Study characteristics for Illumina Preeclampsia Cohort

| | | Early Onset PE | Early Onset Control | Late Onset PE | Late Onset Control |
|---|---|---|---|---|---|
| Sample Size | | n = 12 | n = 12 | n = 12 | n = 12 |
| Gestational Age at Sample Collection (weeks · days) | | 29.2 (+/−2.3) | 29.3 (+/−2.3) | 35.6 (+/−1.3) | 35.9 (+/−0.8) |
| Maternal Characteristics | | | | | |
| Ethnicity | (% Hispanic) | 0% (n = 0) | 0% (n = 0) | 0% (n = 0) | 0% (n = 0) |
| Race | % Caucasian | 91.7% (n = 11) | 100% (n = 12) | 100% (n = 12) | 100% (n = 12) |
| | % African | 8.3% (n = 1) | 0% (n = 0) | 0% (n = 0) | 0% (n = 0) |
| Maternal Age (years, mean +/− SD) | | 29.3 (+/−3.5) | 30.1 (+/−3.8) | 30.2 (+/−4.8) | 29.4 (+/−3.2) |
| Maternal BMI (kg/m2, mean +/− SD) | | 33.6 (+/−9.0) | 28.5 (+/−7.0) | 32.2 (+/−4.9) | 27.9 (+/−4.5) |
| Gravida (% Nulliparous) | | 60% (n = 6) | 58.3% (n = 7) | 75% (n = 9) | 75% (n = 9) |
| Chronic Hypertension | | 13.3% (n = 2) | 8.3% (n = 1) | 8.3% (n = 1) | 0% (n = 0) |
| Type I, II Diabetes | | 13.3% (n = 2) | 0% (n = 0) | 25.0% (n = 3) | 0% (n = 0) |
| Gestational Diabetes | | 13.3% (n = 2) | 33.3% (n = 4) | 8.3% (n = 1) | 16.7% (n = 2) |
| Other Health Condition | | 0% (n = 0) | 8.3% (n = 1) | 0% (n = 0) | 0% (n = 0) |
| Birth Outcomes | | | | | |
| Gestational Age at Birth (weeks · days) | | 30.3 (+/−3.4) | 39.0 (+/−1.5) | 37.0 (+/−1.4) | 39.7 (+/−1.6) |
| Full Term | | 0% (n = 0) | 91.7% (n = 11) | 75.0% (n = 9) | 91.7% (n = 11) |
| Preterm (<37 weeks) | | 100% (n = 12) | 8.3% (n = 1) | 25.0% (n = 3) | 8.3% (n = 1) |
| Sex (% male) | | 75% (n = 9) | 58.3% (n = 7) | 66.7% (n = 8) | 58.3% (n = 7) |
| Birth Weight (kg) | | 1.3 (+/−0.54) | 3.2 (+/−0.40) | 2.7 (+/−0.55) | 3.4 (+/−0.54) |
| Fetal Growth Restriction | | 50.0% (n = 6) | 0% (n = 0) | 8.3% (n = 1) | 0% (n = 0) |
| Small for Gestational Age* | | 25% (n = 3) | 0% (n = 0) | 33.3% (n = 4) | 25% (n = 3) |
| Stillbirth | | 0% (n = 0) | 0% (n = 0) | 0% (n = 0) | 0% (n = 0) |
| HELLP | | 25.0% (n = 3) | 0% (n = 0) | 0% (n = 0) | 0% (n = 0) |
| Medications for treatment of: | | | | | |
| PE/Hypertension | MgSO4 | 83.3% (n = 10) | 0% (n = 0) | 33.3% (n = 4) | 0% (n = 0) |
| | Antenatal Steroids | 100% (n = 12) | 0% (n = 0) | 25.0% (n = 3) | 0% (n = 0) |
| | Anti-Hypertensive | 100% (n = 12) | 8.3% (n = 1) | 75% (n = 9) | 0% (n = 0) |
| | Aspirin | 8.3% (n = 1) | 25.0% (n = 3) | 25.0% (n = 3) | 8.3% (n = 1) |

*Defined as birthweight <10% of population for male or female fetus

Example 7

Circulating Transcriptome Measurements from Maternal Blood Detect a Molecular Signature of Early-Onset Preeclampsia Circulating RNA (C-RNA) is continually released into the bloodstream from tissues throughout the body, offering an opportunity to non-invasively monitor all aspects of pregnancy health from conception to birth. This example determines that C-RNA analysis can detect aberrations in patients diagnosed with preeclampsia (PE), a prevalent and potentially fatal pregnancy complication. As an initial examination, the circulating transcriptome from 40 pregnancies was sequenced at the time of severe, early-onset PE diagnosis along, with 73 gestational age-matched controls. 30 transcripts consistent with the biology of PE were altered, and likely represent placental, fetal, and maternal contributions to the disease. Further, machine learning identified a combination of C-RNA transcripts which robustly classified PE patients in two independent cohorts (85%-89% accuracy). The ability of C-RNA to reflect maternal, placental and fetal health holds great promise for improving the diagnosis and identification of at-risk pregnancies. In summary, the circulating transcriptome reflects biologically relevant changes in patients with early-onset severe preeclampsia and can be used to accurately classify patient status.

Preeclampsia (PE) is one of the most common and serious complications of pregnancy, affecting an estimated 4-5% of pregnancies worldwide (Abalos et al., 2013, *Eur J Obstet Gynecol Reprod Biol;* 170:1-7; and Ananth et al., 2013, *BMJ;* 347:f6564) and is associated with substantial maternal and perinatal morbidity and mortality (Kuklina et al., 2009, *Obstet Gynecol;* 113:1299; and Basso et al., 2006, AMA; 296:1357-1362). In the United States, the incidence of PE is increasing due to advanced maternal age and the increasing prevalence of comorbid conditions such as obesity (Spradley et al., 2015, *Biomolecules;* 5:3142-3176), costing the US healthcare system an estimated 2 billion dollars annually (Stevens et al., 2017, *Am J Obstet Gynecol;* 217:237-248.e16).

PE is diagnosed as new-onset hypertension accompanied by maternal end-organ damage occurring after 20 weeks' gestation (Hypertension in Pregnancy: Executive Summary, 2013, *Obstet Gynecol;* 122:1122; and Tranquilli et al., 2014, *Pregnancy Hypertens;* 4(2): 97-104). However, there is significant heterogeneity in the presentation and progression of PE, including timing of disease onset, symptom severity, clinical manifestations, and maternal and neonatal outcomes (Lisonkova and Joseph, 2013, *Am J Obstet Gynecol;* 209: 544.e1-544.e12). PE is primarily delineated based on whether it manifests before (early-onset) or after (late-onset) 34 weeks and if it presents with severe features, such as sustained elevation in blood pressure ≥160/110 mmHg, neurological symptoms, and/or severe liver or kidney injury (American College of Obstetricians and Gynecologists, Task Force on Hypertension in Pregnancy, 2013, Obstet Gynecol; 122:1122-1131).

The pathophysiology of early-onset PE is incompletely understood, but is thought to occur in two phases (Phipps et al., 2019, Nature Reviews Nephrology; 15:275). Early-onset PE originates with abnormal implantation and placentation in the first trimester, related to maternal immune dysfunction (Hiby et al., 2010, *J Clin Invest;* 120:4102-4110; Ratsep et al., 2015, *Reproduction;* 149:R91-R102; and Girardi, 2018, *Semin Immunopathol;* 40:103-111), incomplete cytotrophoblast differentiation (Zhou et al., 1997, *J Clin Invest;* 99:2152-2164), and/or oxidative stress at the maternal-placental interface (Burton and Jauniaux, 2011, *Best Pract Res Clin Obstet Gynaecol;* 25:287-299), resulting in incomplete remodeling of the maternal spiral arteries and failure to establish the definitive uteroplacental circulation (Lyall et al., 2013, *Hypertension;* 62:1046-1054). This leads to inadequate placental perfusion after 20 weeks' gestation. The resultant placental dysregulation triggers phase two, which manifests predominantly as maternal systemic vascular dysfunction with negative consequences for the fetus, including fetal growth restriction and iatrogenic preterm birth (Hecht et al., 2017, *Hypertens Pregnancy;* 36:259-268; Young et al., 2010, *Annu Rev Pathol;* 5:173-192; and Backes et al., 2011, *J Pregnancy;* 2011:doi:10.1155/2011/214365. In contrast, the placental dysfunction in late-onset PE is thought to be due not to abnormal placentation, but to disturbance in placental perfusion resulting from maternal vascular disease, such as that seen in patients with chronic hypertension, pregestational diabetes (Vambergue and Fajardy, 2011, *World J Diabetes;* 2:196-203), and collagen vascular disorders ("Placental pathology in maternal autoimmune diseases-new insights and clinical implications," 2017, *International Journal of Reproduction, Contraception, Obstetrics and Gynecology;* 6:4090-4097).

The heterogeneity and complexity of this disease have made it difficult to diagnose, to predict risk, and to develop treatments. Further, the inability to easily interrogate the primary affected organ, the placenta, has limited molecular characterization of disease progression. Circulating RNA (C-RNA) has shown great promise for non-invasive monitoring of maternal, placental and fetal dynamics during pregnancy (Tsui et al., 2014, *Clin Chem;* 60:954-962; and Koh et al., 2014, *Proc Natl Acad Sci USA;* 111:7361-7366). C-RNA is released by many tissues into the bloodstream via multiple cellular processes of apoptosis, microvesicle shedding, and exosomal signaling (van Niel et al., 2018, *Nat Rev Mot Cell Biol;* 19:213-228). Due to these diverse origins, C-RNA measurements reflect tissue-specific changes in gene expression, intercellular signaling, as well as the degree of cell death occurring within different tissues throughout the body. Thus, C-RNA has the potential to elucidate the molecular underpinnings of PE and ultimately identify predictive, prognostic and diagnostic biomarkers of the disease (Hahn et al., 2011, *Placenta;* 32:S17-20).

Several studies have begun to investigate and identify potential C-RNA-based biomarkers for a range of pregnancy complications, including preterm birth, PE, and infectious disease (Pan et al., 2017, *Clin Chem;* 63:1695-1704; Ngo et al., 2019, *Science;* 360:1133-1136; and Whitehead et al., 2016, *Prenat Diagn;* 36:997-1008). However, the significant interindividual variability in this sample type threatens to obscure subtle changes in disease specific biomarkers (Meder et al. 2014, *Clin Chem;* 60:1200-1208). Therefore, many PE-focused C-RNA studies have measured RNA of previously identified serum protein biomarkers, including soluble FLT1, soluble endoglin, and oxidative stress and angiogenic markers (Nakamura et al., 2009, *Prenat Diagn;* 29:691-696; Purwosunu et al., 2009, *Reprod Sci;* 16:857-864; and Paiva et al., 2011, *J Clin Endocrinol* Metab; 96:E1807-1815). While protein measurements of these serum markers are known to be altered in PE (Maynard et al., 2003, *J Clin Invest;* 111:649-658; Venkatesha et al., 2006, *Nat Med;* 12:642-649; and Rana et al., 2018, *Pregnancy Hypertens;* 13:100-106), it is unknown whether they will serve as the most effective predictors in C-RNA, thus warranting a broader discovery approach.

In this example, global measurements of the circulating transcriptome detect unique molecular signatures specific to early-onset severe PE. To facilitate discovery, the performance of whole transcriptome enrichment for high throughput sequencing was optimized, allowing for measurement of >14,000 C-RNA transcripts per sample with high confidence. C-RNA profiles were then globally characterized from a preliminary cohort of 113 pregnancies, 40 of which were diagnosed with early-onset severe PE. All analysis methods were tailored to address the high biological variance inherent to C-RNA and identified altered transcripts concordant with PE biology that can classify across cohorts with high accuracy, highlighting that this sample type offers an avenue to developing robust tests for assessing preeclampsia.

Results

Establishing a reproducible whole-transcriptome workflow for C-RNA.

Figure 37A:
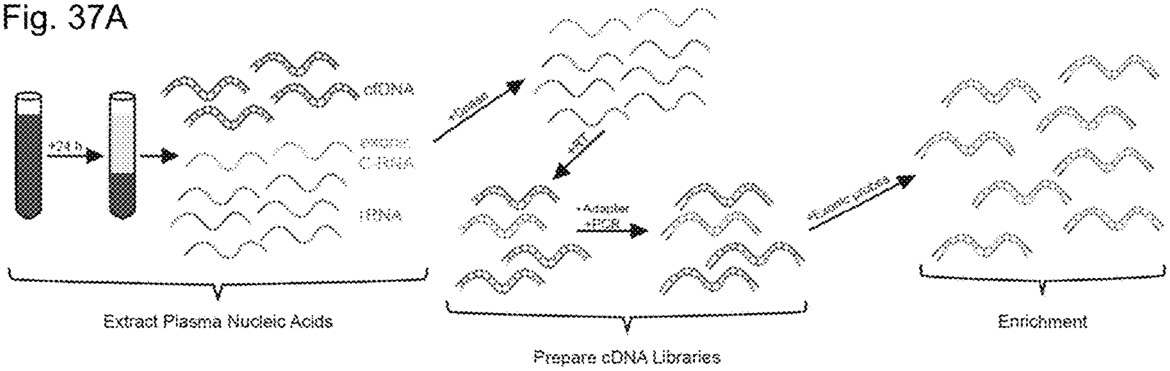
FIGS. 37A and 37B. The C-RNA sample preparation workflow.

C-RNA is present in plasma in relatively low abundance, dominated by ribosomal (rRNA) and globin RNA, and is a mixture of fragmented and full-length transcripts (Crescitelli et al., 2013, *J Extracell Vesicles;* 2:doi:10.3402/jev.v2i0.20677), all of which can affect the efficiency of library preparation methods for next generation sequencing. Thus, workflow was optimized to minimize variability and maximize exonic C-RNA signal (FIG. 37A).

Figure 37B:
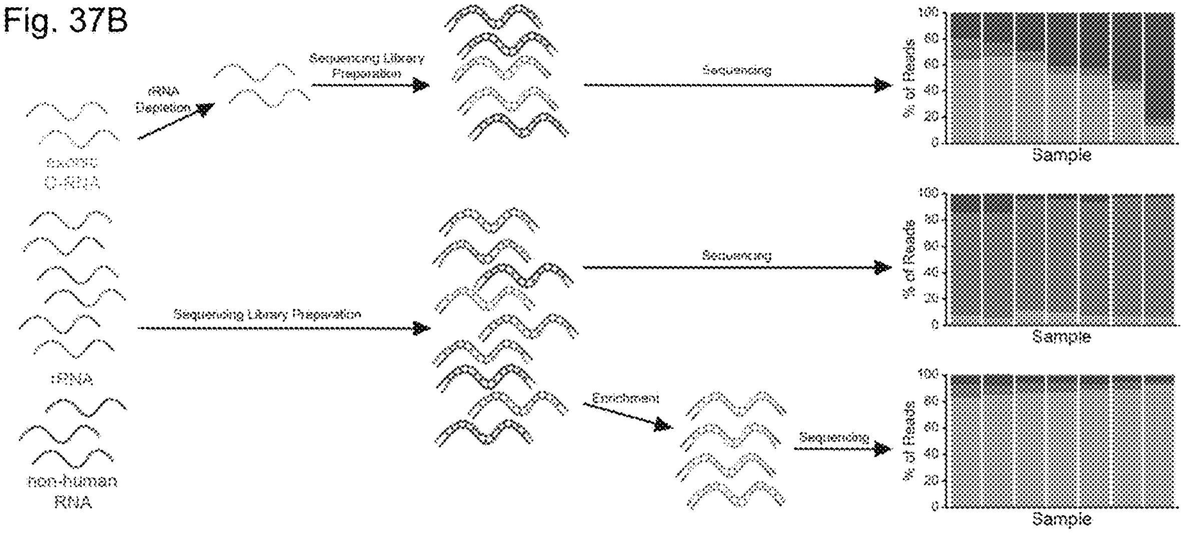

Highly abundant globin and rRNA does not inform biomarker discovery and must be removed. However, standard depletion methods such as Ribo-Zero (Illumina, Inc) or NEBNext rRNA Depletion (New England Biolabs) are not well suited for low starting amounts of RNA (Adiconis et al., 2013, *Nat Methods;* 10:623-629). While upfront depletion with these methods successfully removed unwanted ribosomal sequences from C-RNA (FIG. 37B, gray), sequencing libraries did not consistently exhibit an increase in exonic C-RNA signal (FIG. 37B, orange). Instead, samples varied in the proportion of reads mapping to a complex and variable population of non-human RNA sequences such as GB Virus C (FIG. 37B, pink) (Manso et al., 2017, *Sci Rep;* 7:doi:

10.1038/s41598-017-02239-5; and Whittle et al., 2019, *Front Microbiol;* 9:doi:10.3389/fmicb.2018.03266). Additionally, removal of highly abundant rRNA and globin RNA results in extremely low RNA inputs which increases the failure rate of ligation-based library preparation methods. To avoid these problems, a whole-transcriptome enrichment approach was selected which generates a library from all C-RNA followed by probe-assisted enrichment targeting the whole human exome (FIG. 37A). This method consistently generated high quality sequencing libraries that were composed of >90% exonic C-RNA with minimal contaminating signal from transcripts of limited interest (FIG. 37B, orange).

There is significant interindividual variability in C-RNA plasma concentrations (FIG. 38A), which can vary by an order of magnitude (average 1.1 ng/mL plasma; SD 0.7; range <0.1-5 ng/mL plasma). To ensure reproducible results, the effects of plasma volume input on C-RNA data quality was evaluated. Using less than 2 mL plasma significantly increased the biological coefficient of variation and decreased library complexity (FIGS. 38B and 38C), leading to a decrease in sensitivity. Therefore, a 4 mL plasma input was selected to minimize noise, maximize confidence in data quality and to ensure successful data generation from all individuals regardless of C-RNA plasma concentrations.

Figure 39A:
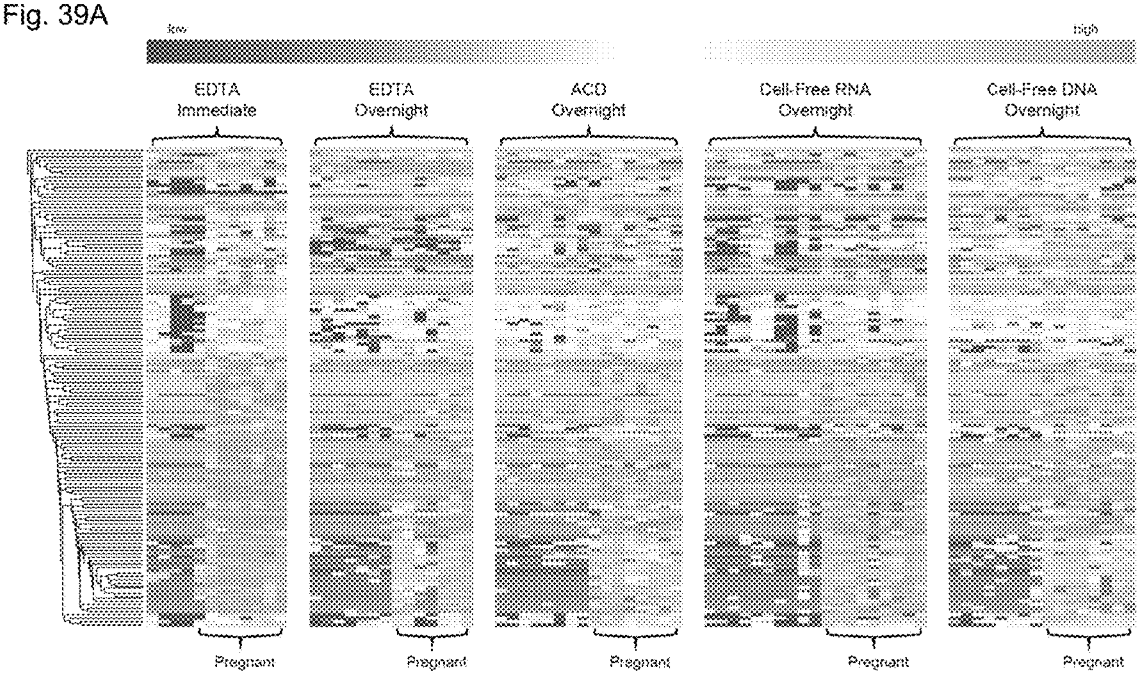
FIGS. 39A-39E. The integrity of C-RNA pregnancy signal after storage in different BCTs.
Figure 39B:
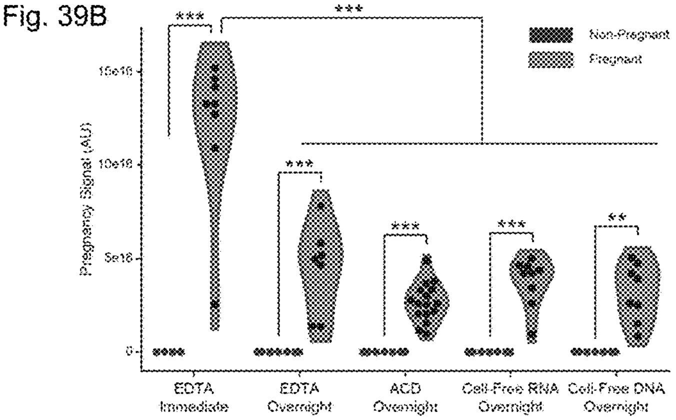
Figure 39C:
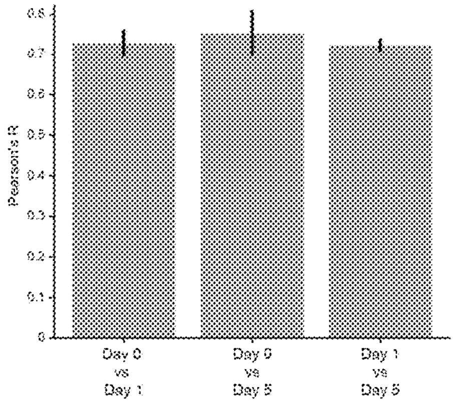
Figure 39D:
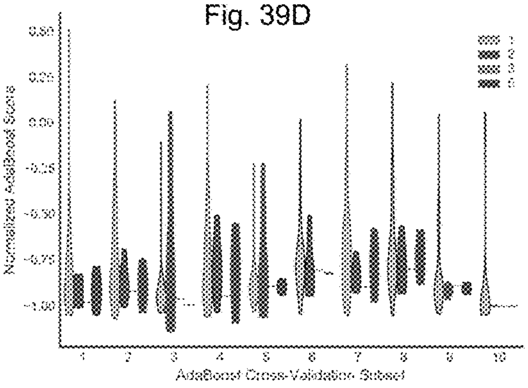
Figure 39E:
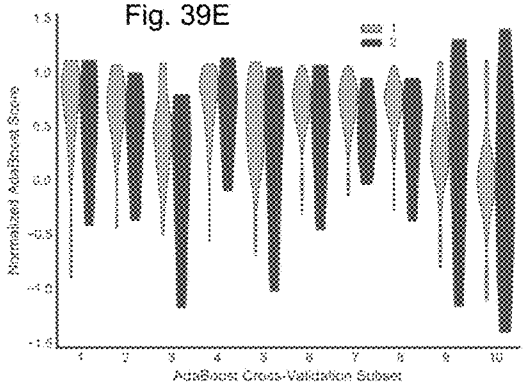

To achieve consistent handling of all samples across diverse collection sites, all processing was centralized and required shipping of the collected blood samples to a single lab. This necessitated an assessment of the impact of overnight shipping on C-RNA data quality. Blood from nonpregnant and pregnant women (gestational age, GA, >28 weeks) was collected in four blood collection tubes (BCTs) and stored overnight at the manufacturer-indicated temperature prior to processing: BD Vacutainer $K_2$EDTA (Beckton Dickinson; 4° C.), BD Vacutainer ACD-A (Beckton Dickinson, 4° C.), Cell-Free DNA BCT (Streck, Inc., RT), Cell-Free RNA BCT (Streck, Inc., RT). A set of samples collected in EDTA BCTs was processed at the clinic within 2 hours to provide a baseline. The C-RNA pregnancy signal in each sample was measured by summing the normalized abundance level of 155 transcripts identified as pregnancy markers in two prior C-RNA publications (Tsui et al., 2014, *Clin Chem;* 60:954-962; and Koh et al., 2014, *Proc Natl Acad Sci USA;* 111:7361-7366). After overnight storage, the C-RNA pregnancy signal was clearly detectable in pregnant samples despite a reduction in overall signal intensity as compared to immediate processing of the EDTA samples (FIGS. 39A and 39B). No major differences were observed between the different BCTs after overnight storage, indicating all are appropriate for C-RNA analysis. Cell-Free DNA BCTs (Streck, Inc) were selected for subsequent sample collections as this enables room temperature shipping. Furthermore, correlation of transcriptomic profiles in a time course experiment confirmed that there is no increase in technical variance after room temperature storage up to five days in these BCTs (FIG. 39C).

Figure 32C:
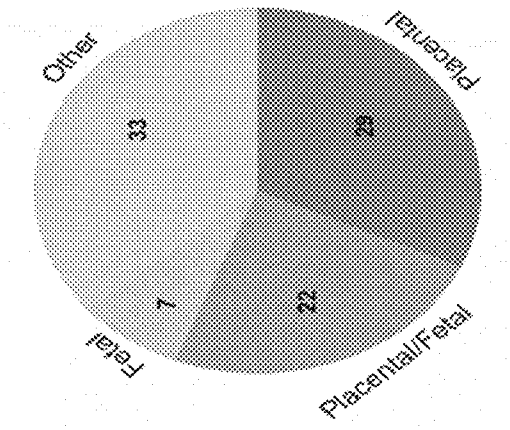
FIGS. 32A-32C. Changes in the C-RNA transcriptome track with pregnancy progression.
Figure 32B:
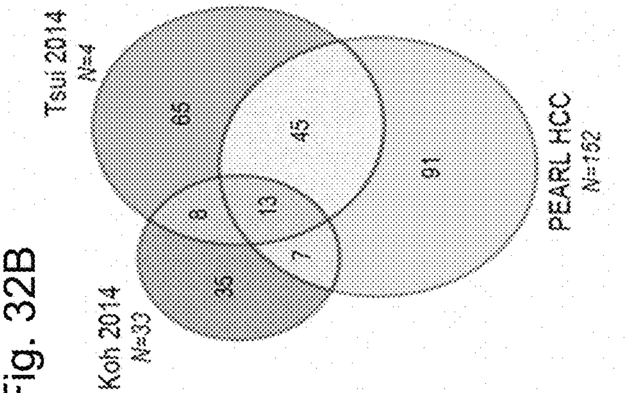
Figure 32A:
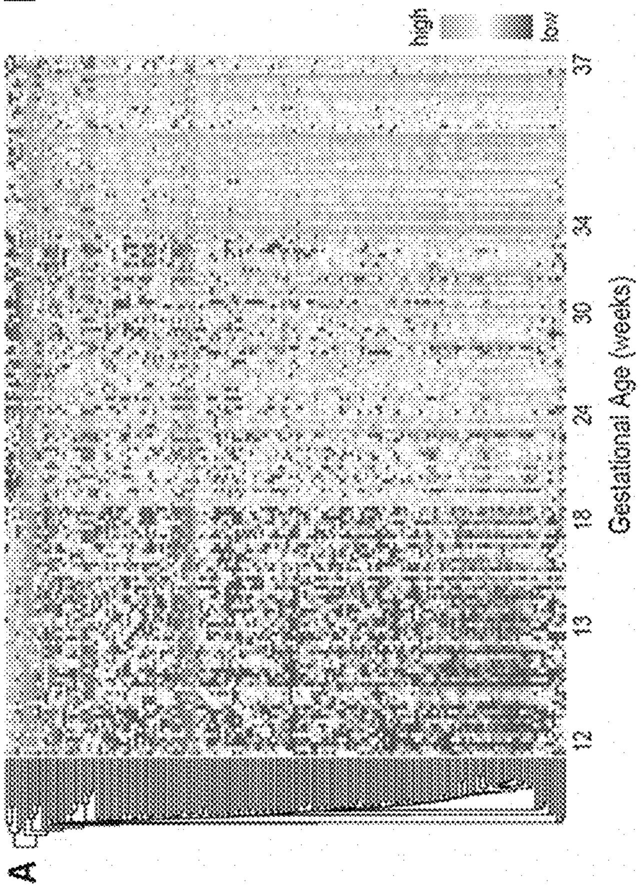

The complete workflow was validated by recapitulating previous work monitoring C-RNA dynamics in healthy pregnancies from first to third trimester. Using 152 samples collected serially from 41 healthy pregnancies (Pre-Eclampsia and Growth Restriction Longitudinal Study Control Cohort—PEARL CC; NCT02379832; Table 13), 156 significantly altered transcripts were identified, with the majority increasing in abundance as pregnancy progresses (FIG. 32A; Table 14). 51% of identified transcripts changed primarily during the first trimester, 6% in the $3^{rd}$ trimester, and 43% were differentially regulated throughout gestation (FIG. 40; Table 14). First trimester genes were enriched for placental steroidogenesis and regulation of trophoblast differentiation, while third trimester genes were involved in the onset of labor. Transcripts that increase throughout gestation are associated with tissue and organ development and morphogenesis (Chatuphonprasert et al., 2018, *Front Pharmacol;* 9:doi:10.3389/fphar.2018. 01027; Debieve et al., 2011, *Mol Hum Reprod;* 17:702-9; Grammatopoulos and Hillhouse, 1999, *Lancet;* 354:1546-1549; and Marshall e al., 2017, *Reprod Sci;* 24:342-354). The results from the PEARL CC were highly concordant with the literature, as 42% of the altered genes were identified in prior C-RNA studies (FIG. 32B) (Tsui et al., 2014, *Clin Chem;* 60:954-962; and Koh et al., 2014, *Proc Natl Acad Sci USA;* 111:7361-7366). Of the 91 transcripts identified only in this study, 64% are expressed by placental and/or fetal tissues (tissue specificity defined as >2 fold higher than median of all tissues in Body Atlas) (FIG. 32C and FIG. 17)(Kupershmidt et al., 2010, *PLOS ONE;* 5:e13066). The remaining genes are hypothesized to reflect maternal tissue responses to pregnancy (Table 14).

Clinical Study Design for Early-Onset Severe PE

After confirming this workflow robustly detects pregnancy-related C-RNA dynamics, changes in C-RNA associated with pregnancy complications were then identified. The workflow was applied to samples collected from two independent PE cohorts, the Illumina Preeclampsia Cohort (iPEC; NCT02808494) and the PEARL Preeclampsia Cohort (PEARL PEC; NCT02379832). The iPEC was used for biomarker identification while the PEARL PEC was used for independent confirmation of our findings. Importantly, all samples in both cohorts were collected in Streck Cell-Free DNA BCTs and libraries were generated in the same manner as discussed in the previous section.

Figure 33A:
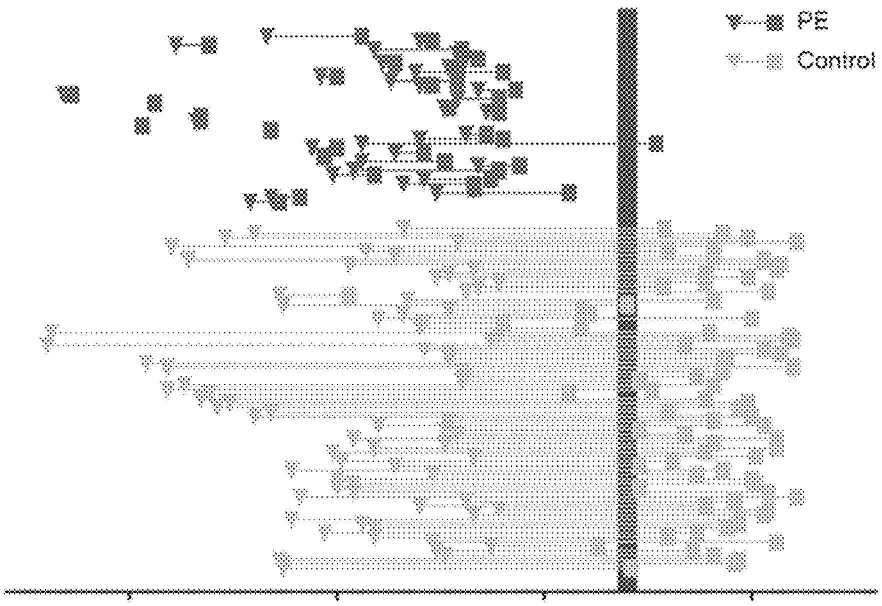
FIGS. 33A-33C. Sample collection but not clinical outcome is matched for control and PE samples. Panels illustrate the time of blood collection (triangles) and gestational age at birth (squares) for each individual in the iPEC study (FIG. 33A) and the PEARL PEC study (FIG. 33B). The red line indicates the threshold for term birth at 37 weeks.

The iPEC study focused on early-onset PE with severe features and excluded women diagnosed with additional health complications such as chronic hypertension or diabetes, to prevent additional heterogeneity from obscuring a consistent PE-associated C-RNA signal (Table 15). 113 samples were collected across 8 sites (Table 17), 40 at the time of early-onset PE diagnosis, and 73 controls that were gestational age-matched to within 1 week (FIG. 33A). Maternal characteristics, pregnancy outcomes, and medications were recorded throughout the study (Table 12 and Table 16). Fetal gender, maternal age, and nulliparity were not significantly different between the PE and control groups. In contrast, BMI was significantly higher in the PE cohort, (p value=0.0007) (O'Brien et al., 2003, *Epidemiology;* 14:368-374). All but one patient with PE gave birth prematurely, in contrast to 9.5% of controls, confirming that our diagnostic criteria identified individuals severely impacted by this disease (FIG. 33C).

Figure 33B:
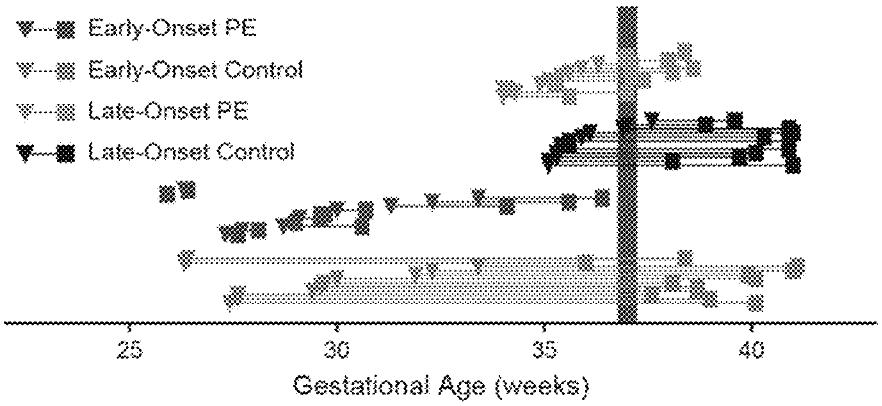
Figure 33C:
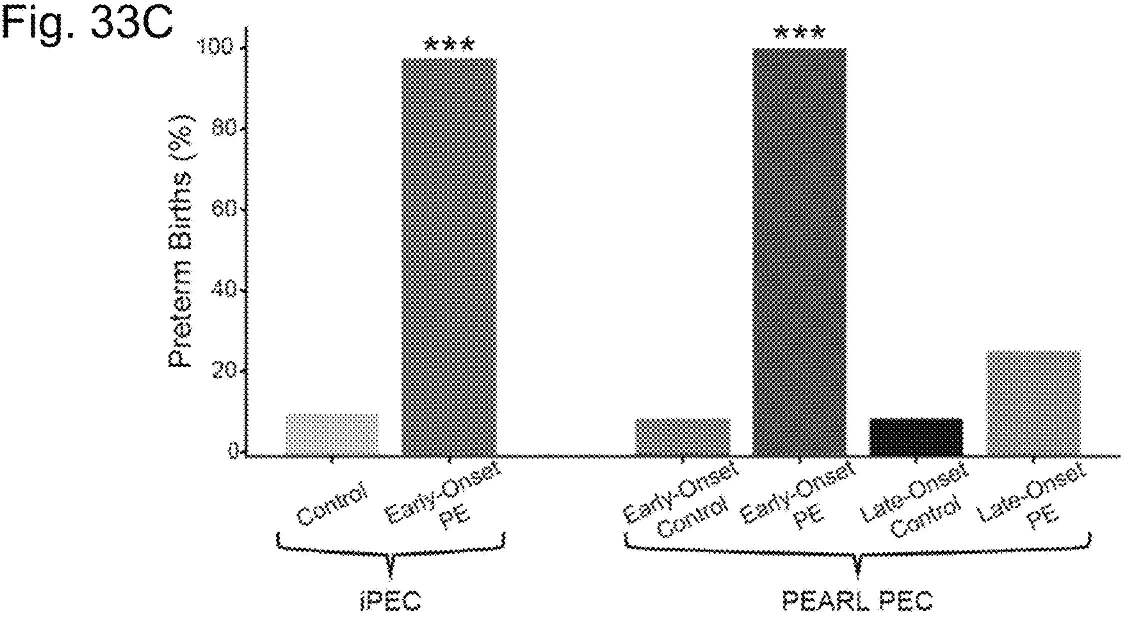

The PEARL PEC samples were collected by an independent institution (CHU de Québec-Université Laval) and consisted of 12 early- and 12 late-onset PE pregnancies with equal numbers of gestational age-matched controls (FIG. 33B). Maternal characteristics, pregnancy outcomes, and medications in use were recorded throughout the study (Table 18). As in iPEC, 100% of early-onset patients delivered prematurely while 75% delivered at term in the late-onset cohort, confirming the differences in severity associated with early- and late-onset PE. Chronic hypertension, diabetes and other maternal health conditions were not grounds for exclusion, making this cohort more representative of the heterogeneity inherent to the pregnant population.

Identification of Transcripts Consistently Altered in Early-Onset PE

Figures 34A, 34B, 34C, 34D, 34E, 34F:
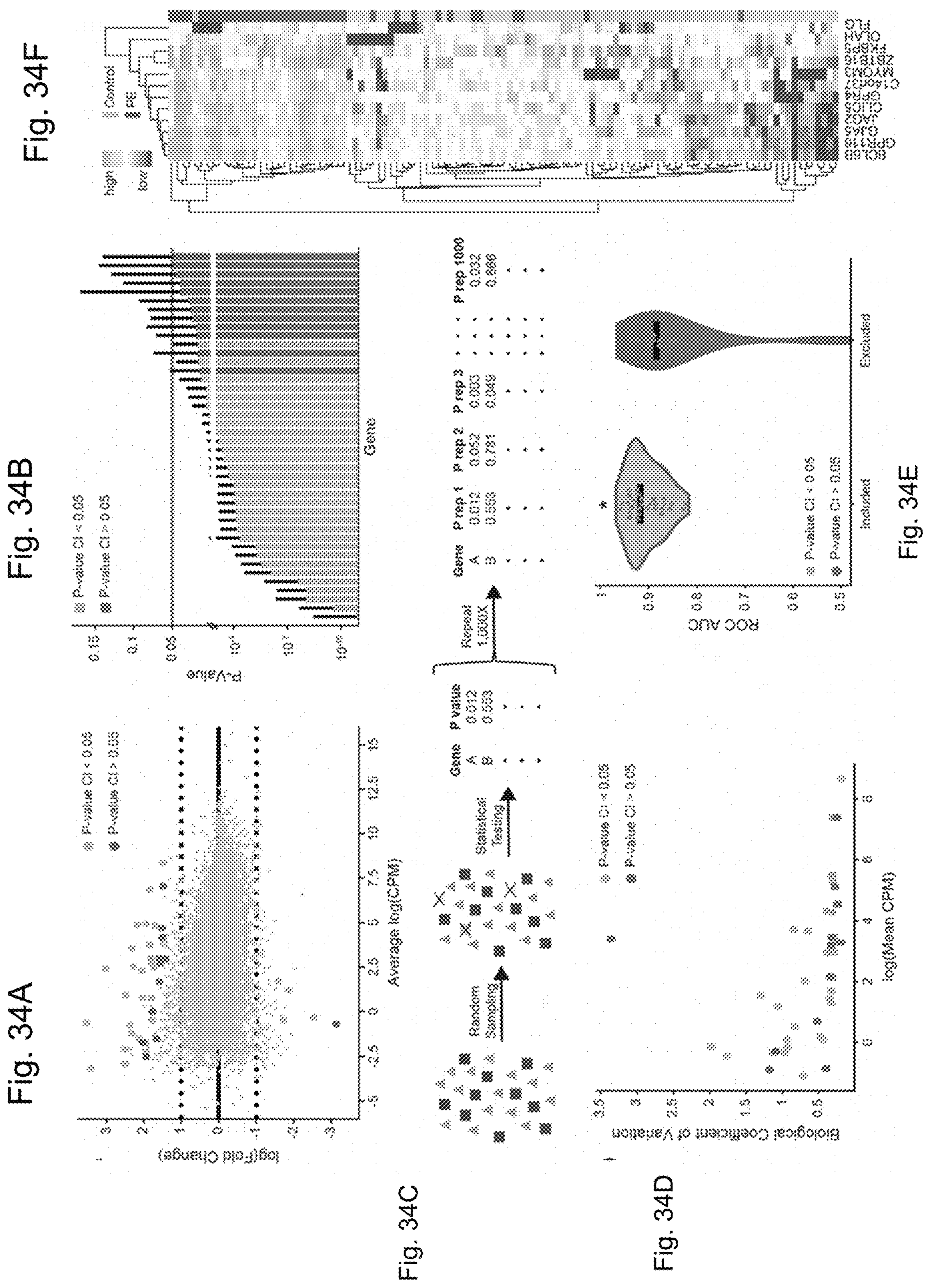
FIGS. 34A-34F. Applying jackknifing to differential expression analysis excludes genes with lower sensitivity for identifying PE samples.

Standard differential expression analysis (Robinson et al., 2010, *Bioinformatics;* 26:139-140) using the full iPEC cohort identified 42 transcripts with altered abundance in plasma, 37 of which were increased in PE (FIG. 34A, blue and orange). However, variability in the differentially abundant transcripts was observed when different subsets of samples were selected for analysis. A jackknifing approach (Library, 1958, *Ann Math Statist;* 29:614-623) was therefore incorporated, enabling the identification of transcript abundances that are most consistently altered when comparing PE to control samples (FIGS. 34A and 34B, orange). One thousand iterations of differential analysis with randomly selected PE and control sample subsets were performed, resulting in the construction of confidence intervals for the p-values associated with each putatively altered transcript (FIG. 34C). Twelve transcripts whose p-value confidence interval exceeded 0.05 were subsequently excluded (FIG. 34B). These transcripts would not have been excluded by simply setting a threshold for baseline abundance or biological variance (FIG. 34D), however these transcripts were observed to have lower predictive value (FIG. 34E). Hierarchical clustering indicates these transcripts are not universally altered in the PE cohort, and thus lack sensitivity (73%) for accurate classification of this condition (FIG. 34F).

Figure 35A:
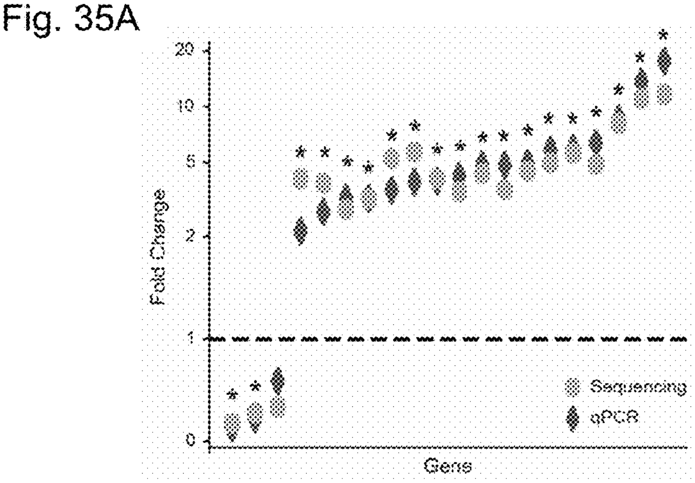
FIGS. 35A-35E. Ubiquitously altered C-RNA transcripts segregate early-onset PE samples from controls.
Figure 35B:
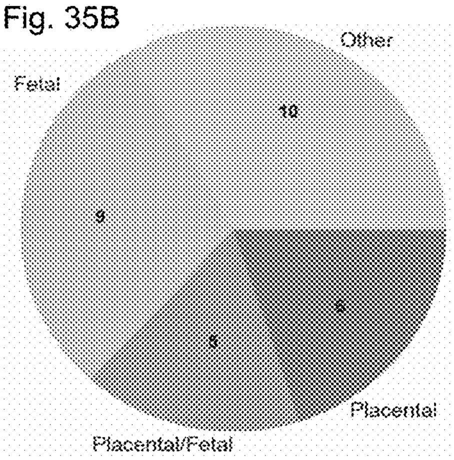

A representative set of 20 transcripts altered in PE were independently quantified by qPCR in a subset of affected and control iPEC patient samples. Fold changes measured by qPCR were highly concordant with the sequencing data, validating our findings (FIG. 35A and Table 19). 58% of the transcripts in the refined list have previously been associated with PE (Table 20). Additionally, nearly all genes can be linked to PE relevant processes, including extracellular matrix (ECM) remodeling, pregnancy duration, placental/fetal development, angiogenesis, and hypoxia response (Table 20). 67% of these genes were expressed by the placenta and/or fetus (FIG. 35B). In the remaining maternally expressed genes, cardiovascular and immune functions were well represented, both of which are altered in PE (Table 20) (Phipps et al., 2019, *Nature Reviews Nephrology;* 15:275).

Figure 35C:
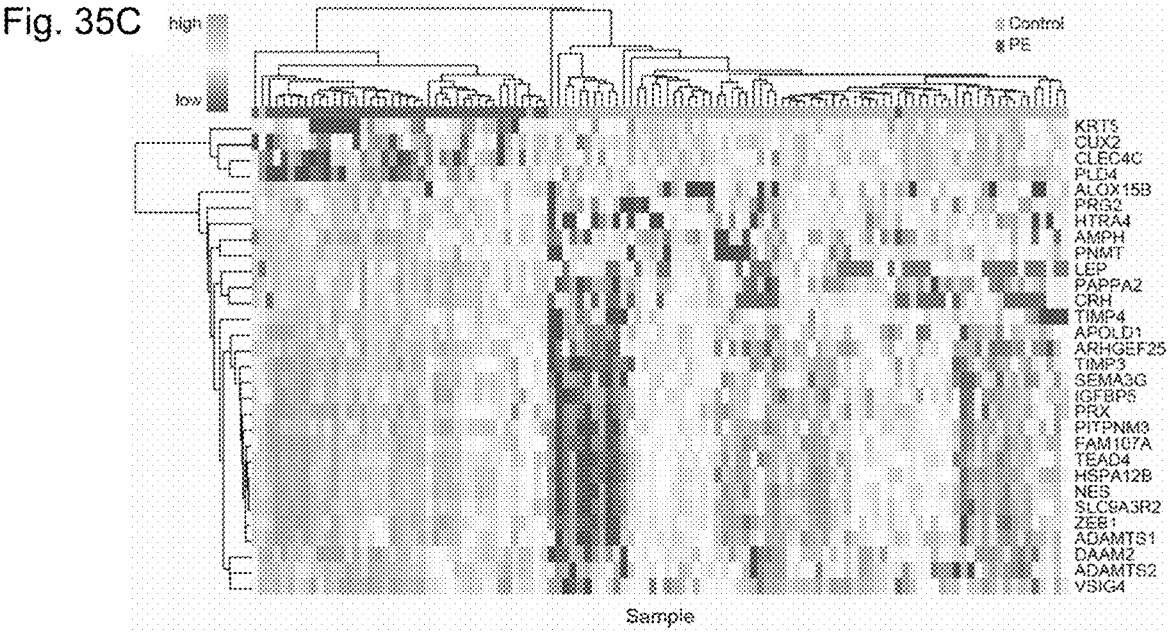
Figure 35D:
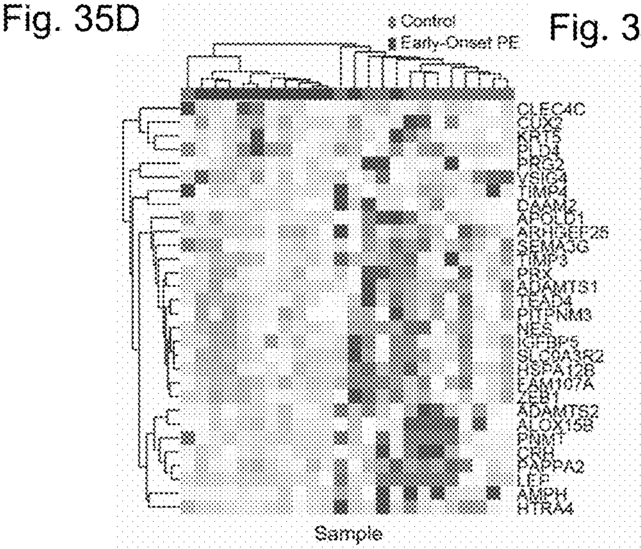
Figure 35E:
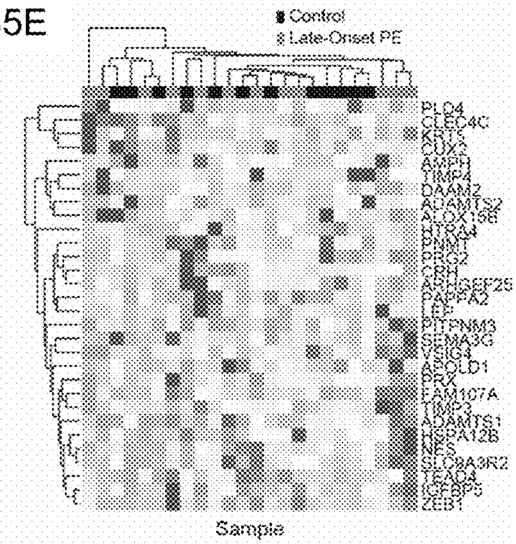

Hierarchical clustering of these transcripts effectively segregated PE and control samples from iPEC with 98% sensitivity and 97% specificity (FIG. 35C). The refined list of 30 transcripts was validated with the independent PEARL PEC. Early-onset PE samples clustered separately from matched controls with 83% sensitivity and 92% specificity, further validating the relevance of these transcripts (FIG. 35D). In contrast, no clustering was observed for the late-onset PE and matched control samples indicating that late-onset PE has a potentially weaker or more likely a different C-RNA signature (FIG. 35E) (Redman, 2017, *An International Journal of Women's Cardiovascular Health;* 7:58; and Hahn et al., 2015, *Expert Rev Mol Diagn;* 15:617-629).

Upon closer inspection of the clinical data for the three misclustered iPEC samples, it was discovered that two controls suffered from potentially confounding health problems, including hypertension and in one case accompanied by preterm delivery. These controls should not have been enrolled in the iPEC due to our stringent exclusion criteria, thus they were excluded from further analyses. The misclustered PE sample showed no clinical abnormalities and was retained in our iPEC dataset.

Development of a Robust Machine Learning Classifier for Early-Onset PE

Figure 42A:
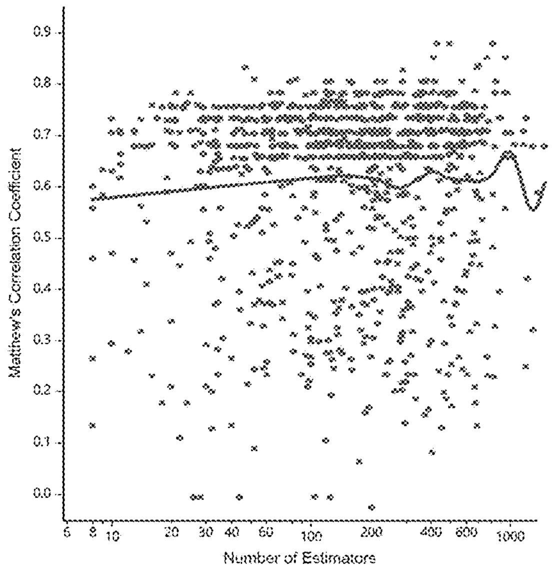
FIGS. 42A and 42B. AdaBoost hyperparameter optimization. Performance, measured by Matthew's Correlation Coefficient, versus the number of estimators (FIG. 42A) or the learning rate (FIG. 42B). Each dot shows the average value obtained from 3-fold cross validation during the random search.
Figure 42B:
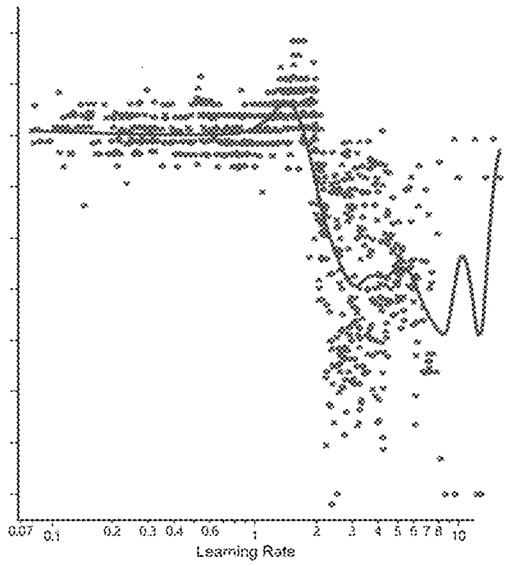
Figure 43A:
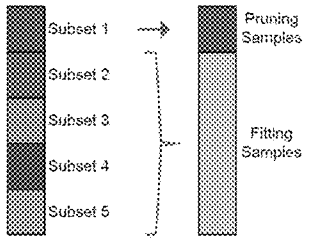
FIGS. 43A-43D. AdaBoost training strategy.
Figure 43B:
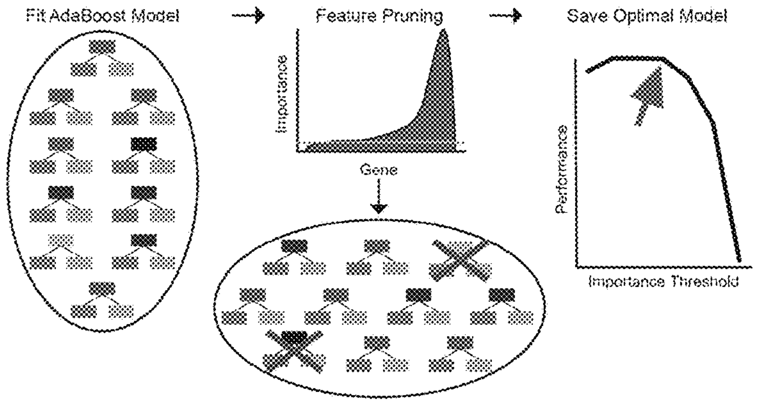
Figure 43C:
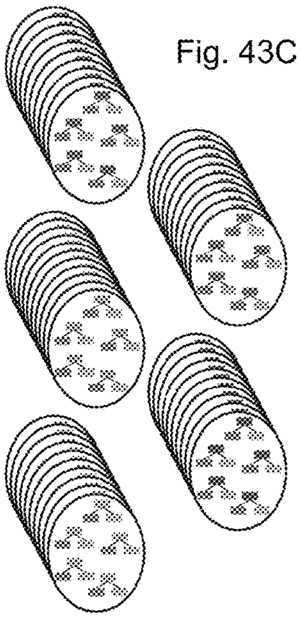
Figure 43D:
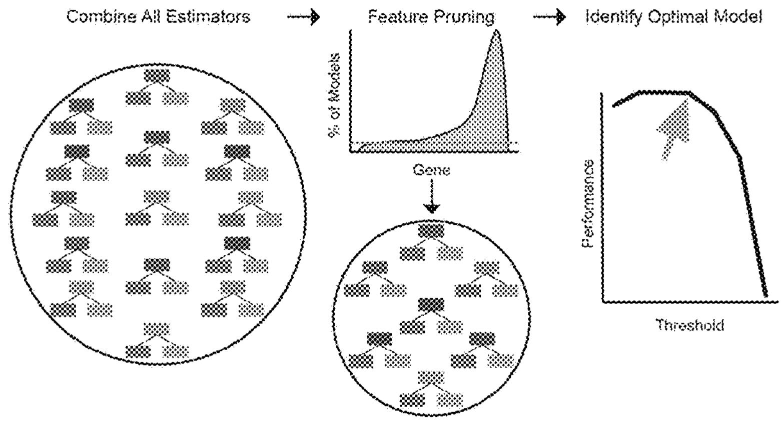

Differential expression analysis confirmed that C-RNA detects biologically relevant changes in PE patients. To assess if C-RNA signatures can robustly classify PE, the data from the iPEC cohort were used to build an AdaBoost model (Freund and Schapire, 1997, *J Comp Sys Sci;* 55:119-139; McPherson et al., 2011, *PLoS Comput Biol;* 7:doi:10.1371/journal.pcbi.1001138; and Lu et al., 2015, *PLOS ONE;* 10:e0130622). A randomly selected 10% of samples were excluded as a holdout set from the entire machine learning process to assess the final model performance. Then, a nested cross-validation approach was used for hyperparameter optimization (FIG. 42) and AdaBoost model building (FIG. 43) (Cawley and Talbot, 2010, *J Machine Learning Res;* 11:2079-2107).

While developing the machine learning approach, a high degree of variability was observed in AdaBoost performance and in the genes selected depending on which samples were included in training (FIG. 44). These observations indicate that different subsets of samples significantly impact model construction (Assessing and improving the stability of chemometric models in small sample size situations | SpringerLink (available on the world wide web at link.springer.com/article/10.1007%2Fs00216-007-1818-6)) which is likely due in part to the heterogeneity of PE. To account for this diversity, AdaBoost models were fit to multiple combinations of the training samples. The estimators from these orthogonally generated models were then combined into a single aggregate and pruned to obtain a minimal gene set (FIG. 43) (Martinez-Munoz and Suarez, 2007, *Pattern Recognition Letters;* 28:156-165; and AveBoost2: Boosting for Noisy Data | SpringerLink ((available on the world wide web at link.springer.com/chapter/10.1007/978-3-540-25966-4_3))). This allowed the capture of wide diversity of PE manifestations in a refined machine learning model with the potential to accurately classify independent samples from a broad pregnancy population.

Figure 36A:
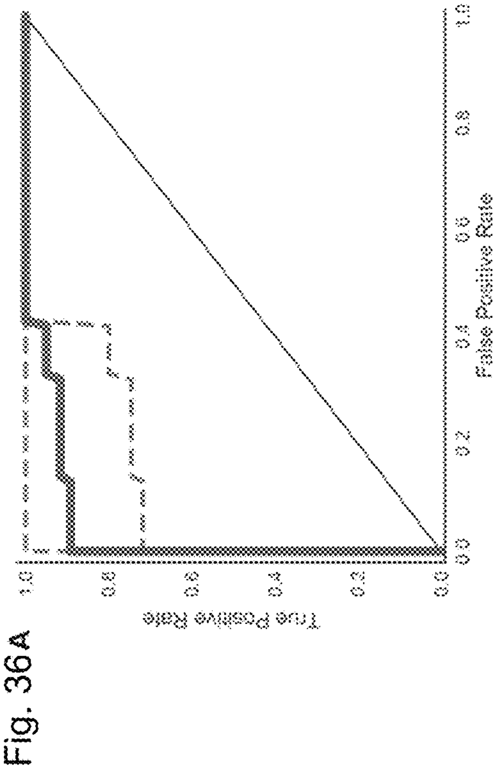
FIGS. 36A-36E. Machine learning accurately classifies PE across independent cohorts.
Figure 36B:
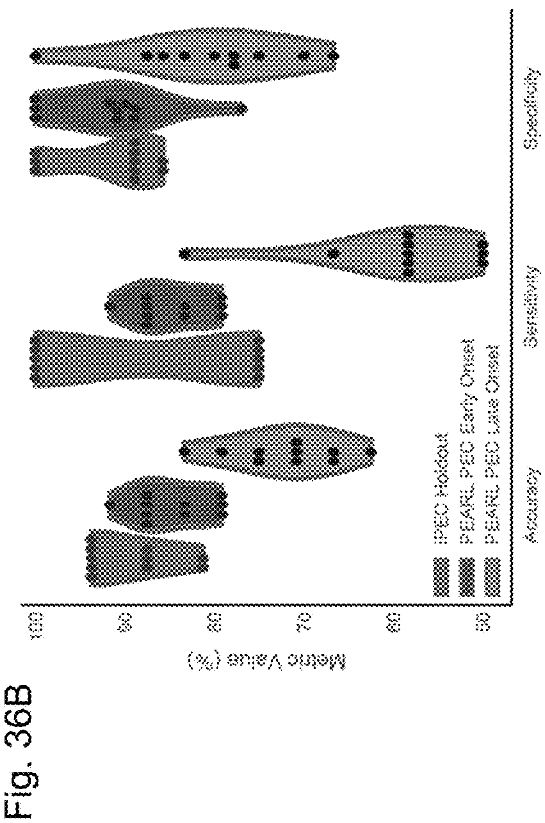
Figure 40A:
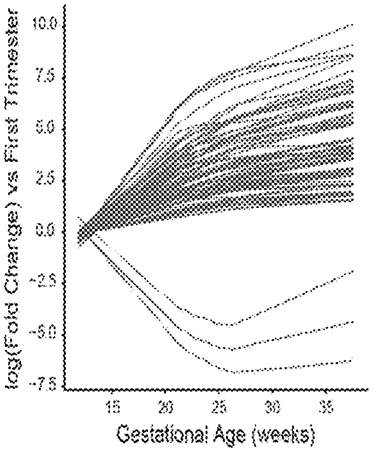
FIGS. 40A-40D. C-RNA transcripts can be altered during specific stages of pregnancy. Dynamic changes in transcripts that primarily change early in pregnancy (FIG. 40A, ~14 weeks), throughout gestation (FIG. 40B), or predominantly late in pregnancy (FIG. 40C, ~33 weeks). Note how transcripts which change from the first to second trimester do not return to baseline levels but remain at the altered abundance for the remainder of gestation.
Figure 40B:
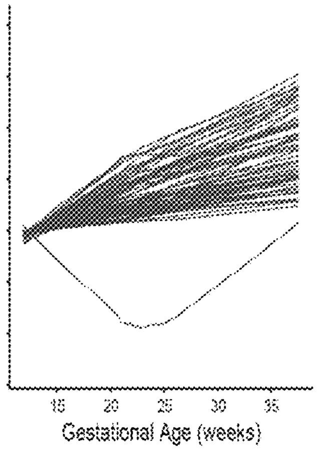
Figure 40C:
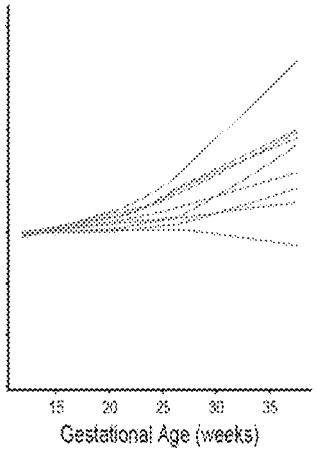
Figure 40D:
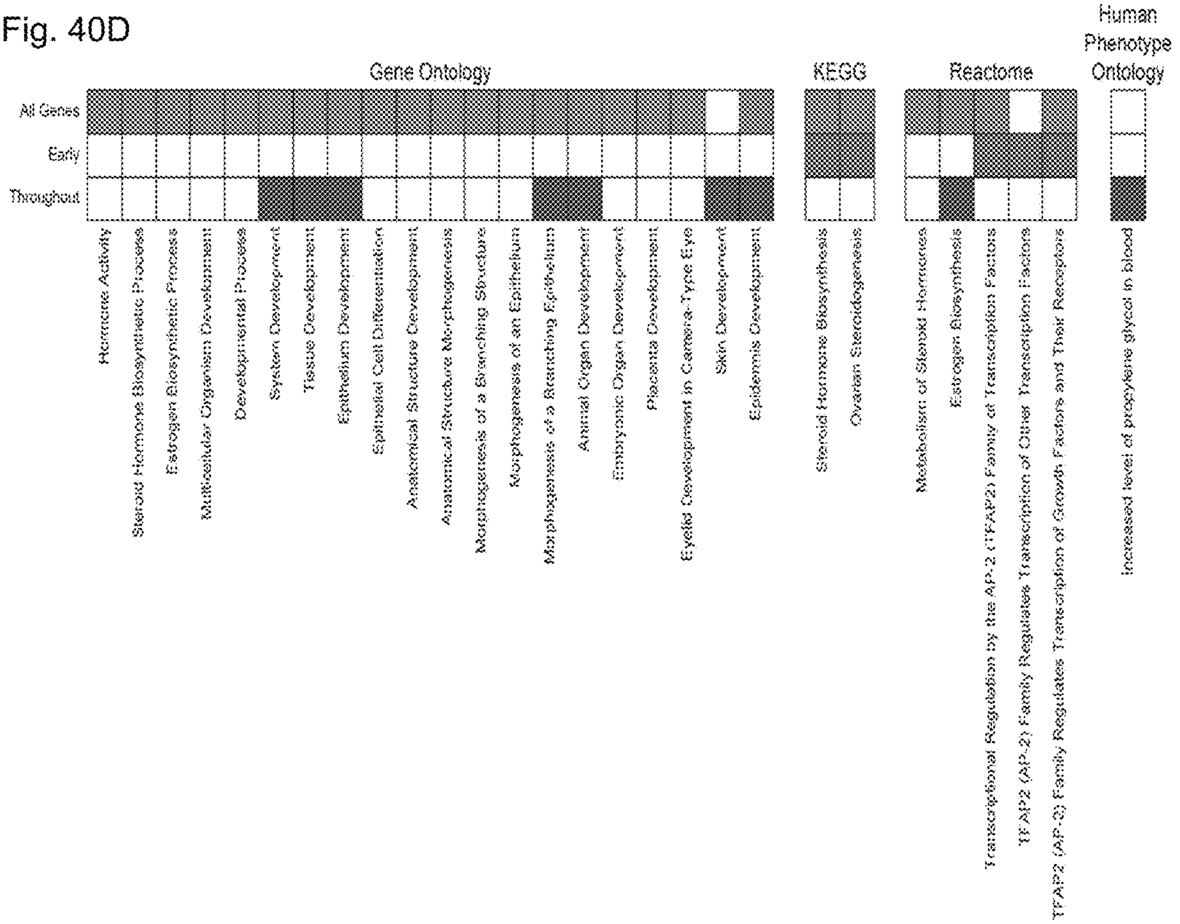
Figure 41A:
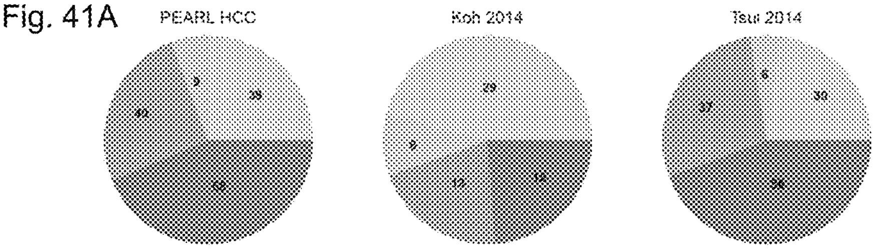
FIGS. 41A-41C. Comparing pregnancy-associated transcript tissue specificity for three independent C-RNA studies.
Figure 41B:
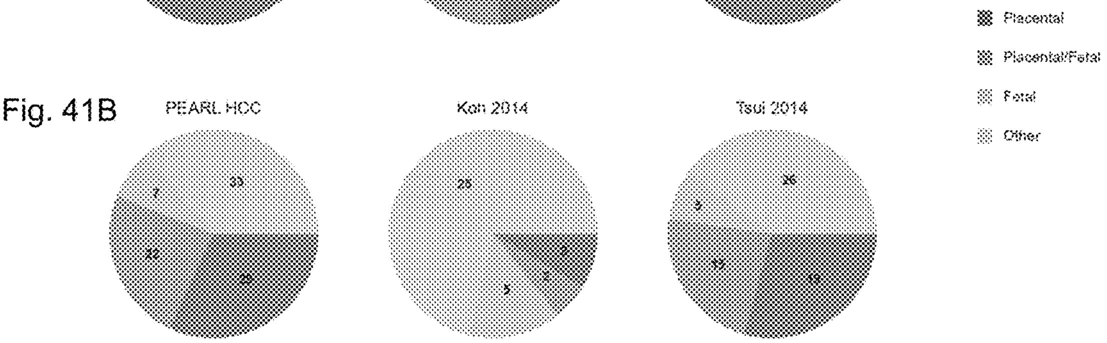
Figure 41C:
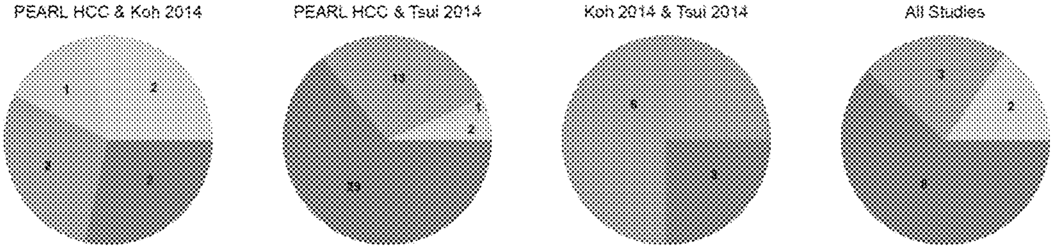

Within each fold of the cross-validation, a threshold AdaBoost score was identified for discriminating PE and control samples which maximized both sensitivity and specificity. Across all ten folds, we obtained an average ROC of 0.964 (+/−0.068 SD) (FIG. 36A). Performance was first assessed in the holdout iPEC samples obtaining 89% (+/−5% SD) accuracy, with 88% (+/−13% SD) sensitivity and 92% (+/−6% SD) specificity (FIG. 36B, blue). AdaBoost classification performance was not affected by the amount of time prior to plasma processing, further supporting the robustness of our sample preparation protocol and analyses (FIGS. 40D and 40E). The model's capabilities to classify the independent PEARL PEC cohort were subsequently investigated. Early-onset PEARL PEC samples achieved 85% (+/−4% SD) accuracy, with 77% (+/−9% SD) sensitivity and 92% (+/−7% SD) specificity (FIG. 36B, pink). Unexpectedly, late-onset PEARL PEC samples were also classified with a reasonable accuracy of 72% (+/−6% SD), sensitivity of 59% (+/−10% SD) and specificity of 80% (+/−10% SD) (FIG. 36B, green).

Figure 36C:
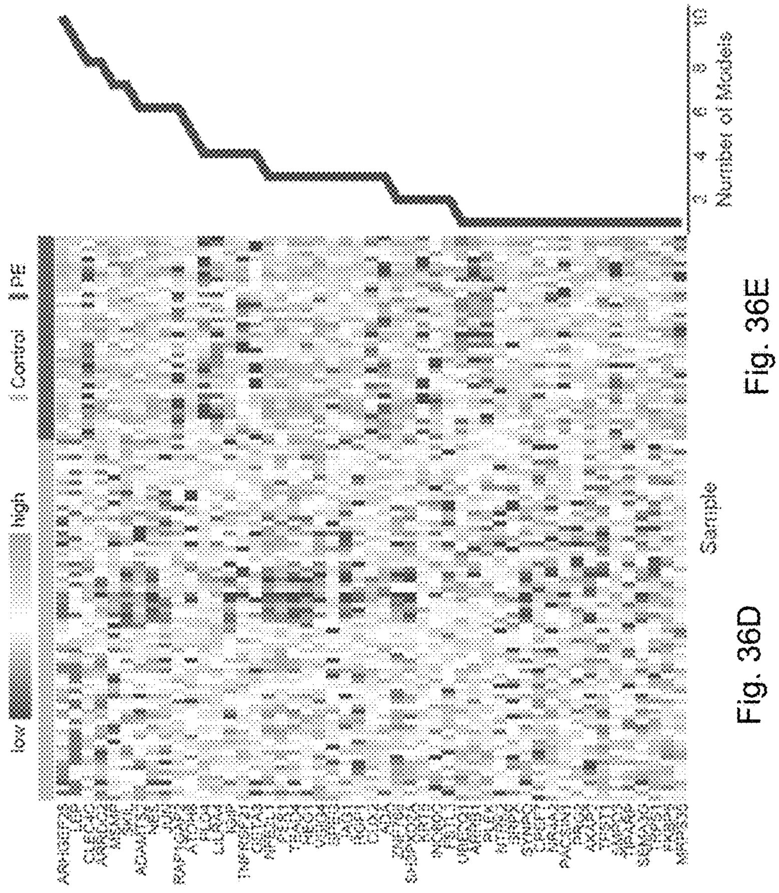
Figure 36D:
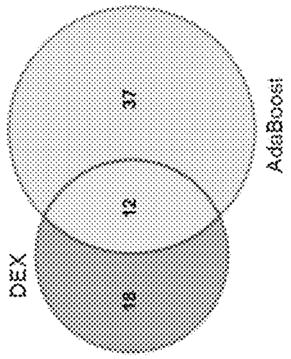
Figure 36E:
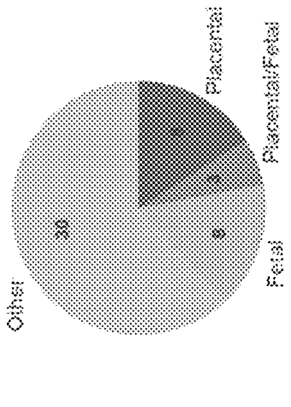

49 total transcripts were used by AdaBoost, with 63% selected in at least 2 rounds of model building (FIG. 36C). Concordance was observed with prior analyses, as 40% of the genes identified in the jackknifing analysis were also used in machine learning (FIG. 36D, Table 21). 38% of the transcripts used by the classifiers have elevated expression in the placenta and/or fetus (FIG. 36E). Transcripts reflecting a diversity of PE-relevant pathways were observed, particularly genes associated with immune regulation and fetal development (Table 21).

Discussion

Whole transcriptome C-RNA analysis casts the wide net necessary for effective biomarker discovery, capturing a molecular snapshot of the diverse and complex interactions of pregnancy at a single point in time. Workflow and analyses were tailored to minimize technical noise, obtain high quality C-RNA measurements, and ultimately detect biologically relevant alterations. Importantly, molecular changes were detected specific to the complex pathophysiology of early-onset severe PE at the time of diagnosis, supporting robust classification across cohorts. The altered C-RNA transcripts identified represent contributions from maternal, placental and fetal tissues, many of which would not be captured in studies focusing on placental tissues collected after delivery. These discoveries highlight the power of C-RNA to comprehensively monitor signals contributed by diverse tissues of origin while the pregnancy is ongoing.

To identify the best method capable of detecting global and potentially subtle changes in pregnancy, the effects of plasma input, library preparation methods, and BCTs on C-RNA data quality were determined. As the majority of transcripts appear to be present in plasma at low abundance, the use 4 mL plasma inputs was chosen in protocols to minimize noise due to sampling error and poor library conversion, both of which plague low input sequencing applications. Upfront depletion of abundant RNA did not eliminate all contaminating RNA species, which were numerous and diverse in our sample population. This made targeted depletion infeasible, thus we selected a whole transcriptome enrichment approach to consistently isolate the exonic C-RNA signal of interest. Overnight shipping was a logistical requirement of the protocol, but runs the risk of introducing both signal loss due to C-RNA degradation as well as contamination with additional RNA from cell lysis. Streck Cell Free DNA BCTs, which inhibit cell lysis at room temperature (Zhao et al., 2019, *J Clin Lab Anal;* 33:e22670), were selected. This BCT is not specifically designed for RNA stabilization, but little evidence of C-RNA degradation was observed after storage for several days. Previous studies have shown that C-RNA has sufficient endogenous protection from extracellular nucleases (Tsui et al., 2002, *Clin Chem;* 48:1647-1653) thus additional precautions to protect the RNA are unnecessary. Together, these optimizations identified a workflow that maximizes C-RNA transcriptomic signal and minimizes technical variability, as illustrated by the numerous biologically relevant alterations observed across healthy and PE pregnancies.

Analyses next focused our analyses on identifying differences in circulating transcriptomes that are ubiquitous to the most extreme phenotype of the disorder, namely early-onset PE with severe features. This required tailoring our approach to account for the variability observed in our data that stems from both the substantial biological noise in C-RNA measurements as well as the phenotypic diversity of PE. C-RNA is inherently more variable than single tissue transcriptomics, because it interrogates RNA from diverse tissues and biological processes, not only detecting changes in gene expression but also differences in the rates of cell death and intercellular signaling. Furthermore, PE exhibits a wide range of maternal and fetal manifestations and outcomes, which may be associated with different underlying molecular causes and responses. While the genes eliminated after jackknifing may be biologically relevant in PE, they were not universally altered in the affected cohort. These transcripts may indicate a molecular subset of the disease and larger cohorts will help elucidate whether C-RNA can further delineate PE subtypes, which is crucial to understanding the diverse pathophysiology of this syndrome.

The transcripts identified by jackknifing represent a diversity of functions spanning the maternal-fetal interface. A majority of the identified changes relate to placental dysfunction and altered fetal development. One of the most striking trends was an increased abundance of ECM remodeling and cell migration proteins (N=10), tracking with dysfunctional extravillous trophoblast invasion characteristic of early-onset PE (Yang et al., 2019, *Gene;* 683:225-232; Zhu et al., 2012, *Rev Obstet Gynecol;* 5:e137-e143; and Wang et al., 2019, *Scientific Reports;* 9:2728). 20% of dysregulated genes identified encode for angiogenic proteins, consistent with a number of observations that the balance of angiogenic factors play a crucial role in regulating placental vascular development (Cerdeira et al., 2012, *Cold Spring Harbor Perspectives in Medicine;* 2:a006585-a006585) and can identify early-onset PE with severe features (Zeisler et al., 2016, *N Engl J Med;* 374:13-22). The data presented here indicated that fetal growth and development was also perturbed in early-onset severe PE, as evidenced by increased abundance of 4 transcripts encoding regulators of IGF signaling (Argente et al., 2017, *EMBO Mol Med;* 9:1338-1345; and Weyer and Glerup, 2011, *Biol. Reprod;* 84:1077-1086), a critical pathway for fetal development (Forbes and Westwood, 2008, *Horm Res;* 69(3):129-137). The remaining transcripts captured the maternal component of PE, namely immune and cardiovascular system dysregulation. Evidence of maternal immune imbalance, a hallmark of PE, appeared as altered abundance of immunological tolerance and pro- and anti-inflammatory factors (Chistiakov et al., 2014, *Front Physiol;* 5 (2014), doi: 10.3389/fphys.2014.00279; Kumar et al., 2012, Cancers (Basel); 4:1252-1299; Qi et al., 2003, *Nature Medicine;* 9:407; and Yang et al., 2014, *Biochim Biophys Acta;* 1840: 3483-3493). Transcripts important to blood pressure regulation as well as several genes linked to atherosclerosis were also identified as altered in PE C-RNA profiles, consistent with maternal vascular disease as an underlying mechanism predisposing some patients to PE (Calò et al., 2014, *J Hypertens;* 32:331-338; and Magnusson et al., 2012, *PLOS ONE;* 7:e43142). The transcripts identified captured a diversity of PE-relevant functions and highlights the ability of C-RNA to simultaneously monitor the numerous molecular processes implicated in complex disease.

Next, it was determined if C-RNA could not only detect biologically relevant changes but also accurately classify pregnancies affected by early-onset severe PE. The careful approach to AdaBoost model building described herein identified combinations of transcripts that can classify across distinct patient subsets, while excluding features that could lead to overfitting and bias in our model. Although 76% of transcripts used by AdaBoost were not identified as differentially abundant, they still reflect the same PE-relevant pathways that were captured in our jackknifing analysis. The success of this strategy was illustrated by the highly accurate classification of the independent early-onset PEARL PEC. These samples were collected at the time of diagnosis from a different population than the one used for training, with less stringent inclusion and exclusion criteria. For example, this cohort included 5 women who had chronic hypertension or gestational diabetes only 1 of which was misclassified by a few AdaBoost models, indicating the C-RNA changes utilized in machine learning were highly specific to PE.

This example provides an important step towards improved understanding and diagnosis of PE. The limited size of our clinical cohorts does not capture the phenotypic diversity of the global pregnant population and this is reflected in the lower values obtained for sensitivity than specificity in the classification analyses. Larger cohorts will better encompass the heterogeneity of PE, identifying signals for diverse manifestations of disease. A second limitation is the targeted nature of whole transcriptome enrichment and as such, does not capture the full range of non-coding or non-human transcripts present in plasma. Certain infections and miRNAs have been associated with PE (Nourollahpour Shiadeh et al., 2017, *Infection;* 45:589-600; and Skalis et al., 2019, *Microrna;* 8:28-35). Thus, future studies should aim to incorporate these measurements with C-RNA transcriptomic data. While the findings of this example are highly consistent with what is reported in the literature, alterations in transcripts of widely reported serum protein biomarkers such as soluble FLT1 (sFLT), vascular endothelial growth factor (VEGF) or placental growth factor (PIGF) were not observed (Phipps et al., 2019, *Nature Reviews Nephrology;* 15:275). This result is unsurprising given that gene expression is not always correlated with protein abundance or release into the circulation.

The iPEC sample collection was focused specifically on early-onset PE with severe features at the time of diagnosis. While this is the most extreme phenotype of the disease, it represents a small percent of PE cases and further in-depth exploration across the clinical PE spectrum is warranted. As a preliminary examination, the AdaBoost model was applied to the late-onset PEARL PEC cohort and achieved reasonably good accuracy (72%). This is surprising, given the substantial evidence that early- and late-onset PE are distinct conditions, despite sharing a final common phenotype of placental dysfunction (Burton et al., 2019, *BMJ;* 366: 12381). Thus, some of the transcripts identified by AdaBoost likely reflect the response to uteroplacental insufficiency rather than its source and therefore may not have predictive value early in disease progression. In contrast, alterations in transcripts involved in angiogenesis and trophoblast invasion (Xie et al., 2018, *Res Commun;* 506:692-697; Hunkapiller et al., 2011, *Development;* 138:2987-2998; and Chrzanowska-Wodnicka, 2017, *Curr Opin Hematol;* 24; 248:255), known molecular drivers of PE initiation, were observed, and may have predictive value early in disease progression. Regardless of whether the changes detected represent cause or effect, or even a combination thereof, the methods and findings described herein show that C-RNA provides a unique opportunity to build robust diagnostic algorithms and investigate mechanisms of disease that were never considered before.

The successful classification of PE patients at the time of diagnosis showcases how C-RNA profiles can be used to robustly monitor maternal, fetal and placental functions in real-time. Future studies should focus earlier in pregnancy to evaluate the potential of this approach to improve prognostication and prediction of outcomes for women with PE. Indeed, such studies hold great promise for uncovering predictive biomarkers for early stratification of all at-risk pregnancies, informing prophylactic interventions or more vigilant monitoring of the pregnancy. The application of C-RNA will ultimately provide comprehensive molecular monitoring of maternal and fetal health throughout the course of pregnancy.

Materials and Methods

Study Design

The objective of this example was to determine whether C-RNA can detect molecular markers associated with early onset PE with severe features. This goal was achieved by (i) optimizing a protocol to obtain robust whole transcriptome C-RNA measurements, (ii) analyzing blood plasma C-RNA profiles from patients at the time of PE diagnosis and gestationally age-matched control pregnancies, and (iii) validating our findings with C-RNA data generated from an independent cohort. The clinical protocol and informed consent forms for the iPEC study were approved by each clinical site's Institutional Review Board; inclusion and exclusion criteria are specified in Table 15. Investigators were blinded to sample status through the bioinformatic processing of sequencing data.

Clinical Sample Collection iPEC. Pregnant patients were recruited in an Illumina sponsored clinical study protocol (NCT02808494) in compliance with the International Conference on Harmonization for Good Clinical Practice. Participants were recruited across 8 different clinical sites: University of Texas Medical Branch (Galveston, Tex.), Tufts Medical Center (Boston, Mass.), Columbia University Irving Medical Center (New York, N.Y.), Winthrop University Hospital (Mineola, N.Y.), St. Peter's University Hospital (New Brunswick, N.J.), Christiana Care (Newark, Del.), Rutgers University Robert Wood Johnson Medical School (New Brunswick, N.J.) and New York Presbyterian/Queens (New York, N.Y.).

After obtaining informed consent, 20 mL whole blood samples were collected from 40 singleton pregnancies with a diagnosis of PE before 34 weeks' gestation with severe features defined per ACOG guidelines (Table 15) (Hypertension in Pregnancy: Executive Summary, 2013, *Obstet Gynecol;* 122:1122). Samples from 76 healthy pregnancies were also collected and were matched for gestational age to the PE group. Three control samples developed term PE after blood collection and were excluded from the study. Maternal characteristics, birth outcomes (Table 32) and medications (Table 16) in use were all recorded during the study.

PEARL. Plasma samples from the PEARL study (NCT02379832) were used as an independent validation cohort. PEARL samples were collected at the Centre Hospitalier Universitaire de Québec (CHU de Québec). Only participants above 18 years of age were eligible, and all pregnancies were singleton. A group of 45 control pregnancies (PEARL Healthy Control Cohort; PEARL HCC) and 45 case pregnancies (PEARL Preeclampsia Cohort; PEARL PEC) were recruited in this study and written informed consent was obtained for all patients. A selection of plasma samples was obtained after the study had reached completion.

The criteria for PE was defined based on the Society of Obstetricians and Gynecologists of Canada (SOGC) June 2014 criteria for PE, with a gestational age requirement between 20 and 41 weeks, encompassing both early (diagnosed <34 weeks; N=12) and late onset (diagnosed >34 weeks, N=12) PE. A blood sample was taken once at the time of diagnosis from the PEARL PEC samples. The PEARL HCC included 45 pregnant women who were expected to have a normal pregnancy and were recruited between 11- and 13-weeks' gestation. Each enrolled patient was followed longitudinally with blood drawn at 4 time-points throughout pregnancy until birth. The control women were divided into three subgroups and subsequent follow up blood draws were staggered to cover the entire range of gestational ages throughout pregnancy (Table 13). In addition to using the PEARL HCC samples to assess C-RNA in healthy pregnancy, samples from 24 unique individuals in the PEARL HCC were selected to serve as gestational age-matched controls for both the early- and late-onset PE cohort.

Sample Preparation

Plasma processing. All samples from the iPEC and the PEARL cohorts were processed in randomized batches by investigators blinded to disease status. Two tubes of blood were collected per patient in Cell-Free DNA BCT tubes (Streck, Inc.). Blood samples collected in iPEC were stored and shipped at room temperature overnight and processed within 120 hours. PEARL blood samples were collected, processed into plasma within 24 hours and stored at −80° C. until shipped to Illumina on dry ice. All blood was centrifuged at 1,600×g for 20 minutes at room temperature, plasma transferred to a new tube and centrifuged additional 10 minutes at 16,000×g. The plasma supernatant was stored at −80° C. until use.

Sequencing library preparation. C-RNA was extracted from 4.5 mL of plasma with the Circulating Nucleic Acid Kit (Qiagen) followed by DNAse I digestion (Thermo Fisher Scientific) according to manufacturer's instructions. C-RNA was fragmented at 94° C. for 8 minutes followed by random hexamer primed cDNA synthesis using the Illumina TruSight Tumor 170 Library Preparation kit (TST170; Illumina, Inc.). Illumina sequencing library preparation was carried out according to the TST170 kit for RNA, with two modifications: all reactions were reduced to 25% of original volume, and the ligation adaptor was used at a 1 in 10 dilution. Library quality was assessed with the High Sensitivity DNA Analysis chips on the Agilent Bioanalyzer 2100 (Agilent Technologies).

Whole-transcriptome enrichment. Sequencing libraries were quantified with Quant-iT PicoGreen dsDNA Kit (Thermo Fisher Scientific), normalized to 200 ng input and 4 samples pooled per enrichment reaction. The Illumina TruSeq RNA Enrichment kit (Illumina, Inc) was used to carry out whole exome enrichment. Briefly, biotinylated oligos targeting the exome were hybridized to sequencing libraries and pulled down by magnetic steptavidin beads to enrich libraries for exonic RNA. This process was performed two times to maximize exonic enrichment. Final enriched library was then re-amplified by PCR to provide sufficient yield for sequencing. Blocking oligos lacking the 5' biotin designed against hemoglobin genes HBA1, HBA2, and HBB were included in the enrichment reaction to minimize contributions from highly abundant hemoglobin. Final enrichment libraries were quantified using Quant-IT Picogreen dsDNA Kit (Thermo Fisher Scientific), normalized and pooled for paired end 50 by 50 sequencing on Illumina HiSeq 2000 platforms to a minimum depth of 40 million reads per sample.

Sequencing Data Analysis

Bioinformatic processing of sequencing data. Fastq files containing over 50 million reads were downsampled to 50 million reads with seqtk (v1.2-r102-dirty). Sequencing reads were mapped to human reference genome (hg19) with TopHat2 (v2.0.13) (Yang et al., 2014, *Biochim Biophys Acta;* 1840:3483-3493), and transcript abundance quantified with featureCounts (subread-1.4.6) (Calò et al., 2014, *J Hypertens;* 32:331-338) against RefGene coordinates (obtained Oct. 27, 2014). Tissue expression data were obtained from Body Atlas (Correlation Engine, Base Space, Illumina, Inc) (Whittle et al., 2019, *Front Microbiol;* 9:doi:10.3389/fmicb.2018.03266). Genes with expression ≥2-fold higher than the median expression across all tissues in the placenta or any of the fetal tissues (brain, liver, lung, and thyroid) were assigned to that group. Subcellular localization was obtained from UniProt (Magnusson et al., 2012, *PLOS ONE;* 7:e43142). Functional enrichment analyses were performed with gProfiler (v e97_eg44_p13 d22abce) (Raudvere et al., 2019, *Nucleic Acids Res;* 47:W191-W198).

Differential expression analysis. Differential expression analysis was performed in R (v3.4.2) with edgeR (v3.20.9), after excluding genes with ≤0.5 counts per million reads sequenced (CPM) in >25% of samples. Datasets were normalized by the TMM method (Debieve et al., 2011, *Mol Hum Reprod;* 17:702-9), and differentially abundant genes identified by the glmTreat test (Shiadeh et al., 2017, *Infection;* 45:589-600) for a log fold change ≥1, followed by Bonferroni-Holm p-value correction. For the iPEC data, this same process was used for each jackknifing iteration, which used 90% of samples in each group selected by random sampling without replacement. After 1,000 jackknifing iterations, the one-sided, normal-based 95% confidence interval for gene-wise p-values was calculated with statsmodels (v0.8.0) (Skalis et al., 2019, *Microrna;* 8:28-35). The one-sided calculation was used because only transcripts with a p-value <0.05 were of interest. Hierarchical clustering analysis was performed with squared Euclidean distance and average linkage.

AdaBoost. AdaBoost was performed in python with scikit-learn (v0.19.1, sklearmensemble.AdaBoostClassifier) (Burton et al., 2019, *BMJ;* 366:12381). A 10% holdout subset of iPEC samples were excluded from all machine learning activities. The remaining samples available for training machine learning were filtered to remove genes with a CPM ≤0.5 in >25% of samples and TMM-normalized. The log(CPM) values of transcripts were then standardized (sklearn.preprocessing.StandardScaler) to mean 0 and standard deviation 1 prior to fitting classifiers.

Optimal hyperparameter values were determined by random search over 1,000 iterations with 3-fold stratified cross-validation and using Matthew's correlation coefficient to quantify performance (FIG. 42) (Bergstra et al., 2012, *J Machine Learning Res;* 13:281-305). The number of estimators was sampled from a geometric distribution (scipy.stats.geom, p=0.004, loc=7) while the learning rate was sampled from an exponential distribution (scipy.stats.expon, loc=0.08, scale=2). Three iterations of the search showed the highest performance, and the median value for each hyperparameter was selected for further use (500 estimators and 1.6 learning rate).

AdaBoost models were trained with 10-fold stratified cross-validation to obtain robust estimates of PE classification capabilities. The full AdaBoost model training strategy is illustrated in FIG. 43. This strategy followed a two-step approach. In the first step, five subsets of samples were created from the training data. Four subsets (80% of training data) were combined and used to fit AdaBoost and one subset (20% of the training data) was used to assess performance during feature pruning. During feature pruning, the performance measure was Matthew's correlation coefficient, and the model with the highest value was retained. In the case of a tie, the model with the fewest transcripts was retained. Due to the probabilistic nature of AdaBoost, model composition varied each time a model was fit. Therefore, to increase the likelihood that the most robust estimators were highly represented, fitting and feature pruning was repeated ten times, generating ten models for a subset. This process was repeated five times, in each round holding out one subset for pruning and combining the four others for fitting. This step ultimately produced 50 total models.

In the second step, the estimators from all 50 models were combined to generate a single aggregate AdaBoost model. This ensemble then underwent feature pruning, in which the importance measure for each transcript was the number of models in which it appeared, and the performance measure was log loss. The model with the best log-scaled average performance across all pruning subsets was selected as the final ensemble.

Within each fold, the validation samples were fully excluded from model training, but were used to construct ROC curves and determine the score threshold which maximized both sensitivity and specificity. The status of the iPEC holdout samples and the PEARL PEC independent cohorts were then classified with each of the 10 AdaBoost models from the cross-validation.

RT-qPCR

25 TaqMan probes (Table 19; Thermo Fisher Scientific) were selected to validate sequencing results in a subset of patients from the iPEC cohort (N=19 PE, N=19 controls). 5 reference probes were used for normalization of fold change differences. These targeted a set of transcripts unchanged between control and PE samples and covered a range of abundances from 0.2 to 20 CPM. Table S20 shows probes selected to span exon junctions.

C-RNA was isolated and converted to cDNA from 2 mL of plasma. cDNA was pre-amplified using the TaqMan Preamp master Mix (Thermo Fisher Scientific) for 16 cycles, then diluted 10-fold. Triplicate TaqMan qPCR reactions were carried out for all probes per the manufacturer's protocol (Thermo Fisher Scientific). Cq values were determined using Bio-Rad CFX manager software. To determine transcript abundance, the ΔΔCq was calculated using the mean Cq values of the reference probes. To determine the fold change in PE samples for each probe, the average ΔΔCq value for PE samples was divided by the average ΔΔCq value for the matched control samples.

Sample Preparation Protocol Optimization rRNA and globin depletion. C-RNA was extracted from 2 mL plasma and DNAse treated prior to depletion. Use of the TruSeq Total RNA Library kit with RiboZero (Illumina, Inc.) followed the manufacturer's protocol. RNAseH depletion followed previously published protocols (Crescitelli et al., 2013, *J Extracell Vesicles;* 2:doi:10.3402/jev.v2i0.20677), except for hybridization which was performed in 6 uL total volume with a final concentration 125 pM/oligo for the depletion oligos.

C-RNA quantification. C-RNA was extracted from 4.5 mL plasma and DNAse treated. One tenth of the extracted C-RNA was used for quantification with the Quant-iT RiboGreen RNA Kit (Thermo Fisher Scientific). C-RNA was diluted 100-fold and quantified against the low range standard curve as recommended by the manufacture.

Plasma input comparison. Although no single experiment simultaneously assessed use of 0.5, 1, 2, and 4 mL plasma input, multiple datasets utilizing different plasma inputs were generated during protocol optimization. A meta-analysis was performed on the data from eight separate experiments to assess the impact of this variable. Biological coefficient of variation (BCV, edgeR) was used to quantify noise (Debieve et al., 2011, *Mol Hum Reprod;* 17:702-9). For every experiment, a BCV measurement was obtained for each set of samples composing a biologically distinct group. The bound population function from Preseq provided library complexity estimates (v2.0.0) (Xie et al., 2018, *Res Commun;* 506:692-697) for each individual sample. All sample preparation was performed as previously described with one exception: for 1 mL and 0.5 mL inputs, the Accel-NGS 1S Plus DNA Library Kit (Swift Biosciences) was used to generate libraries, following manufacturer instructions.

BCT comparison. 8 mL blood was drawn from pregnant and non-pregnant women in the following tube types: K2 EDTA (Beckton Dickinson), ACD (Beckton Dickinson), Cell Free RNA BCT tube (Streck), and Cell Free DNA BCT tube (Streck, Inc.). Blood was shipped overnight either on ice packs (EDTA and ACD) or at room temperature (Cell Free RNA and DNA BCT tubes). As a reference, 8 mL of blood was collected in K2 EDTA tubes and processed within 4 hours into plasma on site and shipped as plasma on dry ice. All other blood samples were processed after shipping after 1 or 5 days of storage at the preferred temperature. 3 mL of plasma was used per condition to generate sequencing libraries for enrichment using Illumina protocols as described previously. To compare pregnant and non-pregnant samples, pregnancy signal was quantified using 155 transcripts reported in prior C-RNA pregnancy studies (Tsui et al., 2014, *Clin Chem;* 60:954-962; and Koh et al., 2014, *Proc Natl Acad Sci USA;* 111:7361-7366) with the following equation:

$$\sum_{i=1}^{155} \frac{x_i - m_i}{s_i}$$

Where i denotes a single transcript, x is the log(CPM) value for the sample of interest, and m and s are the mean and standard deviation, respectively, for non-pregnant samples collected in the same BCT.

Pregnancy Timecourse analysis. Differential expression analysis was performed as described previously, without jackknifing. Transcripts altered during specific stages of gestation were identified as follows. The CPM values for each transcript were normalized within each patient using the first trimester sample (11-14 weeks gestational age) as baseline. The consensus values across all patients was obtained by Lowess smoothing (statsmodels.nonparametric.smoothers_lowess.lowess). A transcript was classified as altered earlier in pregnancy if the slope of the Lowess curve was ≥2-fold higher in absolute magnitude at 14 weeks than at 34 weeks gestational age; transcripts were categorized as altered later in pregnancy if the slope of the Lowess curve was ≥2-fold higher in absolute magnitude at 34 weeks than at 14 weeks gestational age. The remaining transcripts were categorized as altered throughout pregnancy.

Statistical Analysis

Unless otherwise noted, all statistical testing was two-sided. Non-parametric testing was used when data were not normally distributed. P-values were adjusted for multiple comparisons via Bonferroni-Holm or Tukey HSD calculations.

TABLE 12

Study characteristics for the Illumina Preeclampsia Cohort (iPEC). Continuous measurements presented as mean +− SD.

Sample and Maternal Characteristics

| | Sample Size (N) | Sample Gestational Age (weeks) | Male Fetus (%) | Maternal Age (years) | Maternal BMI (kg/m$^2$) | Nulliparous (%) |
|---|---|---|---|---|---|---|
| Control | 73 | 30.5 ± 2.6 | 42.5 | 29.7 ± 5.3 | 30.1 ± 5.6 | 38.4 |
| PE | 40 | 30.4 ± 2.6 | 37.5 | 30.4 ± 5.7 | 34.2 ± 5.8 | 32.5 |

Ethnicity/Race

| | Hispanic (%) | Caucasian (%) | African American (%) | Asian (%) | Other (%) | Unknown (%) |
|---|---|---|---|---|---|---|
| Control | 41.1 | 46.6 | 17.8 | 13.7 | 1.4 | 20.5 |
| PE | 35 | 35 | 27.5 | 7.5 | 0 | 30 |

Birth Outcomes

| | Birth Gestational Age (weeks) | Preterm Delivery (%) | Stillbirth (%) | Birth Weight (kg) | SGA* (%) |
|---|---|---|---|---|---|
| Control | 38.9 ± 1.8 | 9.6 | 0 | 3.2 ± 0.6 | 9.6 |
| PE | 31.5 ± 3.2 | 97.5 | 2.5 | 1.4 ± 0.5 | 45 |

*SGA, small for gestational age, defined as birthweight <10% of population for male or female neonate.

TABLE 13

PEARL HCC Gestational Age Distribution. 45 women with healthy pregnancies were divided into three groups and blood collected at 4 time points.

| Patient Group | Number of Patients | Collection 1 (weeks*) | Collection 2 (weeks*) | Collection 3 (weeks*) | Collection 4 (weeks*) |
|---|---|---|---|---|---|
| 1 | 14 | $11^{0/7}$-$13^{6/7}$ † | $14^{0/7}$-$17^{6/7}$ | $26^{0/7}$-$28^{6/7}$ | $35^{0/7}$-$37^{6/7}$ † |
| 2 | 13 | $11^{0/7}$-$13^{6/7}$ † | $18^{0/7}$-$21^{6/7}$ † | $29^{0/7}$-$31^{6/7}$ † | $35^{0/7}$-$37^{6/7}$ ‡ |
| 3 | 14 | $11^{0/7}$-$13^{6/7}$ § | $22^{0/7}$-$25^{6/7}$ | $32^{0/7}$-$34^{6/7}$ † | $35^{0/7}$-$37^{6/7}$ † |

*Indicated as a range from the minimum gestational age to the maximal gestational age, both in [weeks$^{days/7}$].

†1 sample failed library preparation

‡2 samples failed library preparation

§3 samples failed library preparation

TABLE 14

PEARL HCC pregnancy progression transcripts.

| Gene Symbol | Fold Change* | Timing of Alteration in Pregnancy** | Tissue Expression Category |
|---|---|---|---|
| ACOXL | +27 | Early | Other |
| ADAMI2 | +5.9 | Throughout | Placental/Fetal |
| AIM1L | +8.1 | Throughout | Placental |
| AKR1B15 | +12.7 | Throughout | Other |
| ALDH3B2 | +26 | Early | Other |
| ALPP | +64.5 | Early | Placental/Fetal |
| ANK3 | +3.5 | Early | Placental/Fetal |
| ANKFN1 | +12.1 | Throughout | Placental |
| ANKRD33 | +9.1 | Throughout | Placental |
| AOC1 | +6.1 | Throughout | Other |
| ATP6V1C2 | +11.5 | Early | Placental |
| BCAR4 | +12.9 | Throughout | Placental |
| C2orf72 | +20.6 | Throughout | Placental/Fetal |
| C4orf19 | +8.9 | Early | Placental/Fetal |
| CAMSAP3 | +6.1 | Late | Fetal |
| CAP2 | +4.6 | Throughout | Other |

TABLE 14-continued

PEARL HCC pregnancy progression transcripts.

| Gene Symbol | Fold Change* | Timing of Alteration in Pregnancy** | Tissue Expression Category |
|---|---|---|---|
| CAPN6 | +26.4 | Throughout | Placental |
| CDO1 | +3.7 | Throughout | Placental/Fetal |
| CFB | +3.6 | Early | Placental/Fetal |
| CGB5 | −17.0 | Early | Other |
| CGB8 | −22.0 | Early | Other |
| CRH | +54.4 | Late | Placental/Fetal |
| CRYAB | +8.2 | Early | Other |
| CSH1 | +7.5 | Throughout | Placental/Fetal |
| CSHL1 | +48.4 | Early | Placental/Fetal |
| CYP11A1 | +14.5 | Early | Placental |
| CYP19A1 | +7 | Throughout | Placental/Fetal |
| DACT2 | +9.2 | Throughout | Placental |
| DBET | +9.9 | Throughout | Other |
| DDX3Y | +19.9 | Early | Other |
| DEPDC1B | +4 | Early | Placental/Fetal |
| DLG5 | +4.9 | Throughout | Placental/Fetal |

TABLE 14-continued

PEARL HCC pregnancy progression transcripts.

| Gene Symbol | Fold Change* | Timing of Alteration in Pregnancy** | Tissue Expression Category |
|---|---|---|---|
| DLX3 | +9 | Late | Placental |
| DUSP4 | +3.7 | Throughout | Placental/Fetal |
| EFHD1 | +6.7 | Throughout | Placental |
| EFS | +7 | Throughout | Placental |
| EGFR | +4.3 | Throughout | Placental/Fetal |
| ELF3 | +11 | Early | Fetal |
| EPS8L1 | +6.7 | Throughout | Placental/Fetal |
| EPS8L2 | +3.6 | Throughout | Placental |
| ERVV-1 | +8.5 | Throughout | Other |
| ERVV-2 | +7.5 | Early | Other |
| ESRP2 | +11.5 | Throughout | Other |
| ESRRG | +12.3 | Early | Placental |
| EXPH5 | +37.7 | Throughout | Placental |
| FBN2 | +5.6 | Throughout | Placental/Fetal |
| FER1L6 | +8.3 | Late | Other |
| FOLR1 | +7 | Throughout | Placental/Fetal |
| FRZB | +6 | Early | Placental |
| FXYD3 | +9.1 | Early | Placental/Fetal |
| GADD45G | +5.6 | Throughout | Placental |
| GCM1 | +5.7 | Throughout | Placental |
| GDA | +11.2 | Early | Placental/Fetal |
| GLDN | +8.2 | Early | Placental |
| GOLGA8K | −932.4 | Throughout | Other |
| GPC3 | +6.1 | Throughout | Fetal |
| GRAMD2 | +10.4 | Throughout | Placental |
| GRB7 | +11.6 | Throughout | Placental |
| GRHL2 | +26.8 | Early | Placental |
| GRIP1 | +4.3 | Early | Placental/Fetal |
| GSTA3 | +32.1 | Early | Placental |
| HES2 | +12.5 | Early | Placental |
| HSD17B1 | +9.5 | Early | Placental |
| HSD3B1 | +12.7 | Early | Placental |
| HSPB8 | +4.6 | Early | Placental |
| IL36RN | +9.9 | Early | Other |
| KIAA1522 | +3.2 | Throughout | Other |
| KIF1A | +18.7 | Throughout | Fetal |
| KLF5 | +3.4 | Throughout | Other |
| KRT18 | +3.9 | Early | Placental/Fetal |
| KRT19 | +4.2 | Throughout | Placental/Fetal |
| KRT8 | +4.4 | Early | Placental/Fetal |
| KRT80 | +10.3 | Throughout | Other |
| KRT81 | +13 | Throughout | Other |
| LAD1 | +8.6 | Throughout | Other |
| LEP | −46.2 | Throughout | Placental |
| LGALS13 | +7.7 | Early | Placental/Fetal |
| LGALS14 | +12.2 | Early | Placental |
| LIN28B | +7.2 | Late | Placental |
| LINC00967 | +22.5 | Early | Placental |
| LINC01118 | +6.4 | Early | Placental |
| LY6G6C | +11.2 | Throughout | Other |
| MAGEA4 | +10.4 | Throughout | Other |
| MFSD2A | +3.6 | Throughout | Placental |
| MMP8 | +4.8 | Early | Fetal |
| MOCOS | +5.1 | Early | Other |
| MORN3 | +4 | Throughout | Placental |
| MSX2 | +7.2 | Throughout | Placental |
| MT1G | −68.8 | Early | Fetal |
| MUC15 | +23.1 | Early | Placental |
| NCCRP1 | +5.7 | Throughout | Placental |
| NCMAP | +25 | Early | Other |
| NRK | +13.3 | Early | Placental |
| OLAH | +7.1 | Early | Placental |
| OVOL1 | +13.2 | Throughout | Fetal |
| PACSIN3 | +7.5 | Throughout | Other |
| PAGE4 | +11.5 | Throughout | Placental |
| PAPPA | +15.9 | Early | Placental |
| PAPPA2 | +7 | Late | Placental |
| PCDH11X | +7.3 | Early | Other |
| PCDH11Y | +20.3 | Early | Other |
| PDZD2 | +3.1 | Throughout | Placental/Fetal |
| PGF | +9.5 | Early | Placental |
| PHYHIPL | +12.5 | Early | Placental/Fetal |
| PKIB | +5.6 | Early | Placental |
| PKP3 | +10.5 | Throughout | Placental |

TABLE 14-continued

PEARL HCC pregnancy progression transcripts.

| Gene Symbol | Fold Change* | Timing of Alteration in Pregnancy** | Tissue Expression Category |
|---|---|---|---|
| PLAC1 | +32.7 | Early | Placental/Fetal |
| PLAC4 | +6.9 | Early | Placental |
| PLEKHG6 | +10.5 | Throughout | Other |
| PLEKHH1 | +5.2 | Early | Placental |
| POU2F3 | +10.9 | Throughout | Other |
| PPP1R14C | +10.9 | Throughout | Placental/Fetal |
| PTPN3 | +7.4 | Early | Other |
| PVRL3 | +4.1 | Early | Placental/Fetal |
| PVRL4 | +7.8 | Throughout | Placental |
| RAB25 | +7.8 | Early | Other |
| RAB3B | +43.7 | Early | Placental/Fetal |
| RETN | +4.1 | Early | Other |
| RHOD | +10.6 | Early | Placental/Fetal |
| RLN2 | −125.4 | Late | Other |
| S100P | +4.1 | Early | Placental/Fetal |
| SCIN | +7.1 | Throughout | Placental |
| SEMA3B | +4 | Early | Placental |
| SERPINB2 | +13.4 | Early | Placental |
| SLC27A6 | +10.1 | Throughout | Placental |
| SLC28A1 | +10.4 | Late | Fetal |
| SLC30A2 | +7.5 | Throughout | Placental |
| SLC6A2 | +6.4 | Early | Placental/Fetal |
| SLC7A2 | +6.2 | Throughout | Placental/Fetal |
| SMOC2 | +14.2 | Throughout | Other |
| SPIRE2 | +18.3 | Early | Placental/Fetal |
| SPTLC3 | +5.6 | Throughout | Placental |
| STRA6 | +7.5 | Early | Placental/Fetal |
| SULT2B1 | +35.4 | Early | Other |
| SVEP1 | +12.5 | Early | Placental |
| TACC2 | +36 | Throughout | Placental |
| TBX20 | +9.4 | Early | Other |
| TEAD3 | +9.5 | Early | Placental |
| TFAP2A | +17.9 | Early | Placental |
| TFAP2C | +9.4 | Early | Placental |
| TGM2 | +3.9 | Throughout | Placental/Fetal |
| TMEM54 | +11.2 | Early | Placental |
| TNS4 | +12.7 | Throughout | Placental |
| TPPP3 | +6.2 | Throughout | Placental/Fetal |
| TPRXL | +12.3 | Early | Placental |
| TRIM29 | +18.5 | Early | Placental |
| TRPV6 | +16.7 | Early | Placental |
| TWIST1 | +19.7 | Throughout | Placental |
| USP43 | +11.1 | Early | Placental |
| UTY | +18.6 | Early | Other |
| VGLL1 | +7.1 | Early | Placental/Fetal |
| VGLL3 | +13.6 | Early | Placental |
| WWC1 | +6.1 | Early | Fetal |
| XAGE3 | +11 | Early | Placental |
| ZFY | +16.3 | Late | Other |
| ZNF750 | +12.4 | Early | Placental |

*Reporting the maximal fold change observed between any pairwise comparison of age groups. All changes are relative to the lower GA group-positive change indicates increased abundance later in pregnancy.

**If the slope of the log2(Fold Change) for a transcript is >2-fold higher at 14 weeks GA than at 34 weeks GA, it is considered altered early in pregnancy; if >2-fold higher at 34 weeks than at 14 weeks, it is considered altered late in pregnancy; if both fold changes are <2, it is considered altered throughout pregnancy.

TABLE 15

The iPEC diagnostic and inclusion/exclusion criteria for PE with severe features.

Diagnostic Criteria

| Measurement | Manifestation |
|---|---|
| Blood Pressure | 1. Systolic BP ≥160 mmHG or diastolic BP ≥160 mmHg measured on at least 2 occasions 4 hours apart while on bedrest but before the onset of labor, or measured on 1 occasion only if antihypertensive therapy is initiated due to severe hypertension |
| | Defined by one of the following: |
| Proteinuria | 1. Excretion of ≥300 mg of protein in a 24 hr period |
| | 2. Protein/creatinine value of at least 0.3 |
| | 3. Qualitative determination with urine dipstick of ≥1+, if the above measurements were not available |
| | OR |
| Blood Pressure | 1. Systolic BP ≥140 mmHg or diastolic ≥90 mmHg on at least 2 occasions 4 hours apart while on bedrest but before the onset of labor |
| With one of the following features | 1. Thrombocytopenia (<100,000 platelets/mL) |
| | 2. Impaired liver function |
| | 3. Newly developed renal insufficiency |
| | 4. Pulmonary edema |
| | 5. New-onset cerebral disturbances or scotomata |

Inclusion/Exclusion Criteria

| Category | Requirements |
|---|---|
| PE Inclusion | 1. Women 18 years of age or older |
| | 2. Pregnant women with a viable singleton gestation |
| | 3. Gestational age between 20 0/7 and 33 6/7 weeks determined by ultrasound and/or LMP per ACOG guidelines |
| | 4. Preeclampsia diagnosed with severe features per ACOG guidelines |
| PE Exclusion | 1. Known malignancy |
| | 2. History of maternal organ or bone marrow transplant |
| | 3. Maternal blood transfusion in the last 8 weeks |
| | 4. Chronic hypertension diagnosed prior to current pregnancy |
| | 5. Type I, II or gestational diabetes |
| | 6. Fetal anomaly or known chromosome abnormality |
| Control Inclusion | 1. Women 18 years of age or older |
| | 2. Pregnant women with a viable singleton gestation |
| | 3. Gestational age between 20 0/7 and 33 6/7 weeks determined by ultrasound and/or LMP per ACOG guidelines. |
| Control Exclusion | 1. Known malignancy |
| | 2. History of maternal organ or bone marrow transplant |
| | 3. Maternal blood transfusion in the last 8 weeks |
| | 4. Chronic hypertension diagnosed prior to current pregnancy |
| | 5. Type I, II or gestational diabetes |
| | 6. Fetal anomaly or known chromosome abnormality |
| | 7. Active labor |
| | 8. Thrombocytopenia (<100,000 plts/mL) |
| | 9. Impaired liver function |
| | 10. Newly developed renal insufficiency (serum creatine >1.1 mg/dL) |
| | 11. Pulmonary edema |
| | 12. New-onset cerebral disturbances or scotomata |
| | 13. Preeclampsia in prior or current pregnancy |
| | 14. Fetal growth restriction |
| | 15. |

TABLE 16

Medications in use in the iPEC.

| Treatment Purpose | Medication* | PE Cohort (%) | Control Cohort (%) |
|---|---|---|---|
| PE/Hypertension | Magnesium sulfate | 82.5 | 4.1 |
| | Antenatal Steroids | 95 | 6.8 |
| | Anti-Hypertensive | 75 | 5.3 |
| | Aspirin | 20 | 0 |
| Pregnancy Symptoms | Antiemetics | 25 | 5.5 |
| | Antacids | 27.5 | 8.2 |
| | Anti-constipation | 15 | 11.8 |

TABLE 16-continued

Medications in use in the iPEC.

| Treatment Purpose | Medication* | PE Cohort (%) | Control Cohort (%) |
|---|---|---|---|
| | Prenatal Vitamins | 17.5 | 31.5 |
| | Iron Supplement | 10 | 12.3 |
| Other Conditions | Analgesics | 60 | 11.8 |
| | Antimicrobials | 12.5 | 5.5 |
| | Antihistamines | 32.5 | 13.7 |
| | Antiasthmatics | 10 | 2.7 |
| | Psychoactive | 15 | 5.5 |
| | Hormone Therapy | 7.5 | 2.7 |

TABLE 16-continued

| Medications in use in the iPEC. | | | |
|---|---|---|---|
| Treatment Purpose | Medication* | PE Cohort (%) | Control Cohort (%) |

*Medication category listed for most drugs rather that enumerating all specific pharmaceuticals.

TABLE 17

Medical center collection site patient distribution for the iPEC.

| Clinical Site | Location (city, state) | PE patients (N) | Controls (N) |
|---|---|---|---|
| University of Texas Medical Branch | Galveston, Texas | 4 | 11 |
| Tufts Medical Center | Boston, MA | 10 | 17 |
| Columbia University Irving Medical Center | New York, NY | 4 | 9 |
| Winthrop University Hospital | Mineola, NY | 5 | 9 |
| St. Peter's University Hospital | New Brunswick, NJ | 3 | 6 |
| Christiana Care | Newark, DE | 7 | 13 |
| Rutgers University Robert Wood Johnson Medical School | New Brunswick, NJ | 5 | 8 |
| New York Presbyterian/Queens | New York, NY | 2 | 3 |

TABLE 18

Study characteristics for PEARL PEC. Continuous measurements presented as mean +− SD.

Sample and Maternal Characteristics

| | Sample Size (N) | Sample Gestational Age (weeks) | Male Fetus (%) | Maternal Age (years) | Maternal BMI ($kg/m^2$) | Nulliparous (%) |
|---|---|---|---|---|---|---|
| Early-Onset Control | 12 | 29.3 ± 2.3 | 58.3 | 30.1 ± 3.8 | 28.5 ± 7 | 58.3 |
| Early-Onset PE | 12 | 29.2 ± 2.3 | 75 | 29.3 ± 3.5 | 33.6 ± 9 | 60 |
| Late-Onset Control | 12 | 35.9 ± 0.8 | 58.3 | 29.4 ± 3.2 | 27.9 ± 4.5 | 75 |
| Late-Onset PE | 12 | 35.6 ± 1.3 | 66.7 | 30.2 ± 4.8 | 32.2 ± 4.9 | 75 |

Ethnicity/Race

| | Hispanic (%) | Caucasian (%) | African American (%) | Asian (%) | Other (%) | Unknown (%) |
|---|---|---|---|---|---|---|
| Early-Onset Control | 0 | 100 | 0 | 0 | 0 | 0 |
| Early-Onset PE | 0 | 91.7 | 8.3 | 0 | 0 | 0 |
| Late-Onset Control | 0 | 100 | 0 | 0 | 0 | 0 |
| Late-Onset PE | 0 | 100 | 0 | 0 | 0 | 0 |

Birth Outcomes

| | Birth Gestational Age (weeks) | Term Delivery (%) | Preterm Delivery (%) | Stillbirth (%) | Birth Weight (kg) | SGA* (%) |
|---|---|---|---|---|---|---|
| Early-Onset Control | 39.1 ± 1.5 | 91.7 | 8.3 | 0 | 3.2 ± 0.4 | 0 |
| Early-Onset PE | 30.3 ± 3.4 | 0 | 100 | 0 | 1.3 ± 0.5 | 25 |

TABLE 18-continued

Study characteristics for PEARL PEC. Continuous measurements presented as mean +− SD.

| | | | | | | |
|---|---|---|---|---|---|---|
| Late-Onset Control | 39.7 ± 1.6 | 91.7 | 8.3 | 0 | 3.4 ± 0.5 | 25 |
| Late-Onset PE | 37 ± 1.4 | 75 | 25 | 0 | 2.7 ± 0.6 | 33.3 |

Additional Health Issues

| | Chronic Hypertension | Type I, II Diabetes | Gestational Diabetes | Fetal Growth Restriction | HELLP | Other |
|---|---|---|---|---|---|---|
| Early-Onset Control | 8.3 | 0 | 33.3 | 0 | 0 | 8.3 |
| Early-Onset PE | 16.7 | 16.7 | 16.7 | 50 | 25 | 0 |
| Late-Onset Control | 0 | 0 | 16.7 | 0 | 0 | 0 |
| Late-Onset PE | 8.3 | 25 | 8.3 | 8.3 | 0 | 0 |

PE/Hypertension Medications

| | Magnesium Sulfate | Antenatal Steroids | Anti-Hypertensive | Aspirin |
|---|---|---|---|---|
| Early-Onset Control | 0 | 0 | 8.3 | 25 |
| Early-Onset PE | 83.3 | 100 | 100 | 8.3 |
| Late-Onset Control | 0 | 0 | 0 | 8.3 |
| Late-Onset PE | 33.3 | 25 | 75 | 25 |

*SGA, small for gestational age, defined as birthweight <10% of population for male or female neonate.

TABLE 19

TaqMan Probes for qPCR validation.

| Gene Symbol | Assay ID | RefSeq | Control CPM* (mean ± SD) | PE CPM* (mean ± SD) |
|---|---|---|---|---|
| Reference Probes | | | | |
| ABHD12 | Hs01018050_m1 | NM_001042472.2 | 20.7 ± 6.5 | 20.5 ± 4.7 |
| KRBOX4 | Hs01063506_gH | NM_001129898.1 | 5.1 ± 2 | 5.4 ± 1.8 |
| NME3 | Hs01573872_g1 | NM_002513.2 | 1.6 ± 0.8 | 1.8 ± 0.8 |
| WNT7A | Hs00171699_m1 | NM_004625.3 | 0.3 ± 0.03 | 0.3 ± 0.1 |
| ZNF138 | Hs00864088_gH | NM_001271638.1 | 8.1 ± 3.3 | 7.5 ± 3.2 |
| Target Probes | | | | |
| ADAMTS2 | Hs01029111_m1 | NM_014244.4 | 0.6 ± 1.2 | 7.8 ± 7.5 |
| ALOX15B | Hs00153988_m1 | NM_001039130.1 | 0.3 ± 0.3 | 1.9 +± .1 |
| ARHGEF25 | Hs00384780_g1 | NM_001111270.2 | 1.3 ± 1 | 5.5 ± 2.6 |
| CLEC4C | Hs01092460_m1 | NM_130441.2 | 4.3 ± 2.3 | 1.3 ± 0.9 |
| DAAM2 | Hs00322497_m1 | NM_001201427.1 | 1.6 ± 1.8 | 9.6 ± 9.6 |
| FAM107A | Hs00200376_m1 | NM_001076778.2 | 8.3 ± 5.5 | 44.2 ± 35.4 |
| HSPA12B | Hs00369554_m1 | NM_001197327.1 | 5.9 ± 3.5 | 22.4 ± 11.7 |
| HTRA4 | Hs00538137_m1 | NM_153692.3 | 0.4 ± 0.4 | 1.6 ± 1.2 |
| IGFBP5 | Hs00181213_m1 | NM_000599.3 | 10.3 ± 5.8 | 39.9 ± 26.1 |
| KRT5 | Hs00361185_m1 | NM_000424.3 | 3.1 ± 3.3 | 0.6 ± 0.7 |
| LEP | Hs00174877_m1 | NM_000230.2 | 0.2 ± 0.5 | 1.8 ± 1.5 |
| NES | Hs00707120_s1 | NM_006617.1 | 20.8 ± 12.5 | 101.6 ± 61 |
| PAPPA2 | Hs01060983_m1 | NM_020318.2 | 5.9 ± 9.3 | 26.1 ± 16.6 |
| PITPNM3 | Hs01107787_m1 | NM_001165966.1 | 22.6 ± 12.9 | 76.5 ± 43.6 |
| PLD4 | Hs00975488_m1 | NM_001308174.1 | 5.5 ± 2.6 | 2 ± 1.3 |
| PRG2 | Hs00794928_m1 | NM_001243245.2 | 0.6 ± 0.5 | 3.3 ± 5.6 |
| TIMP3 | Hs00165949_m1 | NM_000362.4 | 3.7 ± 2.3 | 15.8 ± 10.7 |
| TIMP4 | Hs00162784_m1 | NM_003256.3 | 0.4 ± 0.4 | 2 ± 1.9 |

TABLE 19-continued

TaqMan Probes for qPCR validation.

| Gene Symbol | Assay ID | RefSeq | Control CPM* (mean ± SD) | PE CPM* (mean ± SD) |
|---|---|---|---|---|
| VSIG4 | Hs00907325_m1 | NM_001184830.1 | 3.6 ± 3.8 | 30.9 ± 32.9 |
| ZEB1 | Hs01566408_m1 | NM_001128128.2 | 245.9 ± 108.7 | 752.6 ± 434 |

*Calculated from the iPEC sequencing data

TABLE 20

Transcripts with C-RNA abundances altered in early-onset PE with severe features. Delineates the protein expression, functional characteristics, and PE-relevant literature of the genes identified by differential expression analysis with jackknifing (DEX) from the iPEC samples.

Changes in PE

| Gene Symbol | Analysis | Fold Change in PE | PMID of Manuscripts Describing a Role in PE |
|---|---|---|---|
| ALOX15B | DEX | +5.7 | 22078795 |
| AMPH | DEX | +5.0 | NA |
| CUX2 | DEX & AdaBoost | −3.3 | NA |
| FAM107A | DEX | +5.0 | NA |
| IGFBP5 | DEX | +3.6 | 28049695 |
| NES | DEX & AdaBoost | +4.5 | 17653873 |
| PITPNM3 | DEX | +3.2 | NA |
| PRX | DEX | +3.8 | 24657793 |
| TEAD4 | DEX & AdaBoost | +3.3 | NA |
| PNMT | DEX | +3.8 | NA |
| DAAM2 | DEX | +5.6 | 20934677 |
| SLC9A3R2 | DEX | +3.6 | NA |
| HSPA12B | DEX | +3.5 | NA |
| PLD4 | DEX & AdaBoost | −3.0 | NA |
| TIMP4 | DEX | +4.3 | 29231756 |
| KRT5 | DEX & AdaBoost | −5.8 | 24657793 |
| ZEB1 | DEX | +2.8 | 30315928 |
| APOLD1 | DEX | +3.4 | 22013081 |
| HTRA4 | DEX | +3.9 | 25946029 |
| SEMA3G | DEX & AdaBoost | +3.5 | NA |
| ADAMTS1 | DEX | +3.5 | 29135310 |
| CRH | DEX | +5.7 | 12709362 |
| PRG2 | DEX & AdaBoost | +5.2 | 28347715 |
| TIMP3 | DEX | +4.1 | 30715128 |
| ARHGEF25 | DEX & AdaBoost | +4.1 | NA |
| CLEC4C | DEX & AdaBoost | −3.6 | 12699426 |
| LEP | DEX & AdaBoost | +10.7 | 23544093 |
| PAPPA2 | DEX | +4.9 | 26748159 |
| VSIG4 | DEX & AdaBoost | +8.1 | 24349325 |
| ADAMTS2 | DEX & AdaBoost | +11.6 | NA |

Protein Characteristics

| Gene Symbol | Tissue Expression | Sub-Cellular Localization * | Function |
|---|---|---|---|
| ALOX15B | Fetal | Nucleus; Cytoskeleton; Cytosol; | Cell Cycle; Immune Function; Cardiovascular Function |
| AMPH | Fetal | Membrane Cytoskeleton; Membrane | Synaptic Vesicle Endocytosis |
| CUX2 | Fetal | Nucleus | Cell Cycle; Fetal Development; DNA Damage Response |
| FAM107A | Fetal | Cytoskeleton; Membrane; Nucleus | Cell Migration/Invasion; Cell Cycle; ECM Regulation |
| IGFBP5 | Fetal | Extracellular or Secreted | Fetal Development; IGF Signaling |
| NES | Fetal | Cytoskeleton | Fetal Development; Cell Cycle |
| PITPNM3 | Fetal | Membrane | Phosphatidylinositol Regulation |

TABLE 20-continued

Transcripts with C-RNA abundances altered in early-onset PE with severe features. Delineates the protein expression, functional characteristics, and PE-relevant literature of the genes identified by differential expression analysis with jackknifing (DEX) from the iPEC samples.

| | | | |
|---|---|---|---|
| PRX | Fetal | Membrane | Cell Structure/Composition |
| TEAD4 | Fetal | Nucleus | Placental Development |
| PNMT | Other | Cytosol | Epinephrine Synthesis; Cardiovascular Function; Pregnancy Duration |
| DAAM2 | Other | Extracellular or Secreted | Fetal Development |
| SLC9A3R2 | Other | Membrane; Nucleus | ECM Regulation; Cell Structure/Composition |
| HSPA12B | Other | unknown | Angiogenesis; Cardiovascular Function; Cell Migration/Invasion; Hypoxia Response |
| PLD4 | Other | Membrane | Phosphatidylinositol Regulation; Immune Function |
| TIMP4 | Other | Extracellular or Secreted | ECM Regulation; Immune Function |
| KRT5 | Other | Cytoskeleton | Cell Structure/Composition |
| ZEB1 | Other | Nucleus | Immune Function; Cell Migration/Invasion; Fetal Development; Pregnancy Duration |
| APOLD1 | Placental | Plasma Membrane | Angiogenesis; Cardiovascular Function; Hypoxia Response; Fetal Development |
| HTRA4 | Placental | Extracellular or Secreted | IGF Signaling; Placental Development |
| SEMA3G | Placental | Extracellular or Secreted | Cell Migration/Invasion |
| ADAMTS1 | Placental/Fetal | Extracellular or Secreted | ECM Regulation; Fetal Development; Angiogenesis |
| CRH | Placental/Fetal | Extracellular or Secreted | Pregnancy Duration; Fetal Development; Cardiovascular Function |
| PRG2 | Placental/Fetal | Extracellular or Secreted | Immune Function; ECM Regulation; IGF Signaling |
| TIMP3 | Placental/Fetal | Extracellular or Secreted | ECM Regulation; Immune Function; Angiogenesis |
| ARHGEF25 | Other | Membrane; Sarcomere | Cardiovascular function |
| CLEC4C | Other | Membrane | Immune Function |
| LEP | Placental | Extracellular or Secreted | Energy Homeostasis; Immune Function; Angiogenesis; Fetal Development; ECM Regulation |
| PAPPA2 | Placental | Extracellular or Secreted | Fetal Development; IGF Signaling |
| VSIG4 | Placental | Membrane | Immune Function |
| ADAMTS2 | Placental/Fetal | Extracellular or Secreted | ECM Regulation; Angiogenesis; Fetal Development |

* All "membrane" classifications were collapsed to a single category.

TABLE 21

Transcripts used by AdaBoost for classification of early-onset PE with severe features. Delineates the protein expression, functional characteristics, and PE-relevant literature of the genes identified with the iPEC model samples.

| | | Changes in PE | | | |
|---|---|---|---|---|---|
| Gene Symbol | Analysis | Number of Models | Average Relative Importance* | Fold Change in PE | PMID of Manuscripts Describing a Role in PE |
| ADA | AdaBoost | 3 | 0% | −1.44 | 27939490 |
| ADAMTS2 | DEX & AdaBoost | 6 | 18% | +11.57 | NA |
| AKAP2 | AdaBoost | 1 | 1% | +1.95 | NA |
| ARHGEF25 | DEX & AdaBoost | 10 | 25% | +4.09 | NA |
| ARRB1 | AdaBoost | 1 | 19% | −1.17 | 30503206 |

TABLE 21-continued

Transcripts used by AdaBoost for classification of early-onset PE with severe features. Delineates the protein expression, functional characteristics, and PE-relevant literature of the genes identified with the iPEC model samples.

| | | | | | |
|---|---|---|---|---|---|
| ARRDC2 | AdaBoost | 8 | 7% | +1.78 | NA |
| ATOH8 | AdaBoost | 5 | 2% | +2.22 | 30301918 |
| CLEC4C | DEX & AdaBoost | 8 | 8% | −3.64 | 12699426 |
| CPSF7 | AdaBoost | 1 | 1% | +1.2 | NA |
| CUX2 | DEX & AdaBoost | 3 | 1% | −3.3 | NA |
| FKBP5 | AdaBoost | 1 | 0% | +2.8 | 26268791 |
| FSTL3 | AdaBoost | 2 | 1% | +2.57 | 30454705 |
| GSTA3 | AdaBoost | 4 | 1% | −2.54 | 28232601 |
| HEG1 | AdaBoost | 3 | 3% | +2.06 | NA |
| IGIP | AdaBoost | 4 | 1% | +2.49 | 25802182 |
| INO80C | AdaBoost | 2 | 2% | −1.13 | NA |
| JAG1 | AdaBoost | 3 | 2% | +2.13 | 21693515 |
| JUN | AdaBoost | 6 | 3% | +1.75 | 20800894 |
| KRT5 | DEX & AdaBoost | 2 | 3% | −5.78 | 24657793 |
| LEP | DEX & AdaBoost | 9 | 8% | +10.75 | 23544093 |
| LILRA4 | AdaBoost | 4 | 2% | −2.57 | 19368561 |
| MRPS35 | AdaBoost | 1 | 0% | −1.18 | NA |
| MSMP | AdaBoost | 7 | 9% | +1.37 | 29059175 |
| NES | DEX & AdaBoost | 6 | 9% | +4.5 | 17653873 |
| NFE2L1 | AdaBoost | 3 | 7% | +2.39 | 26089598 |
| NR4A2 | AdaBoost | 1 | 1% | +1.42 | 18533121 |
| NTRK2 | AdaBoost | 1 | 1% | +2.67 | 21537405 |
| PACSIN1 | AdaBoost | 1 | 1% | −3.22 | NA |
| PER1 | AdaBoost | 3 | 5% | +2.33 | NA |
| PLD4 | DEX & AdaBoost | 4 | 2% | −3.03 | NA |
| PLEK | AdaBoost | 1 | 19% | −1.37 | NA |
| PRG2 | DEX & AdaBoost | 1 | 1% | +5.24 | 28347715 |
| RAP1GAP2 | AdaBoost | 6 | 2% | −1.23 | 29643944 |
| RGP1 | AdaBoost | 3 | 1% | +1.26 | NA |
| SEMA3G | DEX & AdaBoost | 1 | 0% | +3.48 | NA |
| SH3PXD2A | AdaBoost | 2 | 4% | +2.36 | 23544093 |
| SKIL | AdaBoost | 7 | 7% | +1.46 | 20934677 |
| SMPD3 | AdaBoost | 1 | 0% | −2.3 | 23465879 |
| SPEG | AdaBoost | 3 | 2% | +1.87 | NA |
| SRPX | AdaBoost | 1 | 1% | +2.89 | 20934677 |
| SYNPO | AdaBoost | 1 | 1% | +2.67 | 17255128 |
| TEAD4 | DEX & AdaBoost | 3 | 5% | +3.3 | NA |
| TIPARP | AdaBoost | 1 | 0% | +1.28 | 28347715 |
| TNFRSF21 | AdaBoost | 4 | 1% | −1.52 | NA |
| TPST1 | AdaBoost | 1 | 0% | +1.69 | NA |
| TRPS1 | AdaBoost | 1 | 0% | +1.18 | NA |
| UBE2Q1 | AdaBoost | 1 | 50% | −1.1 | NA |
| VSIG4 | DEX & AdaBoost | 3 | 3% | +8.13 | 24349325 |
| ZNF768 | AdaBoost | 2 | 7% | +1.6 | NA |

Protein Characteristics

| Gene Symbol | Tissue Expression | Sub-Cellular Localization | Function |
|---|---|---|---|
| ADA | Other | Lysosome; Membrane | Metabolism; Inflammation |
| ADAMTS2 | Placental/Fetal | Extracellular or Secreted | ECM regulation; Angiogenesis; Fetal Development |
| AKAP2 | Other | Membrane | Cardiovascular Function |
| ARHGEF25 | Other | Membrane; Sarcomere | Cardiovascular Function |
| ARRB1 | Other | Cytosol | GPCR Signaling; Cardiovascular Function; Immune Function |
| ARRDC2 | Other | Membrane | Protein Trafficking |
| ATOH8 | Other | Nucleus | Transcription Factor; Pregnancy Duration; Trophoblast Regulation |
| CLEC4C | Other | Membrane | Immune Function |
| CPSF7 | Other | Nucleus; Cytoplasm | mRNA Processing |
| CUX2 | Fetal | Nucleus | Cell Cycle; Fetal Development; DNA Damage Response |
| FKBP5 | Other | Nucleus; Cytoplasm | Immune Function; Steroid Hormone Receptor Trafficking |
| FSTL3 | Placental | Extracellular or Secreted; Nucleus | Fetal Development; Trophoblast Regulation |
| GSTA3 | Placental | Cytoplasm | Steroid Hormone Biosynthesis; Placental Development |
| HEG1 | Other | Membrane; Extracellular or Secreted | Fetal Development |
| IGIP | Other | Extracellular or Secreted | Cardiovascular Function |

TABLE 21-continued

Transcripts used by AdaBoost for classification of early-onset PE with severe features. Delineates the protein expression, functional characteristics, and PE-relevant literature of the genes identified with the iPEC model samples.

| | | | |
|---|---|---|---|
| INO80C | Placental | Nucleus | Transcription Regulation; DNA Repair |
| JAG1 | Other | Membrane | Fetal Development; Angiogenesis; Trophoblast Regulation |
| JUN | Other | Nucleus | Transcription Factor; Trophoblast Regulation |
| KRT5 | Other | Cytoskeleton | Cell Structure/Composition |
| LEP | Placental | Extracellular or Secreted | Energy Homeostasis; Immune Function; Angiogenesis; Fetal Development; ECM Regulation |
| LILRA4 | Other | Membrane | Immune Function |
| MRPS35 | Other | Mitochondria | Energy Homeostasis; Cell Structure/Composition |
| MSMP | Other | Extracellular or Secreted | Angiogenesis |
| NES | Fetal | Cytoskeleton | Fetal Development; Cell Cycle Cardiovascular Function; Oxidative |
| NFE2L1 | Other | Membrane; Nucleus | Stress Response; Energy Homeostasis; Transcription Factor |
| NR4A2 | Other | Nucleus; Cytoplasm | Fetal Development; Steroid Hormone Response; Transcription Factor |
| NTRK2 | Fetal | Membrane | Trophoblast Regulation; Fetal Development |
| PACSIN1 | Fetal | Membrane | Cell Structure/Composition; Synaptic Vesicle Endocytosis |
| PER1 | Fetal | Nucleus; Cytoplasm | Circadian Rhythm |
| PLD4 | Other | Membrane | Phosphatidylinositol Regulation; Immune Function |
| PLEK | Fetal | Cytosol | Phosphatidylinositol Regulation; Immune Function; Cell Structure/Composition |
| PRG2 | Placental/Fetal | Extracellular or Secreted | Immune Function; ECM Regulation; IGF Signaling |
| RAP1GAP2 | Placental/Fetal | Cytoplasm | Immune Function; Angiogenesis; Fetal Development |
| RGP1 | Other | Cytosol; Membrane | Protein Trafficking |
| SEMA3G | Placenta | Extracellular or Secreted | Cell Migration/Invasion |
| SH3PXD2A | Other | Cytoplasm | ECM Regulation; Fetal Development |
| SKIL | Placenta | Nucleus | Transcription Factor; Placenta Development |
| SMPD3 | Fetal | Membrane | Lipid Metabolism |
| SPEG | Other | Nucleus | Fetal Development |
| SRPX | Other | Extracellular or Secreted | Angiogenesis |
| SYNPO | Placenta | Cytskeleton; Cytosol | Cell Structure/Composition |
| TEAD4 | Fetal | Nucleus | Placental Development |
| TIPARP | Other | Nucleus | Metabolism; Protein Processing |
| TNFRSF21 | Other | Membrane | Immune Function; Apoptosis |
| TPST1 | Other | Membrane | Protein Processing |
| TRPS1 | Other | Nucleus | Transcription Factor |
| UBE2Q1 | Other | Nucleus; Cytosol | Protein Processing |
| VSIG4 | Placenta | Membrane | Immune Function |
| ZNF768 | Other | Nucleus | Transcription Factor |

*Average for when included in an AdaBoost model.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of detecting and treating preeclampsia in a subject pregnant human female, the method comprising:

detecting in a blood, plasma, or serum sample from the subject pregnant human female a level of circulating RNA (C-RNA) molecules encoding at least a portion of the protein UBE2Q1 protein, wherein the detected level is decreased by about 1.1 fold relative to a level in a gestationally age matched control pregnant human female that does not have preeclampsia, and wherein the detected level indicates the presence of preeclampsia in the subject pregnant human female; and providing the subject pregnant human female with: a therapeutic intervention for the treatment of preeclampsia selected from the group consisting of antihypertensive medications to lower blood pressure, corticosteroid medications, anticonvulsant medications, bed rest, early delivery, and combinations thereof, and/or treating the subject pregnant human female with a low dose of aspirin, wherein a low dose of aspirin comprises about 50 to about 150 mg per day.

2. A method of detecting and treating preeclampsia in a subject pregnant human female, the method comprising:

obtaining a biosample from the subject pregnant human female;

wherein the biosample comprises blood, plasma, or serum;

purifying a population of circulating RNA (C-RNA) molecules from the biosample;

identifying protein coding sequences encoded by the C-RNA molecules within the purified population of C-RNA molecules;

detecting in the blood, plasma, or serum sample from the subject pregnant human female a level of C-RNA molecules encoding at least a portion of the protein UBE2Q1 protein, wherein the detected level is decreased by about 1.1 fold relative to a level in a gestationally age matched control pregnant human female that does not have preeclampsia, and wherein the detected level indicates the presence of preeclampsia in the subject pregnant human female; and providing the subject pregnant human female with a therapeutic intervention for the treatment of preeclampsia selected from the group consisting of antihypertensive medications to lower blood pressure, corticosteroid medications, anticonvulsant medications, bed rest, early delivery, and combinations thereof, and/or treating the subject pregnant human female with a low dose of aspirin, wherein a low dose of aspirin comprises about 50 to about 150 mg per day.

3. The method of claim 1, wherein detecting the level of C-RNA molecules encoding at least a portion of the protein UBE2Q1 protein comprises hybridization, reverse transcriptase PCR, microarray chip analysis, or sequencing.

4. The method of claim 3, wherein sequencing comprises massively parallel sequencing of clonally amplified molecules.

5. The method of claim 3, wherein sequencing comprises RNA sequencing.

6. A method of detecting and treating preeclampsia in a subject pregnant human female, the method comprising:

removing intact cells from a biosample obtained from the subject pregnant human female;

wherein the biosample comprises blood, plasma, or serum;

treating the biosample with a deoxynuclease (DNase) to remove cell free DNA (cfDNA);

synthesizing complementary DNA (cDNA) from circulating RNA (C-RNA) molecules in the biosample;

enriching the cDNA sequences for DNA sequences that encode proteins (exome enrichment);

sequencing the resulting enriched cDNA sequences; and identifying protein coding sequences encoded by enriched C-RNA molecules;

detecting in the blood, plasma, or serum sample from the subject pregnant human female a level of C-RNA molecules encoding at least a portion of the protein UBE2Q1 protein, wherein the detected level is decreased by about 1.1 fold relative to a level in a gestationally age matched control pregnant human female that does not have preeclampsia, and wherein the detected level indicates the presence of preeclampsia in the subject pregnant human female; and providing the subject pregnant human female with a therapeutic intervention for the treatment of preeclampsia selected from the group consisting of antihypertensive medications to lower blood pressure, corticosteroid medications, anticonvulsant medications, bed rest, early delivery, and combinations thereof, and/or treating the subject pregnant human female with a low dose of aspirin, wherein a low dose of aspirin comprises about 50 to about 150 mg per day.

7. The method of claim 1, wherein the blood, plasma, or serum sample is obtained from the subject pregnant human female at less than 16 weeks gestation or at less than 20 weeks gestation.

8. The method of claim 1, wherein the blood, plasma, or serum sample is obtained from the subject pregnant human female at greater than 20 weeks gestation.

9. The method of claim 1, wherein the blood, plasma, or serum sample is a blood sample and the blood sample is collected, shipped, and/or stored in a tube that has cell- and DNA-stabilizing properties prior to processing the blood sample into plasma.

10. The method of claim 1, wherein the biosample blood, plasma, or serum sample is:

a blood sample;

not exposed to EDTA prior to processing the blood sample into plasma;

processed into plasma within about 24 to about 72 hours of the blood draw;

maintained, stored, and/or shipped at room temperature prior to processing into plasma; and/or maintained, stored, and/or shipped without exposure to chilling or freezing prior to processing into plasma.

11. The method of claim 1, further comprising identifying one or more protein coding sequences encoded by the enriched C-RNA molecules comprising one or more of AKAP2, ARRB1, CPSF7, INO80C, JAG1, MSMP, NR4A2, PLEK, RAP1GAP2, SPEG, TRPS1, and ZNF768.

12. The method of claim 2, wherein detecting the level of C-RNA molecules encoding at least a portion of the protein UBE2Q1 protein comprises hybridization, reverse transcriptase PCR, microarray chip analysis, or sequencing.

13. The method of claim 2, wherein the blood, plasma, or serum sample is obtained from the subject pregnant human female at less than 16 weeks gestation or at less than 20 weeks gestation.

14. The method of claim 2, wherein the blood, plasma, or serum sample is obtained from the subject pregnant human female at greater than 20 weeks gestation.

15. The method of claim 6, wherein the blood, plasma, or serum sample is obtained from the subject pregnant human female at less than 16 weeks gestation or at less than 20 weeks gestation.

16. The method of claim 6, wherein the blood, plasma, or serum sample is obtained from the subject pregnant human female at greater than 20 weeks gestation.

17. The method of claim 6, wherein sequencing comprises massively parallel sequencing of clonally amplified molecules.

18. The method of claim 2, wherein the blood, plasma, or serum sample is:

a blood sample;

not exposed to EDTA prior to processing the blood sample into plasma;

processed into plasma within about 24 to about 72 hours of the blood draw;

maintained, stored, and/or shipped at room temperature prior to processing into plasma; and/or maintained, stored, and/or shipped without exposure to chilling or freezing prior to processing into plasma.

* * * * *

UNITED STATES PATENT AND TRADEMARK OFFICE

CERTIFICATE OF CORRECTION

PATENT NO. : 11,753,685 B2
APPLICATION NO. : 16/953480
DATED : September 12, 2023
INVENTOR(S) : Sarah E. Shultzaberger et al.

It is certified that error appears in the above-identified patent and that said Letters Patent is hereby corrected as shown below:

On the Title Page

Column 2, Line 18 Item (56) References Cited, OTHER PUBLICATIONS, delete "2012" and insert -- 2012; -- therefor.

Column 2, Line 29, Item (56) References Cited, OTHER PUBLICATIONS, delete "2008" and insert -- 2008; -- therefor.

In the Claims

Column 109, Line 23, Claim 1, delete "with:" and insert -- with -- therefor.

Column 110, Line 48, Claim 10, delete "biosample" in between "the" and "blood" therefor.

Signed and Sealed this
Thirteenth Day of February, 2024

Katherine Kelly Vidal

Katherine Kelly Vidal
*Director of the United States Patent and Trademark Office*